US008859854B2

(12) United States Patent
Schmulling et al.

(10) Patent No.: US 8,859,854 B2
(45) Date of Patent: Oct. 14, 2014

(54) METHOD FOR MODIFYING PLANT MORPHOLOGY, BIOCHEMISTRY AND PHYSIOLOGY

(76) Inventors: Thomas Schmulling, Berlin (DE); Tomas Werner, Berlin (DE)

(*) Notice: Subject to any disclaimer, the term of this patent is extended or adjusted under 35 U.S.C. 154(b) by 31 days.

(21) Appl. No.: 13/539,876

(22) Filed: Jul. 2, 2012

(65) Prior Publication Data

US 2013/0007922 A1 Jan. 3, 2013

Related U.S. Application Data

(60) Continuation of application No. 12/291,376, filed on Nov. 7, 2008, now Pat. No. 8,227,663, which is a division of application No. 10/871,304, filed on Jun. 18, 2004, now Pat. No. 7,468,475, which is a continuation-in-part of application No. 10/014,101, filed on Dec. 10, 2001, now Pat. No. 7,259,296, which is a continuation-in-part of application No. PCT/EP01/06833, filed on Jun. 18, 2001.

(60) Provisional application No. 60/258,415, filed on Dec. 27, 2000.

(30) Foreign Application Priority Data

Jun. 16, 2000 (EP) .................................... 00870132
Mar. 16, 2001 (EP) .................................... 01870053

(51) Int. Cl.

| | |
|---|---|
| ***A01H 5/00*** | (2006.01) |
| ***A01H 5/10*** | (2006.01) |
| ***C12N 15/82*** | (2006.01) |

(52) U.S. Cl.

USPC ........ 800/298; 536/23.6; 435/320.1; 435/419

(58) Field of Classification Search

None

See application file for complete search history.

(56) References Cited

U.S. PATENT DOCUMENTS 6,310,271 B1 * 10/2001 Hanson et al. ................ 800/278
2004/0237147 A1 11/2004 Habben et al.

FOREIGN PATENT DOCUMENTS

WO 9906571 11/1999
WO 0063401 10/2000

OTHER PUBLICATIONS

Li et al (1994, Cereal Chem. 71(1):87-90).*
Bowie et al.; Science, 247: 1306-1310 (1990).
McConnell et al.; Nature, 411 6838: 709-713 (2001).
Fourgoux-Nicol et al.; Plant Molecular Biology, 40: 857-872 (1999).
Abstract: S.D. Rounsley et al.; XP002151606, Database Accession No. ID/AC=022213 (Jan. 1, 1998).
Abstract: M. Bevan et al.; "Cytokinin oxidase-like protein", XP-002151607, Database Accession No. ID/AC=Q9SU77 (May 1, 2000).
Abstract: X. Lin et al.; "*Arabidopsis thaliana* chromosome II BAC F3P11 genomic sequence, Putative Cytokinin Oxidase", XP-002151608, Database Accession No. ID/AC=Q9ZUP1 (May 1, 1999).
Abstract: Zhang, N., et al.; "Initiation and elongation of lateral roots in Lactuca sativa", XP002151609, Database Accession No. AN=PREV199900326622, International J. of Plant Sciences, 160(3): 511-519 (1999).
Abstract: Y. Koda et al.; "Cytokinin production by tomato root. Identification of a major cytokinin produced by the root and environmental factors effecting the production", XP002151610, Database Accession No. AN=PREV198988038194, J. of the Faculty of Agriculture Hokkaido University, 64(1) 10-20 (1989).
Abstract: M. Frank et al.; "TSD genes negatively regulate merismetic activity in *Arabidopsis*", XP002151616, Database Accession No. AN=PREV200000242628, Biologia Platarum (Prague), 42(Suppl.): S47 (1999).
Doerner et al.; "Control of root growth and development by cyclin expression", Nature, 380: 520-523 (Apr. 11, 1996).
Faiss et al.; Conditional transgenic expression of the ipt gene indicates a function for cytokinins in paracrine signaling in whole tobacco plants, The Plant Journal, 12(2): 401-415 (1997).
Houba-Herin et al.; "Cytokinin oxidase from *Zea mays*: purification, cDNA cloning and expression in moss protoplasts", The Plant Journal, 17(6): pp. 615-626 (1999).
Klee et al.; "Transgenic plants in hormone biology", Plant Hormones: Physiology, Biochemistry and Molecular Biology ed. Davies P.J. (Klower, Dordrdrocht, the Netherlands), 340-353 (1995).
Mok M.C.; "Cytokinins and Plant Development" in Cytokines: Chemistry, Activity and Function Chapter 12 eds. Mok D.W.S & Mok M.C., CRC Press Inc., 155-166 (1994).
Morris et al.; "Isolation of a Gene Encoding a Glycosylated Cytokinin Oxidase from Maize", Biochemical and Biophysical Research Communications, 255: 328-333 (1999).
Motyka et al.; "Changes in Cytokinin Content and Cytokinin Oxidase Activity in Response to Derepression of ipt Gene Transcription in Transgenic Tobacco Calli and Plants", Plant Physiol., 112: 1035-1043 (1996).
Rinaldi et al.; "Cytokinin oxidase strikes again", Trends in Plant Sci., Elsevier Science, 4(8): 300 (Aug. 1999).

(Continued)

*Primary Examiner* — Stuart F Baum

(74) *Attorney, Agent, or Firm* — Ann R. Pokalsky; Dilworth & Baarrese, LLP

(57) ABSTRACT

The present invention provides methods and compositions for increasing seed size and/or weight, embryo size and/or weight, and cotyledon size and/or weight. The methods comprise expression of a cytokinin oxidase or expression of another protein that reduces the level of active cytokinins in plants or plant parts. Methods and compositions for increasing seed yield are also provided. The invention also relates to isolated plant cytokinin oxidase proteins, nucleic acid sequences encoding cytokinin oxidase proteins as well as to vectors, host cells, transgenic cells and plants comprising such sequences.

22 Claims, 21 Drawing Sheets

(56) References Cited

OTHER PUBLICATIONS

Schmulling et al. "Recent advances in cytokinin research: Receptor candidates, primary response genes, mutants and transgenic plants", Advances in Regulation of Plant Growth and Development, 85-96 (1999).
Werner et al. "Regulation of plant growth by cytokinin" PNAS, 98(18) 10487-10492 (Aug. 28, 2001).
Alexandrov, N. et al., (2000), *Arabidopsis thaliana* DNA fragment SEQ ID No. 38444 GeneSeq AAG31640.
Alexandrov, N. et al., (2000), *Arabidopsis thaliana* DNA fragment SEQ ID No. 37443 GeneSeq AAC43214.
Bilyeu, K. et al., (2000), *Arabidopsis thaliana* cytokinin oxidase (CKX2) mRNA, complete cds. EMBL AF303978.
Bilyeu, K. et al., (2001), Molecular and biochemical characterization of a cytokinin oxidase from maize. Plant Physiology 125 378-386.
Burch, L. and Hogan, R., (1989), The purification of cytokinin oxidase from *Zea mays* kernels. Phytochemistry 28 1313-1319.
Hare, P. and van Staden, J., (1994), Cytokinin oxidase: Biochemical features and physiological significance. Physiologia Plantarum 91 128-136.
Kaminek, M. and Armstrong, D. (1990), Genotypic variation in cytokinin oxidase from Phaseolus callus cultures. Plant Physiology 93 1530-1538.
Lin, X. et al., (1989), *Arabidopsis thaliana* chromosome II section 113 of 255 of the complete sequence. Sequence from clones F27F23, F3P11 EMBL AC005917.
Lin, X. et al., (1999), Sequence and analysis of chromosome 2 of the plant *Arabidopsis thaliana*. Nature 402 761-768.
Werner, T. et al. (2003), Cytokinin-deficient transgenic *Arabidopsis* plants show multiple development alterations indicating opposite functions of cytokinins in the regulation of shoot and root meristem activity. Plant Cell 15 2532-2550.

* cited by examiner

A

B

C

D

E

METHOD FOR MODIFYING PLANT MORPHOLOGY, BIOCHEMISTRY AND PHYSIOLOGY

This application is a continuation of U.S. application Ser. No. 12/291,376, filed Nov. 7, 2008, now U.S. Pat. No. 8,227, 663; which is a divisional of U.S. Ser. No. 10/871,304, filed Jun. 18, 2004, now U.S. Pat. No. 7,468,475; which is a continuation-in-part application of U.S. Ser. No. 10/014,101, filed Dec. 10, 2001, now U.S. Pat. No. 7,259,296, which is a continuation-in-part of PCT/EP01/06833, filed Jun. 18, 2001, which claims the benefit under 35 U.S.C. §119(e) of U.S. Provisional Application 60/258,415, filed Dec. 27, 2000, the contents of which are incorporated herein by reference.

FIELD OF THE INVENTION

The present invention generally relates to methods for modifying plant morphological, biochemical and physiological properties or characteristics, such as one or more developmental processes and/or environmental adaptive processes, including but not limited to the modification of initiation or stimulation or enhancement of root growth, and/or adventitious root formation, and/or lateral root formation, and/or root geotropism, and/or shoot growth, and/or apical dominance, and/or branching, and/or timing of senescence, and/or timing of flowering, and/or flower formation, and/or seed development, and/or seed yield. Methods for increasing seed size and/or weight, increasing embryo size and/or weight, and increasing cotyledon size and/or weight are also provided. The methods comprise expressing a cytokinin degradation control protein, in particular cytokinin oxidase, in the plant, operably under the control of a regulatable promoter sequence such as a cell-specific promoter, tissue-specific promoter, or organ-specific promoter sequence. Preferably, the characteristics modified by the present invention are cytokinin-mediated and/or auxin-mediated characteristics. The present invention extends to genetic constructs which are useful for performing the inventive method and to transgenic plants produced therewith having altered morphological and/or biochemical and/or physiological properties compared to their otherwise isogenic counterparts.

BACKGROUND OF THE INVENTION

Roots are an important organ of higher plants. Their main functions are anchoring of the plant in the soil and uptake of water and nutrients (N-nutrition, minerals, etc.). Thus, root growth has a direct or indirect influence on growth and yield of aerial organs, particularly under conditions of nutrient limitation. Roots are also relevant for the production of secondary plant products, such as defense compounds and plant hormones.

Roots are also storage organs in a number of important staple crops. Sugar beet is the most important plant for sugar production in Europe (260 Mill t/year; 38% of world production). Manioc (cassava), yams and sweet potato (batate) are important starch producers (app. 150 Mill t/year each). Their content in starch can be twice as high as that of potato. Roots are also the relevant organ for consumption in a number of vegetables (e.g. carrots, radish), herbs (e.g. ginger, kukuma) and medicinal plants (e.g. ginseng). In addition, some of the secondary plant products found in roots are of economic importance for the chemical and pharmaceutical industry. An example is yams, which contain basic molecules for the synthesis of steroid hormones. Another example is shikonin, which is produced by the roots of *Lithospermum erythrorhizon* in hairy root cultures. Shikonin is used for its anti-inflammatory, anti-tumor and wound-healing properties.

Moreover, improved root growth of crop plants will also enhance competitiveness with weedy plants and will improve growth in arid areas, by increasing water accessibility and uptake.

Improved root growth is also relevant for ecological purposes, such as bioremediation and prevention/arrest of soil erosion.

Root architecture is an area that has remained largely unexplored through classical breeding, because of difficulties with assessing this trait in the field. Thus, biotechnology could have significant impact on the improvement of this trait, because it does not rely on large-scale screenings in the field. Rather, biotechnological approaches require a basic understanding of the molecular components that determine a specific characteristic of the plant. Today, this knowledge is only fragmentary, and as a consequence, biotechnology was so far unable to realize a break-through in this area.

A well-established regulator of root growth is auxin. Application of indole-3-acetic acid (IAA) to growing plants stimulates lateral root development and lateral root elongation (Torrey, Am J Bot 37: 257-264, 1950; Blakely et al., Bot Gaz 143: 341-352, 1982; Muday and Haworth, Plant Physiol Biochem 32: 193-203, 1994). Roots exposed to a range of concentrations of IAA initiated increasing numbers of lateral roots (Kerk et al., Plant Physiol, 122: 925-932, 2000). Furthermore, when roots that had produced laterals in response to a particular concentration of exogenous auxin were subsequently exposed to a higher concentration of IAA, numerous supernumerary lateral roots spaced between existing ones were formed (Kerk et al., Plant Physiol, 122: 925-932, 2000). Conversely, growth of roots on agar containing auxin-transport inhibitors, including NPA, decreases the number of lateral roots (Muday and Haworth, Plant Physiol Biochem 32: 193-203, 1994).

*Arabidopsis* mutants containing increased levels of endogenous IAA have been isolated (Boerjan et al., Plant Cell 7: 1405-141, 1995; Celenza et al., Gene Dev 9: 2131-2142, 1995; King et al., Plant Cell 7: 2023-2037, 1995; Lehman et al., Cell 85: 183-194, 1996). They are now known to be alleles of a single locus located on chromosome 2. These mutant seedlings have excess adventitious and lateral roots, which is in accordance with the above-described effects of external auxin application.

The stimulatory effect of auxins on adventitious and lateral root formation suggests that overproduction of auxins in transgenic plants is a valid strategy for increasing root growth. Yet, it is also questionable whether this would yield a commercial product with improved characteristics. Apart from its stimulatory effect on adventitious and lateral root formation, auxin overproduction triggers other effects, such as reduction in leaf number, abnormal leaf morphology (narrow, curled leaves), aborted inflorescences, increased apical dominance, adventitious root formation on the stem, most of which are undesirable from an agronomic perspective (Klee et al., Genes Devel 1: 86-96, 1987; Kares et al., Plant Mol Biol 15: 225-236, 1990). Therefore, the major problem with approaches that rely on increased auxin synthesis is a problem of containment, namely to confine the effects of auxin to the root. This problem of containment is not likely overcome by using tissue-specific promoters: auxins are transported in the plant and their action is consequently not confined to the site of synthesis. Another issue is whether auxins will always enhance the total root biomass. For agar-grown plants, it has been noticed that increasing concentrations progressively stimulated lateral root formation but concurrently inhibited the outgrowth of these roots (Kerk et al., Plant Physiol, 122: 925-932, 2000).

Seeds are the reproduction unit of higher plants. Plant seeds contain reserve compounds to ensure nutrition of the embryo after germination. These storage organs contribute significantly to human nutrition as well as cattle feeding. Seeds consist of three major parts, namely the embryo, the endosperm and the seed coat. Reserve compounds are deposited in the storage organ which is either the endosperm (resulting form double fertilisation; e.g. in all cereals), the so-called perisperm (derived from the nucellus tissue) or the cotyledons (e.g. bean varieties). Storage compounds are lipids (oil seed rape), proteins (e.g. in the aleuron of cereals) or carbohydrates (starch, oligosaccharides like raffinose).

Starch is the storage compound in the seeds of cereals. The most important species are maize (yearly production ca. 570 mio t; according to FAO 1995), rice (540 mio t p.a.) and wheat (530 mio t p.a.). Protein rich seeds are different kinds of beans (*Phaseolus* spec., *Vicia faba, Vigna* spec.; ca. 20 mio t p.a.), pea (*Pisum sativum;* 14 mio t p.a.) and soybean (*Glycine max;* 136 mio t p.a.). Soybean seeds are also an important source of lipids. Lipid rich seeds are as well those of different *Brassica* species (app. 30 mio t p.a.), cotton, oriental sesame, flax, poppy, castor bean, sunflower, peanut, coconut, oilpalm and some other plants of less economic importance.

After fertilization, the developing seed becomes a sink organ that attracts nutritional compounds from source organs of the plant and uses them to produce the reserve compounds in the storage organ. Increases in seed size and weight, are desirable for many different crop species. In addition to increased starch, protein and lipid reserves and hence enhanced nutrition upon ingestion, increases in seed size and/or weight and cotyledon size and/or weight are correlated with faster growth upon germination (early vigor) and enhanced stress tolerance. Cytokinins are an important factor in determining sink strength. The common concept predicts that cytokinins are a positive regulator of sink strength.

Numerous reports ascribe a stimulatory or inhibitory function to cytokinins in different developmental processes such as root growth and branching, control of apical dominance in the shoot, chloroplast development, and leaf senescence (Mok M. C. (1994) in *Cytokines: Chemistry, Activity and Function*, eds., Mok, D. W. S. & Mok, M. C. (CRC Boca Raton, Fla.), pp. 155-166). Conclusions about the biological functions of cytokinins have mainly been derived from studies on the consequences of exogenous cytokinin application or endogenously enhanced cytokinin levels (Klee, H. J. & Lanehon, M. B. (1995) in *Plant Hormones: Physiology, Biochemistry and Molecular Biology*, ed. Davies, P. J. (Kluwer, Dordrdrocht, the Netherlands), pp. 340-353, Smulling, T., Rupp, H. M. Frank, M& Schafer, S. (1999) in *Advances in Regulation of Plant Growth and Development*, eds. Surnad, M. Pac P. & Beck, E. (Peres, Prague), pp. 85-96). Up to now, it has not been possible to address the reverse question: what are the consequences for plant growth and development if the endogenous cytokinin concentration is decreased? Plants with a reduced cytokinin content are expected to yield more precise information about processes cytokinins limit and, therefore, might regulate. Unlike other plant hormones such as abscisic acid, gibberellins, and ethylene, no cytokinin biosynthetic mutants have been isolated (Hooykens, P. J. J., Hall, M. A. & Libbeuga, K. R., eds. (1999) *Biochemistry and Molecular Biology of Plant Hormones* (Elsevier, Amsterdam).

The catabolic enzyme cytokinin oxidase (CKX) plays a principal role in controlling cytokinin levels in plant tissues. CKX activity has been found in a great number of higher plants and in different plant tissues. The enzyme is a FAD-containing oxidoreductase that catalyzes the degradation of cytokinins bearing unsaturated isoprenoid side chains. The free bases iP and Z, and their respective ribosides are the preferred substrates. The reaction products of iP catabolism are adenine and the unsaturated aldehyde 3-methyl-2-butonal (Armstrong, D. J. (1994) in *Cytokinins: Chemistry, Activity and Functions*, eds. Mok. D. W. S & Mok, M. C. (CRC Boca Raton, Fla.), pp. 139-154). Recently, a cytokinin oxidase gene from *Zea mays* has been isolated (Morris, R. O., Bilyeu, K. D., Laskey, J. G. & Chemch, N, N. (1999) *Biochem. Biophys. Res. Commun.* 255, 328-333, Houba-Heria, N., Pethe, C. d'Alayer, J & Lelouc, M. (1999) *Plant J.* 7:615-626). The manipulation of CKX gene expression could partially overcome the lack of cytokinin biosynthetic mutants and can be used as a powerful tool to study the relevance of iP- and Z-type cytokinins during the whole life cycle of higher plants.

The present invention overcomes problems related to containment of auxin effects, maintenance of root outgrowth, and promotion of increased seed, embryo, and cotyledon size and/or weight through reduction of endogenous cytokinin concentration.

SUMMARY OF THE INVENTION

The present invention provides plant cytokinin oxidase proteins, nucleic acid sequences encoding such proteins, and vectors, host cells and transgenic plant cells, plants, and plant parts comprising the proteins, nucleic acid sequences, and vectors. For example, the present invention relates to a genetic construct comprising a gene encoding a protein with cytokinin oxidase activity from *Arabidopsis thaliana*. This gene may be expressed under control of a regulated promoter. This promoter may be regulated by endogenous tissue-specific or environment-specific factors or, alternatively, it may be induced by application of specific chemicals.

The present invention also relates to a method to modify root architecture and biomass by expression of a cytokinin oxidase gene or expression of a nucleic acid encoding a protein that reduces the level of active cytokinins in plants or plant parts. Preferably, expression is under control of a promoter that is specific to the root or to certain tissues or cell types of the root.

Additionally, the present invention relates to methods of increasing seed size and/or weight, embryo size and/or weight, and cotyledon size and/or weight. The methods involve expression of a cytokinin oxidase gene or expression of a nucleic acid encoding a protein that reduces the level of active cytokinins in plants or plant parts. Preferably, expression is under control of a promoter directs expression preferentially in the seed, embryo, or cotyledon. Methods and compositions for increasing seed yield in a plant are also provided.

Shown are the structures of different cytokinin oxidase genes isolated from maize (ZmCKX1, accession number AF044603, Biochem. Biophys. Res. Com. 255:328-333, 1999) and *Arabidopsis* (AtCKX1 to AtCKX4). Exons are denominated with 'E' and represented by shaded boxes. Introns are represented by white boxes. Further indicated are the gene sizes (in kb, on top of each structure), the gene accession numbers (under the names) and a size bar representing 0.5 kb.

Figure 2:
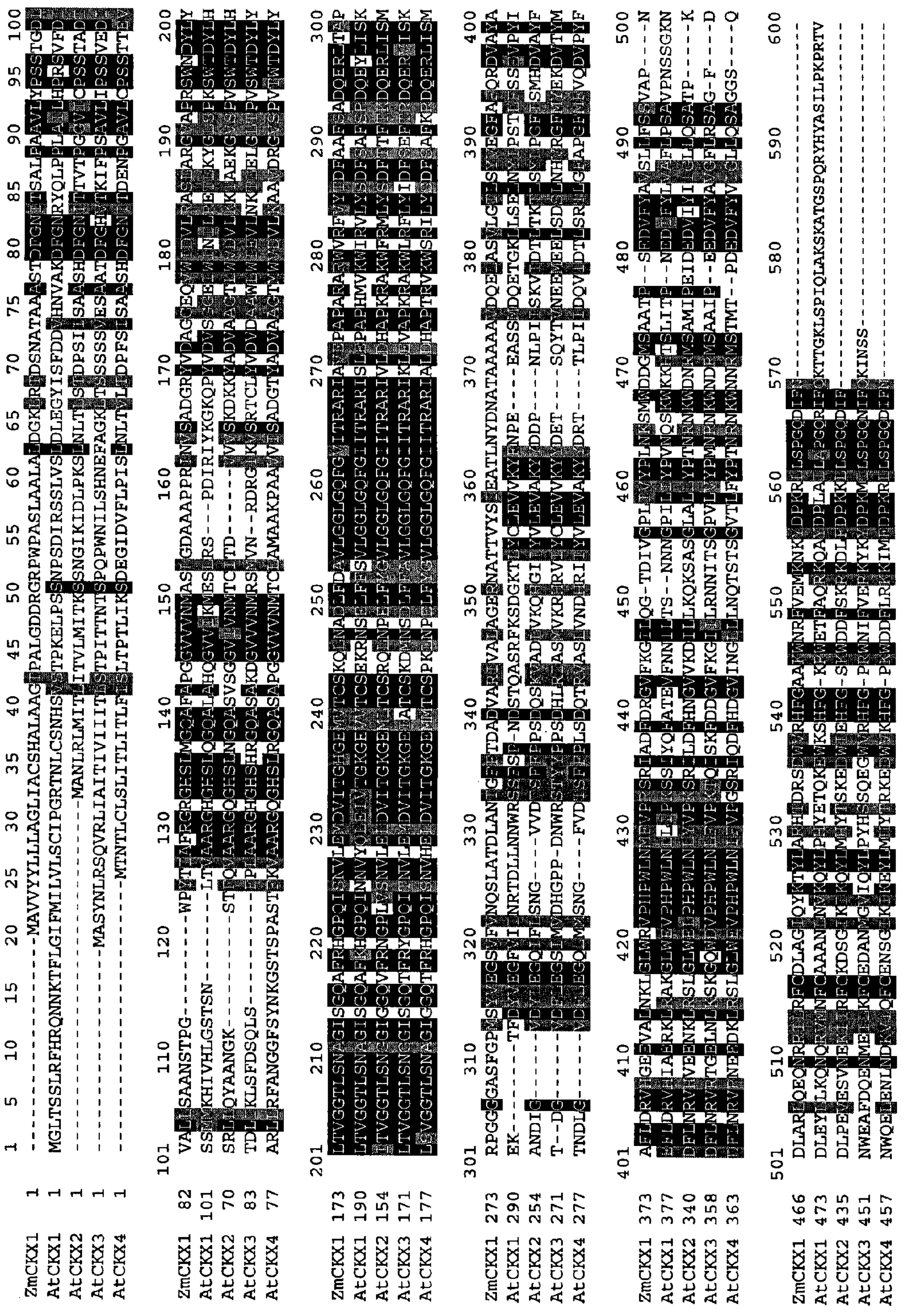

FIG. 2. Alignment of plant cytokinin oxidase amino acid sequences.

The amino acid sequences from cytokinin oxidases from maize (ZmCKX1) (SEQ ID NO:51) and *Arabidopsis* (AtCKX1 to AtCKX4) are aligned. AtCKX1 is SEQ ID NO:2, AtCKX2 is SEQ ID NO:4, AtCKX3 is SEQ ID NO:6, and AtCKX4 is SEQ ID NO:8.

Identical amino acid residues are marked by a black box, similar amino acid residues are in a grey box. Amino acid similarity groups: (M,I,L,V), (F,W,Y), (G,A), (S,T), (R,K,H), (E,D), (N,Q), FIG. 3. Northern blot analysis of AtCKX1-expressing tobacco and *Arabidopsis* plants.

(A) Northern blot analysis of constitutively expressing tobacco plants (lanes 1-8) compared to wild type SNN tobacco (lane 9)

(B) Comparison of tetracycline-induced gene expression in leaves after 12 h of induction with a constitutively expressing clone. Lanes 2-9, leaves of four different AtCKX1-W38TetR clones (+, −, with or without tetracycline treatment), lane 1, constitutively expressing 35S::AtCKX1 clone.

(C) Northern blot analysis of *Arabidopsis* plants constitutively expressing AtCKX1 gene. Lanes 2-4, three different constitutively expressing 35S::AtCKX1 clones compared to wild type *Arabidopsis* plant (lane 1).

Figure 4:
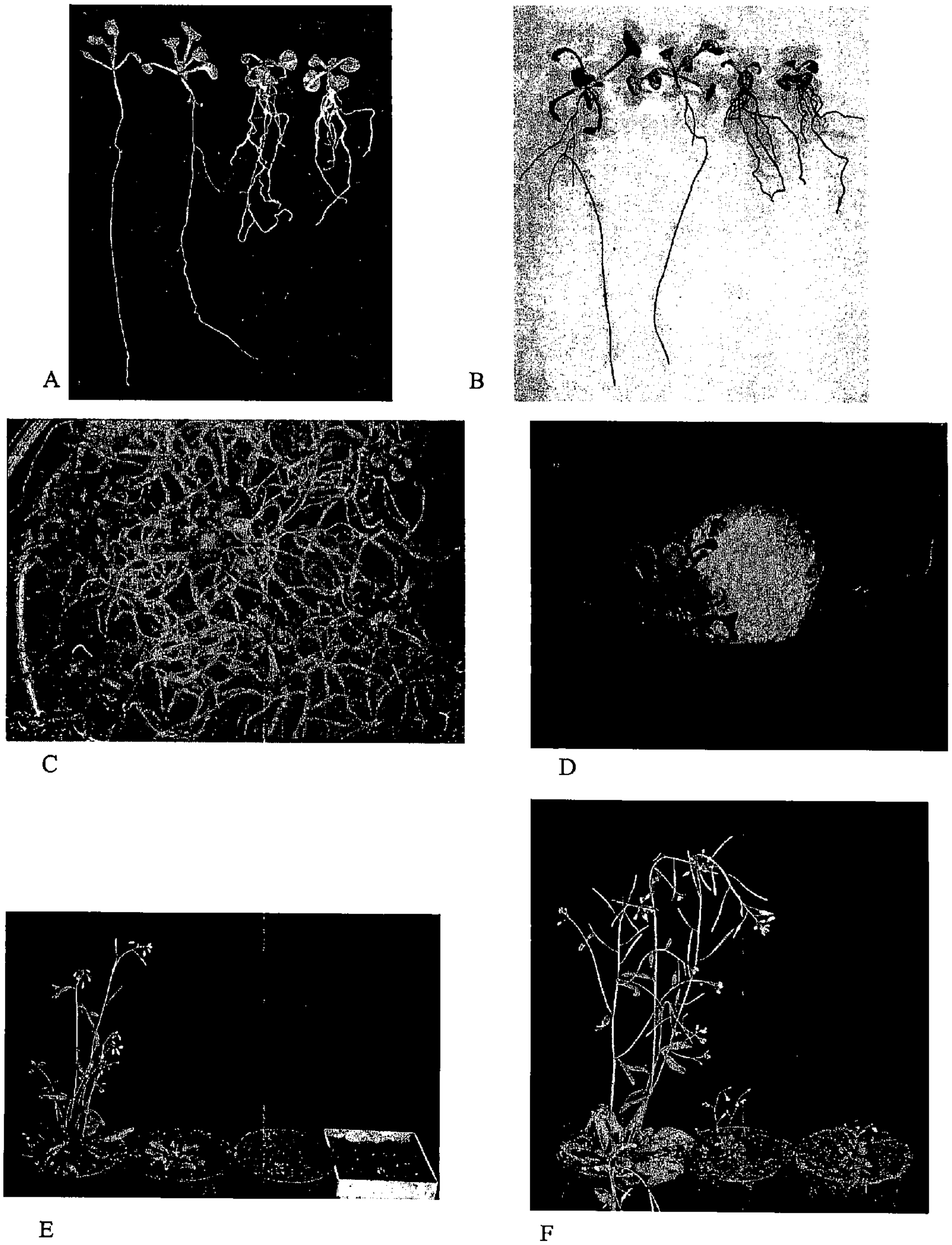

FIG. 4: Growth characteristics of 35S::AtCKX1 transgenic *Arabidopsis* plants.

(A) Two wild type seedlings (left) compared to two 35S::AtCKX1 expressing seedlings (right). Note the increased formation of adventitious roots and increased root branching in the transgenic seedlings. Pictures were taken 14 days after germination. Plants were grown in vitro on MS medium in petri dishes in a vertical position.

(B) Like A, but roots stained with toluidine blue.

(C) Top view of a petri dish with 35S::AtCKX1 transgenic seedlings three weeks after germination.

(D) A 35S::AtCKX1 transgenic plants grown in liquid culture. Roots of wild type seedlings grow poorly under these conditions (not shown).

(E) Transformants (T0) that express the 35S::AtCKX1 gene (three plants on the right), a wild type plant is shown on the left.

(F) Phenotype of T1 plants grown in soil. Wild type plant (left) compared to two 35S::AtCKX1 transgenic plants.

Figure 5:

FIG. 5: Phenotype of AtCKX2 overexpressing *Arabidopsis* plants.

T1 generation of 35S::AtCKX2 expressing *Arabidopsis* plants (two plants on the right) compared to wild type (plant on the left).

Figure 6:
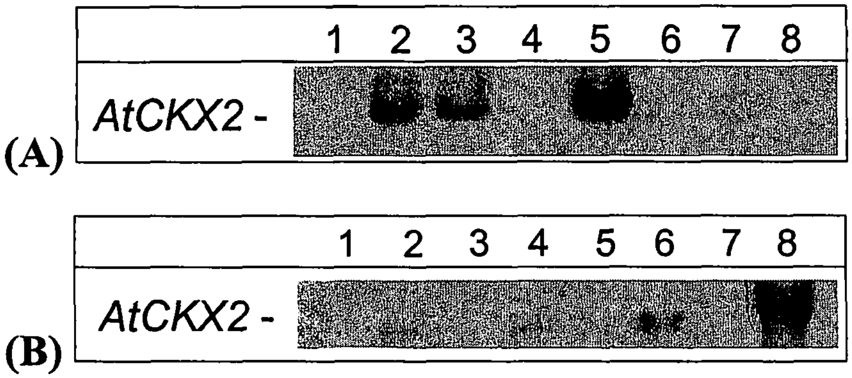

FIG. 6. Northern blot analysis of AtCKX2-expressing tobacco and *Arabidopsis* plants.

(A) Northern blot analysis of constitutively expressing tobacco plants (lanes 1-7) compared to wild type SNN tobacco (lane 8)

(B) Northern blot analysis of *Arabidopsis* plants constitutively expressing AtCKX2 gene. Lanes 2-8, seven different constitutively expressing 35S::AtCKX2 clones compared to wild type *Arabidopsis* plant (lane 1).

Figure 7:
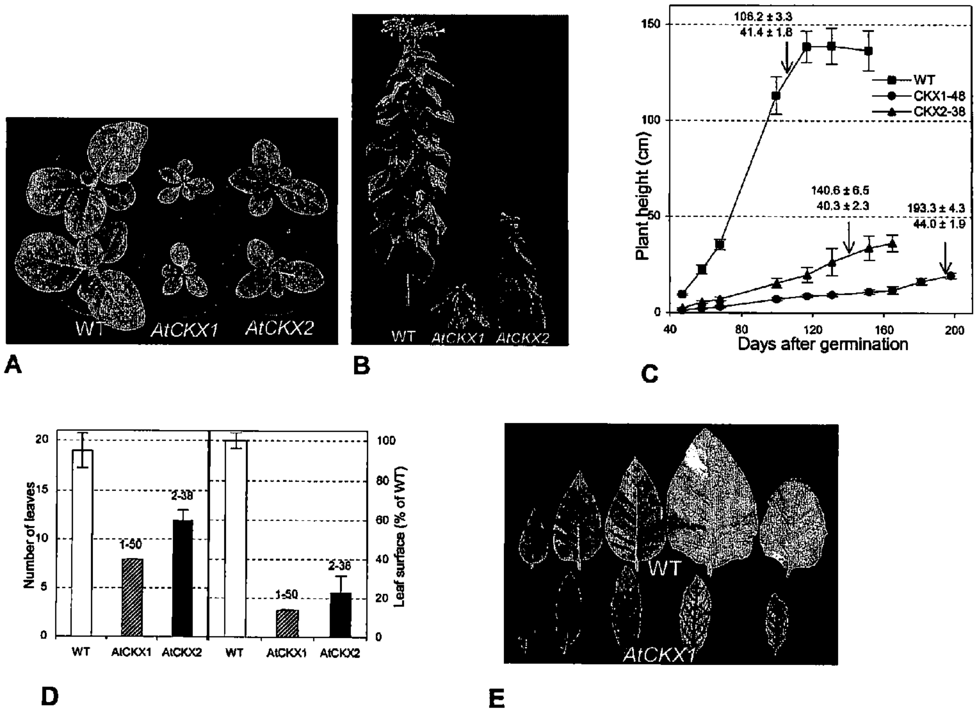

FIG. 7. Shoot phenotype of AtCKX1 and AtCKX2 expressing tobacco plants.

(A) Top view of six week old plants.

(B) Tobacco plants at the flowering stage.

(C) Kinetics of stem elongation. Arrows mark the onset of flowering. Age of plants (days after germination) and leaf number at that stage are indicated above the arrows. Bars indicate SD; n=12.

(D) Number of leaves (n=12) formed between day 68 and day 100 after germination and final surface area of these leaves (100% of wild type is 3646±144 $cm^2$; n=3).

(E) Comparison of leaf size and senescence. Leaves were from nodes number 4, 9, 12, 16 and 20 from the top (from left to right).

Figure 8:
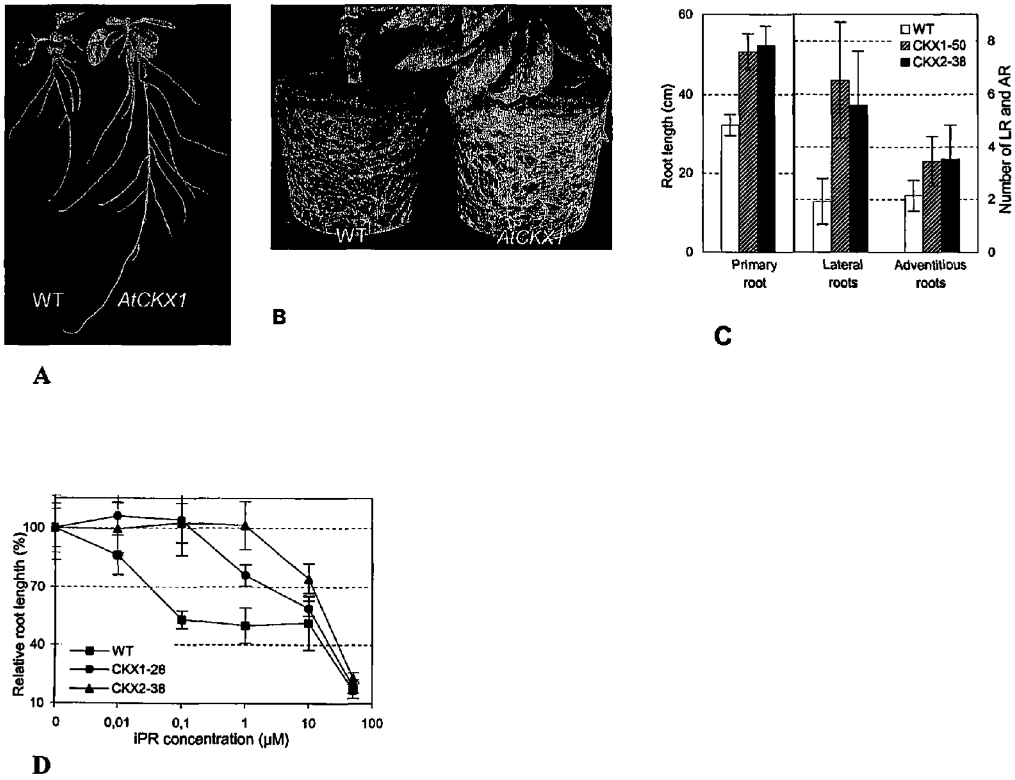

FIG. 8. Root phenotype of AtCKX expressing transgenic tobacco plants.

(A) Seedlings 17 days after germination.

(B) Root system of soil grown plants at the flowering stage.

(C) Root length, number of lateral roots (LR) and adventitious roots (AR) on day 10 after germination.

(D) Dose-response curve of root growth inhibition by exogenous cytokinin. Bars indicate ±SD; n=30.

Figure 9:
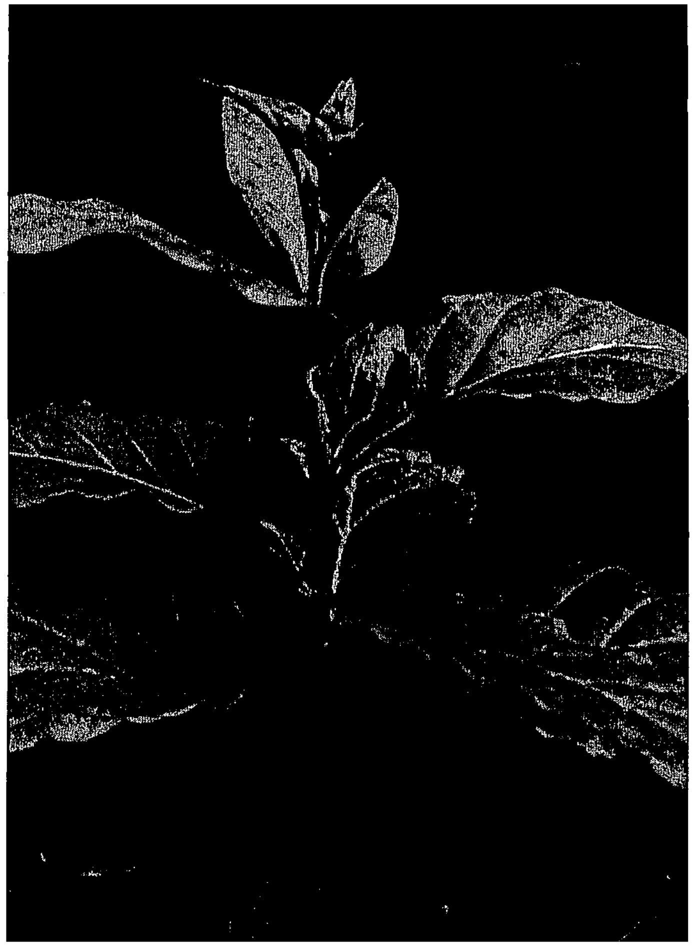

FIG. 9: Growth of axillary shoot meristems in 35S::AtCKX1 expressing tobacco plants.

Figure 10:
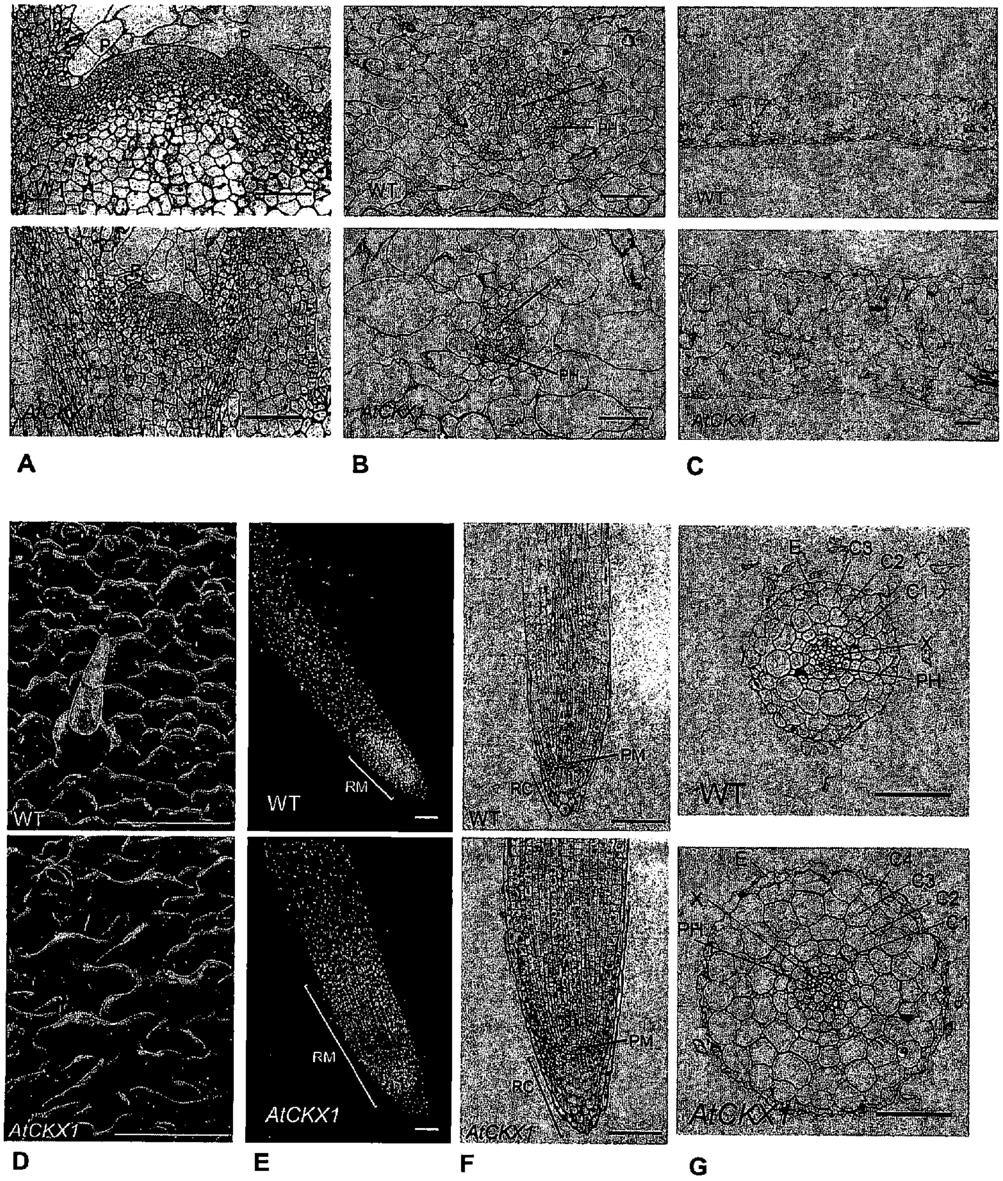

FIG. 10: Histology of shoot meristems, leaves and root meristems of AtCKX1 overexpressing tobacco plants versus wild type (WT) tobacco.

(A) Longitudinal median section through the vegetative shoot apical meristem. P, leaf primordia.

(B) Vascular tissue in second order veins of leaves. X, xylem, PH, a phloem bundle.

(C) Cross sections of fully developed leaves.

(D) Scanning electron microscopy of the upper leaf epidermis.

(E) Root apices stained with DAPI. RM, root meristem.

(F) Longitudinal median sections of root meristems ten days after germination. RC, root cap; PM, promeristem.

(G) Transverse root sections 10 mm from the apex. E, epidermis, C1-C4, cortical cell layer, X, xylem, PH, phloem. Bars are 100 μm.

Figure 11:
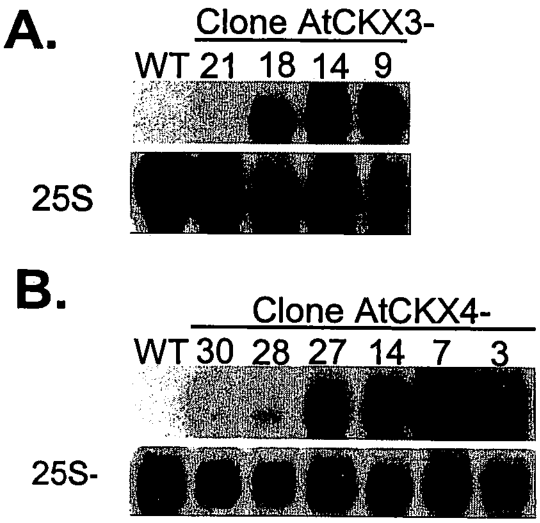

FIG. 11: Northern blot analysis of AtCKX3 and AtCKX4-expressing tobacco plants.

(A) Northern blot analysis of constitutively expressing AtCKX3 tobacco plants. Lane designations indicate individual transgenic plant numbers, WT is wild type SNN tobacco. The blot on top was probed with a AtCKX3 specific probe, the lower blot with a probe specific for the 25S rRNA and serves as a control for RNA loading.

(B) Northern blot analysis of constitutively expressing AtCKX4 tobacco plants. Lane designations indicate individual transgenic plant numbers, WT is wild type SNN tobacco. The blot on top was probed with an AtCKX4 specific probe, the lower blot with a probe specific for the 25S rRNA and serves as a control for RNA loading.

Figure 12:
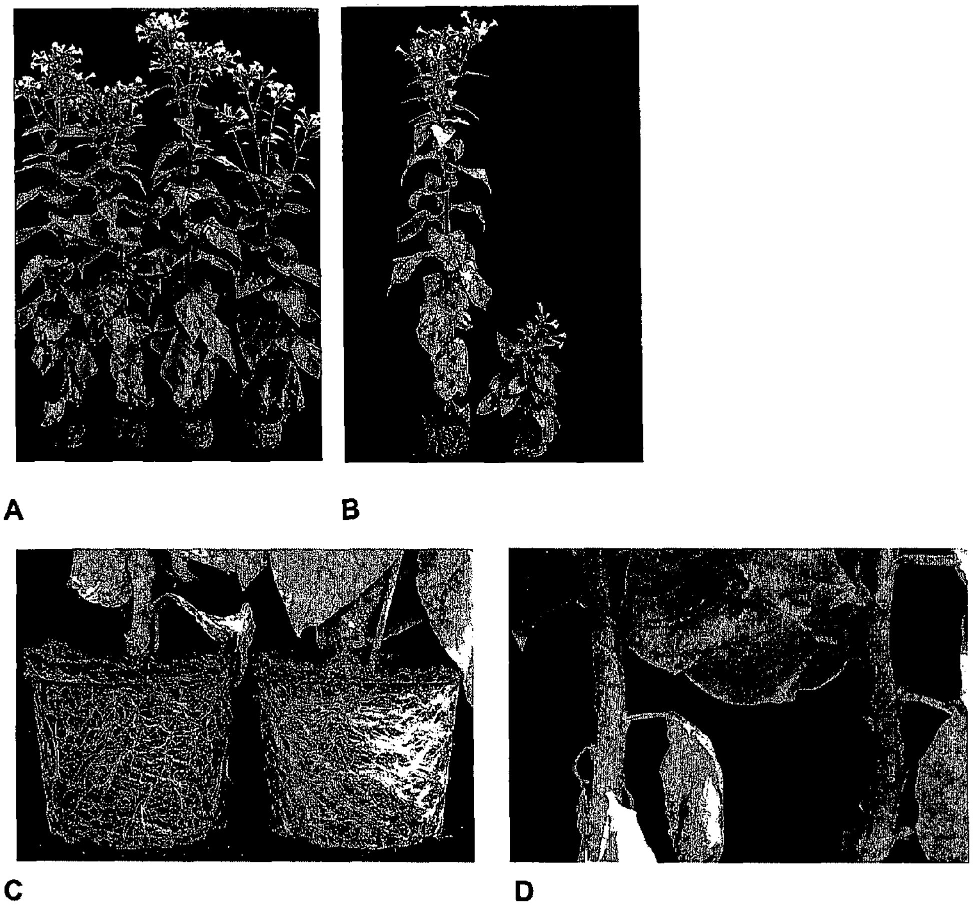
Figure 13A:
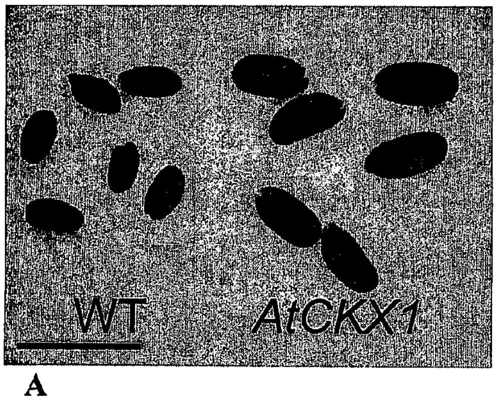
Figure 13B:
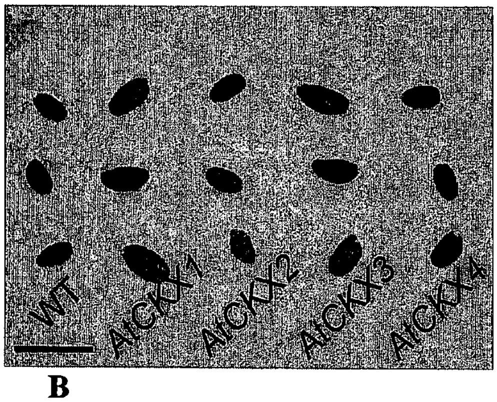
Figure 13C:
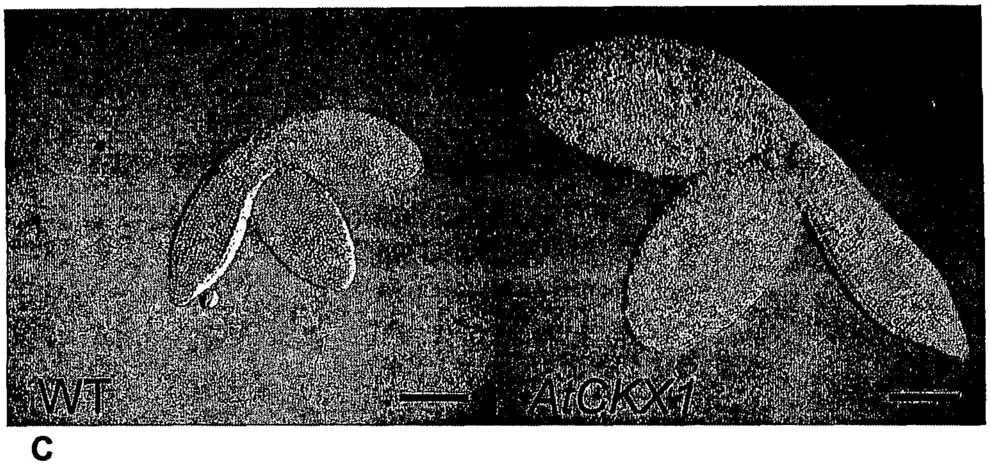
Figure 13D:
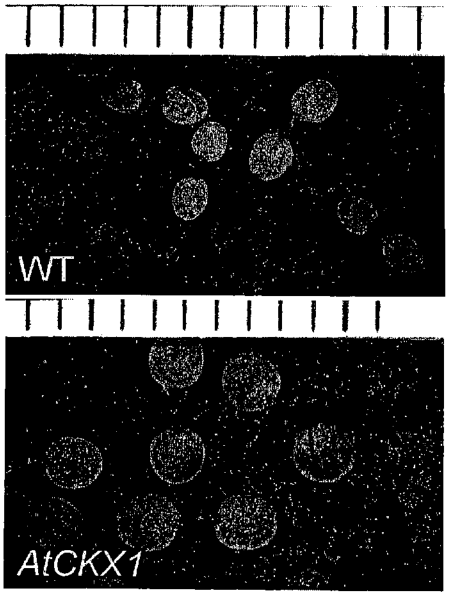
Figure 13E:
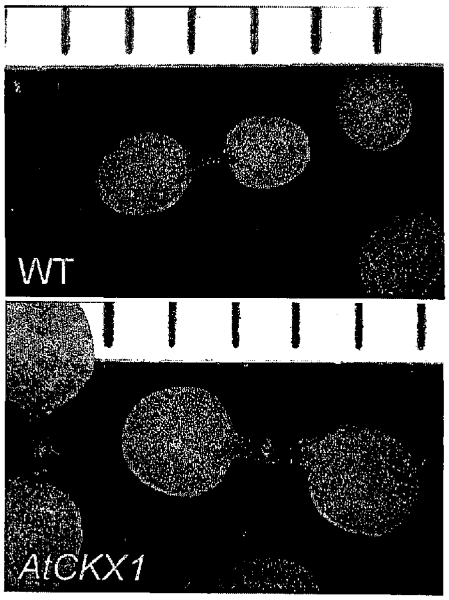

FIG. 12: Reciprocal grafts of AtCKX2 transgenic tobacco plants and wild type plants.

(A) Two plants on the left: Control (WT scion grafted on a WT rootstock).

Two plants on the right: WT scion grafted on a AtCKX2-38 transgenic rootstock.

(B) Left: Control (WT scion grafted on a WT rootstock).

Right: Scion of AtCKX2-38 plant grafted on WT rootstock.

(C) Magnification of root area.

Left: Control (WT scion grafted on a WT rootstock).

Right: WT scion grafted on an AtCKX2-38 transgenic rootstock.

(D) Formation of adventitious roots.

Left: Control (WT scion grafted on an WT rootstock).

Right: WT scion grafted on an AtCKX2-38 transgenic rootstock.

FIG. 13: Phenotype of *Arabidopsis* seeds, embryos and seedlings.

(A) Seeds of an AtCKX1 transgenic line and wild type seeds. Bar size 1 mm (B) Seeds of AtCKX1, AtCKX2, AtCKX3 and AtCKX4 transgenic lines and wild type seeds. Bar size 1 mm.

(C) Mature embryos of AtCKX1 transgenic *Arabidopsis* and of a wild type plant. Bar size 200 μm. Embryos were obtained from mature seeds that had been imbibed for 12 hours in 20% EtOH, squeezed out from the seed coat, cleared with chloralhydrate and photographed using Nomarski optics.

(D) Wild type (top) and AtCKX1 expressing *Arabidopsis* seedlings 4 days after germination.

(E) Close-up of D.

Figure 14:
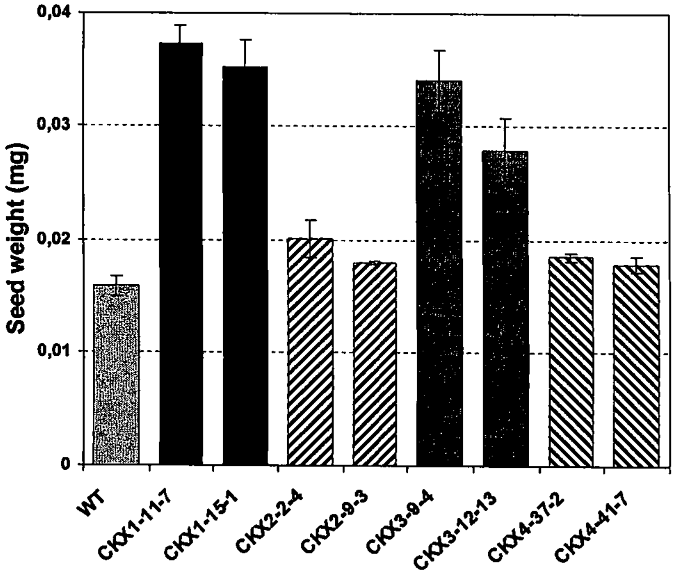

FIG. 14: Seed weight of wild type and two independent clones for each of the four investigated AtCKX genes. Average weight obtained by analysing five different batches of 200 seeds for each clone.

Figure 15:
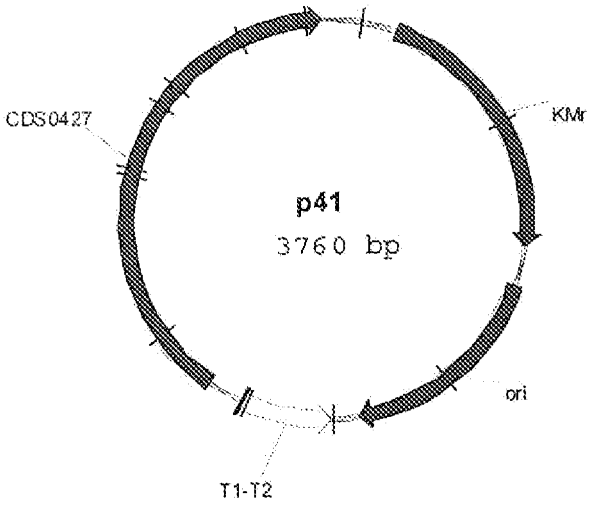

FIG. 15: Schematic presentation of the entry clone p41, containing CDS0427_2 within the AttL1 and AttL2 sites for Gateway® cloning in the pDONR201 backbone. CDS0427_2 is the internal code for the *Arabidopsis thaliana* CKX2 coding sequence (SEQ ID NO: 26). This vector contains also a bacterial kanamycine-resistance cassette and a bacterial origin of replication.

Figure 16:
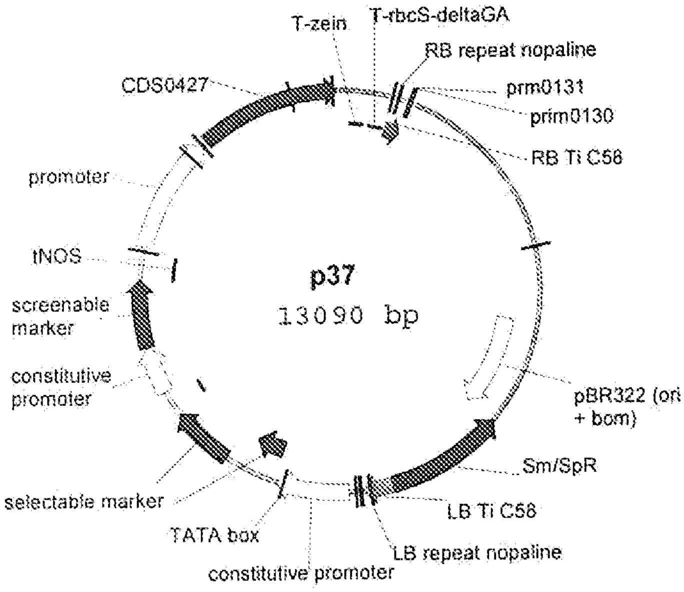

FIG. 16: Binary vector p37 for the expression in *Oryza sativa* of the *Arabidopsis thaliana* CKX2 gene under the control of the PRO0218 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0218-CDS0427_2-zein and rbcS-deltaGA double terminator cassette for expression of the *Arabidopsis thaliana* CKX2 gene. This vector also contains an origin of replication from pBR322 for bacterial replication and a selectable marker (Spe/SmeR) for bacterial selection with spectinomycin and streptomycin.

Figure 17:
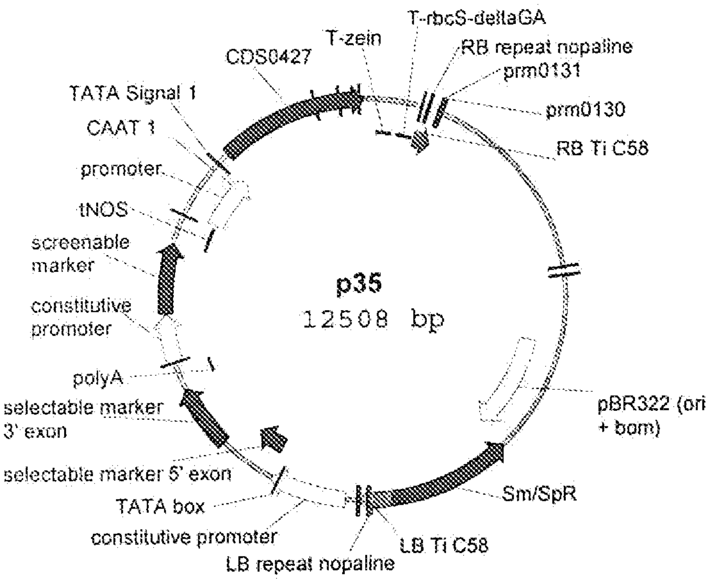

FIG. 17: Binary vector p35 for the expression in *Oryza sativa* of the *Arabidopsis thaliana* CKX2 gene under the control of the PRO0090 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0090-CDS0427_2-zein and rbcS-deltaGA double terminator cassette for expression of the *Arabidopsis thaliana* CKX2 gene. This vector also contains an origin of replication from pBR322 for bacterial replication and a selectable marker (Spe/SmeR) for bacterial selection with spectinomycin and streptomycin.

Figure 18:
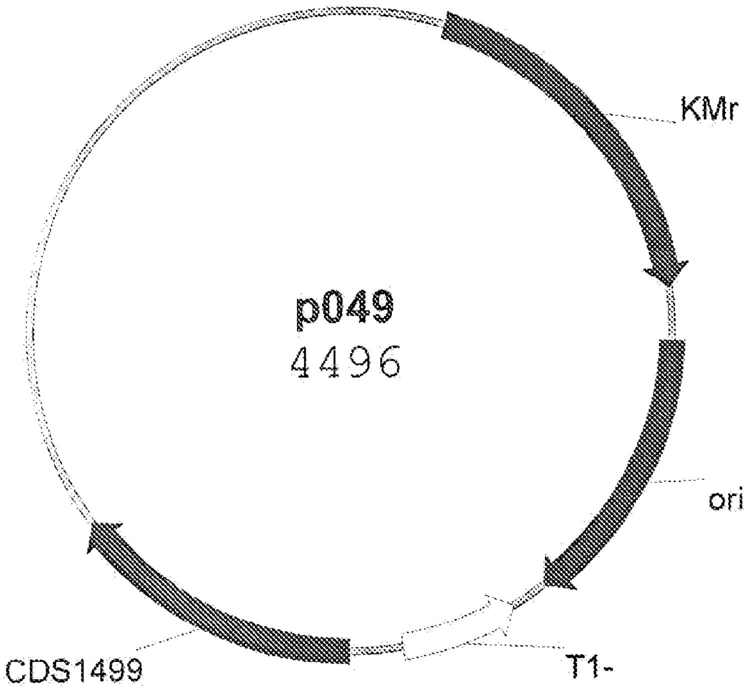

FIG. 18: Schematic presentation of the entry clone p049, containing CDS1499_2 within the AttL1 and AttL2 sites for Gateway® cloning in the pDONR201 backbone. CDS1499_2 is the internal code for the *Arabidopsis thaliana* CKX1 coding sequence (SEQ ID NO:48). This vector contains also a bacterial kanamycine-resistance cassette and a bacterial origin of replication.

Figure 19:
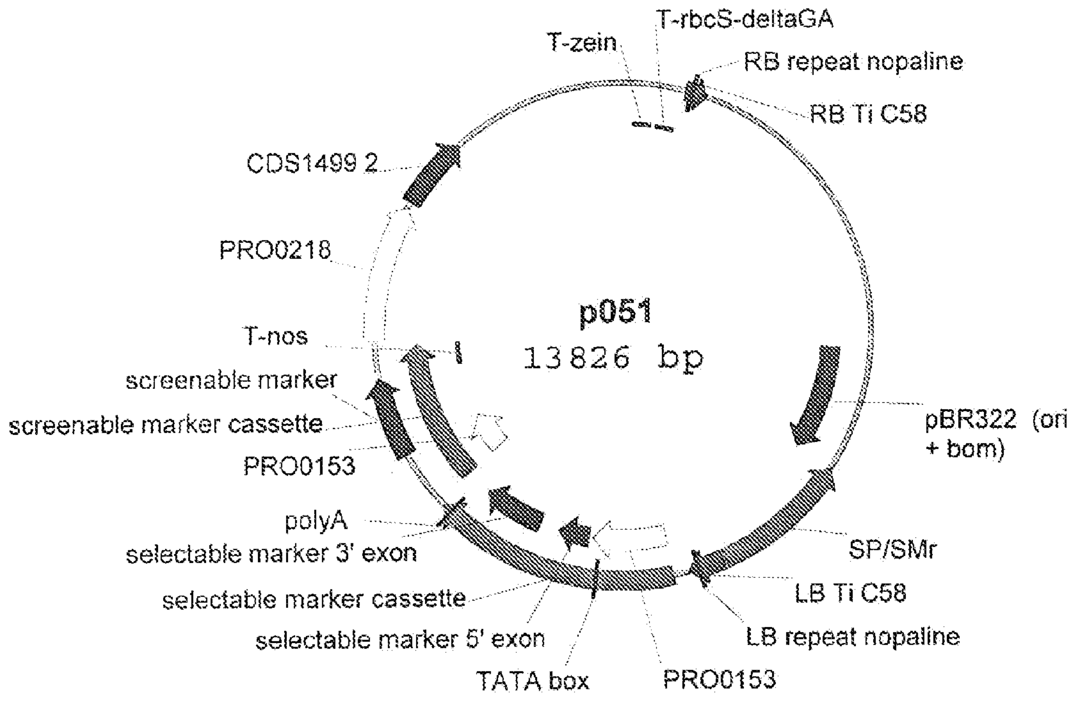

FIG. 19: Binary vector p051 for the expression in *Oryza sativa* of the *Arabidopsis thaliana* CKX1 gene under the control of the PRO0218 promoter. This vector contains a T-DNA derived from the Ti plasmid, limited by a left border (LB repeat, LB Ti C58) and a right border (RB repeat, RB Ti C58)). From the left border to the right border, this T-DNA contains: a selectable and a screenable marker for selection of transformed plants, each under control of a constitutive promoter; the PRO0218-CDS1499_2-zein and rbcS-deltaGA double terminator cassette for expression of the *Arabidopsis thaliana* CKX1 gene. This vector also contains an origin of replication from pBR322 for bacterial replication and a selectable marker (Spe/SmeR) for bacterial selection with spectinomycin and streptomycin.

DETAILED DESCRIPTION OF THE INVENTION

To by-pass above-mentioned problems associated with increasing auxin biosynthesis, it was decided to follow an alternative approach. We reasoned that downregulation of biological antagonists of auxins could evoke similar or even superior effects on root growth as compared to increasing auxin levels. Hormone actions and interactions are extremely complex, but we hypothesized that cytokinins could function as auxin antagonists with respect to root growth. Hormone studies on plant tissue cultures have shown that the ratio of auxin versus cytokinin is more important for organogenesis than the absolute levels of each of these hormones, which indeed indicates that these hormones function as antagonists—at least in certain biological processes. Furthermore, lateral root formation is inhibited by exogenous application of cytokinins. Interestingly, also root elongation is negatively affected by cytokinin treatment, which suggests that cytokinins control both root branching and root outgrowth.

Together, current literature data indicate that increasing cytokinin levels negatively affects root growth, but the mechanisms underlying this process are not understood. The sites of cytokinin synthesis in the plant are root tips and young tissues of the shoot. Endogenous concentrations of cytokinins are in the nM range. However, as their quantification is difficult, rather large tissue amounts need to be extracted and actual local concentrations are not known. Also the subcellular compartmentation of cytokinins is not known. It is generally thought that the free base and ribosides are localized in the cytoplasm and nucleus, while glucosides are localized in the vacuole. There exist also different cytokinins with slightly different chemical structure. As a consequence, it is not known whether the effects of exogenous cytokinins should be ascribed to a raise in total cytokinin concentration or rather to the competing out of other forms of plant-borne cytokinins (which differ either in structure, cellular or subcellular location) for receptors, translocators, transporters, and modifying enzymes.

In order to test the hypothesis that cytokinin levels in the root indeed exceed the level optimal for root growth, novel genes encoding cytokinin oxidases (which are cytokinin metabolizing enzymes) were cloned from *Arabidopsis thaliana* (designated AtCKX) and were subsequently expressed under a strong constitutive promoter in transgenic tobacco and *Arabidopsis*. Transformants showing AtCKX mRNA expression and increased cytokinin oxidase activity also manifested enhanced formation and growth of roots. Negative effects on shoot growth were also observed. The latter is in accordance with the constitutive expression of the cytokinin oxidase gene in these plants, illustrating the importance of confined expression of the cytokinin oxidase gene for general plant growth properties. Containment of cytokinin oxidase activity can be achieved by using cell-, tissue- or organ-specific promoters, since cytokinin degradation is a process limited to the tissues or cells that express the CKX protein, this in contrast to approaches relying on hormone synthesis, as explained above.

The observed negative effects of cytokinin oxidase expression on shoot growth demonstrate that cytokinin oxidases are interesting targets for the design of or screening for growth-promoting chemicals. Such chemicals should inhibit cytokinin oxidase activity, should preferably not be transported to the root and should be rapidly degraded in soil, so that application of these chemicals will not inhibit root growth. Cytokinins also delay leaf senescence, which means that positive effects will include both growth and maintenance of photosynthetic tissues. In addition, the observation that cytokinins delay senescence, enhance greening (chlorophyll content) of leaves and reduce shoot apical dominance shows that strategies based on suppressing CKX activity (such as antisense, ribozyme, and cosuppression technology) in the aerial parts of the plant could result in delayed senescence, enhanced leaf greening and increased branching.

Similarly, the observed positive effects of cytokinin oxidase expression on root growth demonstrate that cytokinin oxidases are interesting targets for the design of or screening for herbicides. Such herbicides should inhibit cytokinin oxidase activity, should preferably not be transported to the shoot, and should be soluble and relatively stable in a solvent that can be administered to the root through the soil.

These effects of cytokinin oxidase overexpression on plant development and architecture were hitherto unknown and, as a consequence, the presented invention and its embodiments could not be envisaged.

The observed negative effects on shoot growth demonstrate that manipulation of cytokinin oxidases can also be used for obtaining dwarfing phenotypes. Dwarfing phenotypes are particularly useful in commercial crops such as cereals and fruit trees for example.

In accordance with the present invention, it has also been surprisingly discovered that transgenic plants overexpressing a cytokinin oxidase gene develop seeds (including embryos) and cotyledons of increased size and/or weight. These results are surprising as a reduced cytokinin content would have been expected to be associated with a reduced organ growth.

Preferable embodiments of the invention relate to the positive effect of cytokinin oxidase expression on plant growth and architecture, and in particular on root growth and architecture, harvest index, seed size and weight, embryo size and weight, and cotyledon size and weight. The cytokinin oxidase gene family contains at least six members in *Arabidopsis* (see examples below) and the present inventors have shown that there are quantitative differences in the effects achieved with some of these genes in transgenic plants. It is anticipated that functional homologs of the described *Arabidopsis* cytokinin oxidases can be isolated from other organisms, given the evidence for the presence of cytokinin oxidase activity in many green plants (Hare and van Staden, Physiol Plant 91:128-136, 1994; Jones and Schreiber, Plant Growth Reg 23:123-134, 1997), as well as in other organisms (Armstrong, in Cytokinins: Chemistry, Activity and Function. Eds Mok and Mok, CRC Press, pp 139-154, 1994). Therefore, the sequence of the cytokinin oxidase, functional in the invention, need not to be identical to those described herein. This invention is particularly useful for cereal crops and monocot crops in general and cytokinin oxidase genes from for example wheat or maize may be used as well (Morris et al., 1999; Rinaldi and Comandini, 1999). It is envisaged that other genes with cytokinin oxidase activity or with any other cytokinin metabolizing activity (see Zažimalová et al., Biochemistry and Molecular Biology of Plant Hormones, Hooykaas, Hall and Libbenga (Eds.), Elsevier Science, pp 141-160, 1997) can also be used for the purpose of this invention. Similarly, genes encoding proteins that would increase endogenous cytokinin metabolizing activity can also be used for the purpose of this invention. In principle, similar phenotypes could also be obtained by interfering with genes that function downstream of cytokinin such as receptors or proteins involved in signal transduction pathways of cytokinin.

For the purpose of this invention, it should be understood that the term ‘root growth’ encompasses all aspects of growth of the different parts that make up the root system at different stages of its development, both in monocotyledonous and dicotyledonous plants. It is to be understood that enhanced growth of the root can result from enhanced growth of one or more of its parts including the primary root, lateral roots, adventitious roots, etc. all of which fall within the scope of this invention.

For purposes of this invention, it should also be understood that increases in seed weight or seed size can include increases in the size of one or more of the embryo, the endosperm, aleurone, and seed coat. Moreover, increases in embryo size and/or weight can include increases in different organs associated therewith such as e.g., cotyledons, hypocotyl, and roots.

According to a first embodiment, the present invention relates to a method for stimulating root growth and/or enhancing the formation of lateral and/or adventitious roots and/or altering root geotropism comprising expression of a plant cytokinin oxidase or comprising expression of another protein that reduces the level of active cytokinins in plants or plant parts.

In another embodiment, the present invention relates to a method for increasing plant seed size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed including different tissues or cell types of the seed.

In another embodiment, the present invention relates to a method for increasing plant embryo size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the seed. Even more preferably, the increased level or activity of a cytokinin oxidase or expression of another protein that reduces the level of active cytokinins in a plant or plant part is localized in the embryo.

In yet another embodiment, the present invention relates to a method for increasing plant cotyledon size and/or weight, by increasing the level or activity of a cytokinin oxidase in the plant or by expression of another protein that reduces the level of active cytokinins in a plant or plant part. Preferably, the increased level or activity of a cytokinin oxidase or expression of another protein that reduces the level of active cytokinins in a plant or plant part is localized in the cotyledon.

In the context of the present invention it should be understood that the term “expression” and/or ‘overexpression’ are used interchangeably and both relate to an “enhanced and/or ectopic expression” of a plant cytokinin oxidase or any other protein that reduces the level of active cytokinins in plants. It should be clear that herewith an enhanced expression of the plant cytokinin oxidase as well as “de novo” expression of plant cytokinin oxidases or of said other proteins is meant. Alternatively, said other protein enhances the cytokinin metabolizing activity of a plant cytokinin oxidase.

It further should be understood that in the context of the present invention the expression “lateral and/or adventitious roots” can mean “lateral and adventitious roots” but also “lateral or adventitious roots”. The enhancement can exist in the formation of lateral roots or in the formation of adventitious roots as well as in the formation of both types of non-primary roots, but not necessarily.

In addition, as used herein, “increasing seed size and/or weight,” can mean increasing seed size and weight, but also size or weight. Thus, the enhancement can exist in an increase in the size of the seed or the weight of the seed or both. Similar interpretations should be applied to “increasing embryo size and/or weight” and “increasing cotyledon size and/or weight.”

The terms “plant” and “plant part” are used interchangeably with the terms “plants” and “plant parts.”

According to a further embodiment, the present invention relates to a method for stimulating root growth and/or enhancing the formation of lateral or adventitious roots and/or altering root geotropism and/or increasing yield and/or enhancing early vigor and/or modifying root/shoot ratio and/or improving resistance to lodging and/or increasing drought tolerance and/or promoting in vitro propagation of explants, comprising expression of a plant cytokinin oxidase or comprising expression of another protein that reduces the level of active cytokinins in plants or plant parts.

According to a preferred embodiment, the present invention relates to a method for stimulating root growth resulting in an increase of root mass by overexpression of a cytokinin oxidase, preferably a cytokinin oxidase according to the invention, or another protein that reduces the level of active cytokinins in plants or plant parts, preferably in roots.

Higher root biomass production due to overexpression of growth promoting sequences has a direct effect on the yield and an indirect effect of production of compounds produced by root cells or transgenic root cells or cell cultures of said transgenic root cells. One example of an interesting compound produced in root cultures is shikonin, the yield of which can be advantageously enhanced by said methods.

According to a more specific embodiment, the present invention relates to methods for stimulating root growth or for enhancing the formation of lateral and/or adventitious roots or for altering root geotropism or for increasing seed size and/or weight, or for increasing embryo size and/or weight, or for increasing cotyledon size and/or weight, or for increasing seed yield or harvest index. The methods comprise expression of a nucleic acid encoding a cytokinin oxidase selected from the group consisting of:

(a) nucleic acids comprising a DNA sequence as given in any of SEQ ID NOs: 48, 44, 38, 27, 1, 3, 5, 7, 9, 11, 25, 26, 28 to 31, 33, or 34, or the complement thereof, (b) nucleic acids comprising the RNA sequences corresponding to any of SEQ ID NOs: 48, 44, 38, 27, 1, 3, 5, 7, 9, 11, 25, 26, 28 to 31, 33, or 34, or the complement thereof, (c) nucleic acids specifically hybridizing to any of SEQ ID NOs: 48, 44, 38, 27, 1, 3, 5, 7, 9, 11, 25, 26, 28 to 31, 33, or 34 or to the complement thereof, (d) nucleic acids encoding a protein comprising the amino acid sequence as given in any of SEQ ID NOs: 2, 4, 6, 8, 10, 12, 32, 35, 37 or 39, or the complement thereof, (e) nucleic acids as defined in any of (a) to (d) characterized in that said nucleic acid is DNA, genomic DNA, cDNA, synthetic DNA or RNA wherein T is replaced by U, (f) nucleic acids which are degenerated compared to a nucleic acid as given in any of SEQ ID NOs: 48, 44, 38, 27, 1, 3, 5, 7, 9, 11, 25, 26, 28 to 31, 33, or 34 or which are degenerated compared to a nucleic acid as defined in any of (a) to (e) as a result of the genetic code, (g) nucleic acids which are diverging from a nucleic acid encoding a protein as given in any of SEQ ID NOs: 2, 4, 6, 8, 10, 12, 35, 37 or 39, or which are diverging from a nucleic acid as defined in any of (a) to (e), due to the differences in codon usage between the organisms, (h) nucleic acids encoding a protein as given in SEQ ID NOs: 2, 4, 6, 8, 10, 12, 35, 37 or 39 or nucleic acids as defined in (a) to (e) which are diverging due to the differences between alleles, (i) nucleic acids encoding a protein as given in any of SEQ ID NOs: 2, 4, 6, 8, 10, 12, 35, 37 or 39, (j) functional fragments of nucleic acids as defined in any of (a) to (i) having the biological activity of a cytokinin oxidase, and (k) nucleic acids encoding a cytokinin oxidase, or comprise expression, preferably in roots, or in seeds (including parts of seeds such as embryo, endosperm, seed coat or aleurone) or in cotyledons, of a nucleic acid encoding a protein that reduces the level of active cytokinins in plants or plant parts.

In the present invention, nucleic acids encoding novel *Arabidopsis thaliana* cytokinin oxidases have been isolated and for the first time, the present inventors have surprisingly shown that the expression of cytokinin oxidases in transgenic plants or in transgenic plant parts resulted in the above-mentioned root and seed-related features. In order that root-related features be effected, the expression of the cytokinin oxidase(s) should take place in roots, preferably under the control of a root-specific promoter. In order that seed-related features be effected (including the embryo), expression of the cytokinin oxidase(s) should take place in seeds, preferably under the control of a seed-specific promoter. One example of such a root-specific promoter is provided in SEQ ID NO: 36. Examples of seed-specific promoters include but are not limited to those listed in Table 4.

In order that cotyledon-related features be effected, the expression of the cytokinin oxidase(s) should take place in the cotyledons, preferably under the control of a promoter which preferentially expresses in cotyledon.

It should be clear that, although the invention is supported in the examples section by several new AtCKX genes and proteins, the inventive concept also relates to the use of other cytokinin oxidases isolated from and expressed in other plants, preferably in the roots and/or seeds and/or cotyledons of said other plants to obtain similar effects in plants as described in the examples section.

Therefore, the present invention more generally relates to the use of a nucleic acid encoding a plant cytokinin oxidase or encoding a protein that reduces the level of active cytokinins in plants or plant parts for stimulating root growth or for enhancing the formation of lateral or adventitious roots or for altering root geotropism. The present invention also relates to the use of a nucleic acid encoding a plant cytokinin oxidase or encoding a protein that reduces the level of active cytokinins in plants or plant parts for increasing seed size and/or weight, or for increasing embryo size and/or weight, or for increasing plant cotyledon size and/or weight or for increasing seed yield. Preferred cytokinin oxidases to be used are encoded by the nucleic acids encoding the cytokinin oxidases as defined below and are encoded by the novel nucleic acids of the invention as defined hereunder.

The invention relates to an isolated nucleic acid encoding a novel plant protein having cytokinin oxidase activity selected from the group consisting of:

(a) a nucleic acid comprising a DNA sequence as given in any of SEQ ID NOs: 48, 44, 38, 29, 3, 5, 9, 26, 27, 31, 33, or 34, or the complement thereof, (b) a nucleic acid comprising the RNA sequences corresponding to any of SEQ ID NOs: 48, 44, 38, 29, 3, 5, 9, 26, 27, 31, 33, 34, or the complement thereof, (c) a nucleic acid specifically hybridizing to a nucleic acid as given in any of SEQ ID NOs: 48, 44, 38, 29, 3, 5, 9, 26, 27, 31, 33, or 34 or the complement thereof, (d) a nucleic acid encoding a protein with an amino acid sequence comprising the polypeptide as given in SEQ ID NO: 32 and which is at least 70% similar, preferably at least 75%, 80% or 85%, more preferably at least 90% or 95%, most preferably at least 99% similar to the amino acid sequence as given in SEQ ID NO: 4, 37 or 39, (e) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 6, (f) a nucleic acid encoding a protein with an amino acid sequence which is at least 35% similar, preferably 37%, 40%, 45%, 47% or 50%, similar, more preferably 55%, 60%, 65%, 70%, 75% or 80% similar, most preferably 85%, 90% or 95% similar to the amino acid sequence as given in SEQ ID NO: 10 or 35, (g) a nucleic acid encoding a protein comprising the amino acid sequence as given in any of SEQ ID NOs: 4, 6, 10, 32, 35, 37 or 39, (h) a nucleic acid which is degenerated compared to a nucleic acid as given in any of SEQ ID NOs: 48, 44, 38, 29, 3, 5, 9, 26, 27, 33, or 34, or which is degenerated compared to a nucleic acid as defined in any of (a) to (g) as a result of the genetic code, (i) a nucleic acid which is diverging from a nucleic acid encoding a protein as given in any of SEQ ID NOs: 4, 6, 10, 35, 37 or 39 or which is diverging from a nucleic acid as defined in any of (a) to (g) due to the differences in codon usage between the organisms, (j) a nucleic acid encoding a protein as given in SEQ ID NOs: 4, 6, 10, 35, 37 or 39, or a nucleic acid as defined in (a) to (g) which is diverging due to the differences between alleles, (k) a nucleic acid encoding an immunologically active fragment of a cytokinin oxidase encoded by a nucleic acid as given in any of SEQ ID NOs: 48, 44, 38, 29, 3, 5, 9, 26, 27, 31, 33, or 34, or an immunologically active fragment of a nucleic acid as defined in any of (a) to (j), (l) a nucleic acid encoding a functional fragment of a cytokinin oxidase encoded by a nucleic acid as given in any of SEQ ID NOs: 48, 44, 38, 29, 3, 5, 9, 26, 27, 31, 33, or 34, or a functional fragment of a nucleic acid as defined in any of (a) to (j), wherein said fragment has the biological activity of a cytokinin oxidase, and (m) a nucleic acid encoding a protein as defined in SEQ ID NOs: 4, 6, 10, 35, 37 or 39, provided that said nucleic acid is not the nucleic acid as deposited under any of the following Genbank accession numbers: AC005917, AB024035, and AC023754.

The invention also relates to an isolated nucleic acid of the invention which is DNA, cDNA, genomic DNA or synthetic DNA, or RNA wherein T is replaced by U.

The invention also relates to a nucleic acid molecule of at least 15 nucleotides in length hybridizing specifically with or specifically amplifying a nucleic acid of the invention.

Different cytokinin forms may have differing roles to play in the various developmental processes. Thus, differential effects of CKX1, CKX2, CKX 3 and CKX4 may relate to distinct effects on the pools of different cytokinins. For example, CKX1 and CKX3 mostly promote root elongation and branching, while CKX2 and CKX4 primarily stimulate the formation of adventitious roots. In addition, CKX1 and CKX3 increase seed size and weight to a greater degree than CKX2 and CKX4. Without being bound to a particular mode of action, this differential effect on cytokinin pools may result from some differences in substrate specificity or from differential compartmentation of cytokinin oxidases in the cell (predicted to be mitochondrial for CKX1 and CKX3, while extracellular for CKX 2, CKX4, CKX5, and CKX6).

According to another embodiment, the invention also relates to a vector comprising a nucleic acid of the invention. In a preferred embodiment, said vector is an expression vector wherein the nucleic acid is operably linked to one or more control sequences allowing the expression of said sequence in prokaryotic and/or eukaryotic host cells.

It should be understood that for expression of the cytokinin oxidase genes of the invention in monocots, a nucleic acid sequence corresponding to the cDNA sequence should be used to avoid mis-splicing of introns in monocots. Preferred cDNA sequences to be expressed in monocots have a nucleic acid sequence as represented in any of SEQ ID NOs: 25 to 30, 34, SEQ ID NO:38, or SEQ ID NO:44.

The invention also relates to a host cell containing any of the nucleic acid molecules or vectors of the invention. Said host cell is chosen from the group comprising bacterial, insect, fungal, plant or animal cells.

Another embodiment of the invention relates to an isolated polypeptide encodable by a nucleic acid of the invention, or a homologue or a derivative thereof, or an immunologically active or a functional fragment thereof. Preferred polypeptides of the invention comprise the amino acid sequences as represented in any of SEQ ID NOs: 2, 4, 6, 8, 10, 12, 32, 35 or 37 or a homologue or a derivative thereof, or an immunologically active and/or functional fragment thereof. In an even more preferred embodiment, the invention relates to a polypeptide which has an amino acid sequence as given in SEQ ID: NO 2, 4, 6, 8, 10, 12, 35 or 37 or a homologue or a derivative thereof, or an immunologically active and/or functional fragment thereof. Preferred functional fragments thereof are those fragments which are devoid of their signal peptide.

According to yet another embodiment, the invention relates to a method for producing a polypeptide of the invention comprising culturing a host cell of the invention under conditions allowing the expression of the polypeptide and recovering the produced polypeptide from the culture.

The invention also relates to an antibody specifically recognizing a polypeptide of the invention or a specific epitope thereof.

The invention further relates to a method for the production of transgenic plants, plant cells or plant tissues comprising the introduction of a nucleic acid molecule of the invention in an expressible format or a vector of the invention in said plant, plant cell or plant tissue.

The invention also relates to a method for the production of altered plants, plant cells or plant tissues comprising the introduction of a polypeptide of the invention directly into a cell, a tissue or an organ of said plant.

According to another embodiment, the invention relates to a method for effecting the expression of a polypeptide of the invention comprising the introduction of a nucleic acid molecule of the invention operably linked to one or more control sequences or a vector of the invention stably into the genome of a plant cell. The invention further relates to the method as described above further comprising regenerating a plant from said plant cell.

The invention also relates to a transgenic plant cell comprising a nucleic acid sequence of the invention which is operably linked to regulatory elements allowing transcription and/or expression of said nucleic acid in plant cells or obtainable by a method as explained above.

According to another preferred embodiment, the invention relates to a transgenic plant cell as described hereinabove wherein the nucleic acid of the invention is stably integrated into the genome of said plant cell.

The invention further relates to a transgenic plant or plant tissue comprising plant cells as herein described and also to a harvestable part of said transgenic plant, preferably selected from the group consisting of seeds, leaves, fruits, stem cultures, roots, tubers, rhizomes and bulbs. The present invention furthermore relates to products directly derived from a harvestable part of a transgenic plant, such as dry pellets or powders, oil, fat and fatty acids, starch, or proteins. The invention also relates to the progeny derived from any of said transgenic plants or plant parts.

According to another embodiment, the invention relates to a method for stimulating root growth comprising expression of a nucleic acid of the invention or comprising expression of another protein that reduces the level of active cytokinins in plants or plant parts.

In another aspect of the invention, there is provided a method of increasing seed size and/or weight. The method comprises increasing the level or activity of a cytokinin oxidase in a plant or increasing the level or activity of a protein that reduces the level of active cytokinins in a plant or plant part, preferably seeds.

Various parts (organs) of the seed may also be increased in size and/or weight such as e.g., embryo, endosperm, seed coat, or aleurone. For example, in accordance with the present invention, there is provided a method of increasing embryo size and/or weight. The method comprises increasing the level or activity of a cytokinin oxidase in a plant or increasing the level or activity of a protein that reduces the level of active cytokinins in a plant or plant part, preferably embryos.

In still another aspect of the invention, there is provided a method of increasing cotyledon size and/or weight. The method comprises increasing the level or activity of a cytokinin oxidase in a plant or increasing the level or activity of a protein that reduces the level of active cytokinins in a plant or plant part, preferably cotyledons.

In accordance with the methods of increasing seed size and/or weight, there is a resultant increase in the speed of growth of seedlings or an increase in early vigor. Increases in yield are also obtained. Similarly, in accordance with the methods of increasing embryo size and/or weight, or cotyledon size and/or weight, there is a resultant increase in speed of growth of seedlings or an increase in early vigor. In many cases, increases in yield are also obtained. Increases in growth of seedlings or early vigor is often associated with increased stress tolerance. For example, faster development of seedlings, including the root systems of seedlings upon germination is critical for survival particularly under adverse conditions such as drought.

Any nucleotide sequence encoding a polypeptide with cytokinin oxidase activity may be used in the methods of the invention. For example, any of the various sequences provided herein encoding a polypeptide with cytokinin oxidase activity may be used in the methods of increasing seed, embryo, or cotyledon size and/or weight.

Preferably, transgenic plants are produced which express a nucleic acid as set forth in any of SEQ ID NOs:1, 5, 25, or 27 or an ortholog of said nucleic acid. Preferably, the ortholog is derived from a related species of the transgenic plant. Even more preferably, the ortholog is specific (native or endogenous) to the species of the transgenic plant.

As described above, promoters which control expression specifically, or preferentially may be used in the methods of the invention. Thus, where increases in seed size or weight are desired, a seed-specific promoter may be used. Where increases in embryo size or weight are desired, an embryo-specific promoter may be used. Where increases in cotyledon size or weight is desired, a promoter which controls expression in cotyledons is preferred. Such promoters are well known, widely available and listed herein in e.g., Table 4.

In another embodiment, the invention relates to a method for increasing seed size or seed weight, or both, said method comprising expression of a nucleic acid of the invention or comprising expression of another protein that reduces the level of active cytokinins in plants or plant parts.

In yet another embodiment, the invention relates to a method for increasing embryo size or weight, or both, said method comprising expression of a nucleic acid of the invention or comprising expression of another protein that reduces the level of active cytokinins in plants or plant parts.

In still another embodiment, the invention relates to a method for increasing cotyledon size comprising expression of a nucleic acid of the invention or comprising expression of another protein that reduces the level of active cytokinins in plants or plant parts. Localized expression of a subject cytokinin oxidase gene or part thereof, or of another protein that reduces the level of active cytokinins in plants or plant parts leads to enhanced growth of cotyledons. In species having cotyledons as storage organs, such enhanced growth of cotyledons leads to enhanced yields and/or to enhanced growth performance of seedlings. Further in this regard, carbohydrates, lipids and proteins are all stored within seeds and are metabolized during germination in order to provide energy and metabolites during early growth of the plant. Seed size is often associated with early vigor, since larger seeds contain more carbohydrates, lipids and proteins and thus confer faster growth. Thus, the methods of the present invention lead to faster growth of seedlings. Such early vigor is associated with enhanced stress tolerance. For example, faster development of a plant's root system is critical for survival, particularly under adverse conditions, such as drought. Early vigor is also related to enhanced yield and shortened time to flowering.

Also in accordance with the present invention, there are provided methods and compositions for increasing seed yield in a plant. Seed yield may be increased by increasing the level or activity of a cytokinin oxidase in the endosperm, embryo or aleurone of a plant seed. Thus for example, seed-preferred promoters may be utilized to drive expression of a cytokinin oxidase in these particular components of a seed. Preferably, a seed-preferred promoter is an embryo and/or aleurone preferred promoter, or an endosperm-preferred promoter. A seedling-preferred promoter may also be used.

In accordance with the present invention, a cytokinin oxidase gene may be placed in a genetic construct such as a vector, under control of an embryo/aleurone-preferred promoter or an endosperm-preferred promoter. For example, the AtCKX2 gene (SEQ ID NO:44) may be placed under control of a seed preferred promoter: (i) an embryo and aleurone preferred promoter which is also active in seedlings, as represented in GenBank under accession number AF019212 (sequence from nucleotide 1 to 1256, hereafter named PRO0218) and (ii) an endosperm preferred promoter as represented in GenBank under accession number X65064 (sequence from nucleotide 1 to 672, hereafter named PRO0090). Since the promoter PRO0090 is not only active in seed tissues but also in seedlings, in another embodiment of the invention, a seedling-preferred promoter may also be used to increase seed yield in a plant.

These constructs may then be used to transform plants, either dicots or monocots. In accordance with the present invention, transgenic plants have, when compared to nullizygous plants, an increased seed yield.

There are different well known parameters which may be used for measuring increased seed yield including but not limited to: total weight of seeds, total number of seeds, total number of filled seeds, harvest index, and Thousand Kernel Weight. As described in the examples, the total weight of seeds, may be measured by weighing all filled seeds harvested from a plant. The total number of seeds may be measured by counting the number of seeds harvested from a plant. The total number of filled seeds may be measured by counting the number of filled seeds harvested from a plant. The harvest index, may be defined as the ratio between the total seed weight and the above ground area ($mm^2$), multiplied by a factor $10^6$. Thousand Kernel Weight may be derived from the number of filled seeds counted and their total weight.

In addition to the cytokinin oxidase genes and corresponding proteins described above, a cytokinin oxidase 2 gene (CKX2) is particularly suited for use in increasing seed yield in a plant. For example, in addition to the *Arabidopsis thaliana* CKX2 protein set forth in SEQ ID NO:37, other CKX proteins from *Arabidopsis thaliana*, such as the ones represented in GenBank Accessions NP_181682, NP_200507, NP_849470, NP_194703, NP_850863 or AAG30909 may be used. CKX proteins from other species like *Zea mays* (for example GenBank Accessions CAE55202, CAE55200 or AAC27500), *Dendrobium* (GenBank CAC17752), *Hordeum vulgare* (GenBank AAN16383, AAO50082, AAM08400), or rice (GenBank NP_913145, NP_916348, NP_922039) are also available for use in the methods and compositions of the present invention. A prokaryotic homologue of SEQ ID NO:37 is represented by GenBank Accession P46377.

A plant cell or tissue culture is an artificially produced culture of plants cells or plant tissues that is grown in a special medium, either liquid or solid, which provides these plant cells or tissues with all requirements necessary for growth and/or production of certain compounds. Plant cell and/or tissue cultures can be used for the rapid propagation of plants and for the production of transgenic plant to name a few examples. Root formation can be difficult for some explants or under some conditions in said cultures and expression of a cytokinin oxidase gene in said cultured plant cells or tissue(s) can be used to enhance root formation. Plant cell and/or tissue culture can also be used for the industrial production of valuable compounds. Possible production compounds are pharmaceuticals, pesticides, pigments, cosmetics, perfumes, food additives, etc. An example of such a product is shikonin, which is produced by the roots of the plant *Lithospermum erythrorhizon*. An example of a plant tissue culture is a hairy root culture, which is an artificially produced mass of hairy roots. Roots of *L. erythrorhizon* are difficult to collect in large numbers and by preparing hairy root cultures, the end product shikonin could be industrially prepared at a faster rate than would normally occur. As disclosed herein, expression of cytokinin oxidases enhances root growth and development and can therefore be used advantageously in said plant cell and tissue culture procedures. Therefore, according to another embodiment of this invention, a method is provided for stimulating root growth and development comprising expression of a nucleic acid encoding a plant cytokinin oxidase, preferably a cytokinin oxidase of the invention, in a transgenic plant cell or tissue culture comprising said transgenic plant cells.

The invention further relates to a method for enhancing the formation of lateral or adventitious roots comprising expression of a nucleic acid of the invention or comprising expression of another protein that reduces the level of active cytokinins in plants or plant parts.

The invention also relates to method for altering root geotropism comprising altering the expression of a nucleic acid of the invention or comprising expression of another protein that that reduces the level of active cytokinins in plants or plant parts.

The invention also relates to methods for enhancing early vigor and/or for modifying root/shoot ratio and/or for improving resistance to lodging and/or for increasing drought tolerance and/or for promoting in vitro propagation of explants comprising expression of a nucleic acid of the invention comprising expression of another protein that reduces the level of active cytokinins in plants or plant parts.

The invention further relates to methods for increasing the root size or the size of the root meristem comprising expression of a nucleic acid of the invention or comprising expression of another protein that reduces the level of active cytokinins in plants or plant parts, preferably in roots.

According to yet another embodiment, the invention relates to a method for increasing the size of the shoot meristem comprising downregulation of expression of a nucleic acid of the invention, preferably in shoots.

According to a preferred embodiment the invention relates to a method for delaying leaf senescence comprising downregulation of expression of any of the cytokinin oxidases of the invention in leaves, preferably in senescing leaves. Also the invention relates to a method for altering leaf senescence comprising expression of one of the cytokinin oxidases in senescing leaves.

The invention also relates to methods for increasing leaf thickness comprising expression of a nucleic acid of the invention or comprising expression of another protein that reduces the level of active cytokinins in plants or plant parts, preferably in leaves.

The invention also relates to a method for reducing the vessel size comprising expression of a nucleic acid of the invention or comprising expression of another protein that reduces the level of active cytokinins in plants or plant parts, preferably in vessels.

The invention further relates to a method for increasing the vessel size comprising downregulation of expression of a nucleic acid of the invention in plants or plant parts.

According to another embodiment, the invention relates to a method for improving standability of seedlings comprising expression of a nucleic acid of the invention or comprising expression of another protein that reduces the level of active cytokinins in seedlings.

Furthermore, the invention relates to any of the above described methods, said method leading to an increase in yield.

The invention further relates to any of the methods of the invention wherein said expression of said nucleic acid occurs under the control of a strong constitutive promoter. With respect to those aspects of the invention having effects on plant roots such as e.g., methods for stimulating root growth, enhancing the formation of lateral or adventitious roots, or for altering root geotropism, preferably, expression of a subject nucleic acid preferably occurs under the control of a promoter that is preferentially expressed in roots. In Table 5 a non-exhaustive list of root specific promoters is included. A preferred promoter to be used in the methods of the invention is the root clavata homolog promoter, having a sequence as given in SEQ ID NO: 36.

With respect to those aspect of the invention having effects on plant seeds such as e.g., methods for increasing seed size or weight, embryo size or weight, or having effects on plant cotyledons such as methods for increasing cotyledon size of weight, expression of a subject nucleic acid occurs under the control of a promoter that is preferentially expressed in seeds. A seed specific promoter may be one which is expressed in all seed organs or one which shows a preference in expression to one or more organs or tissue such as the embryo, endosperm, or aleurone. Examples of such promoters are set forth herein at Table 4.

According to yet another embodiment, the invention relates to a method for modifying cell fate and/or modifying plant development and/or modifying plant morphology and/or modifying plant biochemistry and/or modifying plant physiology and/or modifying the cell cycle progression rate comprising the modification of expression in particular cells, tissues or organs of a plant, of a nucleic acid of the invention.

The invention also relates to a method for obtaining enhanced growth, and/or increased yield and/or altered senescence of a plant cell, tissue and/or organ and/or increased frequency of formation of lateral organs in a plant, comprising the ectopic expression of a nucleic acid of the invention.

The invention also relates to a method for promoting and extending cell division activity in cells in adverse growth conditions and/or in stress, comprising the ectopic expression of a nucleic acid sequence of the invention.

According to yet another embodiment, the invention relates to a method for identifying and obtaining proteins interacting with a polypeptide of the invention comprising a screening assay wherein a polypeptide of the invention is used.

In a more preferred embodiment, the invention relates to a method for identifying and obtaining proteins interacting with a polypeptide of the invention comprising a two-hybrid screening assay wherein a polypeptide of the invention as a bait and a cDNA library as prey are used.

The invention further relates to a method for modulating the interaction between a polypeptide of the invention and interacting protein partners obtainable by a method as described above.

In a further embodiment, the invention relates to a method for identifying and obtaining compounds interacting with a polypeptide of the invention comprising the steps of:

(a) providing a two-hybrid system wherein a polypeptide of the invention and an interacting protein partner obtainable by a method as described above, (b) interacting said compound with the complex formed by the expressed polypeptides as defined in a), and, (c) performing (real-time) measurement of interaction of said compound with said polypeptide or the complex formed by the expressed polypeptides as defined in a).

The invention further relates to a method for identifying compounds or mixtures of compounds which specifically bind to a polypeptide of the invention, comprising:

(a) combining a polypeptide of the invention with said compound or mixtures of compounds under conditions suitable to allow complex formation, and, (b) detecting complex formation, wherein the presence of a complex identifies a compound or mixture which specifically binds said polypeptide.

The invention also relates to a method as described above wherein said compound or mixture inhibits the activity of said polypeptide of the invention and can be used for the rational design of chemicals.

According to another embodiment, the invention relates to the use of a compound or mixture identified by means of a method as described above as a plant growth regulator or herbicide.

The invention also relates to a method for production of a plant growth regulator or herbicide composition comprising the steps of the compound screening methods described above and formulating the compounds obtained from said steps in a suitable form for the application in agriculture or plant cell or tissue culture.

The invention also relates to a method for increasing branching comprising expression of a nucleic acid of the invention in plants or plant parts, preferably in stems or axillary buds.

The invention also relates to a method for improving lodging resistance comprising expression of a nucleic acid of the invention in plants or plant parts, preferably in stems or axillary buds.

The invention also relates to a method for the design of or screening for growth-promoting chemicals or herbicides comprising the use of a nucleic acid of the invention or a vector of the invention.

According to another embodiment, the invention relates to the use of a nucleic acid molecule of the invention, a vector of the invention or a polypeptide of the invention for increasing yield.

The invention also relates to the use of a nucleic acid molecule of the invention, a vector of the invention or a polypeptide of the invention for stimulating root growth.

The invention also relates to the use of a nucleic acid molecule of the invention, a vector of the invention or a polypeptide of the invention for enhancing the formation of lateral or adventitious roots.

The invention also relates to the use of a nucleic acid molecule of the invention, a vector of the invention or a polypeptide of the invention for altering root geotropism.

The invention also relates to the use of a nucleic acid molecule of the invention, a vector of the invention or a polypeptide of the invention for increasing at least one of seed size, seed weight, embryo size, embryo weight, cotyledon size, and cotyledon weight.

The invention further relates to the use of a nucleic acid molecule of the invention, a vector of the invention or a polypeptide of the invention for enhancing early vigor and/or for modifying root/shoot ratio and/or for improving resistance to lodging and/or for increasing drought tolerance and/or for promoting in vitro propagation of explants.

The invention also relates to the use of a nucleic acid molecule of the invention, a recombinant vector of the invention or a polypeptide of the invention for modifying plant development and/or for modifying plant morphology and/or for modifying plant biochemistry and/or for modifying plant physiology.

According to yet another embodiment, the invention relates to a diagnostic composition comprising at least a nucleic acid molecule of the invention, a vector of the invention, a polypeptide of the invention or an antibody of the invention.

Another embodiment of the current invention relates to the use of a transgenic rootstock that has an enhanced root growth and development due to expression of a cytokinin oxidase in grafting procedures with a scion to produce a plant or tree with improved agricultural or horticultural characteristics.

The scion may be transgenic or non-transgenic. Specific characteristics envisaged by this embodiment are those conferred by root systems and include improved anchoring of the plant/tree in the soil and/or improved uptake of water resulting for example in improved drought tolerance, and/or improved nutrient uptake from the soil and/or improved transport of organic substances throughout the plant and/or enhanced secretion of substances into the soil such as for example phytosiderophores, and/or improved respiration and/or improved disease resistance and/or enhanced yield. An advantage of using AtCKX transformed rootstocks for grafting, in addition to their enhanced root system, is the delayed senescence of leaves on the graft, as disclosed herein (see FIG. 12 A). Preferred plants or trees for this particular embodiment include plants or trees that do not grow well on their own roots and are grafted in cultivated settings such as commercially profitable varieties of grapevines, citrus, apricot, almond, plum, peach, apple, pear, cherry, walnut, fig, hazel and loquat.

As mentioned supra, auxins and cytokinins act as antagonists in certain biological processes. For example, the cytokinin/auxin ratio regulates the production of roots and shoots with a high concentration of auxin resulting in organized roots and a high concentration of cytokinins resulting in shoot production. As disclosed in this invention, expression of cytokinin oxidases in tobacco and *Arabidopsis* results in enhanced root development consistent with enhanced auxin effects. Auxins are also involved in the development of fruit. Treatment of female flower parts with auxin results in the development of parthenocarpic fruit in some plant species. Parthenocarpic fruit development has been genetically engineered in several horticultural crop plants through increased biosynthesis of auxins in the female reproductive organs (WO0105985).

Therefore, according to another embodiment, this invention relates to a method for inducing the parthenocarpic trait in plants, said method consisting of downregulating the expression of one or more cytokinin oxidases or of another protein that reduces the level of active cytokinins in plants or plant parts, preferably in the female reproductive organs such as the placenta, ovules and tissues derived therefrom. The DefH9 promoter region from *Antirrhinum majus* or one of its homologues, which confer high expression specificity in placenta and ovules, can be used for this purpose.

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any or more of said steps or features.

The present invention is applicable to any plant, in particular a monocotyledonous plants and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis, Albizia amara, Alsophila tricolor, Andropogon* spp., *Arachis* spp, *Areca catechu, Astelia fragrans, Astragalus cicer, Avena sativa, Baikiaea plurijuga, Betula* spp., *Brassica* spp., *Bruguiera gymnorrhiza, Burkea africana, Butea frondosa, Cadaba farinosa, Calliandra* spp, *Camellia sinensis, Canna indica, Capsicum* spp., *Cassia* spp., *Centroema pubescens, Chaenomeles* spp., *Cinnamomum cassia, Coffea arabica, Colophospermum mopane, Coronillia varia, Cotoneaster serotina, Crataegus* spp., *Cucumis* spp., *Cupressus* spp., *Cyathea dealbata, Cydonia oblonga, Cryptomeria japonica, Cymbopogon* spp., *Cynthea dealbata, Cydonia oblonga, Dalbergia monetaria, Davallia divaricata, Desmodium* spp., *Dicksonia squarosa, Diheteropogon amplectens, Dioclea* spp, *Dolichos* spp., *Dorycnium rectum, Echinochloa pyramidalis, Ehrartia* spp., *Eleusine coracana, Eragrestis* spp., *Erythrina* spp., *Eucalyptus* spp., *Euclea schimperi, Eulalia villosa, Fagopyrum* spp., *Feijoa sellowiana, Fragaria* spp., *Flemingia* spp, *Freycinetia banksii, Geranium thunbergii, Ginkgo biloba, Glycine javanica, Gliricidia* spp, *Gossypium hirsutum, Grevillea* spp., *Guibourtia coleosperma, Hedysarum* spp., *Hemarthia altissima, Heteropogon contortus, Hordeum vulgare, Hyparrhenia rufa, Hypericum erectum, Hyperthelia dissoluta, Indigo incarnata, Iris* spp., *Leptarrhena pyrolifolia, Lespediza* spp., *Lettuca* spp., *Leucaena leucocephala, Loudetia simplex, Lotonus bainesii, Lotus* spp., *Macrotyloma axillare, Malus* spp., *Manihot esculenta, Medicago sativa, Metasequoia glyptostroboides, Musa sapientum, Nicotianum* spp., *Onobrychis* spp., *Ornithopus* spp., *Oryza* spp., *Peltophorum africanum, Pennisetum* spp., *Persea gratissima, Petunia* spp., *Phaseolus* spp., *Phoenix canariensis, Phormium cookianum, Photinia* spp., *Picea glauca, Pinus* spp., *Pisum sativum, Podocarpus totara, Pogonarthria fleckii, Pogonarthria squarrosa, Populus* spp., *Prosopis cineraria, Pseudotsuga menziesii, Pterolobium stellatum, Pyrus communis, Quercus* spp., *Rhaphiolepsis umbellata, Rhopalostylis sapida, Rhus natalensis, Ribes grossularia, Ribes* spp., *Robinia pseudoacacia, Rosa* spp., *Rubus* spp., *Salix* spp., *Schyzachyrium sanguineum, Sciadopitys verticillata, Sequoia sempervirens, Sequoiadendron giganteum, Sorghum bicolor, Spinacia* spp., *Sporobolus fimbriatus, Stiburus alopecuroides, Stylosanthos humilis, Tadehagi* spp, *Taxodium distichum, Themeda triandra, Trifolium* spp., *Triticum* spp., *Tsuga heterophylla, Vaccinium* spp., *Vicia* spp. *Vitis vinifera, Watsonia pyramidata, Zantedeschia aethiopica, Zea mays*, amaranth, artichoke, asparagus, broccoli, brussel sprout, cabbage, canola, carrot, cauliflower, celery, collard greens, flax, kale, lentil, oilseed rape, okra, onion, potato, rice, soybean, straw, sugarbeet, sugar cane, sunflower, tomato, squash, and tea, amongst others, or the seeds of any plant specifically named above or a tissue, cell or organ culture of any of the above species.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps.

As used herein, the term "derived from" shall be taken to indicate that a particular integer or group of integers has originated from the species specified, but has not necessarily been obtained directly from the specified source.

The terms "protein(s)", "peptide(s)" or "oligopeptide(s)", when used herein refer to amino acids in a polymeric form of any length. Said terms also include known amino acid modifications such as disulphide bond formation, cysteinylation, oxidation, glutathionylation, methylation, acetylation, farnesylation, biotinylation, stearoylation, formylation, lipoic acid addition, phosphorylation, sulphation, ubiquitination, myristoylation, palmitoylation, geranylgeranylation, cyclization (e.g. pyroglutamic acid formation), oxidation, deamidation, dehydration, glycosylation (e.g. pentoses, hexosamines, N-acetylhexosamines, deoxyhexoses, hexoses, sialic acid etc.) and acylation as well as non-naturally occurring amino acid residues, L-amino acid residues and D-amino acid residues.

"Homologues" of a protein of the invention are those peptides, oligopeptides, polypeptides, proteins and enzymes which contain amino acid substitutions, deletions and/or additions relative to the said protein with respect to which they are a homologue, without altering one or more of its functional properties, in particular without reducing the activity of the resulting protein. For example, a homologue of said protein will consist of a bioactive amino acid sequence variant of said protein.

Two special forms of homology, orthologous and paralogous homology, are evolutionary concepts used to describe ancestral relationships of genes. The term "paralogous" relates to homologous genes that result from one or more gene duplications within the genome of a species. The term "orthologous" relates to homologous genes in different organisms due to ancestral relationship of these genes. The term "homologues" as used herein also encompasses paralogues and orthologues of the proteins useful in the methods according to the invention. Orthologous genes can be identified by querying one or more gene databases with a query gene of interest, using for example, the BLAST program. The highest-ranking subject genes that result from the search are then again subjected to a BLAST analysis, and only those subject genes that match again with the query gene are retained as true orthologous genes. For example, to find a rice orthologue of an *Arabidopsis thaliana* gene, one may perform a BLASTN or TBLASTX analysis on a rice database (such as (but not limited to) the *Oryza sativa* Nipponbare database available at the NCBI site (ncbi.nlm.nih.gov) or the genomic sequences of rice (cultivars indica or japonica)). In a next step, the obtained rice sequences are used in a reverse BLAST analysis using an *Arabidopsis* database. The results may be further refined when the resulting sequences are analysed with ClustalW and visualised in a neighbour joining tree. The method can be used to identify orthologues from many different species.

To produce such homologues, amino acids present in the said protein can be replaced by other amino acids having similar properties, for example hydrophobicity, hydrophilicity, hydrophobic moment, antigenicity, propensity to form or break $\alpha$-helical structures or $\beta$-sheet structures, and so on. An overview of physical and chemical properties of amino acids is given in Table 2.

The homologues useful in the methods according to the invention can alternatively be defined as having cytokinin oxidase/dehydrogenase activity and comprising at least 2 sequences of 17 and 19 consecutive amino acid residues respectively with a consensus sequence as shown below:

```
Consensus sequence 1 (17 amino acids):
hTDYLhholGGTLSssG

Consensus sequence 2 (19 amino acids):
cLF•ushGsLGQFGlIstA
```

wherein the capital letters are the standard single letter IUPAC codes for the various amino acids and the other letters or signs symbolise the nature of the amino acids, as shown in table 2. The right column lists for each class the particular amino acids that are allowed in the consensus sequences. This classification is based on the amino acid grouping as defined in the SMART database (Schultz et al. (1998) Proc. Natl. Acad. Sci. USA 95, 5857-5864; Letunic et al. (2002) Nucleic Acids Res 30, 242-244).

TABLE 1

| Class | Key | Allowed amino acids |
|---|---|---|
| h | hydrophobic | G, H, L, R, T, W, Y |
| o | alcohol | S, T |
| l | aliphatic | V, I |
| s | small | A, D, G, N, T, V |
| c | charged | D, E, R |
| • | any | Y, R, N, F, D, H |
| u | tiny | A, G, S |
| t | turnlike | R, N |

Substitutional variants of a protein of the invention are those in which at least one residue in said protein amino acid sequence has been removed and a different residue inserted in its place Amino acid substitutions are typically of single residues, but may be clustered depending upon functional constraints placed upon the polypeptide; insertions will usually be of the order of about 1-10 amino acid residues and deletions will range from about 1-20 residues. Preferably, amino acid substitutions will comprise conservative amino acid substitutions, such as those described supra.

TABLE 2

Properties of naturally occurring amino acids.

| Charge properties/ hydrophobicity | Side group | Amino Acid |
|---|---|---|
| Nonpolar | Aliphatic | ala, ile, leu, val |
| hydrophobic | aliphatic, S-containing | met |
| | aromatic | phe, trp |
| | imino | pro |
| polar uncharged | Aliphatic | gly |
| | Amide | asn, gln |
| | Aromatic | tyr |
| | Hydroxyl | ser, thr |
| | Sulfhydryl | cys |
| Positively charged | Basic | arg, his, lys |
| Negatively charged | Acidic | asp, glu |

Insertional amino acid sequence variants of a protein of the invention are those in which one or more amino acid residues are introduced into a predetermined site in said protein. Insertions can comprise amino-terminal and/or carboxy-terminal fusions as well as intra-sequence insertions of single or multiple amino acids. Generally, insertions within the amino acid sequence will be smaller than amino or carboxyl terminal fusions, of the order of about 1 to 10 residues. Examples of amino- or carboxy-terminal fusion proteins or peptides include the binding domain or activation domain of a transcriptional activator as used in a two-hybrid system, phage coat proteins, (histidine)$_6$-tag (SEQ ID NO:52), glutathione S-transferase, protein A, maltose-binding protein, dihydrofolate reductase, Tag•100 epitope (EETARFQPGYRS) (SEQ ID NO:53), c-myc epitope (EQKLISEEDL) (SEQ ID NO:54), FLAG®-epitope (DYKDDDK) (SEQ ID NO:55), lacZ, CMP (calmodulin-binding peptide), HA epitope (YPYDVPDYA) (SEQ ID NO:56), protein C epitope (EDQVDPRLIDGK) (SEQ ID NO:57) and VSV epitope (YTDIEMNRLGK) (SEQ ID NO:58).

Deletional variants of a protein of the invention are characterized by the removal of one or more amino acids from the amino acid sequence of said protein.

Amino acid variants of a protein of the invention may readily be made using peptide synthetic techniques well known in the art, such as solid phase peptide synthesis and the like, or by recombinant DNA manipulations. The manipulation of DNA sequences to produce variant proteins which manifest as substitutional, insertional or deletional variants are well known in the art. For example, techniques for making substitution mutations at predetermined sites in DNA having known sequence are well known to those skilled in the art, such as by M13 mutagenesis, T7-Gen in vitro mutagenesis kit (USB, Cleveland, Ohio), QuickChange Site Directed mutagenesis kit (Stratagene, San Diego, Calif.), PCR-mediated site-directed mutagenesis or other site-directed mutagenesis protocols.

In the current invention "identity" and/or "similarity" percentages between DNA sequences and/or proteins are calculated using computer programs known in the art such as the DNAstar/MegAlign programs in combination with the Clustal method.

"Derivatives" of a protein of the invention are those peptides, oligopeptides, polypeptides, proteins and enzymes which comprise at least about five contiguous amino acid residues of said polypeptide but which retain the biological activity of said protein. A "derivative" may further comprise additional naturally-occurring, altered glycosylated, acylated or non-naturally occurring amino acid residues compared to the amino acid sequence of a naturally-occurring form of said polypeptide. Alternatively or in addition, a derivative may comprise one or more non-amino acid substituents compared to the amino acid sequence of a naturally-occurring form of said polypeptide, for example a reporter molecule or other ligand, covalently or non-covalently bound to the amino acid sequence such as, for example, a reporter molecule which is bound thereto to facilitate its detection.

With "immunologically active" is meant that a molecule or specific fragments thereof such as specific epitopes or haptens are recognized by, i.e. bind to antibodies. Specific epitopes may be determined using, for example, peptide scanning techniques as described in Geysen et al. (1996) (Geysen, H. M., Rodda, S. J. and Mason, T. J. (1986). A priori delineation of a peptide which mimics a discontinuous antigenic determinant. *Mol. Immunol.* 23, 709-715).

The term "fragment of a sequence" or "part of a sequence" means a truncated sequence of the original sequence referred to. The truncated sequence (nucleic acid or protein sequence) can vary widely in length; the minimum size being a sequence of sufficient size to provide a sequence with at least a comparable function and/or activity or the original sequence referred to (e.g. "functional fragment"), while the maximum size is not critical. In some applications, the maximum size usually is not substantially greater than that required to provide the desired activity and/or function(s) of the original sequence. Typically, the truncated amino acid sequence will range from about 5 to about 60 amino acids in length. More typically, however, the sequence will be a maximum of about 50 amino acids in length, preferably a maximum of about 60 amino acids. It is usually desirable to select sequences of at least about 10, 12 or 15 amino acids, up to a maximum of about 20 or 25 amino acids.

Functional fragments can also include those comprising an epitope which is specific for the proteins according to the invention. Preferred functional fragments have a length of at least, for example, 5, 10, 25, 100, 150 or 200 amino acids.

More preferably, functional fragments comprise at least 50 amino acids, include an FAD binding domain (as defined in Pfam (version 14.0, June 2004) accession number 1565, Bateman et al., Nucleic Acids Research Database Issue 32, D138-D141, 2004) and exhibit cytokinin oxidase/dehydrogenase activity. Methods for measuring cytokinin oxidase/dehydrogenase activity are well known in the art. Suitable methods are based on the conversion of [2-$^3$H]iP to adenine (Motyka et al., Plant Physiology 112, 1035-1043, 1996), on colorimetric assays (Libreros-Minotta and Tipton, Anal. Biochem. 231, 339-341, 1995) or on the measurement of reduced electron acceptors (Bilyeu et al., Plant Physiol. 125, 378-386, 2001).

It should thus be understood that functional fragments can also be immunologically active fragments or not.

In the context of the current invention are embodied homologues, derivatives and/or immunologically active and/or functional fragments of the cytokinin oxidases as defined supra. Particularly preferred homologues, derivatives and/or immunologically active and/or functional fragments of the cytokinin oxidase proteins which are contemplated for use in the current invention are derived from plants, more specifically from *Arabidopsis thaliana*, even more specifically said cytokinin oxidases are the *Arabidopsis thaliana* (At)CKX, or are capable of being expressed therein. The present invention clearly contemplates the use of functional homologues or derivatives and/or immunologically active fragments of the AtCKX proteins and is not to be limited in application to the use of a nucleotide sequence encoding one of said AtCKX proteins.

Any of said proteins, polypeptides, peptides and fragments thereof can be produced in a biological system, e.g. a cell culture. Alternatively any of said proteins, polypeptides, peptides and fragments thereof can be chemically manufactured e.g. by solid phase peptide synthesis. Said proteins or fragments thereof can be part of a fusion protein as is the case in e.g. a two-hybrid assay which enables e.g. the identification of proteins interacting with a cytokinin oxidase according to the invention.

The proteins or fragments thereof are furthermore useful e.g. to modulate the interaction between a cytokinin oxidase according to the invention and interacting protein partners obtained by a method of the invention. Chemically synthesized peptides are particularly useful e.g. as a source of antigens for the production of antisera and/or antibodies.

"Antibodies" include monoclonal, polyclonal, synthetic or heavy chain camel antibodies as well as fragments of antibodies such as Fab, Fv or scFv fragments. Monoclonal antibodies can be prepared by the techniques as described in e.g. Liddle and Cryer (1991) which comprise the fusion of mouse myeloma cells to spleen cells derived from immunized animals. Furthermore, antibodies or fragments thereof to a molecule or fragments thereof can be obtained by using methods as described in e.g. Harlow and Lane (1988). In the case of antibodies directed against small peptides such as fragments of a protein of the invention, said peptides are generally coupled to a carrier protein before immunization of animals. Such protein carriers include keyhole limpet hemocyanin (KLH), bovine serum albumin (BSA), ovalbumin and Tetanus toxoid. The carrier protein enhances the immune response of the animal and provides epitopes for T-cell receptor binding sites. The term "antibodies" furthermore includes derivatives thereof such as labeled antibodies. Antibody labels include alkaline phosphatase, PKH2, PKH26, PKH67, fluorescein (FITC), Hoechst 33258, R-phycoerythrin (PE), rhodamine (TRITC), Quantum Red, Texas Red, Cy3, biotin, agarose, peroxidase and gold spheres. Tools in molecular biology relying on antibodies against a protein include protein gel blot analysis, screening of expression libraries allowing gene identification, protein quantitative methods including ELISA and RIA, immunoaffinity purification of proteins, immunoprecipitation of proteins (see e.g. Example 6) and immunolocalization. Other uses of antibodies and especially of peptide antibodies include the study of proteolytic processing (Loffler et al. 1994, Woulfe et al. 1994), determination of protein active sites (Lerner 1982), the study of precursor and post-translational processing (Baron and Baltimore 1982, Lerner et al. 1981, Semier et al. 1982), identification of protein domains involved in protein-protein interactions (Murakami et al. 1992) and the study of exon usage in gene expression (Tamura et al. 1991).

Embodied in the current invention are antibodies specifically recognizing a cytokinin oxidase or homologue, derivative or fragment thereof as defined supra. Preferably said cytokinin oxidase is a plant cytokinin oxidase, more specifically one of the *Arabidopsis thaliana* cytokinin oxidases (AtCKX).

The terms "gene(s)", "polynucleotide(s)", "nucleic acid(s)", "nucleic acid sequence(s)", "nucleotide sequence(s)", or "nucleic acid molecule(s)", when used herein refer to nucleotides, either ribonucleotides or deoxyribonucleotides or a combination of both, in a polymeric form of any length. Said terms furthermore include double-stranded and single-stranded DNA and RNA. Said terms also include known nucleotide modifications such as methylation, cyclization and 'caps' and substitution of one or more of the naturally occurring nucleotides with an analog such as inosine. Modifications of nucleotides include the addition of acridine, amine, biotin, cascade blue, cholesterol, Cy3®, Cy5®, Cy5.5® Dabcyl, digoxigenin, dinitrophenyl, Edans, 6-FAM, fluorescein, 3'-glyceryl, HEX, IRD-700, IRD-800, JOE, phosphate psoralen, rhodamine, ROX, thiol (SH), spacers, TAMRA, TET, AMCA-S®, SE, BODIPY®, Marina Blue®, Pacific Blue®, Oregon Green®, Rhodamine Green®, Rhodamine Red®, Rhodol Green® and Texas Red®. Polynucleotide backbone modifications include methylphosphonate, 2'-OMe-methylphosphonate RNA, phosphorothiorate, RNA, 2'-OMeRNA. Base modifications include 2-amino-dA, 2-aminopurine, 3'-(ddA), 3'dA(cordycepin), 7-deaza-dA, 8-Br-dA, 8-oxo-dA, $N^6$-Me-dA, abasic site (dSpacer), biotin dT, 2'-OMe-5Me-C, 2'-OMe-propynyl-C, 3'-(5-Me-dC), 3'-(ddC), 5-Br-dC, 5-I-dC, 5-Me-dC, 5-F-dC, carboxy-dT, convertible dA, convertible dC, convertible dG, convertible dT, convertible dU, 7-deaza-dG, 8-Br-dG, 8-oxo-dG, $O^6$-Me-dG, S6-DNP-dG, 4-methyl-indole, 5-nitroindole, 2'-OMe-inosine, 2'-dI, $0^6$-phenyl-dI, 4-methyl-indole, 2'-deoxynebularine, 5-nitroindole, 2-aminopurine, dP (purine analogue), dK (pyrimidine analogue), 3-nitropyrrole, 2-thio-dT, 4-thio-dT, biotin-dT, carboxy-dT, $O^4$-Me-dT, $O^4$-triazol dT, 2'-OMe-propynyl-U, 5-Br-dU, 2'-dU, 5-F-dU, 5-I-dU, $O^4$-triazol dU. Said terms also encompass peptide nucleic acids (PNAs), a DNA analogue in which the backbone is a pseudopeptide consisting of N-(2-aminoethyl)-glycine units rather than a sugar. PNAs mimic the behavior of DNA and bind complementary nucleic acid strands. The neutral backbone of PNA results in stronger binding and greater specificity than normally achieved. In addition, the unique chemical, physical and biological properties of PNA have been exploited to produce powerful biomolecular tools, antisense and antigene agents, molecular probes and biosensors.

The present invention also advantageously provides nucleic acid sequences of at least approximately 15 contiguous nucleotides of a nucleic acid according to the invention and preferably from 15 to 50 nucleotides. These sequences may, advantageously be used as probes to specifically hybridize to sequences of the invention as defined above or primers to initiate specific amplification or replication of sequences of the invention as defined above, or the like. Such nucleic acid sequences may be produced according to techniques well known in the art, such as by recombinant or synthetic means. They may also be used in diagnostic kits or the like for detecting the presence of a nucleic acid according to the invention. These tests generally comprise contacting the probe with the sample under hybridising conditions and detecting the presence of any duplex or triplex formation between the probe and any nucleic acid in the sample.

Advantageously, the nucleic acid sequences, according to the invention may be produced using such recombinant or synthetic means, such as for example using PCR cloning mechanisms which generally involve making a pair of primers, which may be from approximately 15 to 50 nucleotides to a region of the gene which is desired to be cloned, bringing the primers into contact with mRNA, cDNA or genomic DNA from a cell, performing a polymerase chain reaction under conditions which bring about amplification of the desired region, isolating the amplified region or fragment and recovering the amplified DNA. Generally, such techniques as defined herein are well known in the art, such as described in Sambrook et al. (Molecular Cloning: a Laboratory Manual, 1989).

A "coding sequence" or "open reading frame" or "ORF" is defined as a nucleotide sequence that can be transcribed into mRNA and/or translated into a polypeptide when placed under the control of appropriate control sequences or regulatory sequences, i.e. when said coding sequence or ORF is present in an expressible format. Said coding sequence of ORF is bounded by a 5' translation start codon and a 3' translation stop codon. A coding sequence or ORF can include, but is not limited to RNA, mRNA, cDNA, recombinant nucleotide sequences, synthetically manufactured nucleotide sequences or genomic DNA. Said coding sequence or ORF can be interrupted by intervening nucleic acid sequences.

Genes and coding sequences essentially encoding the same protein but isolated from different sources can consist of substantially divergent nucleic acid sequences. Reciprocally, substantially divergent nucleic acid sequences can be designed to effect expression of essentially the same protein. Said nucleic acid sequences are the result of e.g. the existence of different alleles of a given gene, of the degeneracy of the genetic code or of differences in codon usage. Thus, as indicated in Table 2, amino acids such as methionine and tryptophan are encoded by a single codon whereas other amino acids such as arginine, leucine and serine can each be translated from up to six different codons. Differences in preferred codon usage are illustrated in Table 4 for *Agrobacterium tumefaciens* (a bacterium), *A. thaliana, M. sativa* (two dicotyledonous plants) and *Oryza sativa* (a monocotyledonous plant). To extract one example, the codon GGC (for glycine) is the most frequently used codon in *A. tumefaciens* (36.2%), is the second most frequently used codon in *O. sativa* but is used at much lower frequencies in *A. thaliana* and *M. sativa* (9% and 8.4% respectively). Of the four possible codons encoding glycine (see Table 3), said GGC codon is most preferably used in *A. tumefaciens* and *O. sativa*. However, in *A. thaliana* this is the GGA (and GGU) codon whereas in *M. sativa* this is the GGU (and GGA) codon.

DNA sequences as defined in the current invention can be interrupted by intervening sequences. With "intervening sequences" is meant any nucleic acid sequence which disrupts a coding sequence comprising said inventive DNA sequence or which disrupts the expressible format of a DNA sequence comprising said inventive DNA sequence. Removal of the intervening sequence restores said coding sequence or said expressible format. Examples of intervening sequences include introns and mobilizable DNA sequences such as transposons. With "mobilizable DNA sequence" is meant any DNA sequence that can be mobilized as the result of a recombination event.

The methods according to the present invention may also be practised using an alternative splice variant of a nucleic acid molecule encoding a CKX protein. The term "alternative splice variant" as used herein encompasses variants of a nucleic acid molecule in which selected introns and/or exons have been excised, replaced or added. Such variants will be ones in which the biological activity of the protein remains unaffected, which can be achieved by selectively retaining functional segments of the protein. Such splice variants may be found in nature or can be manmade. Methods for making such splice variants are well known in the art. Therefore according to another aspect of the present invention, there is provided a method for modifying the growth characteristics of plants, in particular seed yield, comprising modulating expression in a plant of an alternative splice variant of a nucleic acid molecule encoding a CKX and/or by modulating activity and/or levels of a CKX encoded by the alternative splice variant. Preferably, the splice variant is a splice variant of a sequence represented by SEQ ID NO:1, 3, 5, 7, 9, 11, 33 or 48. A preferred splice variant is as represented by SEQ ID NO 38/39.

TABLE 3

Degeneracy of the genetic code.

| Amino Acid | Three-letter code | One-letter code | Possible codons |
|---|---|---|---|
| Alanine | Ala | A | GCA GCC GCG GCU |
| Arginine | Arg | R | AGA AGG CGA CGC CGG CGU |
| Asparagine | Asn | N | AAC AAU |
| Aspartic Acid | Asp | D | GAC GAU |
| Cysteine | Cys | C | UGC UGU |
| Glutamic Acid | Glu | E | GAA GAG |
| Glutamine | Gln | Q | CAA CAG |
| Glycine | Gly | G | GGA GGC GGG GGU |
| Histidine | His | H | CAC CAU |
| Isoleucine | Ile | I | AUA AUC AUU |
| Leucine | Leu | L | UUA UUG CUA CUC CUG CUU |
| Lysine | Lys | K | AAA AAG |
| Methionine | Met | M | AUG |
| Phenylalanine | Phe | F | UUC UUU |
| Proline | Pro | P | CCA CCC CCG CCU |
| Serine | Ser | S | AGC AGU UCA UCC UCG UCU |
| Threonine | Thr | T | ACA ACC ACG ACU |
| Tryptophan | Trp | W | UGG |

TABLE 3-continued

Degeneracy of the genetic code.

| Amino Acid | Three-letter code | One-letter code | |
|---|---|---|---|
| Tyrosine | Tyr | Y | UAC UAU |
| Valine | Val | V | GUA GUC GUG GUU |
| | | | Possible "STOP" codons |
| | | | UAA UAG UGA |

TABLE 4

Usage of the indicated codons in the different organisms given as frequency per thousand codons (kazusa.or.jp/codon).

| Codon | *Agrobacterium tumefaciens* | *Arabidopsis thaliana* | *Medicago sativa* | *Oryza sativa* |
|---|---|---|---|---|
| UUU | 13.9 | 22.5 | 24.1 | 11.3 |
| UUC | 24.3 | 20.7 | 16.9 | 26.3 |
| UUA | 3.5 | 12.9 | 10.4 | 4.7 |
| UUG | 13.2 | 21.0 | 22.4 | 11.8 |
| UCU | 7.0 | 24.6 | 19.8 | 10.1 |
| UCC | 14.8 | 10.8 | 7.7 | 16.9 |
| UCA | 7.4 | 17.8 | 17.2 | 9.7 |
| UCG | 18.2 | 8.9 | 3.2 | 10.8 |
| UAU | 12.3 | 15.2 | 16.6 | 9.2 |
| UAC | 10.3 | 13.7 | 14.0 | 20.6 |
| UAA | 0.9 | 0.9 | 1.2 | 0.9 |
| UAG | 0.6 | 0.5 | 0.8 | 0.8 |
| UGU | 3.0 | 10.8 | 10.6 | 5.0 |
| UGC | 7.4 | 7.2 | 5.8 | 14.3 |
| UGA | 1.8 | 1.0 | 0.8 | 1.3 |
| UGG | 12.2 | 12.7 | 10.0 | 12.8 |
| CUU | 19.1 | 24.3 | 28.3 | 14.6 |
| CUC | 25.7 | 15.9 | 12.0 | 28.0 |
| CUA | 5.2 | 10.0 | 8.8 | 5.7 |
| CUG | 31.6 | 9.9 | 8.5 | 22.1 |
| CCU | 7.7 | 18.3 | 23.2 | 11.8 |
| CCC | 10.6 | 5.3 | 5.3 | 12.5 |
| CCA | 8.9 | 16.1 | 22.6 | 12.2 |
| CCG | 20.7 | 8.3 | 3.6 | 16.7 |
| CAU | 10.6 | 14.0 | 14.6 | 9.2 |
| CAC | 9.1 | 8.7 | 9.1 | 14.6 |
| CAA | 11.2 | 19.7 | 23.2 | 11.9 |

TABLE 4-continued

Usage of the indicated codons in the different organisms given as frequency per thousand codons (kazusa.or.jp/codon).

| Codon | *Agrobacterium tumefaciens* | *Arabidopsis thaliana* | *Medicago sativa* | *Oryza sativa* |
|---|---|---|---|---|
| CAG | 24.9 | 15.2 | 12.3 | 24.6 |
| CGU | 12.2 | 8.9 | 10.1 | 6.8 |
| CGC | 25.5 | 3.7 | 4.2 | 15.9 |
| CGA | 8.2 | 6.2 | 4.2 | 4.2 |
| CGG | 13.2 | 4.8 | 1.8 | 9.7 |
| AUU | 15.4 | 22.0 | 29.4 | 13.8 |
| AUC | 36.9 | 18.5 | 14.7 | 25.5 |
| AUA | 6.2 | 12.9 | 11.7 | 7.2 |
| AUG | 24.7 | 24.5 | 21.7 | 24.4 |
| ACU | 6.4 | 17.8 | 20.8 | 10.3 |
| ACC | 20.9 | 10.3 | 11.7 | 18.6 |
| ACA | 9.1 | 15.9 | 18.9 | 10.0 |
| ACG | 18.8 | 7.6 | 2.8 | 10.8 |
| AAU | 13.5 | 22.7 | 25.0 | 12.9 |
| AAC | 18.7 | 20.9 | 18.7 | 25.1 |
| AAA | 13.6 | 31.0 | 32.2 | 12.0 |
| AAG | 24.4 | 32.6 | 35.1 | 39.4 |
| AGU | 5.7 | 14.0 | 12.6 | 7.3 |
| AGC | 15.8 | 11.1 | 8.8 | 16.9 |
| AGA | 5.3 | 18.7 | 13.6 | 7.7 |
| AGG | 6.5 | 10.9 | 11.7 | 14.9 |
| GUU | 16.6 | 27.3 | 34.7 | 15.0 |
| GUC | 29.3 | 12.7 | 9.9 | 22.8 |
| GUA | 6.1 | 10.1 | 10.0 | 5.7 |
| GUG | 19.7 | 17.5 | 16.5 | 25.0 |
| GCU | 17.4 | 28.0 | 34.6 | 19.8 |
| GCC | 35.8 | 10.3 | 11.4 | 33.2 |
| GCA | 19.5 | 17.6 | 25.9 | 15.6 |
| GCG | 31.7 | 8.8 | 3.4 | 25.3 |
| GAU | 25.8 | 36.8 | 40.0 | 21.5 |
| GAC | 28.0 | 17.3 | 15.5 | 31.6 |
| GAA | 29.9 | 34.4 | 35.9 | 17.1 |
| GAG | 26.3 | 32.2 | 27.4 | 41.1 |
| GGU | 16.5 | 22.2 | 28.7 | 16.3 |
| GGC | 36.2 | 9.0 | 8.4 | 34.7 |

TABLE 4-continued

Usage of the indicated codons in the different organisms given as frequency per thousand codons (kazusa.or.jp/codon).

| Codon | *Agrobacterium tumefaciens* | *Arabidopsis thaliana* | *Medicago sativa* | *Oryza sativa* |
|---|---|---|---|---|
| GGA | 12.5 | 23.9 | 27.3 | 15.0 |
| GGG | 11.3 | 10.2 | 7.4 | 16.6 |

"Hybridization" is the process wherein substantially homologous complementary nucleotide sequences anneal to each other. The hybridization process can occur entirely in solution, i.e. both complementary nucleic acids are in solution. Tools in molecular biology relying on such a process include PCR, subtractive hybridization and DNA sequence determination. The hybridization process can also occur with one of the complementary nucleic acids immobilized to a matrix such as magnetic beads, Sepharose beads or any other resin. Tools in molecular biology relying on such a process include the isolation of poly (A+) mRNA. The hybridization process can furthermore occur with one of the complementary nucleic acids immobilized to a solid support such as a nitrocellulose or nylon membrane or immobilized by e.g. photolithography to e.g. a silicious glass support (the latter known as nucleic acid arrays or microarrays or as nucleic acid chips). Tools in molecular biology relying on such a process include RNA and DNA gel blot analysis, colony hybridization, plaque hybridization and microarray hybridization. In order to allow hybridization to occur, the nucleic acid molecules are generally thermally or chemically (e.g. by NaOH) denatured to melt a double strand into two single strands and/or to remove hairpins or other secondary structures from single stranded nucleic acids. The stringency of hybridization is influenced by conditions such as temperature, salt concentration and hybridization buffer composition. High stringency conditions for hybridization include high temperature and/or low salt concentration (salts include NaCl and Na3-citrate) and/or the inclusion of formamide in the hybridization buffer and/or lowering the concentration of compounds such as SDS (detergent) in the hybridization buffer and/or exclusion of compounds such as dextran sulfate or polyethylene glycol (promoting molecular crowding) from the hybridization buffer. Conventional hybridization conditions are described in e.g. Sambrook et al. (1989) but the skilled craftsman will appreciate that numerous different hybridization conditions can be designed in function of the known or the expected homology and/or length of the nucleic acid sequence. Sufficiently low stringency hybridization conditions are particularly preferred to isolate nucleic acids heterologous to the DNA sequences of the invention defined supra. Elements contributing to said heterology include allelism, degeneration of the genetic code and differences in preferred codon usage as discussed supra.

The term "specifically hybridizing" or "hybridizing specifically" refers to the binding, duplexing, or hybridizing of a molecule to a particular nucleotide sequence under medium to stringent conditions when that sequence is presented in a complex mixture e.g., total cellular DNA or RNA.

"Stringent hybridization conditions" and "stringent hybridization wash conditions" in the context of nucleic acid hybridization experiments such as Southern and Northern hybridizations are sequence dependent and are different under different environmental parameters. For example, longer sequences hybridize specifically at higher temperatures. The $T_m$ is the temperature under defined ionic strength and pH, at which 50% of the target sequence hybridizes to a perfectly matched probe. Specificity is typically the function of post-hybridization washes. Critical factors of such washes include the ionic strength and temperature of the final wash solution.

Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8° \text{ C.} + (18.5 \times \text{Log[Na +]}) + (58.4° \text{ C.} \times \%[G + C]) - (820/\#\ bp \text{ in duplex}) - (0.5 \times \% \text{ formamide})$$

More preferred stringent conditions are when the temperature is 20° C. below $T_m$, and the most preferred stringent conditions are when the temperature is 10° C. below $T_m$. Nonspecific binding may also be controlled using any one of a number of known techniques such as, for example, blocking the membrane with protein-containing solutions, addition of heterologous RNA, DNA, and SDS to the hybridization buffer, and treatment with RNase.

Wash conditions are typically performed at or below stringency. Generally, suitable stringent conditions for nucleic acid hybridization assays or gene amplification detection procedures are as set forth above. More or less stringent conditions may also be selected.

For the purposes of defining the level of stringency, reference can conveniently be made to Sambrook, J., E. F. Fritsch, et al. 1989 "Molecular Cloning: a Laboratory Manual, $2^{nd}$ Edition, Cold Spring Harbor, N.Y., Cold Spring Harbor Laboratory Press, at 11.45. An example of low stringency conditions is 4-6×SSC/0.1-0.5% w/v SDS at 37°-45° C. for 2-3 hours. Depending on the source and concentration of the nucleic acid involved in the hybridization, alternative conditions of stringency may be employed such as medium stringent conditions. Examples of medium stringent conditions include 1-4×SSC/0.25% w/v SDS at ≥45° C. for 2-3 hours. An example of high stringency conditions includes 0.1-1× SSC/0.1% w/v SDS at 60 C for 1-3 hours. The skilled artisan is aware of various parameters which may be altered during hybridization and washing and which will either maintain or change the stringency conditions. For example, another stringent hybridization condition is hybridization at 4×SSC at 65° C., followed by a washing in 0.1×SSC at 65° C. for about one hour. Alternatively, an exemplary stringent hybridization condition is in 50% formamide, 4×SSC, at 42° C. Still another example of stringent conditions include hybridization at 62° C. in 6×SSC, 0.05× BLOTTO, and washing at 2×SSC, 0.1% SDS at 62° C.

Clearly, the current invention embodies the use of the inventive DNA sequences encoding a cytokinin oxidase, homologue, derivative or immunologically active and/or functional fragment thereof as defined higher in any method of hybridization. The current invention furthermore also relates to DNA sequences hybridizing to said inventive DNA sequences. Preferably said cytokinin oxidase is a plant cytokinin oxidase, more specifically the *Arabidopsis thaliana* (At)CKX.

To effect expression of a protein in a cell, tissue or organ, preferably of plant origin, either the protein may be introduced directly to said cell, such as by microinjection or ballistic means or alternatively, an isolated nucleic acid molecule encoding said protein may be introduced into said cell, tissue or organ in an expressible format.

Preferably, the DNA sequence of the invention comprises a coding sequence or open reading frame (ORF) encoding a cytokinin oxidase protein or a homologue or derivative thereof or an immunologically active and/or functional fragment thereof as defined supra. The preferred protein of the invention comprises the amino acid sequence of said cytokinin oxidase. Preferably said cytokinin oxidase is a plant cytokinin oxidase and more specifically a *Arabidopsis thaliana* (At)CKX.

With "vector" or "vector sequence" is meant a DNA sequence which can be introduced in an organism by transformation and can be stably maintained in said organism. Vector maintenance is possible in e.g. cultures of *Escherichia coli, A. tumefaciens, Saccharomyces cerevisiae* or *Schizosaccharomyces pombe*. Other vectors such as phagemids and cosmid vectors can be maintained and multiplied in bacteria and/or viruses. Vector sequences generally comprise a set of unique sites recognized by restriction enzymes, the multiple cloning site (MCS), wherein one or more non-vector sequence(s) can be inserted.

With "non-vector sequence" is accordingly meant a DNA sequence which is integrated in one or more of the sites of the MCS comprised within a vector.

"Expression vectors" form a subset of vectors which, by virtue of comprising the appropriate regulatory or control sequences enable the creation of an expressible format for the inserted non-vector sequence(s), thus allowing expression of the protein encoded by said non-vector sequence(s). Expression vectors are known in the art enabling protein expression in organisms including bacteria (e.g. *E. coli*), fungi (e.g. *S. cerevisiae, S. pombe, Pichia pastoris*), insect cells (e.g. baculoviral expression vectors), animal cells (e.g. COS or CHO cells) and plant cells (e.g. potato virus X-based expression vectors).

The current invention clearly includes any cytokinin oxidase, homologue, derivative and/or immunologically active and/or functional fragment thereof as defined supra. Preferably said cytokinin oxidase is a plant cytokinin oxidase, more specifically a *Arabidopsis thaliana* (At)CKX.

As an alternative to expression vector-mediated protein production in biological systems, chemical protein synthesis can be applied. Synthetic peptides can be manufactured in solution phase or in solid phase. Solid phase peptide synthesis (Merrifield 1963) is, however, the most common way and involves the sequential addition of amino acids to create a linear peptide chain. Solid phase peptide synthesis includes cycles consisting of three steps: (i) immobilization of the carboxy-terminal amino acid of the growing peptide chain to a solid support or resin; (ii) chain assembly, a process consisting of activation, coupling and deprotection of the amino acid to be added to the growing peptide chain; and (iii) cleavage involving removal of the completed peptide chain from the resin and removal of the protecting groups from the amino acid side chains. Common approaches in solid phase peptide synthesis include Fmoc/tBu (9-fluorenylmethyloxycarbonyl/t-butyl) and Boc (t-butyloxycarbonyl) as the amino-terminal protecting groups of amino acids Amino acid side chain protecting groups include methyl (Me), formyl (CHO), ethyl (Et), acetyl (Ac), t-butyl (t-Bu), anisyl, benzyl (Bzl), trifluoroacetyl (Tfa), N-hydroxysuccinimide (ONSu, OSu), benzoyl (Bz), 4-methylbenzyl (Meb), thioanizyl, thiocresyl, benzyloxymethyl (Bom), 4-nitrophenyl (ONp), benzyloxycarbonyl (Z), 2-nitrobenzoyl (NBz), 2-nitrophenylsulphenyl (Nps), 4-toluenesulphonyl (Tosyl, Tos), pentafluorophenyl (Pfp), diphenylmethyl (Dpm), 2-chlorobenzyloxycarbonyl (Cl-Z), 2,4,5-trichlorophenyl, 2-bromobenzyloxycarbonyl (Br-Z), tripheylmethyl (Trityl, Trt), and 2,5,7,8-pentamethyl-chroman-6-sulphonyl (Pmc). During chain assembly, Fmoc or Boc are removed resulting in an activated amino-terminus of the amino acid residue bound to the growing chain. The carboxy-terminus of the incoming amino acid is activated by conversion into a highly reactive ester, e.g. by HBTU. With current technologies (e.g. PerSeptive Biosystems 9050 synthesizer, Applied Biosystems Model 431A Peptide Synthesizer), linear peptides of up to 50 residues can be manufactured. A number of guidelines is available to produce peptides that are suitable for use in biological systems including (i) limiting the use of difficult amino acids such as cys, met, trp (easily oxidized and/or degraded during peptide synthesis) or arg; (ii) minimize hydrophobic amino acids (can impair peptide solubility); and (iii) prevent an amino-terminal glutamic acid (can cyclize to pyroglutamate).

By "expressible format" is meant that the isolated nucleic acid molecule is in a form suitable for being transcribed into mRNA and/or translated to produce a protein, either constitutively or following induction by an intracellular or extracellular signal, such as an environmental stimulus or stress (mitogens, anoxia, hypoxia, temperature, salt, light, dehydration, etc) or a chemical compound such as IPTG (isopropyl-(3-D-thiogalactopyranoside) or such as an antibiotic (tetracycline, ampicillin, rifampicin, kanamycin), hormone (e.g. gibberellin, auxin, cytokinin, glucocorticoid, brassinosteroid, ethylene, abscisic acid etc), hormone analogue (indoleacetic acid (IAA), 2,4-D, etc), metal (zinc, copper, iron, etc), or dexamethasone, amongst others. As will be known to those skilled in the art, expression of a functional protein may also require one or more post-translational modifications, such as glycosylation, phosphorylation, dephosphorylation, or one or more protein-protein interactions, amongst others. All such processes are included within the scope of the term "expressible format".

Preferably, expression of a protein in a specific cell, tissue, or organ, preferably of plant origin, is effected by introducing and expressing an isolated nucleic acid molecule encoding said protein, such as a cDNA molecule, genomic gene, synthetic oligonucleotide molecule, mRNA molecule or open reading frame, to said cell, tissue or organ, wherein said nucleic acid molecule is placed operably in connection with suitable regulatory or control sequences including a promoter, preferably a plant-expressible promoter, and a terminator sequence.

Reference herein to a "promoter" is to be taken in its broadest context and includes the transcriptional regulatory sequences derived from a classical eukaryotic genomic gene, including the TATA box which is required for accurate transcription initiation, with or without a CCAAT box sequence and additional regulatory or control elements (i.e. upstream activating sequences, enhancers and silencers) which alter gene expression in response to developmental and/or external stimuli, or in a tissue-specific manner.

The term "promoter" also includes the transcriptional regulatory sequences of a classical prokaryotic gene, in which case it may include a −35 box sequence and/or a −10 box transcriptional regulatory sequences.

The term "promoter" is also used to describe a synthetic or fusion molecule, or derivative which confers, activates or enhances expression of a nucleic acid molecule in a cell, tissue or organ.

Promoters may contain additional copies of one or more specific regulatory elements, to further enhance expression and/or to alter the spatial expression and/or temporal expression of a nucleic acid molecule to which it is operably connected. Such regulatory elements may be placed adjacent to a heterologous promoter sequence to drive expression of a nucleic acid molecule in response to e.g. copper, glucocorticoids, dexamethasone, tetracycline, gibberellin, cAMP, abscisic acid, auxin, wounding, ethylene, jasmonate or salicylic acid or to confer expression of a nucleic acid molecule to specific cells, tissues or organs such as meristems, leaves, roots, embryo, flowers, seeds or fruits.

In the context of the present invention, the promoter preferably is a plant-expressible promoter sequence. Promoters that also function or solely function in non-plant cells such as bacteria, yeast cells, insect cells and animal cells are not excluded from the invention. By "plant-expressible" is meant that the promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ.

The terms "plant-operable" and "operable in a plant" when used herein, in respect of a promoter sequence, shall be taken to be equivalent to a plant-expressible promoter sequence.

Regulatable promoters as part of a binary viral plant expression system are also known to the skilled artisan (Yadav 1999-WO9922003; Yadav 2000-WO0017365).

In the present context, a "regulatable promoter sequence" is a promoter that is capable of conferring expression on a structural gene in a particular cell, tissue, or organ or group of cells, tissues or organs of a plant, optionally under specific conditions, however does generally not confer expression throughout the plant under all conditions. Accordingly, a regulatable promoter sequence may be a promoter sequence that confers expression on a gene to which it is operably connected in a particular location within the plant or alternatively, throughout the plant under a specific set of conditions, such as following induction of gene expression by a chemical compound or other elicitor.

Preferably, the regulatable promoter used in the performance of the present invention confers expression in a specific location within the plant, either constitutively or following induction, however not in the whole plant under any circumstances. Included within the scope of such promoters are cell-specific promoter sequences, tissue-specific promoter sequences, organ-specific promoter sequences, cell cycle specific gene promoter sequences, inducible promoter sequences and constitutive promoter sequences that have been modified to confer expression in a particular part of the plant at any one time, such as by integration of said constitutive promoter within a transposable genetic element (Ac, Ds, Spm, En, or other transposon).

Similarly, the term "tissue-specific" shall be taken to indicate that expression is predominantly in a particular tissue or tissue-type, preferably of plant origin, albeit not necessarily exclusively in said tissue or tissue-type.

Similarly, the term "organ-specific" shall be taken to indicate that expression is predominantly in a particular organ, preferably of plant origin, albeit not necessarily exclusively in said organ.

Similarly, the term "cell cycle specific" shall be taken to indicate that expression is predominantly cyclic and occurring in one or more, not necessarily consecutive phases of the cell cycle albeit not necessarily exclusively in cycling cells, preferably of plant origin.

Those skilled in the art will be aware that an "inducible promoter" is a promoter the transcriptional activity of which is increased or induced in response to a developmental, chemical, environmental, or physical stimulus. Similarly, the skilled craftsman will understand that a "constitutive promoter" is a promoter that is transcriptionally active throughout most, but not necessarily all parts of an organism, preferably a plant, during most, but not necessarily all phases of its growth and development.

Those skilled in the art will readily be capable of selecting appropriate promoter sequences for use in regulating appropriate expression of the cytokinin oxidase protein from publicly-available or readily-available sources, without undue experimentation.

Placing a nucleic acid molecule under the regulatory control of a promoter sequence, or in operable connection with a promoter sequence, means positioning said nucleic acid molecule such that expression is controlled by the promoter sequence. A promoter is usually, but not necessarily, positioned upstream, or at the 5'-end, and within 2 kb of the start site of transcription, of the nucleic acid molecule which it regulates. In the construction of heterologous promoter/structural gene combinations it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include those listed in Table 5, amongst others. The promoters listed in Table 5 are provided for the purposes of exemplification only and the present invention is not to be limited by the list provided therein. Those skilled in the art will readily be in a position to provide additional promoters that are useful in performing the present invention.

Further examples of promoters suitable for use in the present invention especially with respect to increasing seed yield in a plant may be found in Table 15.

In the case of constitutive promoters or promoters that induce expression throughout the entire plant, it is preferred that such sequences are modified by the addition of nucleotide sequences derived from one or more of the tissue-specific promoters listed in Table 5, or alternatively, nucleotide sequences derived from one or more of the above-mentioned tissue-specific inducible promoters, to confer tissue-specificity thereon. For example, the CaMV 35S promoter may be modified by the addition of maize Adh1 promoter sequence, to confer anaerobically-regulated root-specific expression thereon, as described previously (Ellis et al., 1987). Another example describes conferring root specific or root abundant gene expression by fusing the CaMV35S promoter to elements of the maize glycine-rich protein GRP3 gene (Feix and Wulff 2000-WO0015662). Such modifications can be achieved by routine experimentation by those skilled in the art.

The term "terminator" refers to a DNA sequence at the end of a transcriptional unit which signals termination of transcription. Terminators are 3'-non-translated DNA sequences containing a polyadenylation signal, which facilitates the addition of polyadenylate sequences to the 3'-end of a primary transcript. Terminators active in cells derived from viruses, yeasts, molds, bacteria, insects, birds, mammals and plants are known and described in the literature. They may be isolated from bacteria, fungi, viruses, animals and/or plants.

TABLE 5

Examples of plant-expressible promoters for use in the performance of the present invention

| GENE SOURCE | EXPRESSION PATTERN | REFERENCE |
|---|---|---|
| I: CELL-SPECIFIC, TISSUE-SPECIFIC, AND ORGAN-SPECIFIC PROMOTERS | | |
| α-amylase (Amy32b) | aleurone | Lanahan, M. B., et al., *Plant Cell* 4: 203-211, 1992; Skriver, K., et al. *Proc. Natl. Acad. Sci.* (*USA*) 88: 7266-7270, 1991 |
| cathepsin β-like gene | aleurone | Cejudo, F. J., et al. *Plant Molecular Biology* 20: 849-856, 1992. |
| *Agrobacterium rhizogenes* rolB | cambium | Nilsson et al., *Physiol. Plant.* 100: 456-462, 1997 |
| AtPRP4 | flowers | salus.medium.edu/mmg/tierney/html |
| chalcone synthase (chsA) | flowers | Van der Meer, et al., *Plant Mol. Biol.* 15, 95-109, 1990. |
| LAT52 | anther | Twell et al Mol. Gen Genet. 217: 240-245 (1989) |
| apetala-3 | flowers | |
| Chitinase | fruit (berries, grapes, etc) | Thomas et al. CSIRO Plant Industry, Urrbrae, South Australia, Australia; winetitles.com.au/gwrdc/csh95-1.html |
| rbcs-3A | green tissue (eg leaf) | Lam, E. et al., *The Plant Cell* 2: 857-866, 1990.; Tucker et al., *Plant Physiol.* 113: 1303-1308, 1992. |
| leaf-specific genes | leaf | Baszczynski, et al., *Nucl. Acid Res.* 16: 4732, 1988. |
| AtPRP4 | leaf | salus.medium.edu/mmg/tierney/html |
| chlorella virus adenine | leaf | Mitra and Higgins, 1994, Plant |

TABLE 5-continued

| Examples of plant-expressible promoters for use in the performance of the present invention | | |
|---|---|---|
| methyltransferase gene promoter | | Molecular Biology 26: 85-93 |
| aldP gene promoter from rice | leaf | Kagaya et al., 1995, Molecular and General Genetics 248: 668-674 |
| rbcs promoter from rice or tomato | leaf | Kyozuka et al., 1993, Plant Physiology 102: 991-1000 |
| *Pinus* cab-6 | leaf | Yamamoto et al., *Plant Cell Physiol.* 35: 773-778, 1994. |
| rubisco promoter | leaf | |
| cab (chlorophyll a/b/binding protein | leaf | |
| SAM22 | senescent leaf | Crowell, et al., *Plant Mol. Biol.* 18: 459-466, 1992. |
| ltp gene (lipid transfer gene) | | Fleming, et al, *Plant J.* 2, 855-862. |
| *R. japonicum* nif gene | Nodule | U.S. Pat. No. 4,803,165 |
| *B. japonicum* nifH gene | Nodule | U.S. Pat. No. 5,008,194 |
| GmENOD40 | Nodule | Yang, et al., *The Plant J.* 3: 573-585. |
| PEP carboxylase (PEPC) | Nodule | Pathirana, et al., *Plant Mol. Biol.* 20: 437-450, 1992. |
| Leghaemoglobin (Lb) | Nodule | Gordon, et al., *J. Exp. Bot.* 44: 1453-1465, 1993. |
| *Tungro bacilliform* virus gene | phloem | Bhattacharyya-Pakrasi, et al, *The Plant J.* 4: 71-79, 1992. |
| pollen-specific genes | pollen; microspore | Albani, et al., *Plant Mol. Biol.* 15: 605, 1990; Albani, et al., *Plant Mol. Biol.* 16: 501, 1991) |
| Zm13 | pollen | Guerrero et al Mol. Gen. Genet. 224: 161-168 (1993) |
| apg gene | microspore | Twell et al Sex. Plant Reprod. 6: 217-224 (1993) |
| maize pollen-specific gene | pollen | Hamilton, et al., Plant Mol. Biol. 18: 211-218, 1992. |
| sunflower pollen-expressed gene | pollen | Baltz, et al., The Plant J. 2: 713-721, 1992. |
| *B. napus* pollen-specific gene | pollen; anther; tapetum | Arnoldo, et al., J. Cell. Biochem., Abstract No. Y101, 204, 1992. |
| root-expressible genes | roots | Tingey, et al., EMBO J. 6: 1, 1987. |
| tobacco auxin-inducible gene | root tip | Van der Zaal, et al., Plant Mol. Biol. 16, 983, 1991. |
| β-tubulin | root | Oppenheimer, et al., *Gene* 63: 87, 1988. |
| tobacco root-specific genes | root | Conkling, et al., Plant Physiol. 93: 1203, 1990. |
| *B. napus* G1-3b gene | root | U.S. Pat. No. 5,401,836 |
| SbPRP1 | roots | Suzuki et al., Plant Mol. Biol. 21: 109-119, 1993. |
| AtPRP1; AtPRP3 | roots; root hairs | salus.medium.edu.mmg/tierney/html |
| RD2 gene | root cortex | 2.cnsu.edu/ncsu/research |
| TobRB7 gene | root vasculature | 2.cnsu.edu/ncsu/research |
| AtPRP4 | leaves; flowers; lateral root primordia | salus.medium.edu.mmg/tierney/html |
| seed-specific genes | seed | Simon, et al., *Plant Mol. Biol.* 5: 191, 1985; Scofield, et al., *J. Biol. Chem.* 262: 12202, 1987.; Baszczynski, et al., *Plant Mol. Biol.* 14: 633, 1990. |
| Brazil Nut albumin | seed | Pearson, et al., Plant Mol. Biol. 18: 235-245, 1992. |
| Legumin | seed | Ellis, et al., Plant Mol. Biol. 10: 203-214, 1988. |
| glutelin (rice) | seed | Takaiwa, et al., Mol. Gen. Genet. 208: 15-22, 1986; Takaiwa, et al., FEBS Letts. 221: 43-47, 1987. |
| Zein | seed | Matzke et al Plant Mol Biol, 14(3): 323-32 1990 |
| NapA | seed | Stalberg, et al, *Planta* 199: 515-519, 1996. |
| wheat LMW and HMW glutenin-1 | endosperm | Mol Gen Genet 216: 81-90, 1989; NAR 17: 461-2, 1989 |
| wheat SPA | seed | Albani et al, Plant Cell, 9: 171-184, 1997 |
| wheat α, β, γ-gliadins | endosperm | EMBO 3: 1409-15, 1984 |
| barley Itr1 promoter | endosperm | |
| barley B1, C, D, hordein | endosperm | Theor Appl Gen 98: 1253-62, 1999; Plant J 4: 343-55, 1993; Mol Gen Genet 250: 750-60, 1996 |

TABLE 5-continued

Examples of plant-expressible promoters for use in the performance of the present invention

| | | |
|---|---|---|
| barley DOF | endosperm | Mena et al, The Plant Journal, 116(1): 53-62, 1998 |
| blz2 | endosperm | EP99106056.7 |
| synthetic promoter | endosperm | Vicente-Carbajosa et al., *Plant J.* 13: 629-640, 1998. |
| rice prolamin NRP33 | endosperm | Wu et al, Plant Cell Physiology 39(8) 885-889, 1998 |
| rice α-globulin Glb-1 | endosperm | Wu et al, Plant Cell Physiology 39(8) 885-889, 1998 |
| rice OSH1 | embryo | Sato et al, Proc. Natl. Acad. Sci. USA, 93: 8117-8122, 1996 |
| rice α-globulin REB/OHP-1 | endosperm | Nakase et al. Plant Mol. Biol. 33: 513-522, 1997 |
| rice ADP-glucose PP | endosperm | Trans Res 6: 157-68, 1997 |
| maize ESR gene family | endosperm | Plant J 12: 235-46, 1997 |
| sorgum γ-kafirin | endosperm | PMB 32: 1029-35, 1996 |
| KNOX | embryo | Postma-Haarsma et al, Plant Mol. Biol. 39: 257-71, 1999 |
| rice oleosin | embryo and aleuron | Wu et at, J. Biochem., 123: 386, 1998 |
| sunflower oleosin | seed (embryo and dry seed) | Cummins, et al., Plant Mol. Biol. 19: 873-876, 1992 |
| LEAFY | shoot meristem | Weigel et al., *Cell* 69: 843-859, 1992. |
| *Arabidopsis thaliana* knat1 | shoot meristem | Accession number AJ131822 |
| *Malus domestica* kn1 | shoot meristem | Accession number Z71981 |
| CLAVATA1 | shoot meristem | Accession number AF049870 |
| stigma-specific genes | stigma | Nasrallah, et al., Proc. Natl. Acad. Sci. USA 85: 5551, 1988; Trick, et al., *Plant Mol. Biol.* 15: 203, 1990. |
| class I patatin gene | tuber | Liu et al., Plant Mol. Biol. 153: 386-395, 1991. |
| PCNA rice | meristem | Kosugi et al, *Nucleic Acids Research* 19: 1571-1576, 1991; Kosugi S. and Ohashi Y, *Plant Cell* 9: 1607-1619, 1997. |
| Pea TubA1 tubulin | Dividing cells | Stotz and Long, *Plant Mol. Biol.* 41, 601-614. 1999 |
| *Arabidopsis* cdc2a | cycling cells | Chung and Parish, FEBS Lett, 3; 362(2): 215-9, 1995 |
| *Arabidopsis* Rop1A | Anthers; mature pollen + pollen tubes | Li et al. 1998 *Plant Physiol* 118, 407-417. |
| *Arabidopsis* AtDMC1 | Meiosis-associated | Klimyuk and Jones 1997 *Plant J.* 11, 1-14. |
| Pea PS-IAA4/5 and PS-IAA6 | Auxin-inducible | Wong et al. 1996 *Plant J.* 9, 587-599. |
| Pea farnesyltransferase | Meristematic tissues; phloem near growing tissues; light- and sugar-repressed | Zhou et al. 1997 *Plant J.* 12, 921-930 |
| Tobacco (*N. sylvestris*) cyclin B1; 1 | Dividing cells/ meristematic tissue | Trehin et al. 1997 *Plant Mol. Biol.* 35, 667-672. |
| Mitotic cyclins CYS (A-type) and CYM (B-type) | Dividing cells/ meristematic tissue | Ito et al. 1997 *Plant J.* 11, 983-992 |
| *Arabidopsis* cyc1At (=cyc B1; 1) and cyc3aAt (A-type) | Dividing cells/ meristematic tissue | Shaul et al. 1996 *Proc. Natl. Acad. Sci. U.S.A* 93, 4868-4872. |
| *Arabidopsis* tef1 promoter box | Dividing cells/ meristematic tissue | Regad et al. 1995 *Mol. Gen. Genet.* 248, 703-711. |
| *Catharanthus roseus* cyc07 | Dividing cells/ meristematic tissue | Ito et al. 1994 *Plant Mol. Biol.* 24, 863-878. |
| II: EXAMPLES OF CONSTITUTIVE PROMOTERS | | |
| Actin | constitutive | McElroy et al, Plant Cell, 2: 163-171, 1990 |
| CAMV 35S | constitutive | Odell et al, Nature, 313: 810-812, 1985 |
| CaMV 19S | constitutive | Nilsson et al., Physiol. Plant. 100: 456-462, 1997 |
| GOS2 | constitutive | de Pater et al, Plant J. 2: 837-844, 1992 |
| Ubiquitin | constitutive | Christensen et al, Plant Mol. Biol. 18: 675-689, 1992 |
| rice cyclophilins | constitutive | Buchholz et al, Plant Mol Biol. 25: 837-843, 1994 |

TABLE 5-continued

Examples of plant-expressible promoters for use in the performance of the present invention

| | | |
|---|---|---|
| maize histone H3 | constitutive | Lepetit et al, Mol. Gen. Genet. 231: 276-285, 1992 |
| alfalfa histone H3 | constitutive | Wu et al., Nucleic Acids Res. 17: 3057-3063, 1989; Wu et al., Plant Mol. Biol. 11: 641-649, 1988 |
| actin 2 | constitutive | An et al, Plant J. 10(1); 107-121, 1996 |

III: EXAMPLES OF STRESS-INDUCIBLE PROMOTERS

| NAME | STRESS | REFERENCE |
|---|---|---|
| P5CS (delta(1)-pyrroline-5-carboxylate syntase) | salt, water | Zhang et al. Plant Science. 129: 81-89, 1997 |
| cor15a | cold | Hajela et al., Plant Physiol. 93: 1246-1252, 1990 |
| cor15b | cold | Wlihelm et al., Plant Mol Biol. 23: 1073-1077, 1993 |
| cor15a (−305 to +78 nt) | cold, drought | Baker et al., Plant Mol Biol. 24: 701-713, 1994 |
| rd29 | salt, drought, cold | Kasuga et al., Nature Biotechnology 18: 287-291, 1999 |
| heat shock proteins, including artificial promoters containing the heat shock element (HSE) | heat | Barros et al., Plant Mol Biol 19: 665-75, 1992. Marrs et al., Dev Genet. 14: 27-41, 1993. Schoffl et al., Mol Gen Gent, 217: 246-53, 1989. |
| smHSP (small heat shock proteins) | heat | Waters et al, J Experimental Botany 47: 325-338, 1996 |
| wcs120 | cold | Ouellet et al., FEBS Lett. 423: 324-328, 1998 |
| ci7 | cold | Kirch et al., Plant Mol Biol 33: 897-909, 1997 |
| Adh | cold, drought, hypoxia | Dolferus et al., Plant Physiol 105: 1075-87, 1994 |
| pwsi18 | water: salt and drought | Joshee et al., Plant Cell Physiol 39: 64-72, 1998 |
| ci21A | cold | Schneider et al., Plant Physiol 113: 335-45, 1997 |
| Trg-31 | drought | Chaudhary et al., Plant Mol Biol 30: 1247-57, 1996 |
| Osmotin | osmotic | Raghothama et al., Plant Mol Biol 23: 1117-28, 1993 |
| Rab17 | osmotic, ABA | Vilardell et al., Plant Mol Biol 17: 985-93, 1991 |
| LapA | wounding, enviromental | WO99/03977 University of California/INRA |

IV: EXAMPLES OF PATHOGEN-INDUCIBLE PROMOTERS

| NAME | PATHOGEN | REFERENCE |
|---|---|---|
| RB7 | Root-knot nematodes (*Meloidogyne* spp.) | U.S. Pat. No. 5,760,386 - North Carolina State University; Opperman et al (1994) Science 263: 221-23. |
| PR-1, 2, 3, 4, 5, 8, 11 | fungal, viral, bacterial | Ward et al (1991) Plant Cell 3: 1085-1094; Reiss et al 1996; Lebel et al (1998), Plant J, 16(2): 223-33; Melchers et al (1994), Plant J, 5(4): 469-80; Lawton et al (1992), Plant Mol Biol, 19(5): 735-43. |
| HMG2 | nematodes | WO9503690 - Virginia Tech Intellectual Properties Inc. |
| Abi3 | Cyst nematodes (*Heterodera* spp.) | Unpublished |
| ARM1 | nematodes | Barthels et al., (1997) The Plant Cell 9, 2119-2134. WO 98/31822 - Plant Genetic Systems |
| Att0728 | nematodes | Barthels et al., (1997) The Plant Cell 9, 2119-2134. PCT/EP98/07761 |
| Att1712 | nematodes | Barthels et al., (1997) The Plant Cell 9, 2119-2134. PCT/EP98/07761 |
| Gst1 | Different types of pathogens | Strittmatter et al (1996) Mol. Plant-Microbe Interact. 9, 68-73. |
| LEMMI | nematodes | WO 92/21757 - *Plant Genetic Systems* |

TABLE 5-continued

Examples of plant-expressible promoters for use in the performance of the present invention

| | | |
|---|---|---|
| CLE | geminivirus | PCT/EP99/03445 - CINESTAV |
| PDF1.2 | Fungal including *Alternaria brassicicola* and *Botrytis cinerea* | Manners et al (1998), Plant Mol Biol, 38(6): 1071-80. |
| Thi2.1 | Fungal—*Fusarium oxysporum* f sp. *matthiolae* | Vignutelli et al (1998) Plant J; 14(3): 285-95 |
| DB#226 | nematodes | Bird and Wilson (1994) Mol. Plant-Microbe Interact., 7, 419-42 WO 95.322888 |
| DB#280 | nematodes | Bird and Wilson (1994) Mol. Plant-Microbe Interact., 7, 419-42 WO 95.322888 |
| Cat2 | nematodes | Niebel et al (1995) Mol Plant Microbe Interact 1995 May-June; 8(3): 371-8 |
| □Tub | nematodes | Aristizabal et al (1996), 8th International Congress on Plant-Microbe Interaction, Knoxville US B-29 |
| SHSP | nematodes | Fenoll et al (1997) In: Cellular and molecular aspects of plant-nematode interactions. Kluwer Academic, C. Fenoll, F. M. W. Grundler and S. A. Ohl (Eds.), |
| Tsw12 | nematodes | Fenoll et al (1997) In: Cellular and molecular aspects of plant-nematode interactions. Kluwer Academic, C. Fenoll, F. M. W. Grundler and S.A. Ohl (Eds.) |
| Hs1(pro1) | nematodes | WO 98/122335 - Jung |
| NsLTP | viral, fungal, bacterial | Molina & García-Olmedo (1993) FEBS Lett, 316(2): 119-22 |
| RIP | viral, fungal | Turner et al (1997) Proc Natl Acad Sci USA, 94(8): 3866-71 |

Examples of terminators particularly suitable for use in the gene constructs of the present invention include the *Agrobacterium tumefaciens* nopaline synthase (NOS) gene terminator, the *Agrobacterium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3'Bt2), the *Zea mays* zein gene terminator sequence, the rbcs-1A gene terminator, and the rbcs-3A gene terminator sequences, amongst others.

Preferred promoter sequences of the invention include root specific promoters and seed-specific promoters such as but not limited to the ones listed in Table 6, Table 5, and as outlined in the Examples.

TABLE 6

Examples of root specific promoters for use in the performance of the present invention

| NAME | ORIGIN | REFERENCE |
|---|---|---|
| SbPRP1 | Soybean | Suzuki et al., Plant Mol Biol, 21: 109-119, 1993 |
| 636 bp fragment of TobRB7 | Tobacco | Yamamoto et al., Plant Cell 3: 371-382, 1991 |
| GGPS3 | *Arabidopsis* | Okada et al., Plant Physiol 122: 1045-1056, 2000 |
| 580 bp fragment of prxEa | *Arabidopsis* | Wanapu and Shinmyo, Ann N Y Acad Sci 782: 107-114, 1996 |
| Ids2 promoter | Barley | Okumura et al., Plant Mol Biol 25: 705-719, 1994 |
| AtPRP3 | *Arabidopsis* | Fowler et al., Plant Physiol 121: 1081-1092, 1999 |

Those skilled in the art will be aware of additional promoter sequences and terminator sequences which may be suitable for use in performing the invention. Such sequences may readily be used without any undue experimentation.

In the context of the current invention, "ectopic expression" or "ectopic overexpression" of a gene or a protein are conferring to expression patterns and/or expression levels of said gene or protein normally not occurring under natural conditions, more specifically is meant increased expression and/or increased expression levels. Ectopic expression can be achieved in a number of ways including operably linking of a coding sequence encoding said protein to an isolated homologous or heterologous promoter in order to create a chimeric gene and/or operably linking said coding sequence to its own isolated promoter (i.e. the unisolated promoter naturally driving expression of said protein) in order to create a recombinant gene duplication or gene multiplication effect. With "ectopic co-expression" is meant the ectopic expression or ectopic overexpression of two or more genes or proteins. The same or, more preferably, different promoters are used to confer ectopic expression of said genes or proteins.

Preferably, the promoter sequence used in the context of the present invention is operably linked to a coding sequence or open reading frame (ORF) encoding a cytokinin oxidase protein or a homologue, derivative or an immunologically active and/or functional fragment thereof as defined supra.

"Downregulation of expression" as used herein means lowering levels of gene expression and/or levels of active gene product and/or levels of gene product activity. Decreases in expression may be accomplished by e.g. the addition of coding sequences or parts thereof in a sense orientation (if resulting in co-suppression) or in an antisense orientation relative to a promoter sequence and furthermore by e.g. insertion mutagenesis (e.g. T-DNA insertion or transposon insertion) or by gene silencing strategies as described by e.g. Angell and Baulcombe (1998—WO9836083), Lowe et al. (1989—WO9853083), Lederer et al. (1999—WO9915682) or Wang et al. (1999—WO9953050). Genetic constructs aimed at silencing gene expression may have the nucleotide sequence of said gene (or one or more parts thereof) contained therein in a sense and/or antisense orientation relative to the promoter sequence. Another method to downregulate gene expression comprises the use of ribozymes.

Modulating, including lowering, the level of active gene products or of gene product activity can be achieved by administering or exposing cells, tissues, organs or organisms to said gene product, a homologue, derivative and/or immunologically active fragment thereof. Immunomodulation is another example of a technique capable of downregulation levels of active gene product and/or of gene product activity and comprises administration of or exposing to or expressing antibodies to said gene product to or in cells, tissues, organs or organisms wherein levels of said gene product and/or gene product activity are to be modulated. Such antibodies comprise "plantibodies", single chain antibodies, IgG antibodies and heavy chain camel antibodies as well as fragments thereof.

Modulating, including lowering, the level of active gene products or of gene product activity can furthermore be achieved by administering or exposing cells, tissues, organs or organisms to an agonist of said gene product or the activity thereof. Such agonists include proteins (comprising e.g. kinases and proteinases) and chemical compounds identified according to the current invention as described supra.

In the context of the current invention is envisaged the downregulation of the expression of a cytokinin oxidase gene as defined earlier. Preferably said cytokinin oxidase gene is a plant cytokinin oxidase gene, more specifically an AtCKX. The invention further comprises downregulation of levels of a cytokinin oxidase protein or of a cytokinin oxidase activity whereby said cytokinin oxidase protein has been defined supra. Preferably said cytokinin oxidase protein is a plant cytokinin oxidase, more specifically an AtCKX.

By "modifying cell fate and/or plant development and/or plant morphology and/or biochemistry and/or physiology" is meant that one or more developmental and/or morphological and/or biochemical and/or physiological characteristics of a plant is altered by the performance of one or more steps pertaining to the invention described herein.

"Cell fate" refers to the cell-type or cellular characteristics of a particular cell that are produced during plant development or a cellular process therefor, in particular during the cell cycle or as a consequence of a cell cycle process.

"Plant development" or the term "plant developmental characteristic" or similar term shall, when used herein, be taken to mean any cellular process of a plant that is involved in determining the developmental fate of a plant cell, in particular the specific tissue or organ type into which a progenitor cell will develop. Cellular processes relevant to plant development will be known to those skilled in the art. Such processes include, for example, morphogenesis, photomorphogensis, shoot development, root development, vegetative development, reproductive development, stem elongation, flowering, and regulatory mechanisms involved in determining cell fate, in particular a process or regulatory process involving the cell cycle.

"Plant morphology" or the term "plant morphological characteristic" or similar term will, when used herein, be understood by those skilled in the art to refer to the external appearance of a plant, including any one or more structural features or combination of structural features thereof. Such structural features include the shape, size, number, position, color, texture, arrangement, and patternation of any cell, tissue or organ or groups of cells, tissues or organs of a plant, including the root, stem, leaf, shoot, petiole, trichome, flower, petal, stigma, style, stamen, pollen, ovule, seed, embryo, endosperm, seed coat, aleurone, fiber, fruit, cambium, wood, heartwood, parenchyma, aerenchyma, sieve element, phloem or vascular tissue, amongst others.

"Plant biochemistry" or the term "plant biochemical characteristic" or similar term will, when used herein, be understood by those skilled in the art to refer to the metabolic and catalytic processes of a plant, including primary and secondary metabolism and the products thereof, including any small molecules, macromolecules or chemical compounds, such as but not limited to starches, sugars, proteins, peptides, enzymes, hormones, growth factors, nucleic acid molecules, celluloses, hemicelluloses, calloses, lectins, fibers, pigments such as anthocyanins, vitamins, minerals, micronutrients, or macronutrients, that are produced by plants.

"Plant physiology" or the term "plant physiological characteristic" or similar term will, when used herein, be understood to refer to the functional processes of a plant, including developmental processes such as growth, expansion and differentiation, sexual development, sexual reproduction, seed set, seed development, grain filling, asexual reproduction, cell division, dormancy, germination, light adaptation, photosynthesis, leaf expansion, fiber production, secondary growth or wood production, amongst others; responses of a plant to externally-applied factors such as metals, chemicals, hormones, growth factors, environment and environmental stress factors (e.g. anoxia, hypoxia, high temperature, low temperature, dehydration, light, daylength, flooding, salt, heavy metals, amongst others), including adaptive responses of plants to said externally-applied factors.

Advantageously, performance of the methods according to the present invention results in plants having a variety of modified growth characteristics, such modified growth characteristics including modified yield or biomass, relative to corresponding wild type plants. Preferably, the modified growth characteristics are improved growth characteristics and include increased yield or biomass, relative to corresponding wild type plants.

By "yield" is meant the amount of harvested material per area of production. The term "increased yield" encompasses an increase in biomass in one or more parts of a plant relative to the biomass of corresponding wild-type plants. Depending on the crop, the harvested part of the plant can be a different part or tissue of the plant, such as seed (e.g. rice, sorghum or corn when grown for seed); total above-ground biomass (e.g. corn, when used as silage, sugarcane), root (e.g. sugar beet), fruit (e.g. tomato), cotton fibres, or any other part of the plant which is of economic value. For example, the methods of the present invention are used to increase seed yield of rice and of corn, or also to increase yield of silage corn in terms of overall above ground biomass and energy content. The increase in yield encompasses an increase in seed yield, which includes an increase in the total biomass of the seed (total seed weight), total number of seeds and/or an increase in the number of (filled) seeds. The increase in yield is also reflected in an increase of the Harvest Index, which is expressed as a ratio of the yield of harvestable parts, such as seeds, over the total biomass and is also reflected in an increased Thousand Kernel Weight (derived from the number of filled seeds counted and their total weight).

Therefore, there is provided a method for increasing seed yield of a plant, comprising introducing and overexpressing primarily in the seed of this plant a nucleic acid sequence encoding a cytokinin oxidase/dehydrogenase, a homologue, a derivative or an active fragment thereof compared to corresponding wild type plants, and wherein the increase of seed yield comprises at least one of increased total weight of seeds, increased total number of seeds, increased number of filled seeds, increased harvest index or increased thousand kernel weight, each relative to corresponding wild type plants.

Yield is by its nature a complex parameter whereby total yield depends on a number of yield components. The parameters for increased yield of a crop are well known by a person skilled in the art. By way of example, key yield components for corn include number of plants per hectare or acre, number of ears per plant, number of rows (of seeds) per ear, number of kernels per row, and Thousand Kernel Weight. The improvement in yield as obtained in accordance to the method of the invention, can be obtained as a result of one or more of these yield components. By way of example, key yield components for rice include number of plants per hectare or acre, number of panicles per plant, number of spikelets per panicle, seed filling rate and thousand kernel weight. The improvement in yield as obtained in accordance to the method of the invention can be obtained as a result in one or more of these yield components, preferentially the improvement in yield is obtained primarily on the basis of an increased number of flowers per panicle and an increased seed filling rate.

According to a preferred feature of the present invention, performance of the methods according to the present invention result in plants having modified seed yield. Preferably, the modified yield includes at least an increase in any one or more of total weight of seeds, total seed number, number of filled seeds, thousand kernel weight and harvest index, each relative to control plants. Therefore, according to the present invention, there is provided a method for increasing total seed number, total weight of seeds, number of filled seeds and/or harvest index of plants, which method comprises modulating expression of a nucleic acid molecule encoding a CKX protein and/or modulating activity of the CKX itself in a plant in a seed/seedling preferred way, preferably wherein the CKX protein is encoded by a nucleic acid sequence represented by SEQ ID NO:44 or SEQ ID NO:48, or a portion thereof or by sequences capable of hybridising therewith or wherein the CKX is represented by SEQ ID NO:37 or SEQ ID NO:2, or a homologue, derivative or active fragment thereof. Alternatively, the CKX may be encoded by a nucleic acid sequence represented by SEQ ID NO:38, or by a portion thereof or by sequences capable of hybridising therewith, or wherein the CKX is represented by SEQ ID NO: 39, or a homologue, derivative or active fragment of any thereof.

Means for introducing recombinant DNA into plant tissue or cells include, but are not limited to, transformation using $CaCl_2$ and variations thereof, in particular the method described by Hanahan (1983), direct DNA uptake into protoplasts (Krens et al, 1982; Paszkowski et al, 1984), PEG-mediated uptake to protoplasts (Armstrong et al, 1990) microparticle bombardment, electroporation (Fromm et al., 1985), microinjection of DNA (Crossway et al., 1986), microparticle bombardment of tissue explants or cells (Christou et al, 1988; Sanford, 1988), vacuum-infiltration of tissue with nucleic acid, or in the case of plants, T-DNA-mediated transfer from *Agrobacterium* to the plant tissue as described essentially by An et al. (1985), Dodds et al., (1985), Herrera-Estrella et al. (1983a, 1983b, 1985). Methods for transformation of monocotyledonous plants are well known in the art and include *Agrobacterium*-mediated transformation (Cheng et al., 1997-WO9748814; Hansen 1998-WO9854961; Hiei et al., 1994-WO9400977; Hiei et al., 1998-WO9817813; Rikiishi et al., 1999-WO9904618; Saito et al., 1995-WO9506722), microprojectile bombardment (Adams et al., 1999—U.S. Pat. No. 5,969,213; Bowen et al., 1998—U.S. Pat. No. 5,736,369; Chang et al., 1994-WO9413822; Lundquist et al., 1999—U.S. Pat. No. 5,874,265/U.S. Pat. No. 5,990,390; Vasil and Vasil, 1995—U.S. Pat. No. 5,405,765. Walker et al., 1999—U.S. Pat. No. 5,955,362), DNA uptake (Eyal et al., 1993—WO9318168), microinjection of *Agrobacterium* cells (von Holt, 1994-DE4309203) and sonication (Finer et al., 1997—U.S. Pat. No. 5,693,512).

For microparticle bombardment of cells, a microparticle is propelled into a cell to produce a transformed cell. Any suitable ballistic cell transformation methodology and apparatus can be used in performing the present invention. Exemplary apparatus and procedures are disclosed by Stomp et al. (U.S. Pat. No. 5,122,466) and Sanford and Wolf (U.S. Pat. No. 4,945,050). When using ballistic transformation procedures, the gene construct may incorporate a plasmid capable of replicating in the cell to be transformed. Examples of microparticles suitable for use in such systems include 1 to 5 μm gold spheres. The DNA construct may be deposited on the microparticle by any suitable technique, such as by precipitation.

A whole plant may be regenerated from the transformed or transfected cell, in accordance with procedures well known in the art. Plant tissue capable of subsequent clonal propagation, whether by organogenesis or embryogenesis, may be transformed with a gene construct of the present invention and a whole plant regenerated therefrom. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The term "organogenesis", as used herein, means a process by which shoots and roots are developed sequentially from meristematic centers.

The term "embryogenesis", as used herein, means a process by which shoots and roots develop together in a concerted fashion (not sequentially), whether from somatic cells or gametes.

Preferably, the plant is produced according to the inventive method is transfected or transformed with a genetic sequence, or amenable to the introduction of a protein, by any art-recognized means, such as microprojectile bombardment, microinjection, *Agrobacterium*-mediated transformation (including in planta transformation), protoplast fusion, or electroporation, amongst others. Most preferably said plant is produced by *Agrobacterium*-mediated transformation.

*Agrobacterium*-mediated transformation or agrolistic transformation of plants, yeast, molds or filamentous fungi is based on the transfer of part of the transformation vector sequences, called the T-DNA, to the nucleus and on integration of said T-DNA in the genome of said eukaryote.

With "*Agrobacterium*" is meant a member of the Agrobacteriaceae, more preferably *Agrobacterium* or *Rhizobacterium* and most preferably *Agrobacterium tumefaciens*.

With "T-DNA", or transferred DNA, is meant that part of the transformation vector flanked by T-DNA borders which is, after activation of the *Agrobacterium* vir genes, nicked at the T-DNA borders and is transferred as a single stranded DNA to the nucleus of an eukaryotic cell.

When used herein, with "T-DNA borders", "T-DNA border region", or "border region" are meant either right T-DNA border (RB) or left T-DNA border (LB). Such a border comprises a core sequence flanked by a border inner region as part of the T-DNA flanking the border and/or a border outer region as part of the vector backbone flanking the border. The core sequences comprise 22 bp in case of octopine-type vectors and 25 bp in case of nopaline-type vectors. The core sequences in the right border region and left border region form imperfect repeats. Border core sequences are indispensable for recognition and processing by the *Agrobacterium* nicking complex consisting of at least VirD1 and VirD2. Core sequences flanking a T-DNA are sufficient to promote transfer of said T-DNA. However, efficiency of transformation using transformation vectors carrying said T-DNA solely flanked by said core sequences is low. Border inner and outer regions are known to modulate efficiency of T-DNA transfer (Wang et al. 1987). One element enhancing T-DNA transfer has been characterized and resides in the right border outer region and is called overdrive (Peralta et al. 1986, van Haaren et al. 1987).

With "T-DNA transformation vector" or "T-DNA vector" is meant any vector encompassing a T-DNA sequence flanked by a right and left T-DNA border consisting of at least the right and left border core sequences, respectively, and used for transformation of any eukaryotic cell.

With "T-DNA vector backbone sequence" or "T-DNA vector backbone sequences" is meant all DNA of a T-DNA containing vector that lies outside of the T-DNA borders and, more specifically, outside the nicking sites of the border core imperfect repeats.

The current invention includes optimized T-DNA vectors such that vector backbone integration in the genome of a eukaryotic cell is minimized or absent. With "optimized T-DNA vector" is meant a T-DNA vector designed either to decrease or abolish transfer of vector backbone sequences to the genome of a eukaryotic cell. Such T-DNA vectors are known to the one familiar with the art and include those described by Hanson et al. (1999) and by Stuiver et al. (1999—WO9901563).

The current invention clearly considers the inclusion of a DNA sequence encoding a cytokinin oxidase, homologue, derivative or immunologically active and/or functional fragment thereof as defined supra, in any T-DNA vector comprising binary transformation vectors, super-binary transformation vectors, co-integrate transformation vectors, Ri-derived transformation vectors as well as in T-DNA carrying vectors used in agrolistic transformation. Preferably, said cytokinin oxidase is a plant cytokinin oxidase, more specifically an *Arabidopsis thaliana* (At)CKX.

With "binary transformation vector" is meant a T-DNA transformation vector comprising:

(a) a T-DNA region comprising at least one gene of interest and/or at least one selectable marker active in the eukaryotic cell to be transformed; and (b) a vector backbone region comprising at least origins of replication active in *E. coli* and *Agrobacterium* and markers for selection in *E. coli* and *Agrobacterium.*

The T-DNA borders of a binary transformation vector can be derived from octopine-type or nopaline-type Ti plasmids or from both. The T-DNA of a binary vector is only transferred to a eukaryotic cell in conjunction with a helper plasmid.

With "helper plasmid" is meant a plasmid that is stably maintained in *Agrobacterium* and is at least carrying the set of vir genes necessary for enabling transfer of the T-DNA. Said set of vir genes can be derived from either octopine-type or nopaline-type Ti plasmids or from both.

With "super-binary transformation vector" is meant a binary transformation vector additionally carrying in the vector backbone region a vir region of the Ti plasmid pTiBo542 of the super-virulent *A. tumefaciens* strain A281 (EP0604662, EP0687730). Super-binary transformation vectors are used in conjunction with a helper plasmid.

With "co-integrate transformation vector" is meant a T-DNA vector at least comprising:

(a) a T-DNA region comprising at least one gene of interest and/or at least one selectable marker active in plants; and (b) a vector backbone region comprising at least origins of replication active in *Escherichia coli* and *Agrobacterium*, and markers for selection in *E. coli* and *Agrobacterium*, and a set of vir genes necessary for enabling transfer of the T-DNA.

The T-DNA borders and said set of vir genes of a said T-DNA vector can be derived from either octopine-type or nopaline-type Ti plasmids or from both.

With "Ri-derived plant transformation vector" is meant a binary transformation vector in which the T-DNA borders are derived from a Ti plasmid and said binary transformation vector being used in conjunction with a 'helper' Ri-plasmid carrying the necessary set of vir genes.

As used herein, the term "selectable marker gene" or "selectable marker" or "marker for selection" includes any gene which confers a phenotype on a cell in which it is expressed to facilitate the identification and/or selection of cells which are transfected or transformed with a gene construct of the invention or a derivative thereof. Suitable selectable marker genes contemplated herein include the ampicillin resistance ($Amp^r$), tetracycline resistance gene ($Tc^r$), bacterial kanamycin resistance gene ($Kan^r$), phosphinothricin resistance gene, neomycin phosphotransferase gene (nptII), hygromycin resistance gene, β-glucuronidase (GUS) gene, chloramphenicol acetyltransferase (CAT) gene, green fluorescent protein (gfp) gene (Haseloff et al, 1997), and luciferase gene, amongst others.

With "agrolistics", "agrolistic transformation" or "agrolistic transfer" is meant here a transformation method combining features of *Agrobacterium*-mediated transformation and of biolistic DNA delivery. As such, a T-DNA containing target plasmid is co-delivered with DNA/RNA enabling in planta production of VirD1 and VirD2 with or without VirE2 (Hansen and Chilton 1996; Hansen et al. 1997; Hansen and Chilton 1997-WO9712046).

With "foreign DNA" is meant any DNA sequence that is introduced in the host's genome by recombinant techniques. Said foreign DNA includes e.g. a T-DNA sequence or a part thereof such as the T-DNA sequence comprising the selectable marker in an expressible format. Foreign DNA furthermore include intervening DNA sequences as defined supra.

With "recombination event" is meant either a site-specific recombination event or a recombination event effected by transposon 'jumping'.

With "recombinase" is meant either a site-specific recombinase or a transposase.

With "recombination site" is meant either site-specific recombination sites or transposon border sequences.

With "site specific recombination event" is meant an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e. inverted repeats). If the site-specific recombination sequences are oriented in the same direction relative to one another (i.e. direct repeats), then any intervening sequences will be deleted upon interaction with the site-specific recombinase. Thus, if the site-specific recombination sequences are present as direct repeats at both ends of a foreign DNA sequence integrated into a eukaryotic genome, such integration of said sequences can subsequently be reversed by interaction of the site-specific recombination sequences with the corresponding site specific recombinase.

A number of different site specific recombinase systems can be used including but not limited to the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of the pSR1 plasmid. Recombinases generally are integrases, resolvases or flippases. Also dual-specific recombinases can be used in conjunction with direct or indirect repeats of two different site-specific recombination sites corresponding to the dual-specific recombinase (WO99/25840). The two preferred site-specific recombinase systems are the bacteriophage P1 Cre/lox and the yeast FLP/FRT systems. In these systems a recombinase (Cre or FLP) interact specifically with its respective site-specific recombination sequence (lox or FRT respectively) to invert or excise the intervening sequences. The site-specific recombination sequences for each of these two systems are relatively short (34 bp for lox and 47 bp for FRT). Some of these systems have already been used with high efficiency in plants such as tobacco (Dale et al. 1990) and *Arabidopsis* (Osborne et al. 1995). Site-specific recombination systems have many applications in plant molecular biology including methods for control of homologous recombination (e.g. U.S. Pat. No. 5,527,695), for targeted insertion, gene stacking, etc. (WO99/25821) and for resolution of complex T-DNA integration patterns or for excision of a selectable marker (WO99/23202).

Although the site-specific recombination sequences must be linked to the ends of the DNA to be excised or to be inverted, the gene encoding the site specific recombinase may be located elsewhere. For example, the recombinase gene could already be present in the eukaryote's DNA or could be supplied by a later introduced DNA fragment either introduced directly into cells, through crossing or through cross-pollination. Alternatively, a substantially purified recombinase protein could be introduced directly into the eukaryotic cell, e.g. by micro-injection or particle bombardment. Typically, the site-specific recombinase coding region will be operably linked to regulatory sequences enabling expression of the site-specific recombinase in the eukaryotic cell.

With "recombination event effected by transposon jumping" or "transposase-mediated recombination" is meant a recombination event catalyzed by a system consisting of three elements: a pair of DNA sequences (the transposon border sequences) and a specific enzyme (the transposase). The transposase catalyzes a recombination reaction only between two transposon border sequences which are arranged as inverted repeats.

A number of different transposon/transposase systems can be used including but not limited to the Ds/Ac system, the Spm system and the Mu system. These systems originate from corn but it has been shown that at least the Ds/Ac and the Spm system also function in other plants (Fedoroff et al. 1993, Schlappi et al. 1993, Van Sluys et al. 1987). Preferred are the Ds- and the Spm-type transposons which are delineated by 11 bp- and 13 bp-border sequences, respectively.

Although the transposon border sequences must be linked to the ends of the DNA to be excised, the gene encoding the transposase may be located elsewhere. For example, the recombinase gene could already be present in the eukaryote's DNA or could be supplied by a later introduced DNA fragment either introduced directly into cells, through crossing or through cross-pollination. Alternatively, a substantially purified transposase protein could be introduced directly into cells, e.g. by microinjection or by particle bombardment.

As part of the current invention, transposon border sequences are included in a foreign DNA sequence such that they lie outside said DNA sequence and transform said DNA into a transposon-like entity that can move by the action of a transposase.

As transposons often reintegrate at another locus of the host's genome, segregation of the progeny of the hosts in which the transposase was allowed to act might be necessary to separate transformed hosts containing e.g. only the transposon footprint and transformed hosts still containing the foreign DNA.

In performing the present invention, the genetic element is preferably induced to mobilize, such as, for example, by the expression of a recombinase protein in the cell which contacts the integration site of the genetic element and facilitates a recombination event therein, excising the genetic element completely, or alternatively, leaving a "footprint", generally of about 20 nucleotides in length or greater, at the original integration site. Those hosts and host parts that have been produced according to the inventive method can be identified by standard nucleic acid hybridization and/or amplification techniques to detect the presence of the mobilizable genetic element or a gene construct comprising the same. Alternatively, in the case of transformed host cells, tissues, and hosts wherein the mobilizable genetic element has been excised, it is possible to detect a footprint in the genome of the host which has been left following the excision event, using such techniques. As used herein, the term "footprint" shall be taken to refer to any derivative of a mobilizable genetic element or gene construct comprising the same as described herein which is produced by excision, deletion or other removal of the mobilizable genetic element from the genome of a cell transformed previously with said gene construct. A footprint generally comprises at least a single copy of the recombination loci or transposon used to promote excision. However, a footprint may comprise additional sequences derived from the gene construct, for example nucleotide sequences derived from the left border sequence, right border sequence, origin of replication, recombinase-encoding or transposase-encoding sequence if used, or other vector-derived nucleotide sequences. Accordingly, a footprint is identifiable according to the nucleotide sequence of the recombination locus or transposon of the gene construct used, such as, for example, a sequence of nucleotides corresponding or complementary to a lox site or frt site.

The term "cell cycle" means the cyclic biochemical and structural events associated with growth and with division of cells, and in particular with the regulation of the replication of DNA and mitosis. Cell cycle includes phases called: G0, Gap1 (G1), DNA synthesis (S), Gap2 (G2), and mitosis (M). Normally these four phases occur sequentially, however, the cell cycle also includes modified cycles wherein one or more phases are absent resulting in modified cell cycle such as endomitosis, acytokinesis, polyploidy, polyteny, and endoreduplication.

The term "cell cycle progression" refers to the process of passing through the different cell cycle phases. The term "cell cycle progression rate" accordingly refers to the speed at which said cell cycle phases are run through or the time spans required to complete said cell cycle phases.

With "two-hybrid assay" is meant an assay that is based on the observation that many eukaryotic transcription factors comprise two domains, a DNA-binding domain (DB) and an activation domain (AD) which, when physically separated (i.e. disruption of the covalent linkage) do not effectuate target gene expression. Two proteins able to interact physically with one of said proteins fused to DB and the other of said proteins fused to AD will re-unite the DB and AD domains of the transcription factor resulting in target gene expression. The target gene in the yeast two-hybrid assay is usually a reporter gene such as the β-galactosidase gene. Interaction between protein partners in the yeast two-hybrid assay can thus be quantified by measuring the activity of the reporter gene product (Bartel and Fields 1997). Alternatively, a mammalian two-hybrid system can be used which includes e.g. a chimeric green fluorescent protein encoding reporter gene (Shioda et al., 2000).

Furthermore, folding simulations and computer redesign of structural motifs of the protein of the invention can be performed using appropriate computer programs (Olszewski, Proteins 25 (1996), 286-299; Hoffman, Comput. Appl. Biosci. 1 (1995), 675-679). Computer modeling of protein folding can be used for the conformational and energetic analysis of detailed peptide and protein models (Monge, J. Mol. Biol. 247 (1995), 995-1012; Renouf, Adv. Exp. Med. Biol. 376 (1995), 37-45). In particular, the appropriate programs can be used for the identification of interactive sites of the cytokinin oxidases, its ligands or other interacting proteins by computer assistant searches for complementary peptide sequences (Fassina, Immunomethods 5 (1994), 114-120). Further appropriate computer systems for the design of protein and peptides are described in the prior art, for example in Berry, Biochem. Soc. Trans. 22 (1994), 1033-1036; Wodak, Ann, N.Y. Acac. Sci. 501 (1987), 1-13; Pabo, Biochemistry 25 (1986), 5987-5991. The results obtained form the above-described computer analysis can be used for, e.g. the preparation of peptidomimetics of the protein of the invention or fragments thereof. Such pseudopeptide analogues of the natural amino acid sequence of the protein may very efficiently mimic the parent protein (Benkirane, J. Biol. Chem. 271 (1996), 33218-33224). For example, incorporation of easily available achiral Ω-amino acid residues into a protein of the invention or a fragment thereof results in the substitution of amino bonds by polymethylene units of an aliphatic chain, thereby providing a convenient strategy for constructing a peptidomimetic (Banerjee, Biopolymers 39 (1996), 769-777). Superactive peptidomimetic analogues of small peptide hormones in other systems are described in the prior art (Zhang, Biochem. Biophys. Res. Commun. 224 (1996), 327-331). Appropriate peptidomimetics of the protein of the present invention can also be identified by the synthesis of peptidomimetic combinatorial libraries through successive amine alkylation and testing the resulting compounds, e.g., for their binding, kinase inhibitory and/or immunological properties. Methods for the generation and use of peptidomimetic combinatorial libraries are described in the prior art, for example in Ostresh, Methods in Enzymology 267 (1996), 220-234 and Dorner, Bioorg. Med. Chem. 4 (1996), 709-715.

Furthermore, a three-dimensional and/or crystallographic structure of the protein of the invention can be used for the design of peptidomimetic inhibitors of the biological activity of the protein of the invention (Rose, Biochemistry 35 (1996), 12933-12944; Ruterber, Bioorg. Med. Chem. 4 (1996), 1545-1558).

The compounds to be obtained or identified in the methods of the invention can be compounds that are able to bind to any of the nucleic acids, peptides or proteins of the invention. Other interesting compounds to be identified are compounds that modulate the expression of the genes or the proteins of the invention in such a way that either the expression of said gene or protein is enhanced or decreased by the action of said compound. Alternatively the compound can exert his action by enhancing or decreasing the activity of any of the proteins of the invention. Herein, preferred proteins are novel cytokinin oxidases.

Said compound or plurality of compounds may be comprised in, for example, samples, e.g., cell extracts from, e.g., plants, animals or microorganisms. Furthermore, said compound(s) may be known in the art but hitherto not known to be capable of suppressing or activating cytokinin oxidase interacting proteins. The reaction mixture may be a cell free extract of may comprise a cell or tissue culture. Suitable set ups for the method of the invention are known to the person skilled in the art and are, for example, generally described in Alberts et al., Molecular Biology of the Cell, third edition (1994), in particular Chapter 17. The plurality of compounds may be, e.g., added to the reaction mixture, culture medium or injected into the cell.

If a sample containing a compound or a plurality of compounds is identified in the method of the invention, then it is either possible to isolate the compound form the original sample identified as containing the compound capable of acting as an agonist, or one can further subdivide the original sample, for example, if it consists of a plurality of different compounds, so as to reduce the number of different substances per sample and repeat the method with the subdivisions of the original sample. Depending on the complexity of the samples, the steps described above can be performed several times, preferably until the sample identified according to the method of the invention only comprises a limited number of or only one substance(s). Preferably said sample comprises substances or similar chemical and/or physical properties, and most preferably said substances are identical. Preferably, the compound identified according to the above-described method or its derivative is further formulated in a form suitable for the application in plant breeding or plant cell and tissue culture.

The term "early vigor" refers to the ability of a plant to grow rapidly during early development, and relates to the successful establishment, after germination, of a well-developed root system and a well-developed photosynthetic apparatus.

The term "resistance to lodging" or "standability" refers to the ability of a plant to fix itself to the soil. For plants with an erect or semi-erect growth habit this term also refers to the ability to maintain an upright position under adverse (environmental) conditions. This trait relates to the size, depth and morphology of the root system.

The term 'grafting' as used herein, refers to the joining together of the parts of two different plants so that they bind together and the sap can flow, thus forming a single new plant that can grow and develop. A graft therefore consists of two parts: (i) the lower part is the rootstock as referred to herein and essentially consists of the root system and a portion of the stem, and (ii) the upper part, the scion or graft, which gives rise to the aerial parts of the plant.

As used herein, tblastn refers to an alignment tool that is part of the BLAST (Basic Local Alignment Search Tool)

family of programs (ncbi.nlm nih.gov/BLAST/). BLAST aims to identify regions of optimal local alignment, i.e. the alignment of some portion of two nucleic acid or protein sequences, to detect relationships among sequences which share only isolated regions of similarity (Altschul et al., 1990). In the present invention, tblastn of the BLAST 2.0 suite of programs was used to compare the maize cytokinin oxidase protein sequence against a nucleotide sequence database dynamically translated in all reading frames (Altschul et al., Nucleic Acids Res. 25: 3389-3402 (1997)).

The following examples are given by means of illustration of the present invention and are in no way limiting. The contents of all references included in this application are incorporated by reference herein as if fully set forth.

EXAMPLES

Example 1

Brief Description of the Sequences of the Invention

| SEQ ID NO: | DESCRIPTION |
|---|---|
| 1 | AtCKX1 genomic |
| 2 | AtCKX1 protein |
| 3 | AtCKX2 genomic |
| 4 | AtCKX2 protein |
| 5 | AtCKX3 genomic |
| 6 | AtCKX3 protein |
| 7 | AtCKX4 genomic |
| 8 | AtCKX4 protein |
| 9 | AtCKX5 genomic (short version) |
| 10 | AtCKX5 protein (short version) |
| 11 | AtCKX6 genomic |
| 12 | AtCKX6 protein |
| 13 | 5' primer AtCKX1 |
| 14 | 3' primer AtCKX1 |
| 15 | 5' primer AtCKX2 |
| 16 | 3' primer AtCKX2 |
| 17 | 5' primer AtCKX3 |
| 18 | 3' primer AtCKX3 |
| 19 | 5' primer AtCKX4 |
| 20 | 3' primer AtCKX4 |
| 21 | 5' primer AtCKX5 |
| 22 | 3' primer AtCKX5 |
| 23 | 5' primer AtCKX6 |
| 24 | 3' primer AtCKX6 |
| 25 | AtCKX1 cDNA |
| 26 | AtCKX2 cDNA |
| 27 | AtCKX3 cDNA |
| 28 | AtCKX4 cDNA |
| 29 | AtCKX5 cDNA (short version) |
| 30 | AtCKX6 cDNA |
| 31 | AtCKX2 cDNA fragment |
| 32 | AtCKX2 peptide fragment |
| 33 | AtCKX5 genomic (long version) |
| 34 | AtCKX5 cDNA (long version) |
| 35 | AtCKX5 protein (long version) |
| 36 | root clavata homolog promoter |
| 37 | AtCKX2, CDS0427__2 deduced protein sequence |
| 38 | AtCKX2 splice variant, DNA sequence |
| 39 | AtCKX2 splice variant, deduced protein sequence |
| 40 | PRM3769 (sense, start codon at positions 35 to 37) |
| 41 | PRM1526 (reverse, complementary stop codon at positions 30-32) |
| 42 | Expression cassette with PRO0218 - CDS0427__2 - zein and rbcS-deltaGA double terminator |
| 43 | Expression cassette with PRO0090 - CDS0427__2 - zein and rbcS-deltaGA double terminator |
| 44 | AtCKX2, CDS0427__2 cDNA |
| 45 | PRM02958 (sense, start codon at positions 37 to 37) |
| 46 | PRM02959 (reverse complementary stop codon at positions 30 to 32) |
| 47 | Expression cassette with PRO0218 - CKX1 - zein and rbcS-deltaGA double terminator |
| 48 | AtCKX1 genomic sequence used in example 18 |

Example 2

Identification of Candidate Cytokinin Oxidase Encoding Genes from *Arabidopsis thaliana*

Six different genes were identified from *Arabidopsis thaliana* that bear sequence similarity to a cytokinin oxidase gene from maize (Morris et al., Biochem Biophys Res Comm 255:328-333, 1999; Houda-Herin et al. Plant J 17:615-626; WO 99/06571). These genes were found by screening 6-frame translations of nucleotide sequences from public genomic databases with the maize protein sequence, employing tblastn program. These sequences were designated as *Arabidopsis thaliana* cytokinin oxidase-like genes or AtCKX. They were arbitrarily numbered as AtCKX1 to AtCKX6. The below list summarizes the information on these genes. The predicted ORF borders and protein sequences are indicative, in order to illustrate by approximation the protein sequence divergence between the *Arabidopsis* and maize cytokinin oxidases, as well as amongst the different *Arabidopsis* cytokinin oxidases. The ORF borders and protein sequences shown should not be taken as conclusive evidence for the mode of action of these AtCKX genes. For DNA and protein sequence comparisons the program MegAlign from DNAstar was used. This program uses the Clustal method for alignments. For multiple alignments of protein and cDNA sequences the gap penalty and gap length penalty was set at 10 each. For pairwise alignments of proteins the parameters were as follows: Ktuple at 1; Gap penalty at 3; window at 5; diagonals saved at 5. For pairwise alignments of cDNA's the parameters were as follows: Ktuple at 2; Gap penalty at 5; window at 4; diagonals saved at 4. The similarity groups for protein alignments was: (M,I,L,V), (F,W,Y), (G,A), (S,T), (R,K,H), (E,D), (N,Q). The values that are indicated amongst the *Arabidopsis* cDNA and protein sequences represent the lowest and highest values found with all combinations.

A. Gene name: AtCKX1 (*Arabidopsis thaliana* cytokinin oxidase-like protein 1, SEQ ID NO: 1)

Location in database (accession number, location on bac): AC002510, *Arabidopsis thaliana* chromosome II section 225 of 255 of the complete sequence. Sequence from clones T32G6.

ORF predicted in the database:

15517 . . . 16183, 16415 . . . 16542, 16631 . . . 16891, 16995 . . . 17257, 17344 . . . 17752

The AtCKX1 cDNA sequence is listed as SEQ ID NO: 25

Predicted protein sequence: SEQ ID NO: 2:

Homologies

% identity with *Z. mays* cDNA:

31.5% (Dnastar/MegAlign—Clustal method)

% similarity with *Z. mays* protein:

32.2% (Dnastar/MegAlign—Clustal method)

% identity with other *Arabidopsis* cDNA's (range):

38.2% (AtCKX2) —54.1% (AtCKX6) (Dnastar/MegAlign—Clustal method)

% similarity with other *Arabidopsis* proteins (range):

37.1% (AtCKX2) —58.1% (AtCKX6) (Dnastar/MegAlign—Clustal method)

B. Gene name: AtCKX2 (*Arabidopsis thaliana* cytokinin oxidase-like protein 2, SEQ ID NO: 3)

Location in database (accession number, location on bac): AC005917, *Arabidopsis thaliana* chromosome II section 113 of 255 of the complete sequence. Sequence from clones F27F23, F3P11.

ORF predicted in the database:

complement, 40721.41012, 41054.41364, 41513.41770, 42535.42662, 43153.43711

Please note: The cDNA sequence identified by the inventor using the gene prediction program NetPlantGene (cbs.dtu.dk/services/NetGene2/) was different than the one annotated in the database. Based on the new cDNA sequence the ORF predicted in the database was revised:

complement, 40721 . . . 41012, 41095 . . . 41364, 41513 . . . 41770, 42535 . . . 42662, 43153 . . . 43711

The protein sequence encoded by this cDNA is listed as SEQ ID NO: 4. The cDNA of AtCKX2 was cloned by RT-PCR from total RNA of AtCKX2 transgenic plant tissue with the one-step RT-PCR kit (Qiagen, Hilden, Germany) and sequenced using an ABI PRISM Big Dye Terminator cycle sequencing reaction kit (Perkin Elmer Applied Biosystems Division). This confirmed that the cDNA sequence identified and predicted by the inventor was correct. The new AtCKX2 cDNA sequence is listed as SEQ ID NO: 26. An 84-bp fragment corresponding to nucleotides 1171 through 1254 of the AtCKX2 cDNA is listed as SEQ ID NO: 31. The corresponding peptide sequence of this 84-bp cDNA sequence is listed as SEQ ID NO: 32.

Homologies

% identity with *Z. mays* cDNA:

38.4% (Dnastar/MegAlign—Clustal method)

% similarity with *Z. mays* protein:

37.5% (Dnastar/MegAlign—Clustal method)

% identity with other *Arabidopsis* cDNA's (range):

34.9% (AtCKX6) —64.5% (AtCKX4) (Dnastar/MegAlign—Clustal method)

% similarity with other *Arabidopsis* proteins (range):

36.5% (AtCKX6)-66.1% (AtCKX4) (Dnastar/MegAlign—Clustal method)

C. Gene name: AtCKX3 (*Arabidopsis thaliana* cytokinin oxidase-like protein 3, SEQ ID NO: 5)

Location in database (accession number, location on bac): AB024035, *Arabidopsis thaliana* genomic DNA, chromosome 5, P1 clone: MHM17, complete sequence.

No prediction of the ORF in the database.

The gene was identified by the inventor using several gene prediction programs including GRAIL (arthur.epm.ornl.gov/pub/xgrail), Genscan (http://CCR-081.mit.edu/GENSCAN html) and NetPlantGene (cbs.dtu.dk/services/NetGene2/):

complement, 29415 . . . 29718, 29813 . . . 30081, 30183 . . . 30443, 30529 . . . 30656, 32107 . . . 32716 The new AtCKX3 cDNA sequence identified by the inventor is listed as SEQ ID NO: 27

Predicted protein sequence, based on own ORF prediction: SEQ ID NO: 6

Homologies

% identity with *Z. mays* cDNA:

38.7% (Dnastar/MegAlign—Clustal method)

% similarity with *Z. mays* protein:

39.2% (Dnastar/MegAlign—Clustal method)

% identity with other *Arabidopsis* cDNA's (range):

38.8% (AtCKX6)-51.0% (AtCKX2) (Dnastar/MegAlign—Clustal method)

% similarity with other *Arabidopsis* proteins (range):

39.9% (AtCKX6)-46.7% (AtCKX2) (Dnastar/MegAlign—Clustal method)

D. Gene name: AtCKX4 (*Arabidopsis thaliana* cytokinin oxidase-like protein 4, SEQ ID NO: 7)

Location in database (accession number, location on bac):

1) AL079344, *Arabidopsis thaliana* DNA chromosome 4, BAC clone T16L4 (ESSA project)

2) AL161575, *Arabidopsis thaliana* DNA chromosome 4, contig fragment No. 71.

ORF predicted in the database:

1) 76187 . . . 76814, 77189 . . . 77316, 77823 . . . 78080, 78318 . . . 78586, 78677 . . . 78968

2) 101002 . . . 101629, 102004 . . . 102131, 102638 . . . 102895, 103133 . . . 103401, 103492 . . . 103783

The AtCKX4 cDNA sequence is listed as SEQ ID NO: 28

Predicted protein sequence: SEQ ID NO: 8

Homologies

% identity with *Z. mays* cDNA:

41.0% (Dnastar/MegAlign—Clustal method)

% similarity with *Z. mays* protein:

41.0% (Dnastar/MegAlign—Clustal method)

% identity with other *Arabidopsis* cDNA's (range):

35.2% (AtCKX6) —64.5% (AtCKX2) (Dnastar/MegAlign—Clustal method)

% similarity with other *Arabidopsis* proteins (range):

35.1% (AtCKX6) —66.1% (AtCKX2) (Dnastar/MegAlign—Clustal method)

E. Gene name: AtCKX5 (*Arabidopsis thaliana* cytokinin oxidase-like protein 5, SEQ ID NO: 9)

Location in database (accession number, location on bac): AC023754, F1B16, complete sequence, chromosome 1

No prediction of the ORF in the database.

The gene was identified by the inventors using several gene prediction programs including GRAIL (arthur.emp.ornl.gov/pub/xgrail)), Genscan (CCR-081.mit.edu/GEN SCAN.html) and NetPlantGene (cbs.dtu.dk/services/NetGene2/).

43756 . . . 44347, 44435 . . . 44562, 44700 . . . 44966, 45493 . . . 45755, 46200 . . . 46560

The new AtCKX5 cDNA sequence identified and predicted by the inventor is listed as SEQ ID NO: 29. The predicted protein sequence for this cDNA is listed as SEQ ID NO: 10. A second potential ATG start codon is present 9 nucleotides more upstream in the genomic sequence. It is unclear which of these 2 start codons encodes the first amino acid of the protein. Therefore, a second potential AtCKX5 cDNA starting at this upstream start codon is also listed in this invention as SEQ ID NO: 34. The corresponding genomic sequence is listed as SEQ ID NO: 33 and the encoded protein as SEQ ID NO: 35.

Homologies

% identity with *Z. mays* cDNA:

39.1% (Dnastar/MegAlign—Clustal method)

% similarity with *Z. mays* protein:

36.6% (Dnastar/MegAlign—Clustal method)

% identity with other *Arabidopsis* cDNA's (range):

40.1% (AtCKX2) —44.0% (AtCKX3) (Dnastar/MegAlign—Clustal method)

% similarity with other *Arabidopsis* proteins (range):

41.6% (AtCKX4) —46.4% (AtCKX6) (Dnastar/MegAlign—Clustal method)

F. Gene name: AtCKX6 (*Arabidopsis thaliana* cytokinin oxidase-like protein 6, SEQ ID NO: 11)

Location in database (accession number, location on bac): AL163818, *Arabidopsis thaliana* DNA chromosome 3, P1 clone MAA21 (ESSA project).

ORF predicted in the database:

46630 . . . 47215, 47343 . . . 47470, 47591 . . . 47806, 47899 . . . 48161, 48244 . . . 48565

The AtCKX6 cDNA sequence is listed as SEQ ID NO: 30

Predicted protein sequence: SEQ ID NO: 12

Homologies

% identity with *Z. mays* cDNA:

37.3% (Dnastar/MegAlign—Clustal method) % similarity with *Z. mays* protein:

36.1% (Dnastar/MegAlign—Clustal method)

% identity with other *Arabidopsis* cDNA's (range):

34.9% (AtCKX2) —54.1% (AtCKX1) (Dnastar/MegAlign—Clustal method)

% similarity with other *Arabidopsis* proteins (range):

35.1% (AtCKX4) —58.1% (AtCKX1) (Dnastar/MegAlign—Clustal method)

Genes AtCKX3 and AtCKX5 were not annotated as putative cytokinin oxidases in the database and ORFs for these genes were not given. Furthermore, the ORF (and consequently the protein structures) predicted for AtCKX2 was different from our own prediction and our prediction was confirmed by sequencing the AtCKX2 cDNA.

Figure 1:
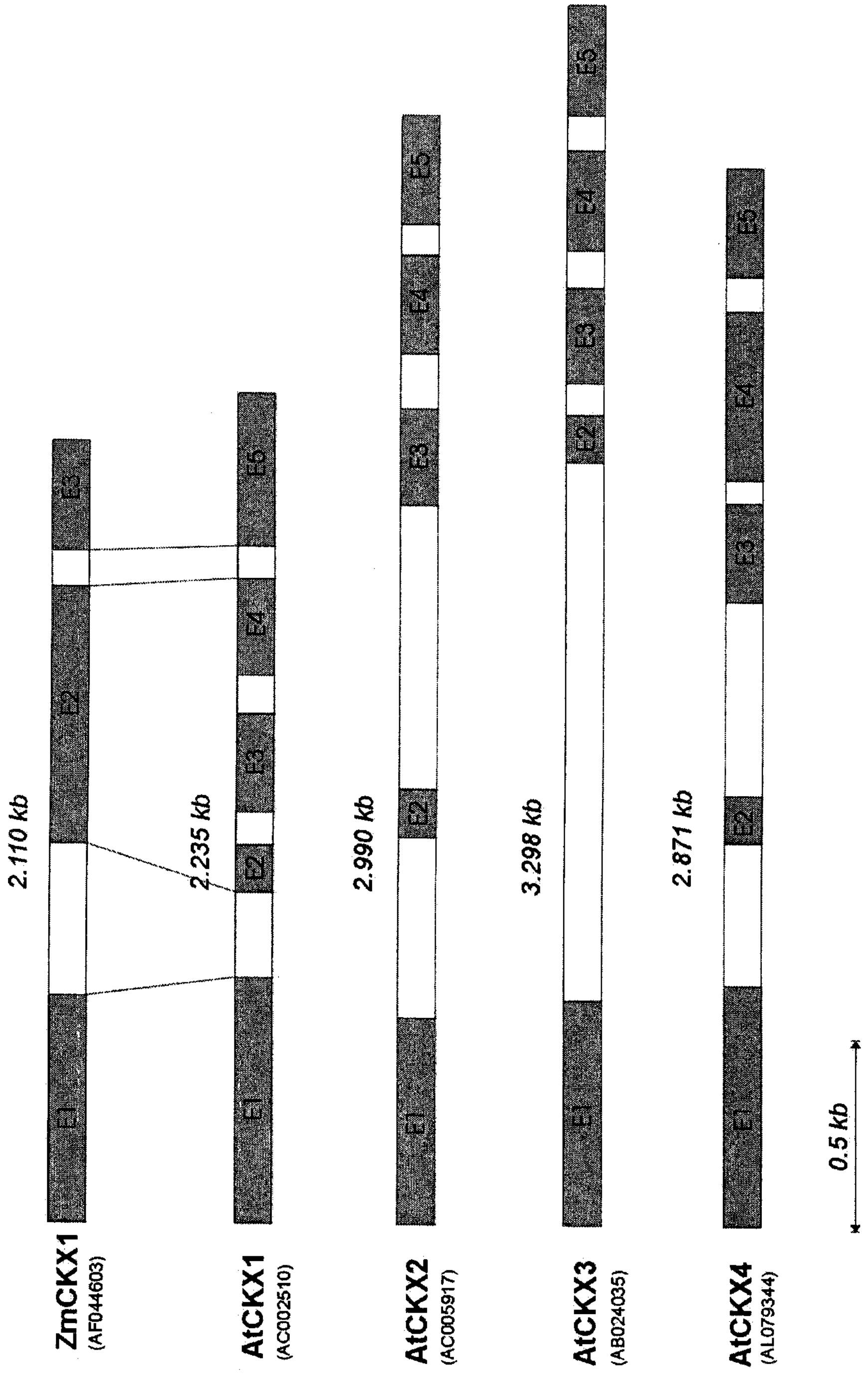
FIG. 1. Schematic representation of plant cytokinin oxidase genes.

A comparison of the gene structure of the *Arabidopsis* AtCKX genes 1 to 4 and the maize CKX gene is shown in FIG. 1.

The predicted proteins encoded by the *Arabidopsis* AtCKX genes show between 32% and 41% sequence similarity with the maize protein, while they show between 35% and 66% sequence similarity to each other. Because of this reduced sequence conservation, it is not clear a priori whether the *Arabidopsis* AtCKX genes encode proteins with cytokinin oxidase activity. An alignment of the *Arabidopsis* AtCKX predicted proteins 1 to 4 and the maize CKX gene is shown in FIG. 2.

Example 3

Transgenic Plants Overexpressing AtCKX1 Showed Increased Cytokinin Oxidase Activity and Altered Plant Morphology 1. Description of the Cloning Process The following primers were used to PCR amplify the AtCKX1 gene from *Arabidopsis thaliana*, accession Columbia (non-homologous sequences used for cloning are in lower case):

```
Sequence of 5' primer:
                                    (SEQ ID NO: 13)
cggtcgacATGGGATTGACCTCATCCTTACG

Sequence of 3' primer:
                                    (SEQ ID NO: 14)
gcgtcgacTTATACAGTTCTAGGTTTCGGCAGTAT
```

A 2235-bp PCR fragment, amplified by these primers, was inserted in the Sal I site of pUC19. The insert was sequenced and confirmed that the PCR amplification product did not contain any mutations. The SalI/SalI fragment of this vector was subcloned in the SalI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Figure 3:
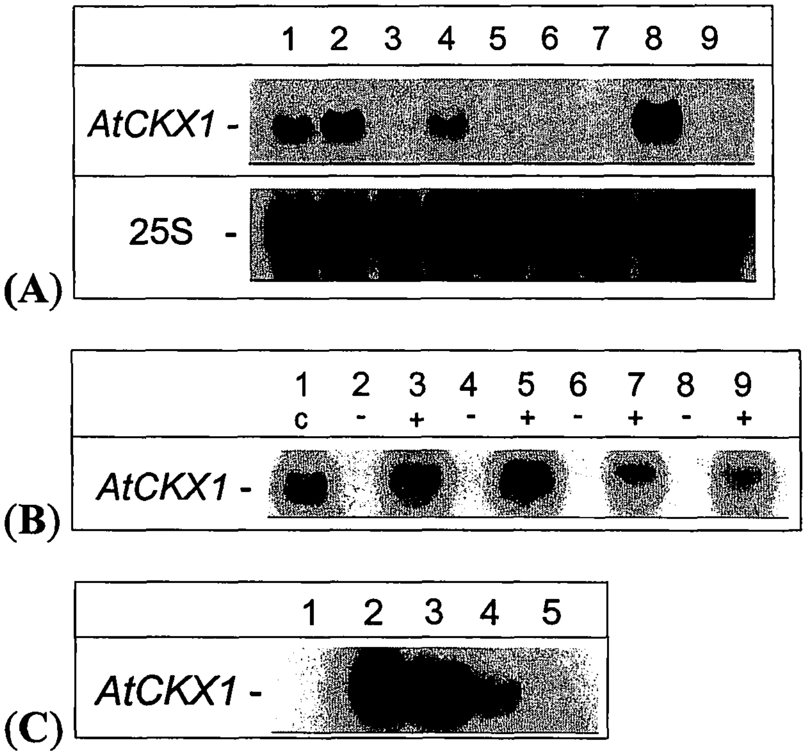

Several transgenic lines were identified that synthesize the AtCKX1 transcript at high levels (FIG. 3). Transgenic lines expressing AtCKX1 transcript also showed increased cytokinin oxidase activity as determined by a standard assay for cytokinin oxidase activity based on conversion of [2-$^3$H]iP to adenine as described (Motyka et al., 1996). This is exemplified for 2 tobacco and 2 *Arabidopsis* lines in Table 7. This result proves that the AtCKX1 gene encodes a protein with cytokinin oxidase activity.

TABLE 7

Cytokinin oxidase activity in AtCKX1 transgenic plant tissues

| Leaf sample | | Cytokinin oxidase activity |
|---|---|---|
| Plant species | Plant line | (nmol Ade/mg protein · h) |
| *Arabidopsis* | Col-0 wild-type | 0.009 |
| | CKX1-11 | 0.024 |
| | CKX1-22 | 0.026 |
| | CKX1-22 | 0.027 |
| Tobacco | SNN wild-type | 0.004 |
| | CKX1-SNN-8 | 0.016 |
| | CKX1-SNN-28 | 0.021 |

3. Phenotypic Description of the Transgenic Lines 3.1 In tobacco:

The plants had a dwarfed phenotype with reduced apical dominance (FIGS. 7 A, B and C) and increased root production (FIG. 8).

Five Categories of Phenotype:

1) strong—2 clones
2) intermediate—3 clones
3) weak—4 clones
4) tall plants (as WT) with large inflorescence—5 clones
5) similar to WT, 9 clones Height (See FIGS. 7 B and C)

WT: between 100-150 cm weak: approximately 75 cm intermediate: appr. 40-45 cm (main stem app. 25 cm but overgrown by side branches.

strong: appr. 10 cm

The transgenics AtCKX1-48 and AtCKX1-50 displayed a strong phenotype. Below are measurements for stem elongation as compared to WT plants:

| | Line | | |
|---|---|---|---|
| Days after germination | Wild-type Height (cm) | AtCKX1-48 Height (cm) | AtCKX1-50 Height (cm) |
| 47 | 9.5 ± 0.5 | 1.3 ± 0.3 | 1.2 ± 0.2 |
| 58 | 22.4 ± 2.3 | 2.2 ± 0.3 | 2.3 ± 0.3 |
| 68 | 35.3 ± 2.6 | 3.1 ± 0.5 | 2.6 ± 0.5 |
| 100 | 113.3 ± 9.8 | 7.1 ± 0.8 | 4.8 ± 0.9 |
| 117 | 138.6 ± 8.1 | 8.7 ± 0.7 | 6.6 ± 0.9 |
| 131 | 139.0 ± 9.3 | 9.3 ± 0.7 | 8.6 ± 1.0 |
| 152 | 136.6 ± 10.4 | 10.9 ± 1.1 | 10.0 ± 1.0 |
| 165 | | 11.8 ± 1.9 | 11.4 ± 1.4 |
| 181 | | 16.5 ± 1.7 | 14.9 ± 1.2 |
| 198 | | 19.5 ± 1.5 | 18.1 ± 1.3 |

Experimental: Plants were grown in soil in greenhouse. Data were collected from at least ten plants per line.

Leaves (See FIGS. 7 D and E)

The shape of leaves of AtCKX1 transgenic expressors was lanceolate (longer and narrow): the width-to-length ratio of mature leaves was reduced from 1:2 in wild type plants to 1:3 in AtCKX1 transgenics (FIG. 7 E). The number of leaves and leaf surface was reduced compared to WT (see FIG. 7 D). A prominent difference was also noted for progression of leaf senescence. In WT tobacco, leaf senescence starts in the most basal leaves and leads to a uniform reduction of leaf pigment (FIG. 7 E). By contrast, ageing leaves of strongly expressing AtCKX1 plants stayed green along the leaf veins and turned yellow in the intercostal regions, indicating altered leaf senescence. The texture of older leaves was more rigid.

Roots

In vitro grown plants highly expressing the gene were easily distinguishable from the WT by their ability to form more roots which are thicker (stronger) (FIG. 8 A), as well as by forming aerial roots along the stem.

The primary root was longer and the number of lateral and adventitious roots was higher as illustrated in FIG. 8 C for AtCKX1-50 overexpressing seedlings (see also Example 9).

The dose-response curve of root growth inhibition by exogenous cytokinin showed that roots of transgenic seedlings are more cytokinin resistant than WT roots (FIG. 8 D). The resistance of AtCKX1 transgenics to iPR was less marked than for AtCKX2, which is consistent with the smaller changes in iP-type cytokinins in the latter (see Table 10). A large increase in root biomass was observed for adult plants grown in soil (see FIG. 8 B for a plant grown in soil for 4 to 5 months) despite the fact that growth of the aerial plant parts was highly reduced.

Internode Distance intermediate phenotype: the $5^{th}$ internode below inflorescence is about 2.5 cm long and $9^{th}$ internode was about 0.5 cm long compared to 5 cm and 2 cm for the length of the $5^{th}$ and $9^{th}$ internode respectively, in WT plants.

strong phenotype: plant AtCKX1-50 The length of the $20^{th}$ internode from the bottom measured at day 131 after germination was 1.3±0 4 mm compared to 39.2±3.8 mm for WT Apical Dominance and Branching More side branches were formed indicating reduced apical dominance compared to WT plants during vegetative growth (see FIG. 9). The side branches overgrew the main stem, reaching a height of 40-45 cm for intermediate AtCKX1 expressors. Even secondary branches appeared. However, the buds were not completely released from apical dominance, i.e. lateral shoots did not really continue to develop. The reduced apical dominance might be due to reduced auxin production by the smaller shoot apical meristem (see Example 10).

Reproductive Development

The onset of flowering in AtCKX1 transgenics was delayed, the number of flowers and the seed yield per capsule was reduced. The size of flowers was not altered in transgenic plants and the weight of the individual seeds was comparable to the weight of seeds from wild type plants. Data for two representative AtCKX1 transgenics is summarized below:

A. Onset of Flowering

| Line | Wild-type | AtCKX1-48 | AtCKX1-50 |
|---|---|---|---|
| Flowering time (DAG) | 106.2 ± 3.3 | 193.3 ± 4.3 | 191.8 ± 3.8 |

Experimental: Data collected for at least ten plants per line. The full elongation of the first flower was defined as onset of flowering. DAG = days after germination.

B. Number of Seed Capsules Per Plant

| Line | Wild-type | AtCKX1-48 | AtCKX1-50 |
|---|---|---|---|
| Number of capsules | 83.33 ± 5.13 | 2.00 ± 1.00 | 2.60 ± 1.67 |

Experimental: Number of seed capsules was determined at least from 5 different plants. Please note that these plants were grown under greenhouse conditions during winter time. This affects negatively the number of flowers that are formed, in particular in the transgenic clones. However, the general picture that they form a reduced number of flowers is correct. n.d., not determined C. Seed Yield/Capsule (Mg)

| Line | Wild-type | AtCKX1-48 | AtCKXl-50 |
|---|---|---|---|
| Seed/capsule (mg) | 87.41 ± 28.75 | 23.83 ± 13.36 | 61.8 ± 40.66 |

Experimental: Seed yield was determined for at least 12 seed capsules. The size of seed capsules was very variable, hence the large standard deviations. n.d., not determined D. Weight of 100 Seeds (Mg)

| Line | Wild-type | AtCKX1-48 | AtCKXl-50 |
|---|---|---|---|
| Seeds weight (mg) | 9.73 ± 0.44 | 10.70 ± 1.60 | 9.54 ± 0.94 |

Experimental; The seed biomass was determined as the weight of 100 seed from at least 5 different seed capsules., n.d., not determined 3.2 In *Arabidopsis* onset of germination was same as for WT the total root system was enlarged and the number of side roots and adventitious roots was enhanced (see FIG. 4 A through D)

the growth of aerial organs was reduced resulting in a dwarfed phenotype (see FIGS. 4 E and F) and the leaf biomass was reduced. Leaf and flower formation is delayed.

the life cycle was longer compared to WT and the seed yield was lower compared to WT The following morphometric data illustrate these phenotypes:

Root Development

A. Total Length of the Root System

| Line | Wild-type | AtCKX1-11 | AtCKX1-15 |
|---|---|---|---|
| Length (mm) | 32.5 | 76.5 | 68.4 |

B. Primary Root Length

| Line | Wild-type | AtCKX1-11 | AtCKX1-15 |
|---|---|---|---|
| Length (mm) | 32.3 ± 3.8 | 52.3 ± 4.8 | 39.9 ± 4.2 |

C. Lateral Roots (LR) Length

| Line | Wild-type | AtCKX1-11 | AtCKX1-15 |
|---|---|---|---|
| Length (mm) | 0.2 ± 0.4 | 15.6 ± 11.0 | 10.4 ± 7.6 |

D. Adventitious Roots Length

| Line | Wild-type | AtCKX1-11 | AtCKX1-15 |
|---|---|---|---|
| Length (mm) | 0.03 ± 0.18 | 8.6 ± 8.5 | 19.1 ± 11.0 |

E. Number of Lateral Roots (LR)

| Line | Wild-type | AtCKX1-11 | AtCKX1-15 |
|---|---|---|---|
| Number of LR | 0.3 ± 0.5 | 10.4 ± 5.4 | 2.6 ± 1.1 |

F. Number of Adventitious Roots (AR)

| Line | Wild-type | AtCKX1-11 | AtCKX1-15 |
|---|---|---|---|
| Number of AR | 0.03 ± 0.18 | 1.6 ± 1.1 | 2.6 ± 1.1 |

Experimental: Measurements were carried out on plants 8 days after germination in vitro on MS medium. At least 17 plants per line were scored.

Shoot Development

A. Leaf Surface

| | Line | | | |
|---|---|---|---|---|
| | Wild-type | AtCKX1-11-7 T3 homozygous plants | AtCKX1-11-12 T3 homozygous plants | AtCKX1-15-1 T3 homozygous plants |
| Leaf surface ($cm^2$) | 21.16 ± 1.73 | 2.28 ± 0.58 | 2.62 ± 0.28 | 1.66 ± 0.22 |

Experimental: Leaf surface area of main rosette leaves formed after 30 days after germination was measured. 3 plants per clone were analyzed.

Reproductive Development

Onset of Flowering

| Onset of flowering | | | | |
|---|---|---|---|---|
| | Line | | | |
| | Wild-type | AtCKX1-11 T3 heterozygous plants | AtCKX2-2 T2 heterozygous plants | AtCKX2-5 T2 heterozygous plants |
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG = days after germination Conclusion The analysis of AtCKX1 transgenic *Arabidopsis* plants confirmed largely the results obtained from tobacco and indicates the general nature of the consequences of a reduced cytokinin content. The total root system was enlarged (the total root length was increased app. 110-140% in AtCKX1 transgenics), the shoot developed more slowly (retarded flowering) and the leaf biomass was reduced. The seed yield was lower in the transgenics as well.

Example 4

Transgenic Plants Overexpressing AtCKX2 Showed Increased Cytokinin Oxidase Activity and Altered Plant Morphology 1. Description of the Cloning Process The following primers were used to PCR amplify the AtCKX2 gene from *Arabidopsis thaliana*, accession Columbia (non-homologous sequences used for cloning are in lower case):

```
Sequence of 5' primer:
                                    (SEQ ID NO: 15)
gcggtaccAGAGAGAGAAACATAAACAAATGGC

Sequence of 3' primer:
                                    (SEQ ID NO: 16)
gcggtaccCAATTTTACTTCCACCAAAATGC
```

A 3104-bp PCR fragment, amplified by these primers, was inserted in the KpnI site of pUC19. The insert was sequenced to check that no differences to the published sequence were introduced by the PCR procedure. The KpnI/KpnI fragment of this vector was subcloned in the KpnI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic lines were identified that synthesize the AtCKX2 transcript at high levels (FIG. 6). Transgenic lines expressing AtCKX2 transcript also showed increased cytokinin oxidase activity. This is exemplified for 2 tobacco and 3 *Arabidopsis* lines in Table 8. This result proves that the AtCKX2 gene encodes a protein with cytokinin oxidase activity.

TABLE 8

Cytokinin oxidase activity in AtCKX2 transgenic plant tissues

| Sample | | |
|---|---|---|
| Plant species and tissue | Plant line | Cytokinin oxidase activity (nmol Ade/mg protein · h) |
| *Arabidopsis* callus | Col-0 wild-type | 0.037 |
| | CKX2-15 | 0.351 |
| | CKX2-17 | 0.380 |
| | CKX2-55 | 0.265 |
| Tobacco leaves | SNN wild-type | 0.009 |
| | CKX2-SNN-18 | 0.091 |
| | CKX2-SNN-19 | 0.091 |

3. Phenotypic Description of the Transgenic Lines 3.1 In Tobacco (See FIG. 7 to 10):

Three categories of phenotype:

1) strong—15 clones (similar to intermediate phenotype of AtCKX1)

2) weak—6 clones 3) others—similar to WT plants, 7 clones

Aerial Plant Parts

The observations concerning plant height, internode distance, branching, leaf form and yellowing were similar as for AtCKX1 transgenics with some generally minor quantitative differences in that the dwarfing characteristics were more severe in AtCKX1 transgenics than in AtCKX2 transgenics (compare AtCKX1 plants with AtCKX2 plants in FIGS. 7 A and B). This is illustrated below for stem elongation and internode distance measurements of clones with a strong phenotype AtCKX2-38 and AtCKX2-40:

| Stem elongation | | | |
|---|---|---|---|
| | Line | | |
| Days after germination | Wild-type Height (cm) | AtCKX2-38 Height (cm) | AtCKX2-40 Height (cm) |
| 47 | 9.5 ± 0.5 | 2.4 ± 0.1 | 2.6 ± 0.2 |
| 58 | 22.4 ± 2.3 | 5.5 ± 0.7 | 5.3 ± 0.5 |
| 68 | 35.3 ± 2.6 | 7.1 ± 0.8 | 7.0 ± 0.7 |
| 100 | 113.3 ± 9.8 | 15.5 ± 2.5 | 20.3 ± 6.4 |
| 117 | 138.6 ± 8.1 | 19.8 ± 3.8 | 29.5 ± 6.0 |
| 131 | 139.0 ± 9.3 | 26.5 ± 7.0 | 33.4 ± 5.8 |
| 152 | 136.6 ± 10.4 | 33.7 ± 6.3 | 33.9 ± 6.4 |
| 165 | | 36.2 ± 4.3 | |

Experimental: Plants were grown in soil in a green house. Data were collected from at least ten plants per line.

| Internode distance | | |
|---|---|---|
| Line | Wild-type | AtCKX2-38 |
| Internode distance (mm) | 39.2 ± 3.8 | 7.2 ± 1.6 |

Experimental: The length of the $20^{th}$ internode from the bottom was measured at day 131 after germination.

Roots

In vitro grown plants highly expressing the gene were easily distinguishable from WT plants by their ability to form more roots which are thicker (stronger) as well as by forming aerial roots along the stem.

The primary root was longer and the number of lateral and adventitious roots was higher as illustrated in FIG. 8 C for AtCKX2-38 overexpressing seedlings (see also Example 9).

The dose-response curve of root growth inhibition by exogenous cytokinin showed that roots of transgenic seedlings were more cytokinin resistant than WT roots (FIG. 8 D). The resistance of AtCKX1-28 transgenics to iPR was less marked than for AtCKX2-38, which is consistent with the smaller changes in iP-type cytokinins in the latter (see Table 10).

An increase in fresh and dry weight of the root biomass of TO lines of AtCKX2 transgenic plants compared to WT was observed for plant grown in soil, as illustrated in the following table:

| Line | Wild-type | AtCKX2 (T0) |
|---|---|---|
| Fresh weight (g) | 45.2 ± 15.4 | 77.1 ± 21.3 |
| Dry weight (g) | 6.3 ± 1.9 | 8.6 ± 2.2 |

Experimental: Six WT plants and six independent T0 lines of 35S::AtCKX2 clone were grown on soil. After flowering the root system was washed with water, the soil was removed as far as possible and the fresh weight and dry weight was measured.

An increase in fresh and dry weight of the root biomass was also observed for F1 progeny of AtCKX2 transgenics grown in hydroponics as compared to WT, as illustrated in the following table:

| Line | Wild-type | AtCKX2-38 | AtCKX2-40 |
|---|---|---|---|
| Fresh weight ROOT (g) | 19.76 ± 6.79 | 33.38 ± 7.76 | 50.04 ± 15.59 |
| Dry weight ROOT (g) | 2.36 ± 0.43 | 2.61 ± 0.39 | 3.52 ± 1.06 |
| Fresh weight SHOOT (g) | 159.8 ± 44.53 | 33.66 ± 2.67 | 48.84 ± 11.83 |
| Fresh weight SHOOT/ROOT ratio | 8.24 ± 0.63 | 1.04 ± 0.18 | 1.08 ± 0.51 |

Experimental: Soil grown plants were transferred 60 days after germination to a hydroponic system (Hoagland's solution) and grown for additional 60 days. The hydroponic solution was aerated continuously and replaced by fresh solution every third day.

In summary, transgenic plants grown in hydroponic solution formed approximately 65-150% more root biomass (fresh weight) than wild type plants. The increase in dry weight was 10-50%. This difference is possibly in part due to the larger cell volume of the transgenics. This reduces the relative portion of cell walls, which forms the bulk of dry matter material. The shoot biomass was reduced to 20%-70% of wild type shoots. The difference in fresh weight leads to a shift in the shoot/root ratio, which was approximately 8 in wild type but approximately 1 in the transgenic clones.

Conclusion

An increase in root growth and biomass was observed for AtCKX2 transgenic seedlings and adult plants grown under different conditions compared to WT controls despite the fact that growth of the aerial plant parts is reduced. Quantitative differences were observed between different transgenic plants: higher increases in root biomass were observed for the strongest expressing clones.

Reproductive Development

The onset of flowering in AtCKX2 transgenics was delayed, the number of flowers and the seed yield per capsule was reduced. These effects were very similar to those observed in the AtCKX1 transgenic plants but they were less prominent in the AtCKX2 transgenics, as indicated in the tables below. The size of flowers was not altered in transgenic plants and the weight of the individual seeds was comparable to the weight of seeds from wild type plants.

A. Onset of Flowering

| Line | Wild-type | AtCKX1-48 | AtCKX1-50 | AtCKX2-38 | AtCKX2-40 |
|---|---|---|---|---|---|
| Flowering time (DAG) | 106.2 ± 3.3 | 193.3 ± 4.3 | 191.8 ± 3.8 | 140.6 ± 6.5 | 121.9 ± 9.8 |

Experimental: Data collected for at least ten plants per line. The full elongation of the first flower was defined as onset of flowering. DAG = days after germination.

B. Number of Seed Capsules Per Plant

| Line | Wild-type | AtCKX1-48 | AtCKX1-50 | AtCKX2-38 | AtCKX2-40 |
|---|---|---|---|---|---|
| Number of capsules | 83.33 ± 5.13 | 2.00 ± 1.00 | 2.60 ± 1.67 | 4.30 ± 2.58 | n.d. |

Experimental: Number of seed capsules was determined at least from 5 different plants. Please note that these plants were grown under green house conditions during winter time. This affects negatively the number of flowers that are formed, in particular in the transgenic clones. However, the general picture that they form a reduced number of flowers is correct. n.d., not determined C. Seed Yield/Capsule (Mg)

| Line | Wild-type | AtCKX1-48 | AtCKX1-50 | AtCKX2-38 | AtCKX2-40 |
|---|---|---|---|---|---|
| Seed/capsule (mg) | 87.41 ± 28.75 | 23.83 ± 13.36 | 61.8 ± 40.66 | 46.98 ± 29.30 | n.d. |

Experimental: Seed yield was determined for at least 12 seed capsules. The size of seed capsules was very variable, hence the large standard deviations. n.d., not determined D. Weight of 100 Seeds (Mg)

| Line | Wild-type | AtCKX1-48 | AtCKX1-50 | AtCKX2-38 | AtCKX2-40 |
|---|---|---|---|---|---|
| Seeds weight (mg) | 9.73 ± 0.44 | 10.70 ± 1.60 | 9.54 ± 0.94 | 10.16 ± 0.47 | n.d. |

Experimental: The seed biomass was determined as the weight of 100 seed from at least 5 different seed capsules. n.d., not determined 3.2 In *Arabidopsis:*

The following morphometric data were obtained for AtCKX2 transgenics:

Root Development

A. Total Length of the Root System

| Line | Wild-type | ACKX2-2 | ACKX2-5 |
|---|---|---|---|
| Length (mm) | 32.5 | 50.6 | 48.5 |

B. Primary Root Length

| Line | Wild-type | AtCKX2-2 | AtCKX2-5 |
|---|---|---|---|
| Length (mm) | 32.3 ± 3.8 | 30.7 ± 4.8 | 31.6 ± 6.8 |

C. Lateral Roots Length

| Line | Wild-type | ACKX2-2 | ACKX2-5 |
|---|---|---|---|
| Length (mm) | 0.2 ± 0.4 | 5.5 ± 9.0 | 1.9 ± 2.5 |

D. Adventitious Roots Length

| Line | Wild-type | ACKX2-2 | ACKX2-5 |
|---|---|---|---|
| Length (mm) | 0.03 ± 0.18 | 14.4 ± 10.2 | 14.9 ± 9.1 |

E. Number of Lateral Roots (LR)

| Line | Wild-type | ACKX2-2 | ACKX2-5 |
|---|---|---|---|
| Number of LR | 0.3 ± 0.5 | 2.9 ± 2.3 | 1.9 ± 1.0 |

F. Number of Adventitious Roots (Ar)

| Line | Wild-type | ACKX2-2 | ACKX2-5 |
|---|---|---|---|
| Number of AR | 0.03 ± 0.18 | 1.8 ± 0.9 | 1.8 ± 1.0 |

Experimental: Measurements were carried out on plants 8 d.a.g. in vitro on MS medium. At least 17 plants per line were scored.

Shoot Development

| Leaf surface | | | | |
|---|---|---|---|---|
| | Line | | | |
| | Wild-type | AtCKX2-2 T2 heterozygous plants | AtCKX2-5 T2 heterozygous plants | AtCKX2-9 T2 heterozygous plants |
| Leaf surface ($cm^2$) | 21.16 ± 1.73 | 8.20 ± 2.35 | 8.22 ± 0.55 | 7.72 ± 0.85 |

Experimental: Leaf surface area of main rosette leaves formed after 30 days after germination was measured. 3 plants per clone were analyzed.

Reproductive Development

| Onset of flowering | | | | |
|---|---|---|---|---|
| | Line | | | |
| | Wild-type | AtCKX1-11 T3 heterozygous plants | AtCKX2-2 T2 heterozygous plants | AtCKX2-5 T2 heterozygous plants |
| Flowering time (DAG) | 43.6 ± 5.8 | 69.7 ± 9.4 | 51.2 ± 4.1 | 45.1 ± 6.9 |

Experimental: Plants were grown under greenhouse condition. At least 13 plants per clone were analyzed. DAG = days after germination.

Conclusion

*Arabidopsis* AtCKX2 transgenics had reduced leaf biomass and a dwarfing phenotype similar to AtCKX1 transgenics (compare FIG. 5 with FIG. 4 F). The total root system was also enlarged in AtCKX2 transgenic *Arabidopsis*. The total root length is increased approximately 50% in AtCKX2 transgenics. The AtCKX1 transgenics have longer primary roots, more side roots and form more adventitious roots. AtCKX2 transgenics lack the enhanced growth of the primary root but form more side roots and lateral roots than WT.

Summary:

The phenotypes observed for AtCKX2 transgenics were very similar but not identical to the AtCKX1 transgenics, which in turn were very similar but not identical to the results obtained for the tobacco transgenics. This confirms the general nature of the consequences of a reduced cytokinin content in these two plant species and therefore, similar phenotypes can be expected in other plant species as well. The main difference between tobacco and *Arabidopsis* is the lack of enhanced primary root growth in AtCKX2 overexpressing plants.

Example 5

Transgenic Plants Overexpressing AtCKX3 Showed Increased Cytokinin Oxidase Activity and Altered Plant Morphology 1. Description of the Cloning Process The following primers were used to PCR amplify the AtCKX3 gene from *Arabidopsis thaliana*, accession Columbia (non-homologous sequences used for cloning are in lower case):

```
Sequence of 5' primer:
                                        (SEQ ID NO: 17)
gcggtaccTTCATTGATAAGAATCAAGCTATTCA

Sequence of 3' primer:
                                        (SEQ ID NO: 18)
gcggtaccCAAAGTGGTGAGAACGACTAACA
```

A 3397-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines were identified that synthesize the AtCKX3 transcript at high levels (FIG. 11A.). Transgenic tobacco lines expressing AtCKX3 transcript also showed increased cytokinin oxidase activity. This is exemplified for three plants in Table 9. This proves that the AtCKX3 gene encodes a protein with cytokinin oxidase activity.

TABLE 9

| Cytokinin oxidase activity in AtCKX4 transgenic plant tissues | | |
|---|---|---|
| Sample | | |
| Plant species and tissue | Plant line | Cytokinin oxidase activity (nmol Ade/mg protein · h) |
| tobacco leaves | SNN wild-type | 0.011 |
| | CKX3-SNN-3 | 0.049 |
| | CKX3-SNN-6 | 0.053 |
| | CKX3-SNN-21 | 0.05 |

3. Plant Phenotypic Analysis

The phenotypes generated by overexpression of the AtCKX3 gene in tobacco and *Arabidopsis* were basically similar as those of AtCKX1 and AtCKX2 expressing plants, i.e. enhanced rooting and dwarfing. However, overexpression of the AtCKX3 gene in tobacco resulted in a stronger phenotype compared to AtCKX2. In this sense AtCKX3 overexpression was more similar to AtCKX1 overexpression.

Example 6

Transgenic Plants Overexpressing AtCKX4 Showed Increased Cytokinin Oxidase Activity and Altered Plant Morphology 1. Description of the Cloning Process The following primers were used to PCR amplify the AtCKX4 gene from *Arabidopsis thaliana*, accession Columbia (non-homologous sequences used for cloning are in lower case):

```
Sequence of 5' primer:
                                        (SEQ ID NO: 19)
gcggtaccCCCATTAACCTACCCGTTTG

Sequence of 3' primer:
                                        (SEQ ID NO: 20)
gcggtaccAGACGATGAACGTACTTGTCTGTA
```

A 2890-bp PCR fragment, produced by this PCR amplification, was inserted in the KpnI site of pBluescript. The insert was sequenced to confirm that the PCR product has no sequence changes as compared to the gene. The KpnI/KpnI fragment of this vector was subcloned in the KpnI site downstream of a modified CaMV 35S promoter (carrying three tetracycline operator sequences) in the binary vector pBinHyg-Tx (Gatz et al., 1992). The resulting construct was introduced into tobacco and *Arabidopsis thaliana* through *Agrobacterium*-mediated transformation, using standard transformation protocols.

2. Molecular Analysis of the Transgenic Lines

Several transgenic tobacco lines synthesized the AtCKX4 transcript at high levels (FIG. 11B.). Transgenic lines expressing AtCKX4 transcript also showed increased cytokinin oxidase activity. This is exemplified for 3 *Arabidopsis* and 3 tobacco lines in Table 10. This result proves that the AtCKX4 gene encodes a protein with cytokinin oxidase activity.

TABLE 10

| Cytokinin oxidase activity in AtCKX4 transgenic plant tissues | | |
|---|---|---|
| Sample | | |
| Plant species and tissue | Plant line | Cytokinin oxidase activity (nmol Ade/mg protein · h) |
| *Arabidopsis* callus | Col-0 wild-type | 0.037 |
| | CKX4-37 | 0.244 |
| | CKX4-40 | 0.258 |
| | CKX4-41 | 0.320 |
| tobacco leaves | SNN wild-type | 0.011 |
| | CKX4-SNN-3 | 0.089 |
| | CKX4-SNN-18 | 0.085 |
| | CKX4-SNN-27 | 0.096 |

Overall, the data showed that the apparent $K_m$ values for the four cytokinin oxidases were in the range of 0.2 to 9.5 μM with iP as substrate, which further demonstrates that the proteins encoded by AtCKX1 through 4 are indeed cytokinin oxidase enzymes as disclosed herein.

3. Plant Phenotypic Analysis

The phenotypes generated by overexpression of the AtCKX4 gene in tobacco and *Arabidopsis* were basically similar as those of AtCKX1 and AtCKX2 expressing plants, i.e. enhanced rooting, reduced apical dominance, dwarfing and yellowing of intercostal regions in older leaves of tobacco. An additional phenotype in tobacco was lanceolate leaves (altered length-to-width ratio).

General Observations of AtCKX Overexpressing Tobacco Plants

Overall, the phenotypic analysis demonstrated that AtCKX gene overexpression caused drastic developmental alterations in the plant shoot and root system in tobacco, including enhanced development of the root system and dwarfing of the aerial plant part. Other effects such as altered leaf senescence, formation of adventitious root on stems, and others were also observed as disclosed herein. The alterations were very similar, but not identical, for the different genes. In tobacco, AtCKX1 and AtCKX3 overexpressors were alike as were AtCKX2 and AtCKX4. Generally, the two former showed higher expression of the traits, particularly in the shoot. Therefore, a particular cytokinin oxidase gene may be preferred for achieving the phenotypes that are described in the embodiments of this invention.

Example 7

Cloning of the AtCKX5 Gene

The following primers were used to PCR amplify the AtCKX5 gene from *Arabidopsis thaliana*, accession Columbia (non-homologous sequences used for cloning are in lower case):

```
Sequence of 5' primer:
                                        (SEQ ID NO: 21)
ggggtaccTTGATGAATCGTGAAATGAC

Sequence of 3' primer:
                                        (SEQ ID NO: 22)
ggggtaccCTTTCCTCTTGGTTTTGTCCTGT
```

The sequence of the 5' primer includes the two potential start codons of the AtCKX5 protein, the most 5' start codon is underlined and a second ATG is indicated in italics.

A 2843-bp PCR fragment, produced by this PCR amplification, was inserted as a blunt-end product in pCR-Blunt II-TOPO cloning vector (Invitrogen).

Example 8

Cloning of the AtCKX6 Gene

The following primers were used to PCR amplify the AtCKX6 gene from *Arabidopsis thaliana*, accession Columbia (non-homologous sequences used for cloning are in lower case):

```
Sequence of 5' primer:
                                        (SEQ ID NO: 23)
gctctagaTCAGGAAAAGAACCATGCTTATAG

Sequence of 3' primer:
                                        (SEQ ID NO: 24)
gctctagaTCATGAGTATGAGACTGCCTTTTG
```

A 1949-bp PCR fragment, produced by this PCR amplification, was inserted as a blunt-end product in pCR-Blunt II-TOPO cloning vector (Invitrogen).

Example 9

Tobacco Seedling Growth Test Demonstrated Early Vigor of AtCKX Transgenics

Seeds of AtCKX1-50 and AtCKX2-38 overexpressing transgenics and WT tobacco were sown in vitro on MS medium, brought to culture room 4 days after cold treatment and germinated after 6 days. Observations on seedling growth were made 10 days after germination (see also FIG. 8C) and are summarized below. At least 20 individuals were scored per clone. Similar data have been obtained in two other experiments.

A. Total Length of the Root System

| Line | Wild-type | AtCKX1-50 | AtCKX2-38 |
|---|---|---|---|
| Length (mm) | 61.1 | 122.0 | 106.5 |

B. Primary Root Length

| Line | Wild-type | AtCKX1-50 | AtCKX2-38 |
|---|---|---|---|
| Length (mm) | 32.3 ± 2.6 | 50.8 ± 4.5 | 52.4 ± 4.8 |

C. Lateral Roots Length

| Line | Wild-type | AtCKX1-50 | AtCKX2-38 |
|---|---|---|---|
| Length (mm) | 9.8 ± 5.5 | 18.0 ± 8.1 | 13.0 ± 6.0 |

D. Adventitious Roots Length

| Line | Wild-type | AtCKX1-50 | AtCKX2-38 |
|---|---|---|---|
| Length (mm) | 19.0 ± 5.0 | 53.0 ± 12.0 | 42.0 ± 9.8 |

E. Number of Lateral Roots (LR)

| Line | Wild-type | AtCKX1-50 | AtCKX2-38 |
|---|---|---|---|
| Number of LR | 1.9 ± 0.9 | 6.5 ± 2.2 | 5.6 ± 2.0 |

F. Number of Adventitious Roots (Ar)

| Line | Wild-type | AtCKX1-50 | AtCKX2-38 |
|---|---|---|---|
| Number of AR | 2.2 ± 0.6 | 3.5 ± 0.9 | 3.6 ± 1.3 |

AtCKX1 and AtCKX2 Plants, General Observations:

Seedlings of AtCKX1 and AtCKX2 overexpressing tobacco plants had 60% more adventitious roots and three times more lateral roots than untransformed control plants 10 days after germination. The length of the primary root was increased by about 70%. This—together with more and longer side roots and secondary roots—resulted in a 70-100% increase in total root length. These results showed that overexpression of cytokinin oxidase enhances the growth and development of both the main root and the adventitious roots, resulting in early vigor.

Example 10

Histological Analysis of Altered Plant Morphology in AtCKX1 Overexpressing Tobacco Plants Microscopic analysis of different tissues revealed that the morphological changes in AtCKX transgenics are reflected by distinct changes in cell number and rate of cell formation (see FIG. 10). The shoot apical meristem (SAM) of AtCKX1 transgenics was smaller than in wild type and fewer cells occupy the space between the central zone and the peripheral zone of lateral organ formation, but the cells were of the same size (FIG. 10 A). The reduced cell number and size of the SAM as a consequence of a reduced cytokinin content indicates that cytokinins have a role in the control of SAM proliferation. No obvious changes in the differentiation pattern occurred, suggesting that the spatial organization of the differentiation zones in the SAM is largely independent from cell number and from the local cytokinin concentration. The overall tissue pattern of leaves in cytokinin oxidase overexpressors was unchanged. However, the size of the phloem and xylem was significantly reduced (FIG. 10 B). By contrast, the average cell size of leaf parenchyma and epidermal cells was increased four- to fivefold (FIG. 10 C, D). New cells of AtCKX1 transgenics are formed at 3-4% of the rate of wild type leaves and final leaf cell number was estimated to be in the range of 5-6% of wild type. This indicates an absolute requirement for cytokinins in leaves to maintain the cell division cycle. Neither cell size nor cell form of floral organs was altered and seed yield per capsule was similar in wild type and AtCKX transgenic plants. The cell population of root meristems of AtCKX1 transgenic plants was enlarged approximately 4-fold and the cell numbers in both the central and lateral columnella were enhanced (FIG. 10 E, F). The final root diameter was increased by 60% due to an increased diameter of all types of root cells. The radial root patterns was identical in wild type and transgenics, with the exception that frequently a fourth layer of cortex cells was noted in transgenic roots (FIG. 10 G). The increased cell number and the slightly reduced cell length indicates that the enhanced root growth is due to an increased number of cycling cells rather than increased cell growth. In the presence of lowered cytokinin content, root meristem cells must undergo additional rounds of mitosis before they leave the meristem and start to elongate. The exit from the meristem is therefore regulated by a mechanism that is sensitive to cytokinins. Apparently, cytokinins have a negative regulatory role in the root meristem and wild type cytokinin concentrations are inhibitory to the development of a maximal root system. Therefore, reducing the level of active cytokinins by overexpressing cytokinin oxidases stimulates root development, which results in an increase in the size of the root with more lateral and adventitious roots as compared to WT plants.

Example 11

AtCKX1 and AtCKX2—Overexpressing Tobacco Plants had a Reduced Cytokinin Content Among the 16 different cytokinin metabolites that were measured, the greatest change occurred in the iP-type cytokinins in AtCKX2 overexpressers (Table 11): the overall decrease in the content of iP-type cytokinins is more pronounced in AtCKX2 expressing plants than in AtCKX1 transgenics. AtCKX1 transgenics showed a stronger phenotype in the shoot. It is not known which cytokinin metabolite is relevant for the different traits that were analysed. It may be that different cytokinin forms play different roles in the various development processes. Smaller alterations were noted for Z-type cytokinins, which could be due to a different accessibility of the substrate or a lower substrate specificity of the protein. The total content of iP and Z metabolites in individual transgenic clones was between 31% and 63% of wild type. The cytokinin reserve pool of O-glucosides was also lowered in the transgenics (Table 11). The concentration of N-glucosides and DHZ-type cytokinins was very low and was not or only marginally, altered in transgenic seedlings (data not shown).

TABLE 11

Cytokinin content of AtCKX transgenic plants. Cytokinin extraction, immunopurification, HPLC separation and quantification by ELISA methods was carried out as described by Faiss et al., 1997. Three independently pooled samples of approximately 100 two week old seedlings (2.5 g per sample) were analysed for each clone. Concentrations are in pmol × g fresh weight$^{-1}$.

| Cytokinin | WT | Line | | | | | | | |
|---|---|---|---|---|---|---|---|---|---|
| | | AtCKX1-2 | | AtCKX1-28 | | ACKX2-38 | | AtCKX2-40 | |
| meta-bolite | Concentration | Concentration | % of WT | Concentration | % of WT | Concentration | % of WT | Concentration | % of WT |
| iP | 5.90 ± 1.80 | 4.76 ± 0.82 | 81 | 4.94 ± 2.62 | 84 | 1.82 ± 0.44 | 31 | 2. 85 ± 0.62 | 48 |
| iPR | 2.36 ± 0.74 | 1.53 ± 0.14 | 65 | 0.75 ± 0.27 | 32 | 0.55 ± 0.39 | 23 | 0.89 ± 0.07 | 38 |
| iPRP | 3.32 ± 0.73 | 0.87 ± 0.26 | 26 | 1.12 ± 0.13 | 34 | 0.80 ± 0.48 | 24 | 1.68 ± 0.45 | 51 |
| Z | 0.24 ± 0.06 | 0.17 ± 0.02 | 71 | 0.22 ± 0.03 | 92 | 0.21 ± 0.06 | 88 | 0.22 ± 0.02 | 92 |

TABLE 11-continued

Cytokinin content of AtCKX transgenic plants. Cytokinin extraction, immunopurification, HPLC separation and quantification by ELISA methods was carried out as described by Faiss et al., 1997. Three independently pooled samples of approximately 100 two week old seedlings (2.5 g per sample) were analysed for each clone. Concentrations are in pmol × g fresh weight$^{-1}$.

| Cytokinin | WT | Line | | | | | | | |
|---|---|---|---|---|---|---|---|---|---|
| | | AtCKX1-2 | | AtCKX1-28 | | ACKX2-38 | | AtCKX2-40 | |
| meta-bolite | Concentration | Concentration | % of WT | Concentration | % of WT | Concentration | % of WT | Concentration | % of WT |
| ZR | 0.60 ± 0.13 | 0.32 ± 0.12 | 53 | 0.34 ± 0.03 | 57 | 0.34 ± 0.15 | 57 | 0.32 ± 0.05 | 53 |
| ZRP | 0.39 ± 0.17 | 0.42 ± 0.11 | 107 | 0.28 ± 0.15 | 72 | 0.06 ± 0.01 | 15 | 0.17 ± 0.06 | 44 |
| ZOG | 0.46 ± 0.20 | 0.32 ± 0.09 | 70 | 0.26 ± 0.13 | 57 | 0.20 ± 0.07 | 43 | 0.12 ± 0.02 | 26 |
| ZROG | 0.48 ± 0.17 | 0.30 ± 0.06 | 63 | 0.47 ± 0.02 | 98 | 0.23 ± 0.05 | 48 | 0.30 ± 0.13 | 63 |
| Total | 13.75 | 8.69 | 63 | 8.38 | 61 | 4.21 | 31 | 6.55 | 48 |

Abbreviations: iP, $N^6$-($\Delta^2$isopentenyl)adenine; iPR, $N^6$-($\Delta^2$isopentenyl)adenine riboside; iPRP, $N^6$-($\Delta^2$isopentenyl)adenine riboside 5'-monophosphate; Z, trans-zeatin; ZR, zeatin riboside; ZRP, zeatin riboside 5'-monophosphate; ZOG, zeatin O-glucoside; ZROG, zeatin riboside O-glucoside.

Example 12

Grafting Experiments Showed that Dwarfing and Enhanced Root Development Due to AtCKX Overexpression is Confined to Transgenic Tissues To investigate which phenotypic effects of cytokinin oxidase overexpression are restricted to expressing tissues, i.e. are cell- or organ-autonomous traits, grafting experiments were performed. Reciprocal grafts were made between an AtCKX2 transgenic tobacco plant and a WT tobacco. The transgenic plant used in this experiment was AtCKX2-38, which displayed a strong phenotype characterized by enhanced root growth and reduced development of the aerial plant parts. As described in Example 3 through 6, these were two important phenotypes that resulted from cytokinin oxidase overexpression in tobacco and *arabidopsis*.

Plants were about 15 cm tall when grafted and the graft junction was about 10 cm above the soil. FIG. 12 shows plants 15 weeks after grafting. The main results were that: (i) the aerial phenotype of a WT scion grafted on a transgenic rootstock was similar to the WT control graft (=WT scion on WT rootstock) Importantly, this showed that overexpression of the AtCKX2 transgene in the rootstock did not induce dwarfing of the non-transgenic aerial parts of the plant (see FIG. 12 A) Improved root growth of the transgenic rootstock was maintained, indicating that improved root growth of AtCKX transgenics is autonomous and does not depend on an AtCKX transgenic shoot (FIG. 12 C). Interestingly, the WT scions grafted on the transgenic rootstocks looked healthier and were better developed. Notably, senescence of the basal leaves was retarded in these plants (see FIG. 12 A); (ii) the transgenic scion grafted on the WT rootstock looked similar to the aerial part of the transgenic plant from which it was derived, i.e. the shoot dwarfing phenotype is also autonomous and not dependent on the improved root growth (see FIG. 12 B).

In addition to the above-mentioned better appearance of WT shoots grafted on a transgenic rootstock, the formation of adventitious roots on the basal part of WT shoots was noted (FIG. 12 D, right plant). Formation of adventitious roots also occurred on the stem of AtCKX transgenics but not on stems of WT control grafts (FIG. 12 D, left plant) and therefore seems to be a non-autonomous trait.

In summary, it is disclosed in this invention that enhanced root formation and dwarfing of the shoot in AtCKX overexpressing tobacco are autonomous traits and can be uncoupled by grafting procedures. Surprisingly, grafting of a WT scion on an AtCKX transgenic rootstock resulted in more vigorously growing plants and retardation of leaf senescence.

As an alternative to grafting, tissue-specific promoters could be used for uncoupling the autonomous phenotypic effects of cytokinin overexpression. Therefore, it is disclosed in this invention that cytokinin oxidase overexpression in a tissue specific manner can be used to alter the morphology of a plant such as the shoot or root system.

Example 13

Expression of an AtCKX Gene Under a Root-Specific Promoter in Transgenic Plants Leads to Increased Root Production An AtCKX gene (see example 4) is cloned under control of the root clavata homolog promoter of *Arabidopsis* (SEQ ID NO: 36), which is a promoter that drives root-specific expression. Other root-specific promoters may also be used for the purpose of this invention. See Table 5 for exemplary root-specific promoters.

Transgenic plants expressing the AtCKX gene specifically in the roots show increased root production without negatively affecting growth and development of the aerial parts of the plant. Positive effects on leaf senescence and growth of aerial plant parts are observed.

Example 14

Suppression of an AtCKX Gene Under a Senescence-Induced Promoter in Transgenic Plants Leads to Delayed Leaf Senescence and Enhanced Seed Yield A chimeric gene construct derived from an AtCKX gene and designed to suppress expression of endogenous cytokinin oxidase gene(s) is cloned under control of a senescence-induced promoter. For example, promoters derived from senescence-associated genes (SAG) such as the SAG12 promoter can be used (Quirino et al., 2000). Transgenic plants suppressing endogenous cytokinin oxidase gene(s) specifically in senescing leaves show delayed leaf senescence and higher seed yield without negatively affecting the morphology and growth and development of the plant.

Example 15

Overexpression of an AtCKX Gene in the Female Reproductive Organs Leads to Parthenocarpic Fruit Development The open reading frame of an AtCKX gene is cloned under control of a promoter that confers overexpression in the female reproductive organs such as for example the DefH9 promoter from *Antirrhinum majus* or one of its homologues, which have high expression specificity in the placenta and ovules. Transgenic plants with enhanced cytokinin oxidase activity in these tissues show parthenocarpic fruit development.

Example 16

Overexpression of AtCKX Genes Result in Increased Seed and Cotyledon Size

Transgenic *Arabidopsis thaliana* plants that overexpress cytokinin oxidase (AtCKX) genes under control of the 35S promoter as described supra. Transgenic plants, in particular those expressing the AtCKX1 and AtCKX3 genes, developed seeds with increased size which was almost entirely due to an enlarged embryo. Details of the seed, embryo and early postembryonic phenotypes are shown in FIGS. 13 A through 13E. Table 12 shows seed weight of wild type and two independent clones for each of the four investigated AtCKX genes. Average weight was obtained by analysing five different batches of 200 seeds for each clone. A quantitative evaluation showed that the seed weight of AtCKX1 and AtCKX3 expressing clones was app. 1.8-2.3-fold higher than in wild type. Gain of weight for seeds of AtCKX2 and AtCKX4 expressing lines was in the range of 10-25% (Table 12 and FIG. 14).

The increases in size and weight for seeds, embryos, and cotyledons are unexpected as a reduced cytokinin content would have been expected to be associated with a reduced organ growth. One possible reason for the increases in seed, embryo, and cotyledon size is a previously unknown negative regulatory function of cytokinins in these storage organs. A negative regulatory functions of cytokinins in the control of organ growth is so far only known from roots (Werner et al. 2001). We propose, therefore, that localized expression of cytokinin oxidase genes in tissues where growth is negatively regulated by cytokinins leads to enhanced growth of this tissue. For example, localized expression of CKX genes during cotyledon development likely leads to enhanced growth of cotyledons and in species with cotyledons as storage organs, to enhanced yield and to an enhanced growth performance of seedlings. Total number of seeds is lowered in AtCKX1 and AtCKX3 expressers. There have been no previous reports however, of lower seed number in *Arabidopsis* being linked to an increase in size.

Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

The *Arabidopsis* CKX2 (corresponding to SEQ ID NO:44) was amplified by PCR using as template an *Arabidopsis thaliana* seedling cDNA library (Invitrogen, Paisley, UK). After reverse transcription of RNA extracted from seedlings, the cDNAs were cloned into pCMV Sport 6.0. Average insert size of the bank was 1.5 kb, and original number of clones was $1.59\times10^7$ cfu. The original titer was determined to be $9.6\times10^5$ cfu/ml, and became after a first amplification $6\times10^{11}$ cfu/ml. After plasmid extraction, 200 ng of template was used in a 500 PCR mix. Primers prm3769 (SEQ ID NO: 40) and prm1526 (SEQ ID NO: 41), which include the AttB sites for Gateway recombination, were used for PCR amplification.

PCR was performed using Hifi Taq DNA polymerase in standard conditions. A PCR fragment of 1506 bp was amplified and purified also using standard methods. The first step of the Gateway procedure, the BP reaction, was then performed, during which the PCR fragment recombines in vivo with the pDONR plasmid to produce, according to the Gateway terminology, an "entry clone", p41 (FIG. 15). pDONR was purchased from Invitrogen, as part of the Gateway technology.

B) Vector Construction

The entry clone p41 was subsequently used in an LR reaction with p831 or p830, both destination vectors according to the Gateway™ terminology, used for rice transformation.

p831 contains as functional elements within the T-DNA borders a plant selectable marker, a screenable marker and a Gateway cassette intended for LR in vivo recombination with the sequence of interest already cloned in the donor vector.

The PRO0218 promoter for embryo and aleurone preferred expression is located upstream of this Gateway cassette.

Similarly, p830 contains as functional elements within the T-DNA borders: a plant selectable marker; a screenable marker; and a Gateway cassette intended for LR in vivo recombination with the sequence of interest already cloned in the donor vector. The PRO0090 promoter for endosperm-preferred expression is located upstream of this Gateway cassette.

After the recombination step, the resulting expression vectors p37 (originating from p831, FIG. 16) and p35 (originating from p830, FIG. 17) were transformed into *Agrobacterium* strain LBA4404 and subsequently into *Oryza sativa* plants.

TABLE 12

| | WT | CKX1-11-7 | CKX1-15-1 | CKX2-2-4 | CKX2-9-3 | CKX3-9-4 | CKX3-12-13 | CKX4-37-2 | CKX4-41-7 |
|---|---|---|---|---|---|---|---|---|---|
| Seed Weight | 0.0158 ± 0.0009 | 0.0372 ± 0.0015 | 0.0352 ± 0.0023 | 0.0201 ± 0.0017 | 0.0180 ± 0.0001 | 0.0340 ± 0.0027 | 0.0280 ± 0.0027 | 0.0185 ± 0.0004 | 0.0179 ± 0.0007 |
| % of WT | 100 | 235.5 | 222.6 | 126.7 | 113.7 | 215.0 | 176.7 | 116.8 | 112.7 |

Example 17

Seed-Preferred or Seedling-Preferred Expression of a CKX2 Gene Results in Increased Seed Yield A) DNA Manipulation and Cloning of AtCKX2

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current C) Transformation of Rice Mature dry seeds of the rice japonica cultivar Nipponbare were dehusked. Sterilization was done by incubating the seeds for one minute in 70% ethanol, followed by 30 minutes in 0.2% $HgCl_2$ and by 6 washes of 15 minutes with sterile distilled water. The sterile seeds were then germinated on a medium containing 2,4-D (callus induction medium). After a 4-week incubation in the dark, embryogenic, scutellum-derived calli were excised and propagated on the same medium. Two weeks later, the calli were multiplied or propagated by subculture on the same medium for another 2 weeks. 3 days before co-cultivation, embryogenic callus pieces were subcultured on fresh medium to boost cell division activity. The *Agrobacterium* strain LBA4404, harbouring T-DNA vectors comprising a suitable selection marker, was used for co-cultivation. *Agrobacterium* was cultured for 3 days at 28° C. on AB medium with the appropriate antibiotics. The bacteria were then collected and suspended in liquid co-cultivation medium at an $OD_{600}$ of about 1. The suspension was transferred to a petri dish and the calli were immersed in the suspension during 15 minutes. Next, the callus tissues were blotted dry on a filter paper, transferred to solidified co-cultivation medium and incubated for 3 days in the dark at 25° C.

Hereafter, co-cultivated callus was grown on 2,4-D-containing medium for 4 weeks in the dark at 28° C. in the presence of a selective agent at a suitable concentration. During this period, rapidly growing resistant callus islands developed. Upon transfer of this material to a regeneration medium and incubation in the light, the embryogenic potential was released and shoots developed in the next four to five weeks. Shoots were excised from the callus and incubated for 2 to 3 weeks on an auxin-containing medium from which they were transferred to soil. Hardened shoots were grown under high humidity and short days in a greenhouse. Finally seeds were harvested three to five months after transplanting. The method yielded single locus transformants at a rate of over 50% (Aldemita and Hodges, 1996, Chan et al., 1993, Hiei et al., 1994).

D) Evaluation of Transformants: Vegetative Growth Measurements

Approximately 15 to 20 independent T0 transformants were generated. The primary transformants were transferred from tissue culture chambers to a greenhouse for growing and harvest of T1 seed. Four events (for p37 transformants, PRO0218 promoter) or five events (for p35 transformants, PRO0090 promoter) of which the T1 progeny segregated 3:1 for presence/absence of the transgene were retained. For each of these events, 10 T1 seedlings containing the transgene (hetero- and homo-zygotes), and 10 T1 seedlings lacking the transgene (nullizygotes), were selected by monitoring visual marker expression. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

In a next step, the mature primary panicles were harvested, bagged, barcode-labelled and then dried for three days in the oven at 37° C. The panicles were then threshed and all the seeds were collected and counted. The filled husks were separated from the empty ones using an air-blowing device. The empty husks were discarded and the remaining fraction was counted again. The filled husks were weighed on an analytical balance and the cross-sectional area of the seeds was measured using digital imaging. This procedure allows deriving a set of seed-related parameters.

The parameters described below were derived in an automated way from the digital images using image analysis software and were analysed statistically. A two factor ANOVA (analysis of variance) corrected for the unbalanced design was used as statistical model for the overall evaluation of plant phenotypic characteristics. An F-test was carried out on all the parameters measured in all the plants and of all the events transformed with that gene. The F-test was carried out to check for an effect of the gene over all the transformation events and to verify for an overall effect of the gene, also named herein "global gene effect". If the value of the F test showed that the data are significant, than it was concluded that there is a "gene" effect, meaning that not only presence or the position of the gene is causing the effect. The threshold for significance for a true global gene effect was set at 5% probability level for the F test.

To check for an effect of the genes within an event, i.e., for a line-specific effect, a t-test was performed within each event using data sets from the transgenic plants and the corresponding null plants. "Null plants" or "Null segregants" or "Nullizygotes" are the plants treated in the same way as the transgenic plant, but from which the transgene has segregated. Null plants can also be described as the homozygous negative transformed plants. The threshold for significance for the t-test was set at a 10% probability level. The results for some events can be under or below this threshold. This is based on the hypothesis that a gene might only have an effect in certain positions in the genome, and that the occurrence of this position-dependent effect is not uncommon. This kind of gene effect is also named herein a "line effect of the gene". The p value was obtained by comparing the t value to the t distribution or alternatively, by comparing the F value to the F distribution. The p value gives the probability of the null hypothesis (i.e., that there is no effect of the transgene) is correct. The threshold for significance was set at a 5% p-value for the F test and a 10% p-value for the t-test.

Vegetative growth and seed yield was measured according to the methods as described above. The inventors surprisingly found that the seed yield (expressed as total weight of seeds, number of (filled) seeds, harvest index, and/or Thousand Kernel Weight) was increased in the rice plants transformed with the AtCKX2 gene when compared with control plants without the AtCKX2 gene, as shown in paragraphs E and F.

The data obtained in the experiment with T1 plants were then confirmed in a further experiment with T2 plants. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation. In particular, four events of p37 T2 transformants and three events of p35 T2 transformants were selected for further analysis. For both p37 T2 transformants and p35 T2 transformants, a total of 120 plants were tested, evenly distributed over each event.

E) Evaluation of p37 Transformants: Measurement of Seed-Related Parameters

Upon analysis of the seeds as described above, the inventors found that plants transformed with the AtCKX2 gene under control of the PRO0218 promoter had a higher total weight of seeds, a higher number of filled seeds, a higher harvest index and a higher Thousand Kernel Weight than plants lacking the CKX2 transgene. These findings were consistent over 2 independent experiments with T1 plants as well as in an experiment with T2 plants, as shown in table 13. In addition to these yield parameters, 3 lines in T1 scored also positive for the total number of seeds. This increase in total seed number was confirmed in T2, where the effect was shown to be a significant global gene effect (mean increase +24%, p-value from the F-test 0.0032).

TABLE 13

| Analysis of seed related parameters for p37 transformants | | | | |
|---|---|---|---|---|
| | T1 generation, 1st experiment | T1 generation, 2nd experiment | T2 generation | |
| parameter | Difference over null plants | Difference over null plants | Difference over null plants | p-value |
| Total weight of seeds | +22% | +22% | +51% | 0.0000 |
| Number of filled seeds | +22% | +17% | +46 | 0.0000 |
| Harvest Index | +25% | +20% | +37% | 0.0025 |
| Thousand Kernel Weight | +1% | +5% | +3% | 0.0000 |

The total seed weight was measured by weighing all filled seeds harvested from a transformed rice plant. The number of filled seeds was determined by counting the number of filled seeds harvested from a transformed rice plant. The total seed number was determined by counting the number of seeds harvested from a plant. The harvest index is defined as the ratio between the total seed weight and the above ground area ($mm^2$), multiplied by a factor $10^6$. Thousand Kernel Weight (TKW) was derived from the number of filled seeds that were counted, and their total weight. The figures gave the mean increase (in %) of each parameter calculated from transgenes versus corresponding nullizygotes of 4 independent events in T1 generation, each event comprising 10 plants carrying the transgene and 10 nullizygotes, and of 4 independent events in the T2 generation, each event comprising 20 plants carrying the transgene and 20 nullizygotes. The p-values of the F-test listed for the data of the T2 generation demonstrate that the obtained increases for the various seed yield parameters are all significant and that there is clearly an overall gene effect.

F) Evaluation of p35 Transformants: Measurement of Seed-Related Parameters

Plants transformed with the AtCKX2 gene under control of the PRO0090 promoter also had a better yield compared to the control nullizygous plants, in particular for total seed weight, number of filled seeds and harvest index. The total seed weight was measured by weighing all filled seeds harvested from a plant. The number of filled seeds was determined by counting the number of filled seeds harvested from a plant. The harvest index in the present invention is defined as the ratio between the total seed weight and the above ground area ($mm^2$), multiplied by a factor $10^6$.

In a first experiment, plants of the T1 generation of five independent events were compared, for each event 10 T1 plants carrying the transgene versus 10 corresponding control T1 plants. For the parameter "total seed weight", two out of the five events had a significant increase (58% and 67%, with a p-value of the t-test of 0.0551 and 0.0211 respectively). Similar results were obtained for the number of filled seeds, for which these two lines showed in increase of 47% and 68% with a p-value of respectively 0.0846 and 0.0166. The two lines also scored positive for Harvest Index (increases of 41% (p-value of 0.0223) and 31% respectively). Besides these two lines, a third line also scored significantly higher than the corresponding nullizygous control plants (+41%, p-value of 0.035).

The positive data for seed yield observed in the T1 generation were confirmed in the T2 generation. Data are given in Table 14.

TABLE 14

| | T2 generation | |
|---|---|---|
| Parameter | Difference over null plants | p-value |
| Total seed weight | +24% | 0.0484 |
| Number of filled seeds | +26% | 0.0254 |
| Harvest index | +19% | 0.0277 |

The figures give the mean increase (in %) of each parameter calculated from transgenes versus corresponding nullizygotes of 3 independent events in the T2 generation, each event comprising 20 plants carrying the transgene and 20 nullizygotes. The p-values of the F-test listed for the data of the T2 generation demonstrate that the obtained increases for the various seed yield parameters are all significant and that there is clearly an overall gene effect.

TABLE 15

| Alternative promoters suitable for seed specific or seedling preferred expression | |
|---|---|
| Gene name | Expression |
| Metallothionein Mte | embryo/scutellum + calli |
| putative beta-amylase | embryo/scutellum |
| unknown | scutellum |
| proteinase inhibitor Rgpi9 | seed |
| structural protein | young tissues, calli, embryo/scutellum |
| prolamine 10 Kda | strong in endosperm |
| allergen RA2 | seed |
| prolamine RP7 | endosperm |
| Metallothioneine-like ML2 | embryo/scutellum + calli |
| prolamine RM9 | strong in endosperm |
| prolamine RP5 | strong in endosperm |
| putative methionine aminopeptidase | embryo |
| putative 40S ribosomal protein | weak in endosperm |
| alpha-globulin | strong in endosperm |
| alanine aminotransferase | aleurone, endosperm |
| cyclophyllin 2 | shoot, embryo/endosperm |
| sucrose synthase SS1 (barley) | medium constitutive, shoot endosperm/aleurone |
| trypsin inhibitor ITR1 (barley) | weak in endosperm |
| WSI18 | embryo/aleurone |
| aquaporine | seedlings |
| RAB21 | embryo/aleurone |
| OSH1 | seedling |
| Arceline 5A | seed |
| Cruciferine | seed |
| Albumine 2S3 | seed |
| Albumine 2S2 | seed |
| FAE1 | embryo |
| Phaseolin Beta subunit | seed |
Lec1 | embryo |
| Gamma zein | seed |
| lipid Transfer Protein | seed |

Example 18

Seed-Preferred Expression the CKX1 Gene Results in Increased Seed Yield

DNA Manipulation

Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Cloning of CKX1

The *Arabidopsis* CKX1 gene (internal reference CDS14992, corresponding to SEQ ID NO:48) was re-amplified by PCR using as template p0432, the pUC19 plasmid containing the *Arabidopsis thaliana* CKX1 2235-bp PCR fragment. The primers used here contained attB sites to be Gateway-compatible. Sequences of the primers used for PCR amplification were SEQ ID NO:45 (PRM02958) and SEQ ID NO:46 (PRM02959), which included the attB sites for Gateway recombination (sequence upstream of the ATG or TTA in PRM02958 respectively PRM02959). PCR was performed using Hifi Taq DNA polymerase in standard conditions. A PCR fragment of 2299 bp was amplified (including the attB sites) and purified also using standard methods. The first step of the Gateway procedure, the BP reaction, was then performed, during which the PCR fragment recombines in vivo with the pDONR plasmid to produce, according to the Gateway terminology, an "entry clone", EC p049 (FIG. 18). pDONR was purchased from Invitrogen, as part of the Gateway technology.

Vector Construction

The entry clone p049 was subsequently used in an LR reaction with p831, a destination vector according to the Gateway™ terminology, used for rice transformation. p831 contains as functional elements within the T-DNA borders a plant selectable marker, a screenable marker and a Gateway cassette intended for LR in vivo recombination with the sequence of interest already cloned in the donor vector. The PRO0218 promoter for embryo and aleurone preferred expression is located upstream of this Gateway cassette.

After the recombination step, the resulting expression vector p051 (originating from p831, FIG. 19) was transformed into *Agrobacterium* strain LBA4404 and subsequently into *Oryza sativa* plants.

Evaluation of p051 Transformants: Measurement of Seed-Related Parameters

Upon analysis of the seeds as described in example 17, the inventors found that plants transformed with the AtCKX1 gene under control of the PRO0218 promoter had a higher number of seeds, and a higher harvest index than plants lacking the CKX1 transgene. These findings were consistent over 2 independent experiments with T1 plants as well as in an experiment with T2 plants, as shown in table 16.

TABLE 16

Analysis of seed related parameters for p051 transformants

| Parameter | T1 generation Difference over null plants | T2 generation Difference over null plants | Combined p-value |
|---|---|---|---|
| Number of seeds | 11% | 5% | 0.0475 |
| Harvest Index | 3% | 10% | 0.0206 |

The total seed number was determined by counting the number of seeds harvested from a plant. The harvest index is defined as the ratio between the total seed weight and the above ground area ($mm^2$), multiplied by a factor $10^6$. The figures gave the mean increase (in %) of each parameter calculated from transgenes versus corresponding nullizygotes of 5 independent events in T1 generation, each event comprising 10 plants carrying the transgene and 10 nullizygotes, and of 4 independent events in the T2 generation, each event comprising 20 plants carrying the transgene and 20 nullizygotes. When two experiments (T1 and T2, for example) with overlapping events have been carried out, a combined analysis can be considered. This is useful to check consistency of the effects over the two experiments, and if this is the case, to accumulate evidence from both experiments in order to increase confidence in the conclusion. The method used is a mixed-model approach that takes into account the multilevel structure of the data (i.e. experiment-event-segregants). P-values are obtained by comparing likelihood ratio test to chi square distributions (for the overall gene effects).

REFERENCES

WO0105985. Method to modulate the expression of genes inducing the parthenocarpic trait in plants.

Alberts, B., Bray, D., Lewis, J., Raff, M., Roberts, K., and Watson, J. D. (1994). "Molecular Biology of the Cell." Garland Publishing Inc.

Aldemita, R. R. and Hodges, T. K. (1996) *Agrobacterium tumefaciens*-mediated transformation of japonica and indica rice varieties. *Planta* 199, 612-617.

Altschul, S. F., Madden, T. L., Schäffer, A. A., Zhang, J., Zhang, Z., Miller, W. & Lipman, D. J. (1997) "Gapped BLAST and PSI-BLAST: a new generation of protein database search programs." *Nucl. Acids Res.* 25, 3389-3402.

Armstrong, D. J. (1994) in *Cytokinins: Chemistry, Activity and Functions*, eds. Mok. D. W. S & Mok, M. C. (CRC Boca Raton, Fla.), pp. 139-154.

An, G., Watson, B. D., Stachel, S., Gordon, M. P., and Nester, E. W. (1985). New cloning vehicles for transformation of higher plants. *EMBO J.* 4, 277-284.

Armstrong, C. L., Petersen, W. P., Buchholz, W. G., Bowen, B. A., and Sulc, S. L. (1990). Factors affecting PEG-mediated stable transformation of maize protoplasts. *Plant Cell Reports* 9, 335-339.

Banerjee, A., Pramanik, A., Bhattacharjya, S., and Balaram, P. (1996). Omega amino acids in peptide design: incorporation into helices. *Biopolymers* 39, 769-777.

Baron, M. H. and Baltimore, D. (1982). Antibodies against the chemically synthesized genome-linked protein of poliovirus react with native virus-specific proteins. *Cell* 28, 395-404.

Bartel, P. L. and Fields, S. (1997). "The Yeast Two-Hybrid System." Oxford University Press.

Benkirane, N., Guichard, G., Briand, J. P., and Muller, S. (1996). Exploration of requirements for peptidomimetic immune recognition. Antigenic and immunogenic properties of reduced peptide bond pseudopeptide analogues of a histone hexapeptide. *J. Biol Chem.* 271, 33218-33224.

Berry, A. and Brenner, S. E. (1994). A prototype computer system for de novo protein design. *Biochem. Soc. Trans.* 22, 1033-1036.

Chan, M. T., Chang, H. H., Ho, S. L., Tong, W. F., and Yu, S. M. (1993) *Agrobacterium* mediated production of transgenic rice plants expressing a chimeric alpha-amylase promoter/beta-glucuronidase gene. *Plant Mol. Biol.* 22, 491-506.

Christou, P., McCabe, D. E., and Swain, W. F. (1988). Stable transformation of soybean callus by DNA-coated gold particles. *Plant Physiol.* 87, 671-674.

Crossway, A., Oakes, J. V., Irvine, J. M., Ward, B., Knauf, V. C., and Shewmaker, C. K. (1986). Integration of foreign DNA following microinjection of tobacco mesophyll protoplasts. *Mol. Gen. Genet.* 202, 179-185.
Dale, E. C. and Ow, D. W. (1990). Intra- and intermolecular site-specific recombination in plant cells mediated by bacteriophage P1 recombinase. *Gene* 91, 79-85.
Dodds, J. H. (1985). "Plant genetic engineering." Cambridge University Press.
Doerner, P., Jorgensen, J. E., You, R., Steppuhn, J., and Lamb, C. (1996). Control of root growth and development by cyclin expression. *Nature* 380, 520-523.
Dorner, B., Husar, G. M., Ostresh, J. M., and Houghten, R. A. (1996). The synthesis of peptidomimetic combinatorial libraries through successive amide alkylations. *Bioorg. Med. Chem.* 4, 709-715.
Ellis, J. G., Llewellyn, D. J., Dennis, E. S., and Peacock, W. J. (1987). Maize Adh-1 promoter sequences control anaerobic regulation: addition of upstream promoter elements from constitutive genes is necessary for expression in tobacco. *EMBO J.* 6, 11-16.
Faiss, M., Zalubilová, J., Strnad, M., Schmülling, T. (1997). Conditional transgenic expression of the ipt gene indicates a function for cytokinins in paracrine signaling in whole tobacco plants. *Plant J.* 12, 401-415.
Fassina, G. and Melli, M. (1994). Identification of interactive sites of proteins and protein receptors by computer-assisted searches for complementary peptide sequences. *Immunomethods.* 5, 114-120.
Fedoroff, N. V. and Smith, D. L. (1993). A versatile system for detecting transposition in *Arabidopsis. Plant J.* 3, 273-289.
Hanahan, D. (1983). Studies on transformation of *Escherichia coli* with plasmids. *J. Mol. Biol* 166, 557-580.
Hansen, G. and Chilton, M. D. (1996). "Agrolistic" transformation of plant cells: integration of T-strands generated in planta. *Proc. Natl. Acad. Sci. U.S.A* 93, 14978-14983.
Hansen, G., Shillito, R. D., and Chilton, M. D. (1997). T-strand integration in maize protoplasts after codelivery of a T-DNA substrate and virulence genes. *Proc. Natl. Acad. Sci. U.S.A* 94, 11726-11730.
Hanson, B., Engler, D., Moy, Y., Newman, B., Ralston, E., and Gutterson, N. (1999). A simple method to enrich an *Agrobacterium*-transformed population for plants containing only T-DNA sequences. *Plant J.* 19, 727-734.
Harlow, E. and Lane, D. (1988). "Antibodies: A Laboratory Manual." Cold Spring Harbor Laboratory Press.
Herrera-Estrella, L., De Block, M., Messens, E. H. J. P., Van Montagu, M., and Schell, J. (1983). Chimeric genes as dominant selectable markers in plant cells. *EMBO J.* 2, 987-995.
Hiei, Y.; Ohta, S.; Komari, T.; and Kumashiro, T. (1994) Efficient transformation of rice (*Oryza sativa* L.) mediated by *Agrobacterium* and sequence analysis of the boundaries of the T-DNA. *Plant J.* 6, 271-282.
Hoffman, D. L., Laiter, S., Singh, R. K., Vaisman, I. I., and Tropsha, A. (1995). Rapid protein structure classification using one-dimensional structure profiles on the bioSCAN parallel computer. *Comput. Appl. Biosci.* 11, 675-679.
Hooykens, P. J. J., Hall, M. A. & Libbeuga, K. R., eds. (1999) *Biochemistry and Molecular Biology of Plant Hormones* (Elsevier, Amsterdam).
Houba-Heria, N., Pethe, C. d'Alayer, J & Lelouc, M. (1999) *Plant J.* 17:615-626.
Klee, H. J. & Lanehon, M. B. (1995) in *Plant Hormones: Physiology, Biochemistry and Molecular Biology*, ed. Davies, P. J. (Kluwer, Dordrdrocht, the Netherlands), pp. 340-353.
Krens, F. A., Molendijk, L., Wullems, G. J., and Schilperoort, R. A. (1982). In vitro transformation of plant protoplasts with Ti-plasmid DNA. *Nature* 296, 72-74.
Lerner, R. A. (1982). Tapping the immunological repertoire to produce antibodies of predetermined specificity. *Nature* 299, 593-596.
Lerner, R. A., Green, N., Alexander, H., Liu, F. T., Sutcliffe, J. G., and Shinnick, T. M. (1981). Chemically synthesized peptides predicted from the nucleotide sequence of the hepatitis B virus genome elicit antibodies reactive with the native envelope protein of Dane particles. *Proc. Natl. Acad. Sci. U.S.A* 78, 3403-3407.
Liddle, J. E. and Cryer, A. (1991). "A Practical Guide to Monoclonal Antibodies." Wiley New York.
Loffler, J., Langui, D., Probst, A., and Huber, G. (1994). Accumulation of a 50 kDa N-terminal fragment of beta-APP695 in Alzheimer's disease hippocampus and neocortex. *Neurochem. Int.* 24, 281-288.
Mok M. C. (1994) in *Cytokines: Chemistry, Activity and Function*, eds., Mok, D. W. S. & Mok, M. C. (CRC Boca Raton, Fla.), pp. 155-166.
Monge, A., Lathrop, E. J., Gunn, J. R., Shenkin, P. S., and Friesner, R. A. (1995). Computer modeling of protein folding: conformational and energetic analysis of reduced and detailed protein models. *J. Mol. Biol* 247, 995-1012.
Morris, R. O. et al. (1999). Isolation of a gene encoding a glycosylated cytokinin oxidase from maize. Bioechem. *Biophys. Res. Commun.* 255, 328-333
Motyka, V., Faiss, M., Strnad, M., Kaminek, M. and Schmuelling, T. (1996). Changes in cytokinin content and cytokinin oxidase activity in response to derepression of ipt gene transcription in transgenic tobacco calli and plants. *Plant Physiol.* 112, 1035-1043.
Murakami, T., Simonds, W. F., and Spiegel, A. M. (1992). Site-specific antibodies directed against G protein beta and gamma subunits: effects on alpha and beta gamma subunit interaction. *Biochemistry* 31, 2905-2911.
Olszewski, K. A., Kolinski, A., and Skolnick, J. (1996). Folding simulations and computer redesign of protein A three-helix bundle motifs. *Proteins* 25, 286-299.
Osborne, B. I., Wirtz, U., and Baker, B. (1995). A system for insertional mutagenesis and chromosomal rearrangement using the Ds transposon and Cre-lox. *Plant J.* 7, 687-701.
Ostresh, J. M., Blondelle, S. E., Dorner, B., and Houghten, R. A. (1996). Generation and use of nonsupport-bound peptide and peptidomimetic combinatorial libraries. *Methods Enzymol.* 267, 220-234.
Pabo, C. O. and Suchanek, E. G. (1986). Computer-aided model-building strategies for protein design. *Biochemistry* 25, 5987-5991.
Paszkowski, J., Shillito, R. D., Saul, M., Mandak, V., and Hohn, T. H. B. P. I. (1984). Direct gene transfer to plants. *EMBO J.* 3, 2717-2722.
Peralta, E. G., Hellmiss, R., and Ream, W. (1986). Overdrive, a T-DNA transmission enhancer on the *A. tumefaciens* tumour-inducing plasmid. *EMBO J.* 5, 1137-1142.
Quirino, B. F., Noh, Y.-S., Himelbau, E., and Amasino, R. M. (2000). Molecular aspects of leaf senescence. *Trends in Plant Science* 5, 278-282.
Renouf, D. V. and Hounsell, E. F. (1995). Molecular modelling of glycoproteins by homology with non-glycosylated protein domains, computer simulated glycosylation and molecular dynamics. *Adv. Exp. Med. Biol* 376, 37-45.
Rinaldi, A. C. and Comandini, O. (1999). Cytokinin oxidase strikes again. *Trends in Plant Sc.* 4, 300.

Rose, R. B., Craik, C. S., Douglas, N. L., and Stroud, R. M. (1996). Three-dimensional structures of HIV-1 and SIV protease product complexes. *Biochemistry* 35, 12933-12944.

Rutenber, E. E., McPhee, F., Kaplan, A. P., Gallion, S. L., Hogan, J. C., Jr., Craik, C. S., and Stroud, R. M. (1996). A new class of HIV-1 protease inhibitor: the crystallographic structure, inhibition and chemical synthesis of an aminimide peptide isostere. *Bioorg. Med. Chem.* 4, 1545-1558.

Sambrook, J., Fritsch, E. F., and Maniatis, T. (1989). "Molecular Cloning: A Laboratory Manual." Cold Spring Harbor Laboratory Press.

Schlappi, M., Smith, D., and Fedoroff, N. (1993). TnpA trans-activates methylated maize Suppressor-mutator transposable elements in transgenic tobacco. *Genetics* 133, 1009-1021.

Shioda, T., Andriole, S., Yahata, T., and Isselbacher, K. J. (2000). A green fluorescent protein-reporter mammalian two-hybrid system with extrachromosomal maintenance of a prey expression plasmid: Application to interaction screening. *Proc. Natl. Acad. Sci. U.S.A* 97, 5220-5224.

Smulling, T., Rupp, H. M. Frank, M& Schafer, S. (1999) in *Advances in Regulation of Plant Growth and Development*, eds. Surnad, M. Pac P. & Beck, E. (Peres, Prague), pp. 85-96.

Tamura, R. N., Cooper, H. M., Collo, G., and Quaranta, V. (1991). Cell type-specific integrin variants with alternative alpha chain cytoplasmic domains. *Proc. Natl. Acad. Sci. U.S.A* 88, 10183-10187.

Werner, T., Vadau Motyka, Miroslav Strnad, and Thomas Schmülling (2001) Regulation of plant growth by cytokinin. *Proc. Nat. Acad. Sci.,* 58 (18) 10487-10492.

Van Haaren, M. J., Sedee, N. J., Schilperoort, R. A., and Hooykaas, P. J. (1987). Overdrive is a T-region transfer enhancer which stimulates T-strand production in *Agrobacterium tumefaciens. Nucleic Acids Res.* 15, 8983-8997.

Van Sluys, M. A., Tempe, J., and Fedoroff, N. (1987). Studies on the introduction and mobility of the maize Activator element in *Arabidopsis thaliana* and *Daucus carota. EMBO J.* 6, 3881-3889.

Wang, K., Genetello, C., Van Montagu, M., and Zambryski, P. C. (1987). Sequence context of the T-DNA border repeat element determines its relative activity during T-DNA transfer to plant cells. *Mol. Gen. Genet.* 210, 338-346.

Woulfe, J., Lafortune, L., de Nadai, F., Kitabgi, P., and Beaudet, A. (1994). Post-translational processing of the neurotensin/neuromedin N precursor in the central nervous system of the rat-II. Immunohistochemical localization of maturation products. *Neuroscience* 60, 167-181.

Zhang, Y. L., Dawe, A. L., Jiang, Y., Becker, J. M., and Naider, F. (1996). A superactive peptidomimetic analog of a farnesylated dodecapeptide yeast pheromone. *Biochem. Biophys. Res. Commun.* 224, 327-331.

What is claimed is:

1. An isolated nucleic acid molecule encoding a cytokinin oxidase operably linked to a heterologous seed-specific promoter, wherein the isolated nucleic acid molecule encoding a cytokinin oxidase is selected from the group consisting of:

a. a nucleic acid molecule comprising the DNA sequence as given in SEQ ID NO: 48, or the complement thereof, b. a nucleic acid molecule comprising the RNA sequences corresponding to SEQ ID NO: 48, or the complement thereof, c. a nucleic acid molecule specifically hybridizing under high stringent conditions to SEQ ID NO:48, or to the complement thereof, wherein the stringent conditions are hybridization at 4×SSC at 65° C., followed by a washing in 0.1×SSC at 65° C., and d. a nucleic acid molecule as defined in any of (a) to (c) characterized in that said nucleic acid molecule is DNA, genomic DNA, cDNA, synthetic DNA or RNA wherein T is replaced by U.

2. The isolated nucleic acid molecule of claim 1 wherein the heterologous seed-specific promoter is an embryo-specific promoter.

3. The isolated nucleic acid molecule of claim 1 wherein the heterologous seed-specific promoter is an endosperm-specific promoter.

4. A vector comprising the isolated nucleic acid molecule of claim 1.

5. The vector of claim 4 wherein the heterologous seed-specific promoter is an embryo-specific promoter.

6. The vector of claim 4 wherein the heterologous seed-specific promoter is an endosperm-specific promoter.

7. A host cell comprising the isolated nucleic acid molecule of claim 1, wherein said host cell is a bacterial, fungal or plant cell.

8. A host cell comprising a vector of claim 4 wherein said host cell is a bacterial, fungal or plant cell.

9. A host cell comprising the vector of claim 5, wherein said host cell is a bacterial, fungal or plant cell.

10. A host cell comprising the vector of claim 6, wherein said host cell is a bacterial, fungal or plant cell.

11. A transgenic plant, plant part, or plant tissue comprising the plant cell of claim 7.

12. A transgenic plant, plant part, or plant tissue comprising the plant cell of claim 8.

13. A transgenic plant, plant part, or plant tissue comprising the plant cell of claim 9.

14. A transgenic plant, plant part, or plant tissue comprising the plant cell of claim 10.

15. A harvestable part of the transgenic plant of claim 11, wherein said harvestable part is selected from the group consisting of seeds, leaves, fruits, stem cultures, rhizomes, roots, tubers and bulbs, and wherein said seeds or fruits comprise said isolated nucleic acid molecule encoding said cytokinin oxidase operably linked to said heterologous seed-specific promoter.

16. A harvestable part of the transgenic plant of claim 12, wherein said harvestable part is selected from the group consisting of seeds, leaves, fruits, stem cultures, rhizomes, roots, tubers and bulbs, and wherein said seeds or fruits comprise said isolated nucleic acid molecule encoding said cytokinin oxidase operably linked to said heterologous seed-specific promoter.

17. A harvestable part of the transgenic plant of claim 13, wherein said harvestable part is selected from the group consisting of seeds, leaves, fruits, stem cultures, rhizomes, roots, tubers and bulbs, and wherein said seeds or fruits comprise said isolated nucleic acid molecule encoding said cytokinin oxidase operably linked to said heterologous seed-specific promoter.

18. A harvestable part of the transgenic plant of claim 14, wherein said harvestable part is selected from the group consisting of seeds, leaves, fruits, stem cultures, rhizomes, roots, tubers and bulbs, and wherein said seeds or fruits comprise said isolated nucleic acid molecule encoding said cytokinin oxidase operably linked to said heterologous seed-specific promoter.

19. Transgenic progeny of the plant or plant part of claim 11 wherein said transgenic progeny comprise said isolated nucleic acid molecule encoding said cytokinin oxidase operably linked to said heterologous seed-specific promoter.

20. Transgenic progeny of the plant or plant part of claim 12 wherein said transgenic progeny comprise said isolated nucleic acid molecule encoding said cytokinin oxidase operably linked to said heterologous seed-specific promoter.

21. Transgenic progeny of the plant or plant part of claim 13 wherein said transgenic progeny comprise said isolated nucleic acid molecule encoding said cytokinin oxidase operably linked to said heterologous seed-specific promoter.

22. Transgenic progeny of the plant or plant part of claim 14 wherein said transgenic progeny comprise said isolated nucleic acid molecule encoding said cytokinin oxidase operably linked to said heterologous seed-specific promoter.

* * * * *

SEQUENCE LISTING

```
<160> NUMBER OF SEQ ID NOS: 58

<210> SEQ ID NO 1
<211> LENGTH: 2236
<212> TYPE: DNA
<213> ORGANISM: Arabidopsis thaliana

<400> SEQUENCE: 1

atgggattga cctcatcctt acggttccat agacaaaaca acaagacttt cctcggaatc     60

ttcatgatct tagttctaag ctgtatacca ggtagaacca atctttgttc caatcattct    120

gttagtaccc caaaagaatt accttcttca aatccttcag atattcgttc ctcattagtt    180

tcactagatt tggagggtta tataagcttc gacgatgtcc acaatgtggc caaggacttt    240

ggcaacagat accagttacc acctttggca attctacatc caaggtcagt ttttgatatt    300

tcatcgatga tgaagcatat agtacatctg ggctccacct caaatcttac agtagcagct    360

agaggccatg gtcactcgct tcaaggacaa gctctagctc atcaaggtgt tgtcatcaaa    420

atggagtcac ttcgaagtcc tgatatcagg atttataagg ggaagcaacc atatgttgat    480

gtctcaggtg gtgaaatatg gataaacatt ctacgcgaga ctctaaaata cggtctttca    540

ccaaagtcct ggacagacta ccttcatttg accgttggag gtacactatc taatgctgga    600

atcagcggtc aagcattcaa gcatggaccc caaatcaaca acgtctacca gctagagatt    660

gttacaggta tttcattcat gctttatctc tgcggtagtc tcaaaaaaat atgcacctgt    720

aaagaatatc catctcttca tgagcaaaaa cactgacgac tttaaataat ttttgactat    780

aaaacaagag tgcataggca caaatgtgaa atatgcaaca cacaattgta acttgcacca    840

agaaaaaagt tataaaaaca aacaactgat aagcaatata tttccaatat ttaatcaggg    900

aaaggagaag tcgtaacctg ttctgagaag cggaattctg aacttttctt cagtgttctt    960

ggcgggcttg gacagtttgg cataatcacc cgggcacgga tctctcttga accagcaccg   1020

catatggtaa agttctatct tgaacaaagt tcaaacaata tacgctatga ttctaagaac   1080
```

```
cactttcctg acacagtcaa ataactttta ataggttaaa tggatcaggg tactctactc   1140

tgacttttct gcattttcaa gggaccaaga atatctgatt tcgaaggaga aaacttttga   1200

ttacgttgaa ggatttgtga taatcaatag aacagacctt ctcaataatt ggcgatcgtc   1260

attcagtccc aacgattcca cacaggcaag cagattcaag tcagatggga aaactcttta   1320

ttgcctagaa gtggtcaaat atttcaaccc agaagaagct agctctatgg atcaggtaag   1380

atgtgaaagc aatatataac tagacttagt ttccacagag agctccaaat caaccgttgg   1440

ctactagcct actaacataa tgaatggttg ccgtgcagga aactggcaag ttactttcag   1500

agttaaatta tattccatcc actttgtttt catctgaagt gccatatatc gagtttctgg   1560

atcgcgtgca tatcgcagag agaaaactaa gagcaaaggg tttatgggag gttccacatc   1620

cctggctgaa tctcctgatt cctaagagca gcatatacca atttgctaca gaagtttcca   1680

acaacattct cacaagcaac aacaacggtc ctatccttat ttatccagtc aatcaatcca   1740

agtaagtgag caaaatgcca aaagcaaatg cgtccagtga ttctgaaaca taaattacta   1800

accatatcca acattttgtg gtttcaggtg gaagaaacat acatctttga taactccaaa   1860

tgaagatata ttctatctcg tagcctttct cccctctgca gtgccaaatt cctcagggaa   1920

aaacgatcta gagtaccttt tgaaacaaaa ccaaagagtt atgaacttct gcgcagcagc   1980

aaacctcaac gtgaagcagt atttgcccca ttatgaaact caaaaagagt ggaaatcaca   2040

ctttggcaaa agatgggaaa catttgcaca gaggaaacaa gcctacgacc ctctagcgat   2100

tctagcacct ggccaaagaa tattccaaaa gacaacagga aaattatctc ccatccaact   2160

cgcaaagtca aaggcaacag gaagtcctca aaggtaccat tacgcatcaa tactgccgaa   2220

acctagaact gtataa                                                    2236
```

<210> SEQ ID NO 2
<211> LENGTH: 575
<212> TYPE: PRT
<213> ORGANISM: Arabidopsis thaliana

<400> SEQUENCE: 2

```
Met Gly Leu Thr Ser Ser Leu Arg Phe His Arg Gln Asn Asn Lys Thr
1               5                   10                  15

Phe Leu Gly Ile Phe Met Ile Leu Val Leu Ser Cys Ile Pro Gly Arg
            20                  25                  30

Thr Asn Leu Cys Ser Asn His Ser Val Ser Thr Pro Lys Glu Leu Pro
        35                  40                  45

Ser Ser Asn Pro Ser Asp Ile Arg Ser Ser Leu Val Ser Leu Asp Leu
    50                  55                  60

Glu Gly Tyr Ile Ser Phe Asp Asp Val His Asn Val Ala Lys Asp Phe
65                  70                  75                  80

Gly Asn Arg Tyr Gln Leu Pro Pro Leu Ala Ile Leu His Pro Arg Ser
                85                  90                  95

Val Phe Asp Ile Ser Ser Met Met Lys His Ile Val His Leu Gly Ser
            100                 105                 110

Thr Ser Asn Leu Thr Val Ala Ala Arg Gly His Gly His Ser Leu Gln
        115                 120                 125

Gly Gln Ala Leu Ala His Gln Gly Val Val Ile Lys Met Glu Ser Leu
    130                 135                 140

Arg Ser Pro Asp Ile Arg Ile Tyr Lys Gly Lys Gln Pro Tyr Val Asp
145                 150                 155                 160
```

```
Val Ser Gly Gly Glu Ile Trp Ile Asn Ile Leu Arg Glu Thr Leu Lys
                165                 170                 175

Tyr Gly Leu Ser Pro Lys Ser Trp Thr Asp Tyr Leu His Leu Thr Val
            180                 185                 190

Gly Gly Thr Leu Ser Asn Ala Gly Ile Ser Gly Gln Ala Phe Lys His
        195                 200                 205

Gly Pro Gln Ile Asn Asn Val Tyr Gln Leu Glu Ile Val Thr Gly Lys
    210                 215                 220

Gly Glu Val Val Thr Cys Ser Glu Lys Arg Asn Ser Glu Leu Phe Phe
225                 230                 235                 240

Ser Val Leu Gly Gly Leu Gly Gln Phe Gly Ile Ile Thr Arg Ala Arg
                245                 250                 255

Ile Ser Leu Glu Pro Ala Pro His Met Val Lys Trp Ile Arg Val Leu
            260                 265                 270

Tyr Ser Asp Phe Ser Ala Phe Ser Arg Asp Gln Glu Tyr Leu Ile Ser
        275                 280                 285

Lys Glu Lys Thr Phe Asp Tyr Val Glu Gly Phe Val Ile Ile Asn Arg
    290                 295                 300

Thr Asp Leu Leu Asn Asn Trp Arg Ser Ser Phe Ser Pro Asn Asp Ser
305                 310                 315                 320

Thr Gln Ala Ser Arg Phe Lys Ser Asp Gly Lys Thr Leu Tyr Cys Leu
                325                 330                 335

Glu Val Val Lys Tyr Phe Asn Pro Glu Glu Ala Ser Ser Met Asp Gln
            340                 345                 350

Glu Thr Gly Lys Leu Leu Ser Glu Leu Asn Tyr Ile Pro Ser Thr Leu
        355                 360                 365

Phe Ser Ser Glu Val Pro Tyr Ile Glu Phe Leu Asp Arg Val His Ile
    370                 375                 380

Ala Glu Arg Lys Leu Arg Ala Lys Gly Leu Trp Glu Val Pro His Pro
385                 390                 395                 400

Trp Leu Asn Leu Leu Ile Pro Lys Ser Ser Ile Tyr Gln Phe Ala Thr
                405                 410                 415

Glu Val Phe Asn Asn Ile Leu Thr Ser Asn Asn Asn Gly Pro Ile Leu
            420                 425                 430

Ile Tyr Pro Val Asn Gln Ser Lys Trp Lys Lys His Thr Ser Leu Ile
        435                 440                 445

Thr Pro Asn Glu Asp Ile Phe Tyr Leu Val Ala Phe Leu Pro Ser Ala
    450                 455                 460

Val Pro Asn Ser Ser Gly Lys Asn Asp Leu Glu Tyr Leu Leu Lys Gln
465                 470                 475                 480

Asn Gln Arg Val Met Asn Phe Cys Ala Ala Ala Asn Leu Asn Val Lys
                485                 490                 495

Gln Tyr Leu Pro His Tyr Glu Thr Gln Lys Glu Trp Lys Ser His Phe
            500                 505                 510

Gly Lys Arg Trp Glu Thr Phe Ala Gln Arg Lys Gln Ala Tyr Asp Pro
        515                 520                 525

Leu Ala Ile Leu Ala Pro Gly Gln Arg Ile Phe Gln Lys Thr Thr Gly
    530                 535                 540

Lys Leu Ser Pro Ile Gln Leu Ala Lys Ser Lys Ala Thr Gly Ser Pro
545                 550                 555                 560

Gln Arg Tyr His Tyr Ala Ser Ile Leu Pro Lys Pro Arg Thr Val
                565                 570                 575
```

<210> SEQ ID NO 3
<211> LENGTH: 2991
<212> TYPE: DNA
<213> ORGANISM: Arabidopsis thaliana

<400> SEQUENCE: 3

```
atggctaatc ttcgtttaat gatcacttta atcacggttt taatgatcac caaatcatca     60
aacggtatta aaattgattt acctaaatcc cttaacctca ccctctctac cgatccttcc    120
atcatctccg cagcctctca tgacttcgga aacataacca ccgtgacccc cggcggcgta    180
atctgcccct cctccaccgc tgatatctct cgtctcctcc aatacgccgc aaacggaaaa    240
agtacattcc aagtagcggc tcgtggccaa ggccactcct taaacggcca agcctcggtc    300
tccggcggag taatcgtcaa catgacgtgt atcactgacg tggtggtttc aaaagacaag    360
aagtacgctg acgtggcggc cgggacgtta tgggtggatg tgcttaagaa gacggcggag    420
aaaggggtgt cgccggtttc ttggacggat tatttgcata taaccgtcgg aggaacgttg    480
tcgaatggtg gaattggtgg tcaagtgttt cgaaacggtc ctcttgttag taacgtcctt    540
gaattggacg ttattactgg tacgcatctt ctaaactttg atgtacatac aacaacaaaa    600
actgtttttg ttttatagta tttttcattt tttgtaccat aggttttatg ttttatagtt    660
gtgctaaact tcttgcacca cacgtaagtc ttcgaaacac aaaatgcgta acgcatctat    720
atgtttttg tacatattga atgttgttca tgagaaataa agtaattaca tatacacaca    780
tttattgtcg tacatatata aataattaaa gacaaatttt cacaattggt agcgtgttaa    840
tttgggattt ttgtaatgta catgcatgac gcatgcatat ggagcttttc ggtttctta    900
gatttgtgta gtatttcaaa tatatcattt attttcttc gaataaagag gtggtatatt    960
tttaaaatag caacatttca gaatttttct ttgaatttac actttttaaa ttgttattgt   1020
taatatggat tttgaataaa taatttcagg gaaaggtgaa atgttgacat gctcgcgaca   1080
gctaaaccca gaattgttct atggagtgtt aggaggtttg ggtcaatttg gaattataac   1140
gagagccaga attgttttgg accatgcacc taaacgggta cgtatcatca tattttacca   1200
tttgttttag tcagcattca tttttcatta gtaattccgt ttcaatttct aaatttttt   1260
agtcaataga aaatgattct tatgtcagag cttgattatt tagtgatttt tattgagata   1320
aaataaaata taacctaacg gaaataatta ttttactaat cggataatgt ctgattaaaa   1380
cattttatga tattacacta agagagttag agacgtatgg atcacaaaac atgaagcttt   1440
cttagatggt atcctaaaac taaagttagg tacaagtttg gaatttaggt caaatgctta   1500
agttgcatta atttgaacaa aatctatgca ttgaataaaa aaaagatatg gattatttta   1560
taaagtatag tccttgtaat cctaggactt gttgtctaat cttgtcttat gcgtgcaaat   1620
ctttttgatg tcaatatata atccttgttt attagagtca agctctttca ttagtcaact   1680
actcaaatat actccaaagt ttagaatata gtcttctgac taattagaat cttacaaccg   1740
ataaacgtta caatttggtt atcattttaa aaaacagatt tggtcataat atacgatgac   1800
gttctgtttt agtttcatct attcacaaat tttatataat tattttcaag aaaatattga   1860
aatactatac tgtaatatgg tttctttata tatgtgtgta taaattaaat gggattgttt   1920
tctctaaatg aaattgtgta ggccaaatgg tttcggatgc tctacagtga tttcacaact   1980
tttacaaagg accaagaacg tttgatatca atggcaaacg atattggagt cgactattta   2040
gaaggtcaaa tatttctatc aaacggtgtc gttgacacct ctttttccc accttcagat   2100
caatctaaag tcgctgatct agtcaagcaa cacggtatca tctatgttct tgaagtagcc   2160
```

-continued

```
aagtattatg atgatcccaa tctccccatc atcagcaagg tactacacat ttacattttc   2220

atcatcgttt ttatcatacc ataagatatt taaatgattc atcattgcac cacattaaga   2280

tattcatcat catcatcgtt acattttttt ttgcatctta tgcttctcat aatctactat   2340

tgtgtaggtt attgacacat taacgaaaac attaagttac ttgcccgggt tcatatcaat   2400

gcacgacgtg gcctacttcg atttcttgaa ccgtgtacat gtcgaagaaa ataaactcag   2460

atctttggga ttatgggaac ttcctcatcc ttggcttaac ctctacgttc ctaaatctcg   2520

gattctcgat tttcataacg gtgttgtcaa agacattctt cttaagcaaa aatcagcttc   2580

gggactcgct cttctctatc caacaaaccg gaataagtac atacttctct tcattcatat   2640

ttatcttcaa gaaccaaagt aaataaattt ctatgaactg attatgctgt tattgttaga   2700

tgggacaatc gtatgtcggc gatgatacca gagatcgatg aagatgttat atatattatc   2760

ggactactac aatccgctac cccaaaggat cttccagaag tggagagcgt taacgagaag   2820

ataattaggt tttgcaagga ttcaggtatt aagattaagc aatatctaat gcattatact   2880

agtaaagaag attggattga gcatttttgga tcaaaatggg atgatttttc gaagaggaaa   2940

gatctatttg atcccaagaa actgttatct ccagggcaag acatcttttg a            2991
```

<210> SEQ ID NO 4
<211> LENGTH: 501
<212> TYPE: PRT
<213> ORGANISM: Arabidopsis thaliana

<400> SEQUENCE: 4

```
Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Gly Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
```

225 230 235 240

Thr Thr Phe Thr Lys Asp Gln Glu Arg Leu Ile Ser Met Ala Asn Asp
245 250 255

Ile Gly Val Asp Tyr Leu Glu Gly Gln Ile Phe Leu Ser Asn Gly Val
260 265 270

Val Asp Thr Ser Phe Phe Pro Pro Ser Asp Gln Ser Lys Val Ala Asp
275 280 285

Leu Val Lys Gln His Gly Ile Ile Tyr Val Leu Glu Val Ala Lys Tyr
290 295 300

Tyr Asp Asp Pro Asn Leu Pro Ile Ile Ser Lys Val Ile Asp Thr Leu
305 310 315 320

Thr Lys Thr Leu Ser Tyr Leu Pro Gly Phe Ile Ser Met His Asp Val
325 330 335

Ala Tyr Phe Asp Phe Leu Asn Arg Val His Val Glu Glu Asn Lys Leu
340 345 350

Arg Ser Leu Gly Leu Trp Glu Leu Pro His Pro Trp Leu Asn Leu Tyr
355 360 365

Val Pro Lys Ser Arg Ile Leu Asp Phe His Asn Gly Val Val Lys Asp
370 375 380

Ile Leu Leu Lys Gln Lys Ser Ala Ser Gly Leu Ala Leu Leu Tyr Pro
385 390 395 400

Thr Asn Arg Asn Lys Trp Asp Asn Arg Met Ser Ala Met Ile Pro Glu
405 410 415

Ile Asp Glu Asp Val Ile Tyr Ile Ile Gly Leu Leu Gln Ser Ala Thr
420 425 430

Pro Lys Asp Leu Pro Glu Val Glu Ser Val Asn Glu Lys Ile Ile Arg
435 440 445

Phe Cys Lys Asp Ser Gly Ile Lys Ile Lys Gln Tyr Leu Met His Tyr
450 455 460

Thr Ser Lys Glu Asp Trp Ile Glu His Phe Gly Ser Lys Trp Asp Asp
465 470 475 480

Phe Ser Lys Arg Lys Asp Leu Phe Asp Pro Lys Lys Leu Leu Ser Pro
485 490 495

Gly Gln Asp Ile Phe
500

<210> SEQ ID NO 5
<211> LENGTH: 3302
<212> TYPE: DNA
<213> ORGANISM: Arabidopsis thaliana

<400> SEQUENCE: 5
atggcgagtt ataatcttcg ttcacaagtt cgtcttatag caataacaat agtaatcatc 60
attactctct caactccgat cacaaccaac acatcaccac aaccatggaa tatcctttca 120
cacaacgaat tcgccggaaa actcacctcc tcctcctcct ccgtcgaatc agccgccaca 180
gatttcggcc acgtcaccaa aatcttccct tccgccgtct taatcccttc ctccgttgaa 240
gacatcacag atctcataaa actctctttt gactctcaac tgtcttttcc tttagccgct 300
cgtggtcacg gacacagcca ccgtggccaa gcctcggcta aagacggagt tgtggtcaac 360
atgcggtcca tggtaaaccg ggatcgaggt atcaaggtgt ctaggacctg tttatatgtt 420
gacgtggacg ctgcgtggct atggattgag gtgttgaata aaactttgga gttagggtta 480
acgccggttt cttggacgga ttatttgtat ttaacagtcg gtgggacgtt atcaaacggc 540

-continued

```
ggaattagtg gacaaacgtt tcggtacggt ccacagatca ctaatgttct agagatggat    600
gttattactg gtacgtacca cgatcttttt cacacagaga ttaaaaaaaa cagtaatagt    660
gattttaact tcgtacgttt ctgatagaca acaaagaact tcgtacgttt ttcgaagttt    720
tttcgtcttt ttcattttag atctgcgcgg ccatttttgg ttatgctatt gtttgtttgt    780
attgtttgtc tctgtttatt tatttctcga acttgttgat agcttttctt cttttcacac    840
atcaatctaa tcaccttttt tggtcttaag attagaaaga agatacggac taggtaaaaa    900
taggtggttg taaacgtaga cgcattaaaa aaatattggt tttttattt tttgataagc     960
aaaattggtg gttggtctaa gattataaac ttgatattaa tgcaaaggtc gatctagcaa   1020
tagaagatta atcaatattc ttggtgtttt aacaacagat tatttcatca ttaaaatcgt   1080
gaaacaaaga aattttggta gtatacatta cgtgtagttt tgttagttta ttaaaaaaaa   1140
tagtatatag ttttgttaaa acgcgattta tttagtaaca cattagtata ttacacgttt   1200
aaccaactaa actttttttt ttgaataatt atgttctata tttcttactc aaattatgca   1260
aatttcgtgg attcgaagtc aaatttctgc gaaatttaca tggtcatata ttataaaact   1320
gttcatataa cccggtgaac aaacagacaa ttaagggttt gaatggttac ggcggttggg   1380
gcggacacaa ccgtcaatag atcagaccgt tttttattta ccattcatca attatattcc   1440
gcagtggttt ggggtaaaaa aaatagaaga aaaccgcagc ggaccaattc cataccgttt   1500
ttacatacaa ataaacatgg tgcgcaacgg tttattgtcc gcctcaaaaa tgaaatggac   1560
taaaccgcag ataaattaga ccgctttgtc cgctgcctcc attcatagac taaaaaaaaa   1620
caaccaaaaa aaaaatggtc ccacgcccat gattttacac gaggtttctt gtggcgtaag   1680
gacaaaactc aaaagttcat aacgtttggt cctaaccagg tgtaatggat taagtaacag   1740
tcaattttct tattatagct gtatccatta tgtccacata tgcatccata tacattacac   1800
tgttggtctc aagtgtagtt agattacgaa gactttcaag ttccattttt tggttaggag   1860
ataaacataa tttaatgata ccgactttag cactctaggc tcaaaacaag tacagaagag   1920
aatagtttta tttcaaactc gttgcattgt tgtatcaatt aattgtgtta gtctttgtat   1980
attcttacat aacggtccaa gtttgttgaa atagtttact tactaaactt ttcctaatgg   2040
ggtcaaattt tattttatag gaaaaggaga gattgcaact tgttccaagg acatgaactc   2100
ggatcttttc ttcgcggtgt taggaggttt gggtcaattc ggcattataa caagagccag   2160
aattaaactt gaagtagctc cgaaaagggt atgttaaatt tgtaaattat gcaactacag   2220
aaaattctat gaaatttatg aatgaacata tatgcatttt tggatttttg taggccaagt   2280
ggttaaggtt tctatacata gatttctccg aattcacaag agatcaagaa cgagtgatat   2340
cgaaaacgga cggtgtagat ttcttagaag gttccattat ggtggaccat ggcccaccgg   2400
ataactggag atccacgtat tatccaccgt ccgatcactt gaggatcgcc tcaatggtca   2460
aacgacatcg tgtcatctac tgccttgaag tcgtcaagta ttacgacgaa acttctcaat   2520
acacagtcaa cgaggtccgt acatacatac aatcataaat catacatgta taattgggag   2580
atctttatgc attattcaat tatattaatt tactttagtt atttaactta tgcaggaaat   2640
ggaggagtta agcgatagtt taaaccatgt aagagggttt atgtacgaga aagatgtgac   2700
gtatatggat ttcctaaacc gagttcgaac cggagagcta aacctgaaat ccaaaggcca   2760
atgggatgtt ccacatccat ggcttaatct cttcgtacca aaaactcaaa tctccaaatt   2820
tgatgatggt gtttttaagg gtattatcct aagaaataac atcactagcg gtcctgttct   2880
tgtttatcct atgaatcgca acaagtaagt ttaactcgat attgcaaaat ttactatcta   2940
```

```
cattttcgtt ttggaatccg aaatattctt acaagctaat tttatgcggc gtttttaggt   3000

ggaatgatcg gatgtctgcc gctatacccg aggaagatgt attttatgcg gtagggtttt   3060

taagatccgc gggttttgac aattgggagg cttttgatca agaaaacatg gaaatactga   3120

agttttgtga ggatgctaat atgggggtta tacaatatct tccttatcat tcatcacaag   3180

aaggatgggt tagacatttt ggtccgaggt ggaatatttt cgtagagaga aaatataaat   3240

atgatcccaa aatgatatta tcaccgggac aaaatatatt tcaaaaaata aactcgagtt   3300

ag                                                                  3302
```

<210> SEQ ID NO 6
<211> LENGTH: 523
<212> TYPE: PRT
<213> ORGANISM: Arabidopsis thaliana

<400> SEQUENCE: 6

```
Met Ala Ser Tyr Asn Leu Arg Ser Gln Val Arg Leu Ile Ala Ile Thr
1               5                   10                  15

Ile Val Ile Ile Ile Thr Leu Ser Thr Pro Ile Thr Thr Asn Thr Ser
            20                  25                  30

Pro Gln Pro Trp Asn Ile Leu Ser His Asn Glu Phe Ala Gly Lys Leu
        35                  40                  45

Thr Ser Ser Ser Ser Ser Val Glu Ser Ala Ala Thr Asp Phe Gly His
    50                  55                  60

Val Thr Lys Ile Phe Pro Ser Ala Val Leu Ile Pro Ser Ser Val Glu
65                  70                  75                  80

Asp Ile Thr Asp Leu Ile Lys Leu Ser Phe Asp Ser Gln Leu Ser Phe
                85                  90                  95

Pro Leu Ala Ala Arg Gly His Gly His Ser His Arg Gly Gln Ala Ser
            100                 105                 110

Ala Lys Asp Gly Val Val Val Asn Met Arg Ser Met Val Asn Arg Asp
        115                 120                 125

Arg Gly Ile Lys Val Ser Arg Thr Cys Leu Tyr Val Asp Val Asp Ala
    130                 135                 140

Ala Trp Leu Trp Ile Glu Val Leu Asn Lys Thr Leu Glu Leu Gly Leu
145                 150                 155                 160

Thr Pro Val Ser Trp Thr Asp Tyr Leu Tyr Leu Thr Val Gly Gly Thr
                165                 170                 175

Leu Ser Asn Gly Gly Ile Ser Gly Gln Thr Phe Arg Tyr Gly Pro Gln
            180                 185                 190

Ile Thr Asn Val Leu Glu Met Asp Val Ile Thr Gly Lys Gly Glu Ile
        195                 200                 205

Ala Thr Cys Ser Lys Asp Met Asn Ser Asp Leu Phe Phe Ala Val Leu
    210                 215                 220

Gly Gly Leu Gly Gln Phe Gly Ile Ile Thr Arg Ala Arg Ile Lys Leu
225                 230                 235                 240

Glu Val Ala Pro Lys Arg Ala Lys Trp Leu Arg Phe Leu Tyr Ile Asp
                245                 250                 255

Phe Ser Glu Phe Thr Arg Asp Gln Glu Arg Val Ile Ser Lys Thr Asp
            260                 265                 270

Gly Val Asp Phe Leu Glu Gly Ser Ile Met Val Asp His Gly Pro Pro
        275                 280                 285

Asp Asn Trp Arg Ser Thr Tyr Tyr Pro Pro Ser Asp His Leu Arg Ile
    290                 295                 300
```

-continued

```
Ala Ser Met Val Lys Arg His Arg Val Ile Tyr Cys Leu Glu Val Val
305                 310                 315                 320

Lys Tyr Tyr Asp Glu Thr Ser Gln Tyr Thr Val Asn Glu Glu Met Glu
                325                 330                 335

Glu Leu Ser Asp Ser Leu Asn His Val Arg Gly Phe Met Tyr Glu Lys
            340                 345                 350

Asp Val Thr Tyr Met Asp Phe Leu Asn Arg Val Arg Thr Gly Glu Leu
        355                 360                 365

Asn Leu Lys Ser Lys Gly Gln Trp Asp Val Pro His Pro Trp Leu Asn
    370                 375                 380

Leu Phe Val Pro Lys Thr Gln Ile Ser Lys Phe Asp Asp Gly Val Phe
385                 390                 395                 400

Lys Gly Ile Ile Leu Arg Asn Asn Ile Thr Ser Gly Pro Val Leu Val
                405                 410                 415

Tyr Pro Met Asn Arg Asn Lys Trp Asn Asp Arg Met Ser Ala Ala Ile
            420                 425                 430

Pro Glu Glu Asp Val Phe Tyr Ala Val Gly Phe Leu Arg Ser Ala Gly
        435                 440                 445

Phe Asp Asn Trp Glu Ala Phe Asp Gln Glu Asn Met Glu Ile Leu Lys
    450                 455                 460

Phe Cys Glu Asp Ala Asn Met Gly Val Ile Gln Tyr Leu Pro Tyr His
465                 470                 475                 480

Ser Ser Gln Glu Gly Trp Val Arg His Phe Gly Pro Arg Trp Asn Ile
                485                 490                 495

Phe Val Glu Arg Lys Tyr Lys Tyr Asp Pro Lys Met Ile Leu Ser Pro
            500                 505                 510

Gly Gln Asn Ile Phe Gln Lys Ile Asn Ser Ser
        515                 520
```

<210> SEQ ID NO 7
<211> LENGTH: 2782
<212> TYPE: DNA
<213> ORGANISM: Arabidopsis thaliana

<400> SEQUENCE: 7

```
atgactaata ctctctgttt aagcctcatc accctaataa cgctttttat aagtttaacc      60

ccaaccttaa tcaaatcaga tgagggcatt gatgttttct tacccatatc actcaacctt     120

acggtcctaa ccgatccctt ctccatctct gccgcttctc acgacttcgg taacataacc     180

gacgaaaatc ccggcgccgt cctctgccct tcctccacca cggaggtggc tcgtctcctc     240

cgtttcgcta acggaggatt ctcttacaat aaaggctcaa ccagccccgc gtctactttc     300

aaagtggctg ctcgaggcca aggccactcc ctccgtggcc aagcctctgc acccggaggt     360

gtcgtcgtga acatgacgtg tctcgccatg gcggctaaac cagcggcggt tgttatctcg     420

gcagacggga cttacgctga cgtggctgcc gggacgatgt gggtggatgt tctgaaggcg     480

gcggtggata gaggcgtctc gccggttaca tggacggatt atttgtatct cagcgtcggc     540

gggacgttgt cgaacgctgg aatcggtggt cagacgttta gacacggccc tcagattagt     600

aacgttcatg agcttgacgt tattaccggt acgtaaatac caaaacttca ctaatctcgt     660

tacaattttt taattttttg gtaatataaa ttttgtacgg ctcaactctt aattaagaat     720

gaaacagtat ctatgatctt ctagatgctc tttttttgtc tgcaagcttt aattgtagta     780

acatcagcga tatatatatc acatgcatgt gtattattga tgataatata taatgtttta     840
```

-continued

```
gttacaaatt tgattctcaa ggtaaaactc acacgccata accagtataa aactccaaaa    900
atcacgtttt ggtcagaaat acatatcctt cattaacagt agttatgcta taatttgtga    960
ttataaataa ctccggagtt tgttcacaat actaaatttc aggaaaaggt gaaatgatga   1020
cttgctctcc aaagttaaac cctgaattgt tctatggagt tttaggaggt ttgggtcaat   1080
tcggtattat aacgagggcc aggattgcgt tggatcatgc acccacaagg gtatgtatca   1140
tgcatctata gtgtaatcaa tttataattt taatgtagtg gtcctaaatc caaaatttga   1200
tttgatttgg ttggaacgta cgtatatata ataagtcaaa aggctgattt tgaagacgaa   1260
tttatatact tttgttgaat taaatctgat tttgcttacg ttttattaga ttctgcgtaa   1320
taaatcctag gacttgctcg agtgtaatct tgtcttatgc ttgcaaatct tgttgatgtc   1380
aatatctaat ctttttttatt atatttccct acgtaagttt tagatatagt tattttaaac   1440
tgctataaat tgtgtacgta tagactttag ataaaaagtt gtggtcgctt gcacctattt   1500
gtttatcgct atagtgattc aaaggtctat atatgattct tggtttttct ttttgaaaaa   1560
aatagaccat acaatccaag gaagatgatc ttaaatggac taatttatgg atataaattg   1620
atatacaaat ctgcaggtga aatggtctcg catactctac agtgacttct cggcttttaa   1680
aagagaccaa gagcgtttaa tatcaatgac caatgatctc ggagttgact ttttggaagg   1740
tcaacttatg atgtcaaatg gcttcgtaga cacctctttc ttcccactct ccgatcaaac   1800
aagagtcgca tctcttgtga atgaccaccg gatcatctat gttctcgaag tagccaagta   1860
ttatgacaga accacccttc ccattattga ccaggtacta aaatccatta ttcatgatga   1920
ttatcttcac acaatcagta tcatcaccaa ttaccatcat cacttgtcat atatgatcca   1980
aagtaaatat atcacatgat ataaataaat cgttcaaatc tttttttttta aagaataaaa   2040
gaatcatttt caagcattac tcatacacat ctacgaatca ccgtgaccat atataaccat   2100
acgcttatta aataatcatt tttgtttgta ggtgattgac acgttaagta gaactctagg   2160
tttcgctcca gggtttatgt tcgtacaaga tgttccgtat ttcgatttct tgaaccgtgt   2220
ccgaaacgaa gaagataaac tcagatcttt aggactatgg gaagttcctc atccatggct   2280
taacatcttt gtcccggggt ctcgaatcca agattttcat gatggtgtta ttaatggcct   2340
tcttctaaac caaacctcaa cttctggtgt tactctcttc tatcccacaa accgaaacaa   2400
gtaaatattt actttttgat tttgttttat ttgaaagtat atcccaataa tgtatgttaa   2460
attgttaaca agaatttatt ttattaatag atggaacaac cgcatgtcaa cgatgacacc   2520
ggacgaagat gtttttttatg tgatcggatt actgcaatca gctggtggat ctcaaaattg   2580
gcaagaactt gaaaatctca acgacaaggt tattcagttt tgtgaaaact cgggaattaa   2640
gattaaggaa tatttgatgc actatacaag aaaagaagat tgggttaaac attttggacc   2700
aaaatgggat gattttttaa gaaagaaaat tatgtttgat cccaaaagac tattgtctcc   2760
aggacaagac atatttaatt aa                                            2782
```

```
<210> SEQ ID NO 8
<211> LENGTH: 524
<212> TYPE: PRT
<213> ORGANISM: Arabidopsis thaliana

<400> SEQUENCE: 8

Met Thr Asn Thr Leu Cys Leu Ser Leu Ile Thr Leu Ile Thr Leu Phe
1               5                   10                  15

Ile Ser Leu Thr Pro Thr Leu Ile Lys Ser Asp Glu Gly Ile Asp Val
            20                  25                  30
```

```
Phe Leu Pro Ile Ser Leu Asn Leu Thr Val Leu Thr Asp Pro Phe Ser
        35                  40                  45

Ile Ser Ala Ala Ser His Asp Phe Gly Asn Ile Thr Asp Glu Asn Pro
    50                  55                  60

Gly Ala Val Leu Cys Pro Ser Ser Thr Thr Glu Val Ala Arg Leu Leu
65                  70                  75                  80

Arg Phe Ala Asn Gly Gly Phe Ser Tyr Asn Lys Gly Ser Thr Ser Pro
                85                  90                  95

Ala Ser Thr Phe Lys Val Ala Ala Arg Gly Gln Gly His Ser Leu Arg
            100                 105                 110

Gly Gln Ala Ser Ala Pro Gly Gly Val Val Val Asn Met Thr Cys Leu
        115                 120                 125

Ala Met Ala Ala Lys Pro Ala Ala Val Val Ile Ser Ala Asp Gly Thr
    130                 135                 140

Tyr Ala Asp Val Ala Ala Gly Thr Met Trp Val Asp Val Leu Lys Ala
145                 150                 155                 160

Ala Val Asp Arg Gly Val Ser Pro Val Thr Trp Thr Asp Tyr Leu Tyr
                165                 170                 175

Leu Ser Val Gly Gly Thr Leu Ser Asn Ala Gly Ile Gly Gly Gln Thr
            180                 185                 190

Phe Arg His Gly Pro Gln Ile Ser Asn Val His Glu Leu Asp Val Ile
        195                 200                 205

Thr Gly Lys Gly Glu Met Met Thr Cys Ser Pro Lys Leu Asn Pro Glu
    210                 215                 220

Leu Phe Tyr Gly Val Leu Gly Gly Leu Gly Gln Phe Gly Ile Ile Thr
225                 230                 235                 240

Arg Ala Arg Ile Ala Leu Asp His Ala Pro Thr Arg Val Lys Trp Ser
                245                 250                 255

Arg Ile Leu Tyr Ser Asp Phe Ser Ala Phe Lys Arg Asp Gln Glu Arg
            260                 265                 270

Leu Ile Ser Met Thr Asn Asp Leu Gly Val Asp Phe Leu Glu Gly Gln
        275                 280                 285

Leu Met Met Ser Asn Gly Phe Val Asp Thr Ser Phe Phe Pro Leu Ser
    290                 295                 300

Asp Gln Thr Arg Val Ala Ser Leu Val Asn Asp His Arg Ile Ile Tyr
305                 310                 315                 320

Val Leu Glu Val Ala Lys Tyr Tyr Asp Arg Thr Thr Leu Pro Ile Ile
                325                 330                 335

Asp Gln Val Ile Asp Thr Leu Ser Arg Thr Leu Gly Phe Ala Pro Gly
            340                 345                 350

Phe Met Phe Val Gln Asp Val Pro Tyr Phe Asp Phe Leu Asn Arg Val
        355                 360                 365

Arg Asn Glu Glu Asp Lys Leu Arg Ser Leu Gly Leu Trp Glu Val Pro
    370                 375                 380

His Pro Trp Leu Asn Ile Phe Val Pro Gly Ser Arg Ile Gln Asp Phe
385                 390                 395                 400

His Asp Gly Val Ile Asn Gly Leu Leu Leu Asn Gln Thr Ser Thr Ser
                405                 410                 415

Gly Val Thr Leu Phe Tyr Pro Thr Asn Arg Asn Lys Trp Asn Asn Arg
            420                 425                 430

Met Ser Thr Met Thr Pro Asp Glu Asp Val Phe Tyr Val Ile Gly Leu
        435                 440                 445
```

```
Leu Gln Ser Ala Gly Gly Ser Gln Asn Trp Gln Glu Leu Glu Asn Leu
    450                 455                 460

Asn Asp Lys Val Ile Gln Phe Cys Glu Asn Ser Gly Ile Lys Ile Lys
465                 470                 475                 480

Glu Tyr Leu Met His Tyr Thr Arg Lys Glu Asp Trp Val Lys His Phe
                485                 490                 495

Gly Pro Lys Trp Asp Asp Phe Leu Arg Lys Lys Ile Met Phe Asp Pro
            500                 505                 510

Lys Arg Leu Leu Ser Pro Gly Gln Asp Ile Phe Asn
        515                 520


<210> SEQ ID NO 9
<211> LENGTH: 2805
<212> TYPE: DNA
<213> ORGANISM: Arabidopsis thaliana

<400> SEQUENCE: 9

atgacgtcaa gctttcttct cctgacgttc gccatatgta aactgatcat agccgtgggt      60

ctaaacgtgg gccccagtga gctcctccgc atcggagcca tagatgtcga cggccacttc     120

accgtccacc cttccgactt agcctccgtc tcctcagact tcggtatgct gaagtcacct     180

gaagagccat tggccgtgct tcatccatca tcggccgaag acgtggcacg actcgtcaga     240

acagcttacg gttcagccac ggcgtttccg gtctcagccc gaggccacgg ccattccata     300

aacggacaag ccgcggcggg gaggaacggt gtggtggttg aaatgaacca cggcgtaacc     360

gggacgccca agccactcgt ccgaccggat gaaatgtatg tggatgtatg gggtggagag     420

ttatgggtcg atgtgttgaa gaaaacgttg gagcatggct tagcaccaaa atcatggacg     480

gattacttgt atctaaccgt tggaggtaca ctctccaatg caggaatcag tggtcaagct     540

tttcaccatg gtcctcaaat tagtaacgtc cttgagctcg acgttgtaac tggttagtat     600

taaaacattc aagttcatat attttaaatg cttttgtctg aagttttact aataacaaga     660

aattgatacc aaaaagtagg gaaaggagag gtgatgagat gctcagaaga agagaacaca     720

aggctattcc atggagttct tggtggatta ggtcaatttg ggatcatcac tcgagcacga     780

atctctctcg aaccagctcc ccaaagggta atattttttt aatgactagc tatcaaaaat     840

ccctggcggg tccatacgtt gtaatctttt tagtttttac tgttgatggt atttttttata     900

tattttggat aataaaaccc taaaatggta tattgtgatg acaggtgaga tggatacggg     960

tattgtattc gagcttcaaa gtgtttacgg aggaccaaga gtacttaatc tcaatgcatg    1020

gtcaattaaa gtttgattac gtggaaggtt ttgtgattgt ggacgaagga ctcgtcaaca    1080

attggagatc ttctttcttc tctccacgta accccgtcaa gatctcctct gttagttcca    1140

acggctctgt tttgtattgc cttgagatca ccaagaacta ccacgactcc gactccgaaa    1200

tcgttgatca ggtcactttc attattcact tagaaaaaag cgatattttc atttttttata    1260

ttgatgaata tctggaagga tttaacgcta tgcgactatt gggaaatcat tatgaaaaaa    1320

tatttagttt atatgattga aagtggtctc catagtattt ttgttgtgtc gactttatta    1380

taacttaaat ttggaagagg acatgaagaa gaagccagag aggatctaca gagatctagc    1440

ttttccacct gaacttaata atgcacattt atataattat ttttcttctt ctaaagttta    1500

gtttatcact agcgaattaa tcatggttac taattaagta gtggacaggg tcatggacca    1560

ctcactcacc aaataatgat tcctctttac tcttaagttt aattttaata aaaccaactc    1620

tactggaatc ttaacttatc cttggttttg gtaggctttt atagcaacac ggttttttta    1680
```

-continued

```
attttcctat tccagatttt gtatattaaa tgtcgatttt ttttcttttt gtttcaggaa   1740

gttgagattc tgatgaagaa attgaatttc ataccgacat cggtctttac aacggattta   1800

caatatgtgg actttctcga ccgggtacac aaggccgaat tgaagctccg gtccaagaat   1860

ttatgggagg ttccacaccc atggctcaac ctcttcgtgc caaaatcaag aatctctgac   1920

ttcgataaag gcgttttcaa gggcattttg ggaaataaaa caagtggccc tattcttatc   1980

taccccatga acaaagacaa gtaagtcttg acattaccat tgattactac ttctaaattt   2040

cttctctaga aaaaagaata aaacgagttt tgcattgcat gcatgcaaag ttacacttgt   2100

ggggattaat tagtggtcca agaaaaaaag tttgtcaaaa ttgaaaaaaa ctagacacgt   2160

ggtacatggg attgtccgaa aaacgttgtc cacatgtgca tcgaaccagc taagattgac   2220

aacaacactt cgtcggctcg tatttctctt tttgttttgt gaccaaatcc gatggtccag   2280

attgggttta tttgttttta agttcctaga actcatggtg ggtgggtccc aatcagattc   2340

tcctagacca aaccgatctc aacgaaccct ccgcacatca ttgattatta cattaatata   2400

gatattgtcg ttgctgacgt gtcgtaattt gatgttattg tcagatggga cgagaggagc   2460

tcagccgtga cgccggatga ggaagttttc tatctggtgg ctctattgag atcagcttta   2520

acggacggtg aagagacaca gaagctagag tatctgaaag atcagaaccg tcggatcttg   2580

gagttctgtg aacaagccaa gatcaatgtg aagcagtatc ttcctcacca cgcaacacag   2640

gaagagtggg tggctcattt tggggacaag tgggatcggt tcagaagctt aaaggctgag   2700

tttgatccgc gacacatact cgctactggt cagagaatct ttcaaaaccc atctttgtct   2760

ttgtttcctc cgtcgtcgtc ttcttcgtca gcggcttcat ggtga                   2805
```

```
<210> SEQ ID NO 10
<211> LENGTH: 536
<212> TYPE: PRT
<213> ORGANISM: Arabidopsis thaliana

<400> SEQUENCE: 10

Met Thr Ser Ser Phe Leu Leu Leu Thr Phe Ala Ile Cys Lys Leu Ile
1               5                   10                  15

Ile Ala Val Gly Leu Asn Val Gly Pro Ser Glu Leu Leu Arg Ile Gly
            20                  25                  30

Ala Ile Asp Val Asp Gly His Phe Thr Val His Pro Ser Asp Leu Ala
        35                  40                  45

Ser Val Ser Ser Asp Phe Gly Met Leu Lys Ser Pro Glu Glu Pro Leu
    50                  55                  60

Ala Val Leu His Pro Ser Ser Ala Glu Asp Val Ala Arg Leu Val Arg
65                  70                  75                  80

Thr Ala Tyr Gly Ser Ala Thr Ala Phe Pro Val Ser Ala Arg Gly His
                85                  90                  95

Gly His Ser Ile Asn Gly Gln Ala Ala Ala Gly Arg Asn Gly Val Val
            100                 105                 110

Val Glu Met Asn His Gly Val Thr Gly Thr Pro Lys Pro Leu Val Arg
        115                 120                 125

Pro Asp Glu Met Tyr Val Asp Val Trp Gly Gly Glu Leu Trp Val Asp
    130                 135                 140

Val Leu Lys Lys Thr Leu Glu His Gly Leu Ala Pro Lys Ser Trp Thr
145                 150                 155                 160

Asp Tyr Leu Tyr Leu Thr Val Gly Gly Thr Leu Ser Asn Ala Gly Ile
                165                 170                 175
```

```
Ser Gly Gln Ala Phe His His Gly Pro Gln Ile Ser Asn Val Leu Glu
            180                 185                 190

Leu Asp Val Val Thr Gly Lys Gly Glu Val Met Arg Cys Ser Glu Glu
        195                 200                 205

Glu Asn Thr Arg Leu Phe His Gly Val Leu Gly Gly Leu Gly Gln Phe
    210                 215                 220

Gly Ile Ile Thr Arg Ala Arg Ile Ser Leu Glu Pro Ala Pro Gln Arg
225                 230                 235                 240

Val Arg Trp Ile Arg Val Leu Tyr Ser Ser Phe Lys Val Phe Thr Glu
                245                 250                 255

Asp Gln Glu Tyr Leu Ile Ser Met His Gly Gln Leu Lys Phe Asp Tyr
            260                 265                 270

Val Glu Gly Phe Val Ile Val Asp Glu Gly Leu Val Asn Asn Trp Arg
        275                 280                 285

Ser Ser Phe Phe Ser Pro Arg Asn Pro Val Lys Ile Ser Ser Val Ser
    290                 295                 300

Ser Asn Gly Ser Val Leu Tyr Cys Leu Glu Ile Thr Lys Asn Tyr His
305                 310                 315                 320

Asp Ser Asp Ser Glu Ile Val Asp Gln Glu Val Glu Ile Leu Met Lys
                325                 330                 335

Lys Leu Asn Phe Ile Pro Thr Ser Val Phe Thr Thr Asp Leu Gln Tyr
            340                 345                 350

Val Asp Phe Leu Asp Arg Val His Lys Ala Glu Leu Lys Leu Arg Ser
        355                 360                 365

Lys Asn Leu Trp Glu Val Pro His Pro Trp Leu Asn Leu Phe Val Pro
    370                 375                 380

Lys Ser Arg Ile Ser Asp Phe Asp Lys Gly Val Phe Lys Gly Ile Leu
385                 390                 395                 400

Gly Asn Lys Thr Ser Gly Pro Ile Leu Ile Tyr Pro Met Asn Lys Asp
                405                 410                 415

Lys Trp Asp Glu Arg Ser Ser Ala Val Thr Pro Asp Glu Glu Val Phe
            420                 425                 430

Tyr Leu Val Ala Leu Leu Arg Ser Ala Leu Thr Asp Gly Glu Glu Thr
        435                 440                 445

Gln Lys Leu Glu Tyr Leu Lys Asp Gln Asn Arg Arg Ile Leu Glu Phe
    450                 455                 460

Cys Glu Gln Ala Lys Ile Asn Val Lys Gln Tyr Leu Pro His His Ala
465                 470                 475                 480

Thr Gln Glu Glu Trp Val Ala His Phe Gly Asp Lys Trp Asp Arg Phe
                485                 490                 495

Arg Ser Leu Lys Ala Glu Phe Asp Pro Arg His Ile Leu Ala Thr Gly
            500                 505                 510

Gln Arg Ile Phe Gln Asn Pro Ser Leu Ser Leu Phe Pro Pro Ser Ser
        515                 520                 525

Ser Ser Ser Ser Ala Ala Ser Trp
    530                 535
```

<210> SEQ ID NO 11
<211> LENGTH: 1936
<212> TYPE: DNA
<213> ORGANISM: Arabidopsis thaliana

<400> SEQUENCE: 11

```
atgcttatag taagaagttt caccatcttg cttctcagct gcatagcctt taagttggct      60
```

-continued

```
tgctgcttct ctagcagcat ttcttctttg aaggcgcttc ccctagtagg ccatttggag    120

tttgaacatg tccatcacgc ctccaaagat tttggaaatc gataccagtt gatccctttg    180

gcggtcttac atcccaaatc ggtaagcgac atcgcctcaa cgatacgaca catctggatg    240

atgggcactc attcacagct tacagtggca gcgagaggtc gtggacattc actccaaggc    300

caagctcaaa caagacatgg aattgttata cacatggaat cactccatcc ccagaagctg    360

caggtctaca gtgtggattc ccctgctcca tatgttgatg tgtctggtgg tgagctgtgg    420

ataaacattt tgcatgagac cctcaagtac gggcttgcac caaaatcatg gacggattac    480

ctgcatttaa ctgtaggtgg tactctgtcc aatgctggaa taagcggcca ggcattccga    540

catggaccac agatcagcaa tgttcatcaa ctggagattg tcacaggtta gttcagagtt    600

gcagtattcg tgttttgaaa gcatagactc tatatggttg gtgactatta acaacatgaa    660

gagattcccg agaatagcta cccactaatg tcatgcctat ttattgactg caggaaaagg    720

cgagatccta aactgtacaa agaggcagaa cagcgactta tttaatggtg ttcttggtgg    780

tttaggtcag tttggcatca taacgcgggc aagaatagca ttggaaccag caccaaccat    840

ggtaaacaat aaataaataa aaaacttaaa aactgaacac gcgtgtgtcc tcctaactct    900

gtataatgga caggtaaaat ggataagagt gttatacctg gattttgcag cttttgccaa    960

ggaccaagag caactaatat ctgcccaggg ccacaaattc gattacatag aagggtttgt   1020

gataataaac aggacaggcc tcctgaacag ctggaggttg tctttcaccg cagaagagcc   1080

tttagaagca agccaattca agtttgatgg aaggactctg tattgtctgg agctagccaa   1140

gtatttgaag caagataaca aagacgtaat caaccaggtg agaaaacaga gtagaagcaa   1200

tcggtagaat cttctttggt agatgacatt cattggaact gaaaatatat atatatttgt   1260

ccaatccagg aagtgaaaga aacattatca gagctaagct acgtgacgtc gacactgttt   1320

acaacggagg tagcatatga agcattcttg gacagggtac atgtgtctga ggtaaaactc   1380

cgatcgaaag ggcagtggga ggtgccacat ccatggctga acctcctggt accaagaagc   1440

aaaatcaatg aatttgcaag aggtgtattt ggaaacatac taacggatac aagcaacggc   1500

ccagtcatcg tctacccagt gaacaaatca aagtaagaaa gaaagaaaga aagagctagt   1560

catgattttg tttcttttca cttgttgaca aaacaaaagc atgttggtga gcaggtggga   1620

caatcaaaca tcagcagtaa caccggagga agaggtattc tacctggtgg cgatcctaac   1680

atcggcatct ccagggtcgg caggaaagga tggagtagaa gagatcttga ggcggaacag   1740

aagaatactg gaattcagtg aagaagcagg gatagggttg aagcagtatc tgccacatta   1800

cacgacaaga gaagagtgga gatcccattt cggggacaag tggggagaat ttgtgaggag   1860

gaaatccaga tatgatccat tggcaattct tgcgcctggc caccgaattt ttcaaaaggc   1920

agtctcatac tcatga                                                   1936

<210> SEQ ID NO 12
<211> LENGTH: 504
<212> TYPE: PRT
<213> ORGANISM: Arabidopsis thaliana

<400> SEQUENCE: 12

Met Leu Ile Val Arg Ser Phe Thr Ile Leu Leu Leu Ser Cys Ile Ala
1               5                   10                  15

Phe Lys Leu Ala Cys Cys Phe Ser Ser Ser Ile Ser Ser Leu Lys Ala
            20                  25                  30

Leu Pro Leu Val Gly His Leu Glu Phe Glu His Val His His Ala Ser
```

```
        35                  40                  45

Lys Asp Phe Gly Asn Arg Tyr Gln Leu Ile Pro Leu Ala Val Leu His
    50                  55                  60

Pro Lys Ser Val Ser Asp Ile Ala Ser Thr Ile Arg His Ile Trp Met
65                  70                  75                  80

Met Gly Thr His Ser Gln Leu Thr Val Ala Ala Arg Gly Arg Gly His
                85                  90                  95

Ser Leu Gln Gly Gln Ala Gln Thr Arg His Gly Ile Val Ile His Met
            100                 105                 110

Glu Ser Leu His Pro Gln Lys Leu Gln Val Tyr Ser Val Asp Ser Pro
        115                 120                 125

Ala Pro Tyr Val Asp Val Ser Gly Gly Glu Leu Trp Ile Asn Ile Leu
    130                 135                 140

His Glu Thr Leu Lys Tyr Gly Leu Ala Pro Lys Ser Trp Thr Asp Tyr
145                 150                 155                 160

Leu His Leu Thr Val Gly Gly Thr Leu Ser Asn Ala Gly Ile Ser Gly
                165                 170                 175

Gln Ala Phe Arg His Gly Pro Gln Ile Ser Asn Val His Gln Leu Glu
            180                 185                 190

Ile Val Thr Gly Lys Gly Glu Ile Leu Asn Cys Thr Lys Arg Gln Asn
        195                 200                 205

Ser Asp Leu Phe Asn Gly Val Leu Gly Gly Leu Gly Gln Phe Gly Ile
    210                 215                 220

Ile Thr Arg Ala Arg Ile Ala Leu Glu Pro Ala Pro Thr Met Asp Gln
225                 230                 235                 240

Glu Gln Leu Ile Ser Ala Gln Gly His Lys Phe Asp Tyr Ile Glu Gly
                245                 250                 255

Phe Val Ile Ile Asn Arg Thr Gly Leu Leu Asn Ser Trp Arg Leu Ser
            260                 265                 270

Phe Thr Ala Glu Glu Pro Leu Glu Ala Ser Gln Phe Lys Phe Asp Gly
        275                 280                 285

Arg Thr Leu Tyr Cys Leu Glu Leu Ala Lys Tyr Leu Lys Gln Asp Asn
    290                 295                 300

Lys Asp Val Ile Asn Gln Glu Val Lys Glu Thr Leu Ser Glu Leu Ser
305                 310                 315                 320

Tyr Val Thr Ser Thr Leu Phe Thr Thr Glu Val Ala Tyr Glu Ala Phe
                325                 330                 335

Leu Asp Arg Val His Val Ser Glu Val Lys Leu Arg Ser Lys Gly Gln
            340                 345                 350

Trp Glu Val Pro His Pro Trp Leu Asn Leu Leu Val Pro Arg Ser Lys
        355                 360                 365

Ile Asn Glu Phe Ala Arg Gly Val Phe Gly Asn Ile Leu Thr Asp Thr
    370                 375                 380

Ser Asn Gly Pro Val Ile Val Tyr Pro Val Asn Lys Ser Lys Trp Asp
385                 390                 395                 400

Asn Gln Thr Ser Ala Val Thr Pro Glu Glu Val Phe Tyr Leu Val
                405                 410                 415

Ala Ile Leu Thr Ser Ala Ser Pro Gly Ser Ala Gly Lys Asp Gly Val
            420                 425                 430

Glu Glu Ile Leu Arg Arg Asn Arg Arg Ile Leu Glu Phe Ser Glu Glu
        435                 440                 445

Ala Gly Ile Gly Leu Lys Gln Tyr Leu Pro His Tyr Thr Thr Arg Glu
    450                 455                 460
```

```
Glu Trp Arg Ser His Phe Gly Asp Lys Trp Gly Glu Phe Val Arg Arg
465                 470                 475                 480

Lys Ser Arg Tyr Asp Pro Leu Ala Ile Leu Ala Pro Gly His Arg Ile
                485                 490                 495

Phe Gln Lys Ala Val Ser Tyr Ser
            500


<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 13

cggtcgacat gggattgacc tcatccttac g                                    31


<210> SEQ ID NO 14
<211> LENGTH: 35
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 14

gcgtcgactt atacagttct aggtttcggc agtat                                35


<210> SEQ ID NO 15
<211> LENGTH: 33
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 15

gcggtaccag agagagaaac ataaacaaat ggc                                  33


<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 16

gcggtaccca attttacttc caccaaaatg c                                    31


<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 17

gcggtacctt cattgataag aatcaagcta ttca                                 34


<210> SEQ ID NO 18
<211> LENGTH: 31
<212> TYPE: DNA
```

```
<213> ORGANISM: Artificial Sequence
<220> FEATURE:
<223> OTHER INFORMATION: Description of Artificial Sequence:
      oligonucleotide: primer or probe

<400> SEQUENCE: 18

gcggtaccca aagtggtgag aacgactaac a                                31


<210> SEQ ID NO 19
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 19

gcggtacccc cattaaccta cccgtttg                                    28


<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 20

gcggtaccag acgatgaacg tacttgtctg ta                               32


<210> SEQ ID NO 21
<211> LENGTH: 28
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 21

ggggtacctt gatgaatcgt gaaatgac                                    28


<210> SEQ ID NO 22
<211> LENGTH: 31
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 22

ggggtaccct ttcctcttgg ttttgtcctg t                                31


<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence:
      oligonucleotide: primer or probe

<400> SEQUENCE: 23

gctctagatc aggaaaagaa ccatgcttat ag                               32


<210> SEQ ID NO 24
<211> LENGTH: 32
<212> TYPE: DNA
<213> ORGANISM: Artificial Sequence
```

<220> FEATURE:
<223> OTHER INFORMATION: Description of Artificial Sequence: oligonucleotide: primer or probe

<400> SEQUENCE: 24
gctctagatc atgagtatga gactgccttt tg 32

<210> SEQ ID NO 25
<211> LENGTH: 1728
<212> TYPE: DNA
<213> ORGANISM: Arabidopsis thaliana

<400> SEQUENCE: 25
atgggattga cctcatcctt acggttccat agacaaaaca acaagacttt cctcggaatc 60
ttcatgatct tagttctaag ctgtatacca ggtagaacca atctttgttc caatcattct 120
gttagtaccc caaaagaatt accttcttca aatccttcag atattcgttc ctcattagtt 180
tcactagatt tggagggtta tataagcttc gacgatgtcc acaatgtggc caaggacttt 240
ggcaacagat accagttacc acctttggca attctacatc caaggtcagt tttgatattt 300
tcatcgatga tgaagcatat agtacatctg ggctccacct caaatcttac agtagcagct 360
agaggccatg gtcactcgct tcaaggacaa gctctagctc atcaaggtgt tgtcatcaaa 420
atggagtcac ttcgaagtcc tgatatcagg atttataagg ggaagcaacc atatgttgat 480
gtctcaggtg gtgaaatatg gataaacatt ctacgcgaga ctctaaaata cggtctttca 540
ccaaagtcct ggacagacta ccttcatttg accgttggag gtacactatc taatgctgga 600
atcagcggtc aagcattcaa gcatggaccc caaatcaaca acgtctacca gctagagatt 660
gttacaggga aaggagaagt cgtaacctgt tctgagaagc ggaattctga actttcttc 720 agtgttcttg gcgggcttgg acagtttggc ataatcaccc gggcacggat ctctcttgaa 780
ccagcaccgc atatggttaa atggatcagg gtactctact ctgacttttc tgcattttca 840
agggaccaag aatatctgat ttcgaaggag aaaacttttg attacgttga aggatttgtg 900
ataatcaata gaacagacct tctcaataat tggcgatcgt cattcagtcc caacgattcc 960
acacaggcaa gcagattcaa gtcagatggg aaaactcttt attgcctaga agtggtcaaa 1020
tatttcaacc cagaagaagc tagctctatg gatcaggaaa ctggcaagtt actttcagag 1080
ttaaattata ttccatccac tttgttttca tctgaagtgc catatatcga gtttctggat 1140
cgcgtgcata tcgcagagag aaaactaaga gcaaagggtt tatgggaggt tccacatccc 1200
tggctgaatc tcctgattcc taagagcagc atataccaat ttgctacaga agttttcaac 1260
aacattctca caagcaacaa caacggtcct atccttattt atccagtcaa tcaatccaag 1320
tggaagaaac atacatcttt gataactcca aatgaagata tattctatct cgtagccttt 1380
ctcccctctg cagtgccaaa ttcctcaggg aaaaacgatc tagagtacct tttgaaacaa 1440
aaccaaagag ttatgaactt ctgcgcagca gcaaacctca acgtgaagca gtatttgccc 1500
cattatgaaa ctcaaaaaga gtggaaatca cactttggca aaagatggga aacatttgca 1560
cagaggaaac aagcctacga ccctctagcg attctagcac ctggccaaag aatattccaa 1620
aagacaacag gaaaattatc tcccatccaa ctcgcaaagt caaaggcaac aggaagtcct 1680
caaaggtacc attacgcatc aatactgccg aaacctagaa ctgtataa 1728

<210> SEQ ID NO 26
<211> LENGTH: 1506
<212> TYPE: DNA
<213> ORGANISM: Arabidopsis thaliana

<400> SEQUENCE: 26
atggctaatc ttcgtttaat gatcacttta atcacggttt taatgatcac caaatcatca 60
aacggtatta aaattgattt acctaaatcc cttaacctca ccctctctac cgatccttcc 120
atcatctccg cagcctctca tgacttcgga aacataacca ccgtgacccc cggcggcgta 180
atctgcccct cctccaccgc tgatatctct cgtctcctcc aatacgccgc aaacggaaaa 240
agtacattcc aagtagcggc tcgtggccaa ggccactcct taaacggcca agcctcggtc 300
tccggcggag taatcgtcaa catgacgtgt atcactgacg tggtggtttc aaaagacaag 360
aagtacgctg acgtggcggc cgggacgtta tgggtggatg tgcttaagaa gacggcggag 420
aaaggggtgt cgccggtttc ttggacggat tatttgcata taaccgtcgg aggaacgttg 480
tcgaatggtg gaattggtgg tcaagtgttt cgaaacggtc ctcttgttag taacgtcctt 540
gaattggacg ttattactgg gaaaggtgaa atgttgacat gctcgcgaca gctaaaccca 600
gaattgttct atggagtgtt aggaggtttg ggtcaatttg gaattataac gagagccaga 660
attgttttgg accatgcacc taaacgggcc aaatggtttc ggatgctcta cagtgatttc 720
acaactttta caaaggacca agaacgtttg atatcaatgg caaacgatat tggagtcgac 780
tatttagaag gtcaaatatt tctatcaaac ggtgtcgttg acacctcttt tttcccacct 840
tcagatcaat ctaaagtcgc tgatctagtc aagcaacacg gtatcatcta tgttcttgaa 900
gtagccaagt attatgatga tcccaatctc cccatcatca gcaaggttat tgacacatta 960
acgaaaacat taagttactt gcccgggttc atatcaatgc acgacgtggc ctacttcgat 1020
ttcttgaacc gtgtacatgt cgaagaaaat aaactcagat ctttgggatt atgggaactt 1080
cctcatcctt ggcttaacct ctacgttcct aaatctcgga ttctcgattt tcataacggt 1140
gttgtcaaag acattcttct taagcaaaaa tcagcttcgg gactcgctct tctctatcca 1200
acaaaccgga ataaatggga caatcgtatg tcggcgatga taccagagat cgatgaagat 1260
gttatatata ttatcggact actacaatcc gctaccccaa aggatcttcc agaagtggag 1320
agcgttaacg agaagataat taggttttgc aaggattcag gtattaagat taagcaatat 1380
ctaatgcatt atactagtaa agaagattgg attgagcatt ttggatcaaa atgggatgat 1440
ttttcgaaga ggaaagatct atttgatccc aagaaactgt tatctccagg gcaagacatc 1500
ttttga 1506

<210> SEQ ID NO 27
<211> LENGTH: 1572
<212> TYPE: DNA
<213> ORGANISM: Arabidopsis thaliana

<400> SEQUENCE: 27
atggcgagtt ataatcttcg ttcacaagtt cgtcttatag caataacaat agtaatcatc 60
attactctct caactccgat cacaaccaac acatcaccac aaccatggaa tatcctttca 120
cacaacgaat tcgccggaaa actcacctcc tcctcctcct ccgtcgaatc agccgccaca 180
gatttcggcc acgtcaccaa aatcttccct tccgccgtct taatcccttc ctccgttgaa 240
gacatcacag atctcataaa actctctttt gactctcaac tgtcttttcc tttagccgct 300
cgtggtcacg gacacagcca ccgtggccaa gcctcggcta aagacggagt tgtggtcaac 360
atgcggtcca tggtaaaccg ggatcgaggt atcaaggtgt ctaggacctg tttatatgtt 420
gacgtggacg ctgcgtggct atggattgag gtgttgaata aaactttgga gttagggtta 480

```
acgccggttt cttggacgga ttatttgtat ttaacagtcg gtgggacgtt atcaaacggc    540
ggaattagtg gacaaacgtt tcggtacggt ccacagatca ctaatgttct agagatggat    600
gttattactg gaaaaggaga gattgcaact tgttccaagg acatgaactc ggatcttttc    660
ttcgcggtgt taggaggttt gggtcaattc ggcattataa caagagccag aattaaactt    720
gaagtagctc cgaaaagggc caagtggtta aggtttctat acatagattt ctccgaattc    780
acaagagatc aagaacgagt gatatcgaaa acggacggtg tagatttctt agaaggttcc    840
attatggtgg accatggccc accggataac tggagatcca cgtattatcc accgtccgat    900
cacttgagga tcgcctcaat ggtcaaacga catcgtgtca tctactgcct tgaagtcgtc    960
aagtattacg acgaaacttc tcaatacaca gtcaacgagg aaatggagga gttaagcgat   1020
agtttaaacc atgtaagagg gtttatgtac gagaaagatg tgacgtatat ggatttccta   1080
aaccgagttc gaaccggaga gctaaacctg aaatccaaag gccaatggga tgttccacat   1140
ccatggctta atctcttcgt accaaaaact caaatctcca aatttgatga tggtgttttt   1200
aagggtatta tcctaagaaa taacatcact agcggtcctg ttcttgttta tcctatgaat   1260
cgcaacaagt ggaatgatcg gatgtctgcc gctatacccg aggaagatgt attttatgcg   1320
gtagggtttt taagatccgc gggttttgac aattgggagg cttttgatca agaaaacatg   1380
gaaatactga agttttgtga ggatgctaat atgggggtta tacaatatct tccttatcat   1440
tcatcacaag aaggatgggt tagacatttt ggtccgaggt ggaatatttt cgtagagaga   1500
aaatataaat atgatcccaa aatgatatta tcaccgggac aaaatatatt tcaaaaaata   1560
aactcgagtt ag                                                       1572
```

<210> SEQ ID NO 28
<211> LENGTH: 1575
<212> TYPE: DNA
<213> ORGANISM: Arabidopsis thaliana

<400> SEQUENCE: 28

```
atgactaata ctctctgttt aagcctcatc accctaataa cgctttttat aagtttaacc     60
ccaaccttaa tcaaatcaga tgagggcatt gatgttttct tacccatatc actcaacctt    120
acggtcctaa ccgatccctt ctccatctct gccgcttctc acgacttcgg taacataacc    180
gacgaaaatc ccggcgccgt cctctgccct tcctccacca cggaggtggc tcgtctcctc    240
cgtttcgcta acggaggatt ctcttacaat aaaggctcaa ccagccccgc gtctactttc    300
aaagtggctg ctcgaggcca aggccactcc ctccgtggcc aagcctctgc acccggaggt    360
gtcgtcgtga acatgacgtg tctcgccatg gcggctaaac cagcggcggt tgttatctcg    420
gcagacggga cttacgctga cgtggctgcc gggacgatgt gggtggatgt tctgaaggcg    480
gcggtggata gaggcgtctc gccggttaca tggacggatt atttgtatct cagcgtcggc    540
gggacgttgt cgaacgctgg aatcggtggt cagacgttta gacacggccc tcagattagt    600
aacgttcatg agcttgacgt tattaccgga aaaggtgaaa tgatgacttg ctctccaaag    660
ttaaaccctg aattgttcta tggagtttta ggaggtttgg gtcaattcgg tattataacg    720
agggccagga ttgcgttgga tcatgcaccc acaagggtga aatggtctcg catactctac    780
agtgacttct cggcttttaa aagagaccaa gagcgtttaa tatcaatgac caatgatctc    840
ggagttgact tttggaagg tcaacttatg atgtcaaatg gcttcgtaga cacctctttc     900
ttcccactct ccgatcaaac aagagtcgca tctcttgtga atgaccaccg gatcatctat    960
gttctcgaag tagccaagta ttatgacaga accacccttc ccattattga ccaggtgatt   1020
```

gacacgttaa gtagaactct aggtttcgct ccagggttta tgttcgtaca agatgttccg 1080
tatttcgatt tcttgaaccg tgtccgaaac gaagaagata aactcagatc tttaggacta 1140
tgggaagttc ctcatccatg gcttaacatc tttgtcccgg ggtctcgaat ccaagatttt 1200
catgatggtg ttattaatgg ccttcttcta aaccaaacct caacttctgg tgttactctc 1260
ttctatccca caaaccgaaa caaatggaac aaccgcatgt caacgatgac accggacgaa 1320
gatgtttttt atgtgatcgg attactgcaa tcagctggtg gatctcaaaa ttggcaagaa 1380
cttgaaaatc tcaacgacaa ggttattcag ttttgtgaaa actcgggaat taagattaag 1440
gaatatttga tgcactatac aagaaaagaa gattgggtta aacattttgg accaaaatgg 1500
gatgattttt taagaaagaa aattatgttt gatcccaaaa gactattgtc tccaggacaa 1560
gacatattta attaa 1575

<210> SEQ ID NO 29
<211> LENGTH: 1611
<212> TYPE: DNA
<213> ORGANISM: Arabidopsis thaliana

<400> SEQUENCE: 29
atgacgtcaa gctttcttct cctgacgttc gccatatgta aactgatcat agccgtgggt 60
ctaaacgtgg gccccagtga gctcctccgc atcggagcca tagatgtcga cggccacttc 120
accgtccacc cttccgactt agcctccgtc tcctcagact tcggtatgct gaagtcacct 180
gaagagccat tggccgtgct tcatccatca tcggccgaag acgtggcacg actcgtcaga 240
acagcttacg gttcagccac ggcgtttccg gtctcagccc gaggccacgg ccattccata 300
aacggacaag ccgcggcggg gaggaacggt gtggtggttg aaatgaacca cggcgtaacc 360
gggacgccca agccactcgt ccgaccggat gaaatgtatg tggatgtatg gggtggagag 420
ttatgggtcg atgtgttgaa gaaaacgttg gagcatggct tagcaccaaa atcatggacg 480
gattacttgt atctaaccgt tggaggtaca ctctccaatg caggaatcag tggtcaagct 540
tttcaccatg gtcctcaaat tagtaacgtc cttgagctcg acgttgtaac tgggaaagga 600
gaggtgatga gatgctcaga agaagagaac acaaggctat tccatggagt tcttggtgga 660
ttaggtcaat ttgggatcat cactcgagca cgaatctctc tcgaaccagc tccccaaagg 720
gtgagatgga tacgggtatt gtattcgagc ttcaaagtgt ttacggagga ccaagagtac 780
ttaatctcaa tgcatggtca attaaagttt gattacgtgg aaggttttgt gattgtggac 840
gaaggactcg tcaacaattg gagatcttct ttcttctctc cacgtaaccc cgtcaagatc 900
tcctctgtta gttccaacgg ctctgttttg tattgccttg agatcaccaa gaactaccac 960
gactccgact ccgaaatcgt tgatcaggaa gttgagattc tgatgaagaa attgaatttc 1020
ataccgacat cggtctttac aacggattta caatatgtgg actttctcga ccgggtacac 1080
aaggccgaat tgaagctccg gtccaagaat ttatgggagg ttccacaccc atggctcaac 1140
ctcttcgtgc caaaatcaag aatctctgac ttcgataaag gcgttttcaa gggcattttg 1200
ggaaataaaa caagtggccc tattcttatc taccccatga acaaagacaa atgggacgag 1260
aggagctcag ccgtgacgcc ggatgaggaa gttttctatc tggtggctct attgagatca 1320
gctttaacgg acggtgaaga gacacagaag ctagagtatc tgaaagatca gaaccgtcgg 1380
atcttggagt tctgtgaaca agccaagatc aatgtgaagc agtatcttcc tcaccacgca 1440
acacaggaag agtgggtggc tcattttggg gacaagtggg atcggttcag aagcttaaag 1500

-continued gctgagtttg atccgcgaca catactcgct actggtcaga gaatctttca aaacccatct 1560
ttgtctttgt ttcctccgtc gtcgtcttct tcgtcagcgg cttcatggtg a 1611

<210> SEQ ID NO 30
<211> LENGTH: 1515
<212> TYPE: DNA
<213> ORGANISM: Arabidopsis thaliana

<400> SEQUENCE: 30
atgcttatag taagaagttt caccatcttg cttctcagct gcatagcctt taagttggct 60
tgctgcttct ctagcagcat ttcttctttg aaggcgcttc ccctagtagg ccatttggag 120
tttgaacatg tccatcacgc ctccaaagat tttggaaatc gataccagtt gatccctttg 180
gcggtcttac atcccaaatc ggtaagcgac atcgcctcaa cgatacgaca catctggatg 240
atgggcactc attcacagct tacagtggca gcgagaggtc gtggacattc actccaaggc 300
caagctcaaa caagacatgg aattgttata cacatggaat cactccatcc ccagaagctg 360
caggtctaca gtgtggattc ccctgctcca tatgttgatg tgtctggtgg tgagctgtgg 420
ataaacattt tgcatgagac cctcaagtac gggcttgcac caaaatcatg gacggattac 480
ctgcatttaa ctgtaggtgg tactctgtcc aatgctggaa taagcggcca ggcattccga 540
catggaccac agatcagcaa tgttcatcaa ctggagattg tcacaggaaa aggcgagatc 600
ctaaactgta caaagaggca gaacagcgac ttatttaatg gtgttcttgg tggtttaggt 660
cagtttggca tcataacgcg ggcaagaata gcattggaac cagcaccaac catggaccaa 720
gagcaactaa tatctgccca gggccacaaa ttcgattaca tagaagggtt tgtgataata 780
aacaggacag gcctcctgaa cagctggagg ttgtctttca ccgcagaaga gcctttagaa 840
gcaagccaat tcaagtttga tggaaggact ctgtattgtc tggagctagc caagtatttg 900
aagcaagata acaaagacgt aatcaaccag gaagtgaaag aaacattatc agagctaagc 960
tacgtgacgt cgacactgtt tacaacggag gtagcatatg aagcattctt ggacagggta 1020
catgtgtctg aggtaaaact ccgatcgaaa gggcagtggg aggtgccaca tccatggctg 1080
aacctcctgg taccaagaag caaaatcaat gaatttgcaa gaggtgtatt tggaaacata 1140
ctaacggata caagcaacgg cccagtcatc gtctacccag tgaacaaatc aaagtgggac 1200
aatcaaacat cagcagtaac accggaggaa gaggtattct acctggtggc gatcctaaca 1260
tcggcatctc cagggtcggc aggaaaggat ggagtagaag agatcttgag gcggaacaga 1320
agaatactgg aattcagtga agaagcaggg atagggttga agcagtatct gccacattac 1380
acgacaagag aagagtggag atcccatttc ggggacaagt ggggagaatt tgtgaggagg 1440
aaatccagat atgatccatt ggcaattctt gcgcctggcc accgaatttt tcaaaaggca 1500
gtctcatact catga 1515

<210> SEQ ID NO 31
<211> LENGTH: 84
<212> TYPE: DNA
<213> ORGANISM: Arabidopsis thaliana

<400> SEQUENCE: 31
tcagcttcgg gactcgctct tctctatcca acaaaccgga ataaatggga caatcgtatg 60
tcggcgatga taccagagat cgat 84

<210> SEQ ID NO 32
<211> LENGTH: 28

<212> TYPE: PRT
<213> ORGANISM: Arabidopsis thaliana

<400> SEQUENCE: 32

Ser Ala Ser Gly Leu Ala Leu Leu Tyr Pro Thr Asn Arg Asn Lys Trp
1 5 10 15

Asp Asn Arg Met Ser Ala Met Ile Pro Glu Ile Asp
20 25

<210> SEQ ID NO 33
<211> LENGTH: 2814
<212> TYPE: DNA
<213> ORGANISM: Arabidopsis thaliana

<400> SEQUENCE: 33
atgaatcgta tgacgtcaag ctttcttctc ctgacgttcg ccatatgtaa actgatcata 60
gccgtgggtc taaacgtggg ccccagtgag ctcctccgca tcggagccat agatgtcgac 120
ggccacttca ccgtccaccc ttccgactta gcctccgtct cctcagactt cggtatgctg 180
aagtcacctg aagagccatt ggccgtgctt catccatcat cggccgaaga cgtggcacga 240
ctcgtcagaa cagcttacgg ttcagccacg gcgtttccgg tctcagcccg aggccacggc 300
cattccataa acggacaagc cgcggcgggg aggaacggtg tggtggttga aatgaaccac 360
ggcgtaaccg ggacgcccaa gccactcgtc cgaccggatg aaatgtatgt ggatgtatgg 420
ggtggagagt tatgggtcga tgtgttgaag aaaacgttgg agcatggctt agcaccaaaa 480
tcatggacgg attacttgta tctaaccgtt ggaggtacac tctccaatgc aggaatcagt 540
ggtcaagctt ttcaccatgg tcctcaaatt agtaacgtcc ttgagctcga cgttgtaact 600
ggttagtatt aaaacattca agttcatata ttttaaatgc ttttgtctga agttttacta 660
ataacaagaa attgatacca aaaagtaggg aaaggagagg tgatgagatg ctcagaagaa 720
gagaacacaa ggctattcca tggagttctt ggtggattag gtcaatttgg gatcatcact 780
cgagcacgaa tctctctcga accagctccc caaagggtaa tattttttta atgactagct 840
atcaaaaatc cctggcgggt ccatacgttg taatcttttt agtttttact gttgatggta 900 tttttatat attttggata ataaaaccct aaaatggtat attgtgatga caggtgagat 960
ggatacgggt attgtattcg agcttcaaag tgtttacgga ggaccaagag tacttaatct 1020
caatgcatgg tcaattaaag tttgattacg tggaaggttt tgtgattgtg gacgaaggac 1080
tcgtcaacaa ttggagatct tctttcttct ctccacgtaa ccccgtcaag atctcctctg 1140
ttagttccaa cggctctgtt ttgtattgcc ttgagatcac caagaactac cacgactccg 1200
actccgaaat cgttgatcag gtcactttca ttattcactt agaaaaaagc gatattttca 1260 tttttatat tgatgaatat ctggaaggat ttaacgctat gcgactattg ggaaatcatt 1320
atgaaaaaat atttagttta tatgattgaa agtggtctcc atagtatttt tgttgtgtcg 1380
actttattat aacttaaatt tggaagagga catgaagaag aagccagaga ggatctacag 1440
agatctagct tttccacctg aacttaataa tgcacattta tataattatt tttcttcttc 1500
taaagtttag tttatcacta gcgaattaat catggttact aattaagtag tggacagggt 1560
catggaccac tcactcacca aataatgatt cctctttact cttaagttta attttaataa 1620
aaccaactct actggaatct taacttatcc ttggttttgg taggctttta tagcaacacg 1680
gtttttttaa ttttcctatt ccagattttg tatattaaat gtcgattttt tttcttttttg 1740 tttcaggaag ttgagattct gatgaagaaa ttgaatttca taccgacatc ggtctttaca 1800

-continued

```
acggatttac aatatgtgga ctttctcgac cgggtacaca aggccgaatt gaagctccgg   1860
tccaagaatt tatgggaggt tccacaccca tggctcaacc tcttcgtgcc aaaatcaaga   1920
atctctgact tcgataaagg cgttttcaag ggcattttgg gaaataaaac aagtggccct   1980
attcttatct accccatgaa caaagacaag taagtcttga cattaccatt gattactact   2040
tctaaatttc ttctctagaa aaaagaataa aacgagtttt gcattgcatg catgcaaagt   2100
tacacttgtg ggattaatt agtggtccaa gaaaaaaagt ttgtcaaaat tgaaaaaaac   2160
tagacacgtg gtacatggga ttgtccgaaa aacgttgtcc acatgtgcat cgaaccagct   2220
aagattgaca acaacacttc gtcggctcgt atttctcttt ttgttttgtg accaaatccg   2280
atggtccaga ttgggtttat ttgtttttaa gttcctagaa ctcatggtgg gtgggtccca   2340
atcagattct cctagaccaa accgatctca acgaaccctc cgcacatcat tgattattac   2400
attaatatag atattgtcgt tgctgacgtg tcgtaatttg atgttattgt cagatgggac   2460
gagaggagct cagccgtgac gccggatgag gaagttttct atctggtggc tctattgaga   2520
tcagctttaa cggacggtga agagacacag aagctagagt atctgaaaga tcagaaccgt   2580
cggatcttgg agttctgtga acaagccaag atcaatgtga agcagtatct tcctcaccac   2640
gcaacacagg aagagtgggt ggctcatttt ggggacaagt gggatcggtt cagaagctta   2700
aaggctgagt ttgatccgcg acacatactc gctactggtc agagaatctt tcaaaaccca   2760
tctttgtctt tgtttcctcc gtcgtcgtct tcttcgtcag cggcttcatg gtga         2814
```

<210> SEQ ID NO 34
<211> LENGTH: 1620
<212> TYPE: DNA
<213> ORGANISM: Arabidopsis thaliana

<400> SEQUENCE: 34

```
atgaatcgta tgacgtcaag ctttcttctc ctgacgttcg ccatatgtaa actgatcata     60
gccgtgggtc taaacgtggg ccccagtgag ctcctccgca tcggagccat agatgtcgac    120
ggccacttca ccgtccaccc ttccgactta gcctccgtct cctcagactt cggtatgctg    180
aagtcacctg aagagccatt ggccgtgctt catccatcat cggccgaaga cgtggcacga    240
ctcgtcagaa cagcttacgg ttcagccacg gcgtttccgg tctcagcccg aggccacggc    300
cattccataa acggacaagc cgcggcgggg aggaacggtg tggtggttga aatgaaccac    360
ggcgtaaccg ggacgcccaa gccactcgtc cgaccggatg aaatgtatgt ggatgtatgg    420
ggtggagagt tatgggtcga tgtgttgaag aaaacgttgg agcatggctt agcaccaaaa    480
tcatggacgg attacttgta tctaaccgtt ggaggtacac tctccaatgc aggaatcagt    540
ggtcaagctt ttcaccatgg tcctcaaatt agtaacgtcc ttgagctcga cgttgtaact    600
gggaaaggag aggtgatgag atgctcagaa gaagagaaca caaggctatt ccatggagtt    660
cttggtggat taggtcaatt tgggatcatc actcgagcac gaatctctct cgaaccagct    720
ccccaaaggg tgagatggat acgggtattg tattcgagct tcaaagtgtt tacggaggac    780
caagagtact taatctcaat gcatggtcaa ttaaagtttg attacgtgga aggttttgtg    840
attgtggacg aaggactcgt caacaattgg agatcttctt tcttctctcc acgtaacccc    900
gtcaagatct cctctgttag ttccaacggc tctgttttgt attgccttga gatcaccaag    960
aactaccacg actccgactc cgaaatcgtt gatcaggaag ttgagattct gatgaagaaa   1020
ttgaatttca taccgacatc ggtctttaca acggatttac aatatgtgga ctttctcgac   1080
cgggtacaca aggccgaatt gaagctccgg tccaagaatt tatgggaggt tccacaccca   1140
```

```
tggctcaacc tcttcgtgcc aaaatcaaga atctctgact tcgataaagg cgttttcaag   1200

ggcattttgg gaaataaaac aagtggccct attcttatct accccatgaa caaagacaaa   1260

tgggacgaga ggagctcagc cgtgacgccg gatgaggaag ttttctatct ggtggctcta   1320

ttgagatcag ctttaacgga cggtgaagag acacagaagc tagagtatct gaaagatcag   1380

aaccgtcgga tcttggagtt ctgtgaacaa gccaagatca atgtgaagca gtatcttcct   1440

caccacgcaa cacaggaaga gtgggtggct cattttgggg acaagtggga tcggttcaga   1500

agcttaaagg ctgagtttga tccgcgacac atactcgcta ctggtcagag aatctttcaa   1560

aacccatctt tgtctttgtt tcctccgtcg tcgtcttctt cgtcagcggc ttcatggtga   1620


<210> SEQ ID NO 35
<211> LENGTH: 539
<212> TYPE: PRT
<213> ORGANISM: Arabidopsis thaliana

<400> SEQUENCE: 35

Met Asn Arg Met Thr Ser Ser Phe Leu Leu Leu Thr Phe Ala Ile Cys
1               5                   10                  15

Lys Leu Ile Ile Ala Val Gly Leu Asn Val Gly Pro Ser Glu Leu Leu
            20                  25                  30

Arg Ile Gly Ala Ile Asp Val Asp Gly His Phe Thr Val His Pro Ser
        35                  40                  45

Asp Leu Ala Ser Val Ser Ser Asp Phe Gly Met Leu Lys Ser Pro Glu
    50                  55                  60

Glu Pro Leu Ala Val Leu His Pro Ser Ser Ala Glu Asp Val Ala Arg
65                  70                  75                  80

Leu Val Arg Thr Ala Tyr Gly Ser Ala Thr Ala Phe Pro Val Ser Ala
                85                  90                  95

Arg Gly His Gly His Ser Ile Asn Gly Gln Ala Ala Ala Gly Arg Asn
            100                 105                 110

Gly Val Val Val Glu Met Asn His Gly Val Thr Gly Thr Pro Lys Pro
        115                 120                 125

Leu Val Arg Pro Asp Glu Met Tyr Val Asp Val Trp Gly Gly Glu Leu
    130                 135                 140

Trp Val Asp Val Leu Lys Lys Thr Leu Glu His Gly Leu Ala Pro Lys
145                 150                 155                 160

Ser Trp Thr Asp Tyr Leu Tyr Leu Thr Val Gly Gly Thr Leu Ser Asn
                165                 170                 175

Ala Gly Ile Ser Gly Gln Ala Phe His His Gly Pro Gln Ile Ser Asn
            180                 185                 190

Val Leu Glu Leu Asp Val Val Thr Gly Lys Gly Glu Val Met Arg Cys
        195                 200                 205

Ser Glu Glu Glu Asn Thr Arg Leu Phe His Gly Val Leu Gly Gly Leu
    210                 215                 220

Gly Gln Phe Gly Ile Ile Thr Arg Ala Arg Ile Ser Leu Glu Pro Ala
225                 230                 235                 240

Pro Gln Arg Val Arg Trp Ile Arg Val Leu Tyr Ser Ser Phe Lys Val
                245                 250                 255

Phe Thr Glu Asp Gln Glu Tyr Leu Ile Ser Met His Gly Gln Leu Lys
            260                 265                 270

Phe Asp Tyr Val Glu Gly Phe Val Ile Val Asp Glu Gly Leu Val Asn
        275                 280                 285
```

```
Asn Trp Arg Ser Ser Phe Phe Ser Pro Arg Asn Pro Val Lys Ile Ser
    290                 295                 300

Ser Val Ser Ser Asn Gly Ser Val Leu Tyr Cys Leu Glu Ile Thr Lys
305                 310                 315                 320

Asn Tyr His Asp Ser Asp Ser Glu Ile Val Asp Gln Glu Val Glu Ile
                325                 330                 335

Leu Met Lys Lys Leu Asn Phe Ile Pro Thr Ser Val Phe Thr Thr Asp
            340                 345                 350

Leu Gln Tyr Val Asp Phe Leu Asp Arg Val His Lys Ala Glu Leu Lys
        355                 360                 365

Leu Arg Ser Lys Asn Leu Trp Glu Val Pro His Pro Trp Leu Asn Leu
    370                 375                 380

Phe Val Pro Lys Ser Arg Ile Ser Asp Phe Asp Lys Gly Val Phe Lys
385                 390                 395                 400

Gly Ile Leu Gly Asn Lys Thr Ser Gly Pro Ile Leu Ile Tyr Pro Met
                405                 410                 415

Asn Lys Asp Lys Trp Asp Glu Arg Ser Ser Ala Val Thr Pro Asp Glu
            420                 425                 430

Glu Val Phe Tyr Leu Val Ala Leu Leu Arg Ser Ala Leu Thr Asp Gly
        435                 440                 445

Glu Glu Thr Gln Lys Leu Glu Tyr Leu Lys Asp Gln Asn Arg Arg Ile
    450                 455                 460

Leu Glu Phe Cys Glu Gln Ala Lys Ile Asn Val Lys Gln Tyr Leu Pro
465                 470                 475                 480

His His Ala Thr Gln Glu Glu Trp Val Ala His Phe Gly Asp Lys Trp
                485                 490                 495

Asp Arg Phe Arg Ser Leu Lys Ala Glu Phe Asp Pro Arg His Ile Leu
            500                 505                 510

Ala Thr Gly Gln Arg Ile Phe Gln Asn Pro Ser Leu Ser Leu Phe Pro
        515                 520                 525

Pro Ser Ser Ser Ser Ser Ser Ala Ala Ser Trp
    530                 535
```

<210> SEQ ID NO 36
<211> LENGTH: 842
<212> TYPE: DNA
<213> ORGANISM: Arabidopsis thaliana

<400> SEQUENCE: 36

```
aagcttaaat gacaatttag taccttgggt tggtcatgat ttagagcgga acaaatatac     60

catacatcaa acgaggatat acagagaaaa ttcatggaag tatggaattt agaggacaat    120

ttctcttctg ggctacaacg gaccggccca ttcgctcatt tacccagagg tatcgagttt    180

gtggactttt gatgccgcta gagactattg gcatcggatt gaaaaaaatg tttacttcgt    240

tgttaacaat tttctgaatg caatattttc cttgtcatga atatttaaac ttgttattac    300

tttcttttag cttaggtgtg gacaattatg gagtttactt caaacgagga agaatcttaa    360

acgctcggtt caggtctcga aaacaaacca actcacaatc ctgacttaat tgaggaaaac    420

aatgcaaaac cacatgcatg cttccatatt tctatcataa tcttataaga aaaaacacta    480

ctaagtgaaa tgattctgta tatatataac caatgccttt tgttttgtga tattttatgt    540

atatataact attgactttt gtcatctatg gatagtgtct cgggctcttg gcaaacatat    600

ttcaaagaaa agttaatgac tgtaattaat taatctgaag ctagaaacag aaccccgagg    660

taaaagaaaa agacagagca catgaagttt agtactttta tatatttaat atatcattct    720
```

```
ttcttattgc ttatctctaa agcaaaaact tccctaaacc ctaagccaaa ggactcagat    780

cgatgcagaa ccaagaaggc ttgttttgga tttgagagcc aaatgcaaag aaaaaaactc    840

tt                                                                   842


<210> SEQ ID NO 37
<211> LENGTH: 501
<212> TYPE: PRT
<213> ORGANISM: Arabidopsis thaliana

<400> SEQUENCE: 37

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Arg Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Ala Lys Trp Phe Arg Met Leu Tyr Ser Asp Phe
225                 230                 235                 240

Thr Thr Phe Thr Lys Asp Gln Glu Arg Leu Ile Ser Met Ala Asn Asp
                245                 250                 255

Ile Gly Val Asp Tyr Leu Glu Gly Gln Ile Phe Leu Ser Asn Gly Val
            260                 265                 270

Val Asp Thr Ser Phe Phe Pro Pro Ser Asp Gln Ser Lys Val Ala Asp
        275                 280                 285

Leu Val Lys Gln His Gly Ile Ile Tyr Val Leu Glu Val Ala Lys Tyr
    290                 295                 300

Tyr Asp Asp Pro Asn Leu Pro Ile Ile Ser Lys Val Ile Asp Thr Leu
305                 310                 315                 320

Thr Lys Thr Leu Ser Tyr Leu Pro Gly Phe Ile Ser Met His Asp Val
                325                 330                 335

Ala Tyr Phe Asp Phe Leu Asn Arg Val His Val Glu Glu Asn Lys Leu
```

-continued

```
            340                 345                 350

Arg Ser Leu Gly Leu Trp Glu Leu Pro His Pro Trp Leu Asn Leu Tyr
        355                 360                 365

Val Pro Lys Ser Arg Ile Leu Asp Phe His Asn Gly Val Val Lys Asp
    370                 375                 380

Ile Leu Leu Lys Gln Lys Ser Ala Ser Gly Leu Ala Leu Leu Tyr Pro
385                 390                 395                 400

Thr Asn Arg Asn Lys Trp Asp Asn Arg Met Ser Ala Met Ile Pro Glu
                405                 410                 415

Ile Asp Glu Asp Val Ile Tyr Ile Ile Gly Leu Leu Gln Ser Ala Thr
            420                 425                 430

Pro Lys Asp Leu Pro Glu Val Glu Ser Val Asn Glu Lys Ile Ile Arg
        435                 440                 445

Phe Cys Lys Asp Ser Gly Ile Lys Ile Lys Gln Tyr Leu Met His Tyr
    450                 455                 460

Thr Ser Lys Glu Asp Trp Ile Glu His Phe Gly Ser Lys Trp Asp Asp
465                 470                 475                 480

Phe Ser Lys Arg Lys Asp Leu Phe Asp Pro Lys Lys Leu Leu Ser Pro
                485                 490                 495

Gly Gln Asp Ile Phe
            500


<210> SEQ ID NO 38
<211> LENGTH: 1455
<212> TYPE: DNA
<213> ORGANISM: Arabidopsis thaliana

<400> SEQUENCE: 38

atggctaatc ttcgtttaat gatcacttta atcacggttt taatgatcac caaatcatca      60

aacggtatta aaattgattt acctaaatcc cttaacctca ccctctctac cgatccttcc     120

atcatctccg cagcctctca tgacttcgga aacataacca ccgtgacccc cggcggcgta     180

atctgcccct cctccaccgc tgatatctct cgtctcctcc aatacgccgc aaacggaaaa     240

agtacattcc aagtagcggc tcgtggccaa ggccactcct taaacggcca agcctcggtc     300

tccggcggag taatcgtcaa catgacgtgt atcactgacg tggtggtttc aaaagacaag     360

aagtacgctg acgtggcggc cgggacgtta tgggtggatg tgcttaagaa gacggcggag     420

aaaggggtgt cgccggtttc ttggacggat tatttgcata taaccgtccg aggaacgttg     480

tcgaatggtg gaattggtgg tcaagtgttt cgaaacggtc ctcttgttag taacgtcctt     540

gaattggacg ttattactgg gaaaggtgaa atgttgacat gctcgcgaca gctaaaccca     600

gaattgttct atggagtgtt aggaggtttg ggtcaatttg gaattataac gagagccaga     660

attgttttgg accatgcacc taaacggcaa gaacgtttga tatcaatggc aaacgatatt     720

ggagtcgact atttagaagg tcaaatattt ctatcaaacg gtgtcgttga cacctctttt     780

ttcccacctt cagatcaatc taaagtcgct gatctagtca agcaacacgg tatcatctat     840

gttcttgaag tagccaagta ttatgatgat cccaatctcc ccatcatcag caaggttatt     900

gacacattaa cgaaaacatt aagttacttg cccgggttca tatcaatgca cgacgtggcc     960

tacttcgatt tcttgaaccg tgtacatgtc gaagaaaata aactcagatc tttgggatta    1020

tgggaacttc ctcatccttg gcttaacctc tacgttccta aatctcggat tctcgatttt    1080

cataacggtg ttgtcaaaga cattcttctt aagcaaaaat cagcttcggg actcgctctt    1140

ctctatccaa caaaccggaa taaatgggac aatcgtatgt cggcgatgat accagagatc    1200
```

```
gatgaagatg ttatatatat tatcggacta ctacaatccg ctaccccaaa ggatcttcca   1260

gaagtggaga gcgttaacga gaagataatt aggttttgca aggattcagg tattaagatt   1320

aagcaatatc taatgcatta tactagtaaa gaagattgga ttgagcattt tggatcaaaa   1380

tgggatgatt tttcgaagag gaaagatcta tttgatccca agaaactgtt atctccaggg   1440

caagacatct tttga                                                    1455


<210> SEQ ID NO 39
<211> LENGTH: 484
<212> TYPE: PRT
<213> ORGANISM: Arabidopsis thaliana

<400> SEQUENCE: 39

Met Ala Asn Leu Arg Leu Met Ile Thr Leu Ile Thr Val Leu Met Ile
1               5                   10                  15

Thr Lys Ser Ser Asn Gly Ile Lys Ile Asp Leu Pro Lys Ser Leu Asn
            20                  25                  30

Leu Thr Leu Ser Thr Asp Pro Ser Ile Ile Ser Ala Ala Ser His Asp
        35                  40                  45

Phe Gly Asn Ile Thr Thr Val Thr Pro Gly Gly Val Ile Cys Pro Ser
    50                  55                  60

Ser Thr Ala Asp Ile Ser Arg Leu Leu Gln Tyr Ala Ala Asn Gly Lys
65                  70                  75                  80

Ser Thr Phe Gln Val Ala Ala Arg Gly Gln Gly His Ser Leu Asn Gly
                85                  90                  95

Gln Ala Ser Val Ser Gly Gly Val Ile Val Asn Met Thr Cys Ile Thr
            100                 105                 110

Asp Val Val Val Ser Lys Asp Lys Lys Tyr Ala Asp Val Ala Ala Gly
        115                 120                 125

Thr Leu Trp Val Asp Val Leu Lys Lys Thr Ala Glu Lys Gly Val Ser
    130                 135                 140

Pro Val Ser Trp Thr Asp Tyr Leu His Ile Thr Val Arg Gly Thr Leu
145                 150                 155                 160

Ser Asn Gly Gly Ile Gly Gly Gln Val Phe Arg Asn Gly Pro Leu Val
                165                 170                 175

Ser Asn Val Leu Glu Leu Asp Val Ile Thr Gly Lys Gly Glu Met Leu
            180                 185                 190

Thr Cys Ser Arg Gln Leu Asn Pro Glu Leu Phe Tyr Gly Val Leu Gly
        195                 200                 205

Gly Leu Gly Gln Phe Gly Ile Ile Thr Arg Ala Arg Ile Val Leu Asp
    210                 215                 220

His Ala Pro Lys Arg Gln Glu Arg Leu Ile Ser Met Ala Asn Asp Ile
225                 230                 235                 240

Gly Val Asp Tyr Leu Glu Gly Gln Ile Phe Leu Ser Asn Gly Val Val
                245                 250                 255

Asp Thr Ser Phe Phe Pro Pro Ser Asp Gln Ser Lys Val Ala Asp Leu
            260                 265                 270

Val Lys Gln His Gly Ile Ile Tyr Val Leu Glu Val Ala Lys Tyr Tyr
        275                 280                 285

Asp Asp Pro Asn Leu Pro Ile Ile Ser Lys Val Ile Asp Thr Leu Thr
    290                 295                 300

Lys Thr Leu Ser Tyr Leu Pro Gly Phe Ile Ser Met His Asp Val Ala
305                 310                 315                 320
```

Tyr Phe Asp Phe Leu Asn Arg Val His Val Glu Glu Asn Lys Leu Arg
325 330 335

Ser Leu Gly Leu Trp Glu Leu Pro His Pro Trp Leu Asn Leu Tyr Val
340 345 350

Pro Lys Ser Arg Ile Leu Asp Phe His Asn Gly Val Val Lys Asp Ile
355 360 365

Leu Leu Lys Gln Lys Ser Ala Ser Gly Leu Ala Leu Leu Tyr Pro Thr
370 375 380

Asn Arg Asn Lys Trp Asp Asn Arg Met Ser Ala Met Ile Pro Glu Ile
385 390 395 400

Asp Glu Asp Val Ile Tyr Ile Ile Gly Leu Leu Gln Ser Ala Thr Pro
405 410 415

Lys Asp Leu Pro Glu Val Glu Ser Val Asn Glu Lys Ile Ile Arg Phe
420 425 430

Cys Lys Asp Ser Gly Ile Lys Ile Lys Gln Tyr Leu Met His Tyr Thr
435 440 445

Ser Lys Glu Asp Trp Ile Glu His Phe Gly Ser Lys Trp Asp Asp Phe
450 455 460

Ser Lys Arg Lys Asp Leu Phe Asp Pro Lys Lys Leu Leu Ser Pro Gly
465 470 475 480

Gln Asp Ile Phe

<210> SEQ ID NO 40
<211> LENGTH: 60
<212> TYPE: DNA
<213> ORGANISM: Artificial Sequence
<220> FEATURE:
<223> OTHER INFORMATION: oligonucleotide

<400> SEQUENCE: 40
ggggacaagt ttgtacaaaa aagcaggctt cacaatggct aatcttcgtt taatgatcac 60

<210> SEQ ID NO 41
<211> LENGTH: 49
<212> TYPE: DNA
<213> ORGANISM: Artificial Sequence
<220> FEATURE:
<223> OTHER INFORMATION: oligonucleotide

<400> SEQUENCE: 41
ggggaccact ttgtacaaga aagctgggtt caaaagatgt cttgccctg 49

<210> SEQ ID NO 42
<211> LENGTH: 3328
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (2495)..(2496)
<223> OTHER INFORMATION: n is a, c, g, or t

<400> SEQUENCE: 42
ggtcagccaa tacattgatc cgttgccaat catgcaaagt attttggctg tggccgagtg 60
ccggaattga taattgtgtt ctgactaaat taaatgacca gaagtcgcta tcttccaatg 120
tatccgaaac ctggattaaa caatcctgtt ctgttctcta gcccctcctg catggccgga 180
ttgttttttt gacatgtttt cttgactgag gcctgtttgt tctaaacttt ttcttcaaac 240
ttttaacttt ttcatcacat cagaactttt ctacacatat aaacttttaa cttttccgtc 300

```
acatcgttcc aatttcaatc aaactttcaa ttttggcgtg aactaaacac accctgagtc    360
ttttattgct cctccgtacg ggttggctgg ttgagaatag gtattttcag agagaaaatc    420
tagatattgg gaggaacttg gcatgaatgg ccactatatt tagagcaatt ctacggtcct    480
tgaggaggta ccatgaggta ccaaaatttt agtgtaaatt ttagtatctc attataacta    540
ggtattatga ggtaccaaat ttacaataga aaaaatagta cttcatggta ctttcttaag    600
taccgtaaaa ttgctcctat atttaagggg atgtttatat ctatccatat ccataatttg    660
attttgataa gaaaaaatgt gagcacacca agcatgtcca tgaccttgca ctcttggctc    720
actcgtcaac tgtgaagaac ctcaaaaatg ctcaatatag ctacaggtgc ctgaaaaaat    780
aactttaaag ttttgaacat cgatttcact aaacaacaat tattatctcc ctctgaaaga    840
tgatagttta gaactctaga atcattgtcg gcggagaaag taaattattt tccccaaatt    900
tccagctatg aaaaaaccct caccaaacac catcaaacaa gagttcacca aaccgcccat    960
gcggccatgc tgtcacgcaa cgcaccgcat tgcctgatgg ccgctcgatg catgcatgct   1020
tccccgtgca catatccgac agacgcgccg tgtcagcgag ctcctcgacc gacctgtgta   1080
gcccatgcaa gcatccaccc ccgccacgta cacccccctcc tcctccctac gtgtcaccgc   1140
tctctccacc tatatatgcc cacctggccc ctctcctccc atctccactt cacccgatcg   1200
cttcttcttc ttcttcgttg cattcatctt gctagcattt aaatcaacta gggatatcac   1260
aagtttgtac aaaaaagcag gcttcacaat ggctaatctt cgtttaatga tcactttaat   1320
cacggtttta atgatcacca aatcatcaaa cggtattaaa attgatttac ctaaatccct   1380
taacctcacc ctctctaccg atccttccat catctccgca gcctctcatg acttcggaaa   1440
cataaccacc gtgacccccg gcggcgtaat ctgcccctcc tccaccgctg atatctctcg   1500
tctcctccaa tacgccgcaa acggaaaaag tacattccaa gtagcggctc gtggccaagg   1560
ccactcctta aacggccaag cctcggtctc cggcggagta atcgtcaaca tgacgtgtat   1620
cactgacgtg gtggtttcaa aagacaagaa gtacgctgac gtggcggccg ggacgttatg   1680
ggtggatgtg cttaagaaga cggcggagaa aggggtgtcg ccggtttctt ggacggatta   1740
tttgcatata accgtcggag gaacgttgtc gaatggtgga attggtggtc aagtgtttcg   1800
aaacggtcct cttgttagta acgtccttga attggacgtt attactggga aaggtgaaat   1860
gttgacatgc tcgcgacagc taaacccaga attgttctat ggagtgttag gaggtttggg   1920
tcaatttgga attataacga gagccagaat tgttttggac catgcaccta aacggcaaga   1980
acgtttgata tcaatggcaa acgatattgg agtcgactat ttagaaggtc aaatatttct   2040
atcaaacggt gtcgttgaca cctctttttt cccaccttca gatcaatcta aagtcgctga   2100
tctagtcaag caacacggta tcatctatgt tcttgaagta gccaagtatt atgatgatcc   2160
caatctcccc atcatcagca aggttattga cacattaacg aaaacattaa gttacttgcc   2220
cgggttcata tcaatgcacg acgtggccta cttcgatttc ttgaaccgtg tacatgtcga   2280
agaaaataaa ctcagatctt tgggattatg ggaacttcct catccttggc ttaacctcta   2340
cgttcctaaa tctcggattc tcgattttca taacggtgtt gtcaaagaca ttcttcttaa   2400
gcaaaaatca gcttcgggac tcgctcttct ctatccaaca aaccggaata agtacatact   2460
tctcttcatt catatttatc ttcaagaacc aaagnnatgg gacaatcgta tgtcggcgat   2520
gataccagag atcgatgaag atgttatata tattatcgga ctactacaat ccgctacccc   2580
aaaggatctt ccagaagtgg agagcgttaa cgagaagata attaggtttt gcaaggattc   2640
```

aggtattaag attaagcaat atctaatgca ttatactagt aaagaagatt ggattgagca 2700
ttttggatca aaatgggatg atttttcgaa gaggaaagat ctatttgatc ccaagaaact 2760
gttatctcca gggcaagaca tcttttgaac ccagctttct tgtacaaagt ggtgatatca 2820
caagcccggg cggtcttcta gggataacag ggtaattata tccctctaga tcacaagccc 2880
gggcggtctt ctacgatgat tgagtaataa tgtgtcacgc atcaccatgg gtggcagtgt 2940
cagtgtgagc aatgacctga atgaacaatt gaaatgaaaa gaaaaaaagt actccatctg 3000
ttccaaatta aaattcattt taacctttta ataggtttat acaataattg atatatgttt 3060
tctgtatatg tctaatttgt tatcatccgg gcggtcttct agggataaca gggtaattat 3120
atccctctag acaacacaca acaaataaga gaaaaaacaa ataatattaa tttgagaatg 3180
aacaaaagga ccatatcatt cattaactct tctccatcca tttccatttc acagttcgat 3240
agcgaaaacc gaataaaaaa cacagtaaat tacaagcaca acaaatggta caagaaaaac 3300
agttttccca atgccataat actcgaac 3328

<210> SEQ ID NO 43
<211> LENGTH: 2746
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (1913)..(1914)
<223> OTHER INFORMATION: n is a, c, g, or t

<400> SEQUENCE: 43
cttctacatc ggcttaggtg tagcaacacg actttattat tattattatt attattatta 60
ttattttaca aaaatataaa atagatcagt ccctcaccac aagtagagca agttggtgag 120
ttattgtaaa gttctacaaa gctaatttaa aagttattgc attaacttat ttcatattac 180
aaacaagagt gtcaatggaa caatgaaaac catatgacat actataattt tgtttttatt 240
attgaaatta tataattcaa agagaataaa tccacatagc cgtaaagttc tacatgtggt 300
gcattaccaa aatatatata gcttacaaaa catgacaagc ttagtttgaa aaattgcaat 360
ccttatcaca ttgacacata aagtgagtga tgagtcataa tattattttc tttgctaccc 420
atcatgtata tatgatagcc acaaagttac tttgatgatg atatcaaaga acatttttag 480
gtgcacctaa cagaatatcc aaataatatg actcacttag atcataatag agcatcaagt 540
aaaactaaca ctctaaagca accgatggga aagcatctat aaatagacaa gcacaatgaa 600
aatcctcatc atccttcacc acaattcaaa tattatagtt gaagcatagt agtaatttaa 660
atcaactagg gatatcacaa gtttgtacaa aaaagcaggc ttcacaatgg ctaatcttcg 720
tttaatgatc actttaatca cggttttaat gatcaccaaa tcatcaaacg gtattaaaat 780
tgatttacct aaatccctta acctcaccct ctctaccgat ccttccatca tctccgcagc 840
ctctcatgac ttcggaaaca taaccaccgt gacccccggc ggcgtaatct gcccctcctc 900
caccgctgat atctctcgtc tcctccaata cgccgcaaac ggaaaaagta cattccaagt 960
agcggctcgt ggccaaggcc actccttaaa cggccaagcc tcggtctccg gcggagtaat 1020
cgtcaacatg acgtgtatca ctgacgtggt ggtttcaaaa gacaagaagt acgctgacgt 1080
ggcggccggg acgttatggg tggatgtgct taagaagacg gcggagaaag gggtgtcgcc 1140
ggtttcttgg acggattatt tgcatataac cgtcggagga acgttgtcga atggtggaat 1200
tggtggtcaa gtgtttcgaa acggtcctct tgttagtaac gtccttgaat tggacgttat 1260

```
tactgggaaa ggtgaaatgt tgacatgctc gcgacagcta aacccagaat tgttctatgg   1320
agtgttagga ggtttgggtc aatttggaat tataacgaga gccagaattg ttttggacca   1380
tgcacctaaa cggcaagaac gtttgatatc aatggcaaac gatattggag tcgactattt   1440
agaaggtcaa atatttctat caaacggtgt cgttgacacc tctttttcc caccttcaga    1500
tcaatctaaa gtcgctgatc tagtcaagca acacggtatc atctatgttc ttgaagtagc   1560
caagtattat gatgatccca atctccccat catcagcaag gttattgaca cattaacgaa   1620
aacattaagt tacttgcccg ggttcatatc aatgcacgac gtggcctact tcgatttctt   1680
gaaccgtgta catgtcgaag aaaataaact cagatctttg ggattatggg aacttcctca   1740
tccttggctt aacctctacg ttcctaaatc tcggattctc gattttcata acggtgttgt   1800
caaagacatt cttcttaagc aaaaatcagc ttcgggactc gctcttctct atccaacaaa   1860
ccggaataag tacatacttc tcttcattca tatttatctt caagaaccaa agnnatggga   1920
caatcgtatg tcggcgatga taccagagat cgatgaagat gttatatata ttatcggact   1980
actacaatcc gctaccccaa aggatcttcc agaagtggag agcgttaacg agaagataat   2040
taggttttgc aaggattcag gtattaagat taagcaatat ctaatgcatt atactagtaa   2100
agaagattgg attgagcatt ttggatcaaa atgggatgat ttttcgaaga ggaaagatct   2160
atttgatccc aagaaactgt tatctccagg gcaagacatc ttttgaaccc agctttcttg   2220
tacaaagtgg tgatatcaca agcccgggcg gtcttctagg gataacaggg taattatatc   2280
cctctagatc acaagcccgg gcggtcttct acgatgattg agtaataatg tgtcacgcat   2340
caccatgggt ggcagtgtca gtgtgagcaa tgacctgaat gaacaattga aatgaaaaga   2400
aaaaaagtac tccatctgtt ccaaattaaa attcatttta accttttaat aggtttatac   2460
aataattgat atatgtttc tgtatatgtc taatttgtta tcatccgggc ggtcttctag    2520
ggataacagg gtaattatat ccctctagac aacacacaac aaataagaga aaaaacaaat   2580
aatattaatt tgagaatgaa caaaaggacc atatcattca ttaactcttc tccatccatt   2640
tccatttcac agttcgatag cgaaaaccga ataaaaaaca cagtaaatta caagcacaac   2700
aaatggtaca agaaaaacag ttttcccaat gccataatac tcgaac                  2746
```

<210> SEQ ID NO 44
<211> LENGTH: 1506
<212> TYPE: DNA
<213> ORGANISM: Arabidopsis thaliana

<400> SEQUENCE: 44

```
atggctaatc ttcgtttaat gatcacttta atcacggttt taatgatcac caaatcatca     60
aacggtatta aaattgattt acctaaatcc cttaacctca ccctctctac cgatccttcc    120
atcatctccg cagcctctca tgacttcgga aacataacca ccgtgacccc cggcggcgta    180
atctgcccct cctccaccgc tgatatctct cgtctcctcc aatacgccgc aaacggaaaa    240
agtacattcc aagtagcggc tcgtggccaa ggccactcct taaacggcca agcctcggtc    300
tccggcggag taatcgtcaa catgacgtgt atcactgacg tggtggtttc aaaagacaag    360
aagtacgctg acgtggcggc cgggacgtta tgggtggatg tgcttaagaa gacggcggag    420
aaaggggtgt cgccggtttc ttggacggat tatttgcata taaccgtccg aggaacgttg    480
tcgaatggtg gaattggtgg tcaagtgttt cgaaacggtc ctcttgttag taacgtcctt    540
gaattggacg ttattactgg gaaaggtgaa atgttgacat gctcgcgaca gctaaaccca    600
```

gaattgttct atggagtgtt aggaggtttg ggtcaatttg gaattataac gagagccaga 660
attgttttgg accatgcacc taaacgggcc aaatggtttc ggatgctcta cagtgatttc 720
acaactttta caaaggacca agaacgtttg atatcaatgg caaacgatat tggagtcgac 780
tatttagaag gtcaaatatt tctatcaaac ggtgtcgttg acacctcttt tttcccacct 840
tcagatcaat ctaaagtcgc tgatctagtc aagcaacacg gtatcatcta tgttcttgaa 900
gtagccaagt attatgatga tcccaatctc cccatcatca gcaaggttat tgacacatta 960
acgaaaacat taagttactt gcccgggttc atatcaatgc acgacgtggc ctacttcgat 1020
ttcttgaacc gtgtacatgt cgaagaaaat aaactcagat ctttgggatt atgggaactt 1080
cctcatcctt ggcttaacct ctacgttcct aaatctcgga ttctcgattt tcataacggt 1140
gttgtcaaag acattcttct taagcaaaaa tcagcttcgg gactcgctct tctctatcca 1200
acaaaccgga ataaatggga caatcgtatg tcggcgatga taccagagat cgatgaagat 1260
gttatatata ttatcggact actacaatcc gctaccccaa aggatcttcc agaagtggag 1320
agcgttaacg agaagataat taggttttgc aaggattcag gtattaagat taagcaatat 1380
ctaatgcatt atactagtaa agaagattgg attgagcatt ttggatcaaa atgggatgat 1440
ttttcgaaga ggaaagatct atttgatccc aagaaactgt tatctccagg gcaagacatc 1500
ttttga 1506

<210> SEQ ID NO 45
<211> LENGTH: 56
<212> TYPE: DNA
<213> ORGANISM: Artificial Sequence
<220> FEATURE:
<223> OTHER INFORMATION: oligonucleotide

<400> SEQUENCE: 45
ggggacaagt ttgtacaaaa aagcaggctt cacaatggga ttgacctcat ccttac 56

<210> SEQ ID NO 46
<211> LENGTH: 53
<212> TYPE: DNA
<213> ORGANISM: Artificial Sequence
<220> FEATURE:
<223> OTHER INFORMATION: oligonucleotide

<400> SEQUENCE: 46
ggggaccact ttgtacaaga aagctgggtt tatacagttc taggtttcgg cag 53

<210> SEQ ID NO 47
<211> LENGTH: 2746
<212> TYPE: DNA
<213> ORGANISM: Artificial Sequence
<220> FEATURE:
<223> OTHER INFORMATION: expression cassette
<220> FEATURE:
<221> NAME/KEY: misc_feature
<222> LOCATION: (1913)..(1914)
<223> OTHER INFORMATION: n is a, c, g, or t

<400> SEQUENCE: 47
cttctacatc ggcttaggtg tagcaacacg actttattat tattattatt attattatta 60
ttattttaca aaaatataaa atagatcagt ccctcaccac aagtagagca agttggtgag 120
ttattgtaaa gttctacaaa gctaatttaa aagttattgc attaacttat ttcatattac 180
aaacaagagt gtcaatggaa caatgaaaac catatgacat actataattt tgtttttatt 240
attgaaatta tataattcaa agagaataaa tccacatagc cgtaaagttc tacatgtggt 300

-continued

```
gcattaccaa aatatatata gcttacaaaa catgacaagc ttagtttgaa aaattgcaat    360
ccttatcaca ttgacacata aagtgagtga tgagtcataa tattattttc tttgctaccc    420
atcatgtata tatgatagcc acaaagttac tttgatgatg atatcaaaga acatttttag    480
gtgcacctaa cagaatatcc aaataatatg actcacttag atcataatag agcatcaagt    540
aaaactaaca ctctaaagca accgatggga aagcatctat aaatagacaa gcacaatgaa    600
aatcctcatc atccttcacc acaattcaaa tattatagtt gaagcatagt agtaatttaa    660
atcaactagg gatatcacaa gtttgtacaa aaaagcaggc ttcacaatgg ctaatcttcg    720
tttaatgatc actttaatca cggttttaat gatcaccaaa tcatcaaacg gtattaaaat    780
tgatttacct aaatccctta acctcaccct ctctaccgat ccttccatca tctccgcagc    840
ctctcatgac ttcggaaaca taaccaccgt gacccccggc ggcgtaatct gcccctcctc    900
caccgctgat atctctcgtc tcctccaata cgccgcaaac ggaaaaagta cattccaagt    960
agcggctcgt ggccaaggcc actccttaaa cggccaagcc tcggtctccg gcggagtaat   1020
cgtcaacatg acgtgtatca ctgacgtggt ggtttcaaaa gacaagaagt acgctgacgt   1080
ggcggccggg acgttatggg tggatgtgct taagaagacg gcggagaaag gggtgtcgcc   1140
ggtttcttgg acggattatt tgcatataac cgtcggagga acgttgtcga atggtggaat   1200
tggtggtcaa gtgtttcgaa acggtcctct tgttagtaac gtccttgaat tggacgttat   1260
tactgggaaa ggtgaaatgt tgacatgctc gcgacagcta aacccagaat tgttctatgg   1320
agtgttagga ggtttgggtc aatttggaat tataacgaga gccagaattg ttttggacca   1380
tgcacctaaa cggcaagaac gtttgatatc aatggcaaac gatattggag tcgactattt   1440
agaaggtcaa atatttctat caaacggtgt cgttgacacc tctttttttcc caccttcaga   1500
tcaatctaaa gtcgctgatc tagtcaagca acacggtatc atctatgttc ttgaagtagc   1560
caagtattat gatgatccca atctccccat catcagcaag gttattgaca cattaacgaa   1620
aacattaagt tacttgcccg ggttcatatc aatgcacgac gtggcctact tcgatttctt   1680
gaaccgtgta catgtcgaag aaaataaact cagatctttg ggattatggg aacttcctca   1740
tccttggctt aacctctacg ttcctaaatc tcggattctc gattttcata acggtgttgt   1800
caaagacatt cttcttaagc aaaaatcagc ttcgggactc gctcttctct atccaacaaa   1860
ccggaataag tacatacttc tcttcattca tatttatctt caagaaccaa agnnatggga   1920
caatcgtatg tcggcgatga taccagagat cgatgaagat gttatatata ttatcggact   1980
actacaatcc gctaccccaa aggatcttcc agaagtggag agcgttaacg agaagataat   2040
taggttttgc aaggattcag gtattaagat taagcaatat ctaatgcatt atactagtaa   2100
agaagattgg attgagcatt ttggatcaaa atgggatgat tttcgaaga ggaaagatct   2160
atttgatccc aagaaactgt tatctccagg gcaagacatc ttttgaaccc agctttcttg   2220
tacaaagtgg tgatatcaca agcccgggcg gtcttctagg gataacaggg taattatatc   2280
cctctagatc acaagcccgg gcggtcttct acgatgattg agtaataatg tgtcacgcat   2340
caccatgggt ggcagtgtca gtgtgagcaa tgacctgaat gaacaattga aatgaaaaga   2400
aaaaaagtac tccatctgtt ccaaattaaa attcatttta accttttaat aggtttatac   2460
aataattgat atatgttttc tgtatatgtc taatttgtta tcatccgggc ggtcttctag   2520
ggataacagg gtaattatat ccctctagac aacacacaac aaataagaga aaaaacaaat   2580
aatattaatt tgagaatgaa caaaaggacc atatcattca ttaactcttc tccatccatt   2640
```

tccatttcac agttcgatag cgaaaaccga ataaaaaaca cagtaaatta caagcacaac 2700
aaatggtaca agaaaaacag ttttcccaat gccataatac tcgaac 2746

<210> SEQ ID NO 48
<211> LENGTH: 2291
<212> TYPE: DNA
<213> ORGANISM: Arabidopsis thaliana

<400> SEQUENCE: 48
caaagtagaa atgggattga cctcatcctt acggttccat agacaaaaca acaagacttt 60
cctcggaatc ttcatgatct tagttctaag ctgtatacca ggtagaacca atctttgttc 120
caatcattct gttagtaccc caaaagaatt accttcttca aatccttcag atattcgttc 180
ctcattagtt tcactagatt tggagggtta tataagcttc gacgatgtcc acaatgtggc 240
caaggacttt ggcaacagat accagttacc acctttggca attctacatc caaggtcagt 300
ttttgatatt tcatcgatga tgaagcatat agtacatctg ggctccacct caaatcttac 360
agtagcagct agaggccatg gtcactcgct tcaaggacaa gctctagctc atcaaggtgt 420
tgtcatcaaa atggagtcac ttcgaagtcc tgatatcagg atttataagg ggaagcaacc 480
atatgttgat gtctcaggtg gtgaaatatg gataaacatt ctacgcgaga ctctaaaata 540
cggtctttca ccaaagtcct ggacagacta ccttcatttg accgttggag gtacactatc 600
taatgctgga atcagcggtc aagcattcaa gcatggaccc caaatcaaca acgtctacca 660
gctagagatt gttacaggta tttcattcat gctttatctc tgcggtagtc tcaaaaaaat 720
atgcacctgt aaagaatatc catctcttca tgagcaaaaa cactgacgac tttaaataat 780
ttttgactat aaaacaagag tgcataggca caaatgtgaa atatgcaaca cacaattgta 840
acttgcacca agaaaaaagt tataaaaaca aacaactgat aagcaatata tttccaatat 900
ttaatcaggg aaaggagaag tcgtaacctg ttctgagaag cggaattctg aacttttctt 960
cagtgttctt ggcgggcttg gacagtttgg cataatcacc cgggcacgga tctctcttga 1020
accagcaccg catatggtaa agttctatct tgaacaaagt tcaaacaata tacgctatga 1080
ttctaagaac cactttcctg acacagtcaa ataactttta ataggttaaa tggatcaggg 1140
tactctactc tgacttttct gcattttcaa gggaccaaga atatctgatt tcgaaggaga 1200 aaactttga ttacgttgaa ggatttgtga taatcaatag aacagacctt ctcaataatt 1260
ggcgatcgtc attcagtccc aacgattcca cacaggcaag cagattcaag tcagatggga 1320
aaactcttta ttgcctagaa gtggtcaaat atttcaaccc agaagaagct agctctatgg 1380
atcaggtaag atgtgaaagc aatatataac tagacttagt ttccacagag agctccaaat 1440
caaccgttgg ctactagcct actaacataa tgaatggttg ccgtgcagga aactggcaag 1500
ttactttcag agttaaatta tattccatcc actttgtttt catctgaagt gccatatatc 1560
gagtttctgg atcgcgtgca tatcgcagag agaaaactaa gagcaaaggg tttatgggag 1620
gttccacatc cctggctgaa tctcctgatt cctaagagca gcatatacca atttgctaca 1680
gaagttttca acaacattct cacaagcaac aacaacggtc ctatccttat ttatccagtc 1740
aatcaatcca agtaagtgag caaaatgcca aaagcaaatg cgtccagtga ttctgaaaca 1800
taaattacta accatatcca acattttgtg gtttcaggtg gaagaaacat acatctttga 1860
taactccaaa tgaagatata ttctatctcg tagcctttct cccctctgca gtgccaaatt 1920
cctcagggaa aaacgatcta gagtaccttt tgaaacaaaa ccaaagagtt atgaacttct 1980
gcgcagcagc aaacctcaac gtgaagcagt atttgcccca ttatgaaact caaaaagagt 2040

```
ggaaatcaca ctttggcaaa agatgggaaa catttgcaca gaggaaacaa gcctacgacc   2100

ctctagcgat tctagcacct ggccaaagaa tattccaaaa gacaacagga aaattatctc   2160

ccatccaact cgcaaagtca aaggcaacag gaagtcctca aaggtaccat tacgcatcaa   2220

tactgccgaa acctagaact gtataaaagt ttcctgtgtc cgtccttgta accgctcagg   2280

ctaggcagca a                                                        2291


<210> SEQ ID NO 49
<211> LENGTH: 17
<212> TYPE: PRT
<213> ORGANISM: Artificial
<220> FEATURE:
<221> NAME/KEY: PEPTIDE
<222> LOCATION: (1)...(17)
<223> OTHER INFORMATION: Peptide is consensus sequence for cytokinin
      oxidase/dehydrogenase
<220> FEATURE:
<221> NAME/KEY: misc_feature
<222> LOCATION: (1)...(1)
<223> OTHER INFORMATION: Xaa at position 1 is Gly, His, Leu, Arg, Thr,
      Trp, or Tyr
<220> FEATURE:
<221> NAME/KEY: misc_feature
<222> LOCATION: (6)...(6)
<223> OTHER INFORMATION: Xaa at position 6 is Gly, His, Leu, Arg, Thr,
      Trp, or Tyr
<220> FEATURE:
<221> NAME/KEY: misc_feature
<222> LOCATION: (7)...(7)
<223> OTHER INFORMATION: Xaa at position 7 is Gly, His, Leu, Arg, Thr,
      Trp, or Tyr
<220> FEATURE:
<221> NAME/KEY: misc_feature
<222> LOCATION: (8)...(8)
<223> OTHER INFORMATION: Xaa at position 8 is Ser or Thr
<220> FEATURE:
<221> NAME/KEY: misc_feature
<222> LOCATION: (9)...(9)
<223> OTHER INFORMATION: Xaa at position 9 is Val or Ile
<220> FEATURE:
<221> NAME/KEY: misc_feature
<222> LOCATION: (15)...(15)
<223> OTHER INFORMATION: Xaa at position 15 is Ala, Asp, Gly, Asn, Thr
      or Val
<220> FEATURE:
<221> NAME/KEY: misc_feature
<222> LOCATION: (16)...(16)
<223> OTHER INFORMATION: Xaa at position 16 is Ala, Asp, Gly, Asn, Thr
      or Val

<400> SEQUENCE: 49

Xaa Thr Asp Tyr Leu Xaa Xaa Xaa Xaa Gly Gly Thr Leu Ser Xaa Xaa
1               5                   10                  15

Gly


<210> SEQ ID NO 50
<211> LENGTH: 19
<212> TYPE: PRT
<213> ORGANISM: Artificial
<220> FEATURE:
<221> NAME/KEY: PEPTIDE
<222> LOCATION: (1)...(19)
<223> OTHER INFORMATION: Peptide is consensus sequence for cytokinin
      oxidase/dehydrogenase
<220> FEATURE:
<221> NAME/KEY: misc_feature
<222> LOCATION: (1)...(1)
<223> OTHER INFORMATION: Xaa at position 1 is Asp, Glu, or Arg
<220> FEATURE:
<221> NAME/KEY: misc_feature
<222> LOCATION: (4)...(4)
```

<223> OTHER INFORMATION: Xaa at position 4 is Tyr, Arg, Asn, Phe, Asp, or His
<220> FEATURE:
<221> NAME/KEY: misc_feature
<222> LOCATION: (5)...(5)
<223> OTHER INFORMATION: Xaa at position 5 is Ala, Gly, or Ser
<220> FEATURE:
<221> NAME/KEY: misc_feature
<222> LOCATION: (6)...(6)
<223> OTHER INFORMATION: Xaa at position 6 is Ala, Asp, Gly, Asn, Thr, or Val
<220> FEATURE:
<221> NAME/KEY: misc_feature
<222> LOCATION: (7)...(7)
<223> OTHER INFORMATION: Xaa at position 7 is Gly, His, Leu, Arg, Thr, Trp, or Tyr
<220> FEATURE:
<221> NAME/KEY: misc_feature
<222> LOCATION: (9)...(9)
<223> OTHER INFORMATION: Xaa at position 9 is Ala, Asp, Gly, Asn, Thr, or Val
<220> FEATURE:
<221> NAME/KEY: misc_feature
<222> LOCATION: (15)...(15)
<223> OTHER INFORMATION: Xaa at position 15 is Val or Ile
<220> FEATURE:
<221> NAME/KEY: misc_feature
<222> LOCATION: (17)...(17)
<223> OTHER INFORMATION: Xaa at position 17 is Ala, Asp, Gly, Asn, Thr, or Val
<220> FEATURE:
<221> NAME/KEY: misc_feature
<222> LOCATION: (18)...(18)
<223> OTHER INFORMATION: Xaa at position 18 is Arg or Asn

<400> SEQUENCE: 50

```
Xaa Leu Phe Xaa Xaa Xaa Xaa Gly Xaa Leu Gly Gln Phe Gly Xaa
1               5                   10                  15

Ile Xaa Xaa Ala
```

<210> SEQ ID NO 51
<211> LENGTH: 534
<212> TYPE: PRT
<213> ORGANISM: Zea mays

<400> SEQUENCE: 51

```
Met Ala Val Val Tyr Tyr Leu Leu Leu Ala Gly Leu Ile Ala Cys Ser
1               5                   10                  15

His Ala Leu Ala Ala Gly Thr Pro Ala Leu Gly Asp Asp Arg Gly Arg
            20                  25                  30

Pro Trp Pro Ala Ser Leu Ala Ala Leu Ala Leu Asp Gly Lys Leu Arg
        35                  40                  45

Thr Asp Ser Asn Ala Thr Ala Ala Ala Ser Thr Asp Phe Gly Asn Ile
    50                  55                  60

Thr Ser Ala Leu Pro Ala Ala Val Leu Tyr Pro Ser Ser Thr Gly Asp
65                  70                  75                  80

Leu Val Ala Leu Leu Ser Ala Ala Asn Ser Thr Pro Gly Trp Pro Tyr
                85                  90                  95

Thr Ile Ala Phe Arg Gly Arg Gly His Ser Leu Met Gly Gln Ala Phe
            100                 105                 110

Ala Pro Gly Gly Val Val Val Asn Met Ala Ser Leu Gly Asp Ala Ala
        115                 120                 125

Ala Pro Pro Arg Ile Asn Val Ser Ala Asp Gly Arg Tyr Val Asp Ala
    130                 135                 140

Gly Gly Glu Gln Val Trp Ile Asp Val Leu Arg Ala Ser Leu Ala Arg
145                 150                 155                 160
```

```
Gly Val Ala Pro Arg Ser Trp Asn Asp Tyr Leu Tyr Leu Thr Val Gly
                165                 170                 175

Gly Thr Leu Ser Asn Ala Gly Ile Ser Gly Gln Ala Phe Arg His Gly
            180                 185                 190

Pro Gln Ile Ser Asn Val Leu Glu Met Asp Val Ile Thr Gly His Gly
        195                 200                 205

Glu Met Val Thr Cys Ser Lys Gln Leu Asn Ala Asp Leu Phe Asp Ala
    210                 215                 220

Val Leu Gly Gly Leu Gly Gln Phe Gly Val Ile Thr Arg Ala Arg Ile
225                 230                 235                 240

Ala Val Glu Pro Ala Pro Ala Arg Ala Arg Trp Val Arg Phe Val Tyr
                245                 250                 255

Thr Asp Phe Ala Ala Phe Ser Ala Asp Gln Glu Arg Leu Thr Ala Pro
            260                 265                 270

Arg Pro Gly Gly Gly Gly Ala Ser Phe Gly Pro Met Ser Tyr Val Glu
        275                 280                 285

Gly Ser Val Phe Val Asn Gln Ser Leu Ala Thr Asp Leu Ala Asn Thr
    290                 295                 300

Gly Phe Phe Thr Asp Ala Asp Val Ala Arg Ile Val Ala Leu Ala Gly
305                 310                 315                 320

Glu Arg Asn Ala Thr Thr Val Tyr Ser Ile Glu Ala Thr Leu Asn Tyr
                325                 330                 335

Asp Asn Ala Thr Ala Ala Ala Ala Ala Val Asp Gln Glu Leu Ala Ser
            340                 345                 350

Val Leu Gly Thr Leu Ser Tyr Val Glu Gly Phe Ala Phe Gln Arg Asp
        355                 360                 365

Val Ala Tyr Ala Ala Phe Leu Asp Arg Val His Gly Glu Glu Val Ala
    370                 375                 380

Leu Asn Lys Leu Gly Leu Trp Arg Val Pro His Pro Trp Leu Asn Met
385                 390                 395                 400

Phe Val Pro Arg Ser Arg Ile Ala Asp Phe Asp Arg Gly Val Phe Lys
                405                 410                 415

Gly Ile Leu Gln Gly Thr Asp Ile Val Gly Pro Leu Ile Val Tyr Pro
            420                 425                 430

Leu Asn Lys Ser Met Trp Asp Asp Gly Met Ser Ala Ala Thr Pro Ser
        435                 440                 445

Glu Asp Val Phe Tyr Ala Val Ser Leu Leu Phe Ser Ser Val Ala Pro
    450                 455                 460

Asn Asp Leu Ala Arg Leu Gln Glu Gln Asn Arg Arg Ile Leu Arg Phe
465                 470                 475                 480

Cys Asp Leu Ala Gly Ile Gln Tyr Lys Thr Tyr Leu Ala Arg His Thr
                485                 490                 495

Asp Arg Ser Asp Trp Val Arg His Phe Gly Ala Ala Lys Trp Asn Arg
            500                 505                 510

Phe Val Glu Met Lys Asn Lys Tyr Asp Pro Lys Arg Leu Leu Ser Pro
        515                 520                 525

Gly Gln Asp Ile Phe Asn
    530
```

<210> SEQ ID NO 52
<211> LENGTH: 6
<212> TYPE: PRT
<213> ORGANISM: Artificial Sequence
<220> FEATURE:

<223> OTHER INFORMATION: peptide; (histidine)6-tag

<400> SEQUENCE: 52

His His His His His His
1 5

<210> SEQ ID NO 53
<211> LENGTH: 12
<212> TYPE: PRT
<213> ORGANISM: Artificial Sequence
<220> FEATURE:
<223> OTHER INFORMATION: peptide; Tag.100 epitope

<400> SEQUENCE: 53

Glu Glu Thr Ala Arg Phe Gln Pro Gly Tyr Arg Ser
1 5 10

<210> SEQ ID NO 54
<211> LENGTH: 10
<212> TYPE: PRT
<213> ORGANISM: Artificial Sequence
<220> FEATURE:
<223> OTHER INFORMATION: Peptide; c-myc epitope

<400> SEQUENCE: 54

Glu Gln Lys Leu Ile Ser Glu Glu Asp Leu
1 5 10

<210> SEQ ID NO 55
<211> LENGTH: 7
<212> TYPE: PRT
<213> ORGANISM: Artifical Sequence
<220> FEATURE:
<223> OTHER INFORMATION: Peptide; FLAG-epitope

<400> SEQUENCE: 55

Asp Tyr Lys Asp Asp Asp Lys
1 5

<210> SEQ ID NO 56
<211> LENGTH: 9
<212> TYPE: PRT
<213> ORGANISM: Artificial Sequence
<220> FEATURE:
<223> OTHER INFORMATION: Peptide; HA-epitope

<400> SEQUENCE: 56

Tyr Pro Tyr Asp Val Pro Asp Tyr Ala
1 5

<210> SEQ ID NO 57
<211> LENGTH: 12
<212> TYPE: PRT
<213> ORGANISM: Artificial Sequence
<220> FEATURE:
<223> OTHER INFORMATION: Peptide; protein C epitope

<400> SEQUENCE: 57

Glu Asp Gln Val Asp Pro Arg Leu Ile Asp Gly Lys
1 5 10

<210> SEQ ID NO 58
<211> LENGTH: 11
<212> TYPE: PRT

-continued

```
<213> ORGANISM: Artificial Sequence
<220> FEATURE:
<223> OTHER INFORMATION: Peptide; VSV epitope

<400> SEQUENCE: 58

Tyr Thr Asp Ile Glu Met Asn Arg Leu Gly Lys
1               5                   10
```